United States Patent
Lin et al.

(10) Patent No.: US 12,331,332 B2
(45) Date of Patent: Jun. 17, 2025

(54) GH61 VARIANTS AND POLYNUCLEOTIDES ENCODING SAME

(71) Applicants: Novozymes A/S, Bagsvaerd (DK); Novozymes, Inc., Davis, CA (US)

(72) Inventors: Janine Lin, Davis, CA (US); Doreen Bohan, Fairfield, CA (US); Michelle Maranta, Davis, CA (US); Leslie Beresford, Roseville, CA (US); Michael Lamsa, Woodland, CA (US); Matt Sweeney, Sacramento, CA (US); Mark David Wogulis, Davis, CA (US); Elizabeth Znameroski, Davis, CA (US); Frank Winther Rasmussen, Roskilde (DK)

(73) Assignees: Novozymes A/S, Bagsvaerd (DK); Novozymes, Inc., Davis, CA (US)

( * ) Notice: Subject to any disclaimer, the term of this patent is extended or adjusted under 35 U.S.C. 154(b) by 0 days.

(21) Appl. No.: 18/524,366

(22) Filed: Nov. 30, 2023

(65) Prior Publication Data

US 2024/0110169 A1 Apr. 4, 2024

Related U.S. Application Data

(62) Division of application No. 17/714,461, filed on Apr. 6, 2022, now Pat. No. 11,891,637, which is a division of application No. 16/269,212, filed on Feb. 6, 2019, now Pat. No. 11,345,905, which is a division of application No. 14/395,984, filed as application No. PCT/US2013/038477 on Apr. 26, 2013, now Pat. No. 10,227,579.

(60) Provisional application No. 61/639,648, filed on Apr. 27, 2012.

(51) Int. Cl.
| | |
|---|---|
| *C12N 9/24* | (2006.01) |
| *C11D 3/386* | (2006.01) |
| *C12N 9/02* | (2006.01) |
| *C12N 9/42* | (2006.01) |
| *C12P 19/02* | (2006.01) |
| *C12P 19/14* | (2006.01) |
| *D21C 5/00* | (2006.01) |
| *D21H 17/00* | (2006.01) |

(52) U.S. Cl.
CPC ........ *C12N 9/2437* (2013.01); *C11D 3/38645* (2013.01); *C12N 9/0071* (2013.01); *C12N 9/2434* (2013.01); *C12P 19/02* (2013.01); *C12P 19/14* (2013.01); *C12Y 302/01021* (2013.01); *D21C 5/005* (2013.01); *D21H 17/005* (2013.01); *C12P 2203/00* (2013.01); *C12Y 114/00* (2013.01); *C12Y 302/01004* (2013.01)

(58) Field of Classification Search
None
See application file for complete search history.

(56) References Cited

U.S. PATENT DOCUMENTS

| | | |
|---|---|---|
| 9,260,704 B2 | 2/2016 | Schooneveld-Bergmans et al. |
| 2010/0143971 A1 | 6/2010 | Spodsberg et al. |
| 2010/0159535 A1 | 6/2010 | Xu et al. |
| 2011/0078829 A1 | 3/2011 | Tang et al. |
| 2011/0078831 A1 | 3/2011 | Tang et al. |

FOREIGN PATENT DOCUMENTS

| | | |
|---|---|---|
| WO | 2011050038 A2 | 4/2011 |
| WO | 2012044835 A1 | 4/2012 |

OTHER PUBLICATIONS

Dimarogona_2012_Bioresourse_Technology_110_480-487.
Fedorova_2007_EBI_Accession_no._A1CH98.
Fedorova_2007_Uniprot_Access_No_A1CX17.
Harris 2010 Biochem 49 (15) 3305-3316.
Heijne_2015_NCBI_Reference_no._XP_013325186.1.
Horn 2012 Biotechnology for Biofuels 5(45) 1-12.
Kusuya_2015_Genbank_Accession_GAO83771.
Langston, 2011 Appl Environ Microbiol 77(19) 7007-7015.
Machida_2006_Uniprot_Access_No_Q2UGM5.
Nguyen_2015_Genbank_accession_KOS47081.
Quinlan 2011 PNAS 108(37) 15079-15084.
WO 2012-021410—Geneseq Access No. AZT54345.
WO 2011-080267—Geneseq Access No. AZJ19469.

*Primary Examiner* — Brent T Page
(74) *Attorney, Agent, or Firm* — David A. Fazzolare

(57) ABSTRACT

The present invention relates to GH61 polypeptide variants. The present invention also relates to polynucleotides encoding the variants; nucleic acid constructs, vectors, and host cells comprising the polynucleotides; and methods of using the variants.

32 Claims, 11 Drawing Sheets

Specification includes a Sequence Listing.

```
      M  T  L  S  K  I  T  S  I  A  G  L  L  A  S  A  S  L  V  A  G  H  G  F  V  S  G
  1   ATGACTTTGT CCAAGATCAC TTCCATTGCT GGCCTTCTGG CCTCAGCGTC TCTCGTGGCT GGCCACGGCT TTGTTTCTGG
      I  V  A  D  G  K  Y                                                              Y  G
 81   CATTGTTGCT GATGGGAAAT AGTATGTGCT TGAACCACAC AAATGACAGC TGCAACAGCT AACTTCTATT CCAGTTACGG
      G  Y  L  V  N  Q  Y  P  Y  M  S  N  P  P  D  T  I  A  W  S  T  T  A  T  D  L
161   AGGGTACCTT GTTAACCAAT ACCCCTACAT GAGCAACCCT CCCGACACCA TTGCCTGGTC CACCACCGCC ACCGACCTCG
      G  F  V  D  G  T  G  Y  Q  S  P  D  I  I  C  H  R  D  A  K  N  G  K  L  T  A  T
241   GCTTTGTGGA CGGCACCGGC TACCAGTCTC CGGATATTAT CTGCCACAGA GACGCAAAGA ATGGCAAGTT GACCGCAACC
      V  A  A  G  S  Q  I  E  F  Q  W  T  T  W  P  E  S  H  H  G  P
321   GTTGCAGCCG GTTCACAGAT CGAATTCCAG TGGACGACGT GGCCAGAGTC TCACCATGGA CCGGTACGAC GCCGAAGAGA
                                                                 L  I  T  Y  L  A  P  C  N  G  D  C  A  T
401   AGAGAACATA TTGTGACCAG ATAGGCTAAC ATAGCATAGT TGATTACTTA CCTCGCTCCA TGCAACGGCG ACTGTGCCAC
      V  D  K  T  T  L  K  F  V  K  I  A  A  Q  G  L  I  D  G  S  N  P  P  G  V  W
481   CGTGGACAAG ACCACCCTGA AGTTTGTCAA GATCGCGGCT CAAGGCTTGA TCGACGGCTC CAACCCACCT GGTGTTTGGG
      A  D  D  E  M  I  A  N  N  N  T  A  T  V  T  I  P  A  S  Y  A  P  G  N  Y  V  L
561   CTGATGATGA AATGATCGCC AACAACAACA CGGCCACAGT GACCATTCCT GCCTCCTATG CCCCCGGAAA CTACGTCCTT
      R  H  E  I  I  A  L  H  S  A  G  N  L  N  G  A  Q  N  Y  P  Q  C  F  N  I  Q  I
641   CGCCACGAGA TCATCGCCCT TCACTCTGCG GGTAACCTGA ACGGCGCGCA GAACTACCCC CAGTGTTTCA ACATCCAAAT
      T  G  G  S  A  Q  G  S  G  T  A  G  T  S  L  Y  K  N  T  D  P  G  I  K  F
721   CACCGGTGGC GGCAGTGCTC AGGGATCTGG CACCGCTGGC ACGTCCCTGT ACAAGAATAC TGATCCTGGC ATCAAGTTTG
      D  I  Y  S  D  L  S  G  G  Y  P  I  P  G  P  A  L  F  N  A  *
801   ACATCTACTC GGATCTGAGC GGTGGATACC CTATTCCTGG TCCTGCACTG TTCAACGCTT AA
```

Fig. 1

GH61 VARIANTS AND POLYNUCLEOTIDES ENCODING SAME

CROSS-REFERENCE TO RELATED APPLICATIONS

This application is a divisional application of U.S. patent application Ser. No. 17/714,461, filed on Apr. 6, 2022, issued U.S. Pat. No. 11,891,637, granted on Feb. 6, 2024, which is a divisional application of U.S. patent application Ser. No. 16/269,212, filed on Feb. 6, 2019, issued U.S. Pat. No. 11,345,905, granted on May 31, 2022, which is a divisional application of U.S. patent application Ser. No. 14/395,984, filed on Oct. 21, 2014, issued U.S. Pat. No. 10,227,579, granted on Mar. 12, 2019 which is a 35 U.S.C. § 371 national application of PCT/US2013/038477, filed on Apr. 26, 2013, which claims priority from U.S. Provisional Application Ser. No. 61/639,648, filed on Apr. 27, 2012. The contents of these applications are fully incorporated herein by reference.

REFERENCE TO A SEQUENCE LISTING

This application contains a Sequence Listing in computer-readable form created on Nov. 28, 2023 as an xml file, 568 kb in size, and named SQ_ST26.xml, which is incorporated herein by reference.

BACKGROUND OF THE INVENTION

Field of the Invention

The present invention relates to GH61 polypeptide variants, polynucleotides encoding the variants, methods of producing the variants, and methods of using the variants.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars can easily be fermented by yeast into ethanol.

WO 2005/074647, WO 2008/148131, and WO 2011/035027 disclose isolated GH61 polypeptides having cellulolytic enhancing activity and the polynucleotides thereof from *Thielavia terrestris*. WO 2005/074656 and WO 2010/065830 disclose isolated GH61 polypeptides having cellulolytic enhancing activity and the polynucleotides thereof from *Thermoascus aurantiacus*. WO 2007/089290 and WO 2012/149344 disclose isolated GH61 polypeptides having cellulolytic enhancing activity and the polynucleotides thereof from *Trichoderma reesei*. WO 2009/085935, WO 2009/085859, WO 2009/085864, and WO 2009/085868 disclose isolated GH61 polypeptides having cellulolytic enhancing activity and the polynucleotides thereof from *Myceliophthora thermophila*. WO 2010/138754 discloses an isolated GH61 polypeptide having cellulolytic enhancing activity and the polynucleotide thereof from *Aspergillus fumigatus*. WO 2011/005867 discloses an isolated GH61 polypeptide having cellulolytic enhancing activity and the polynucleotide thereof from *Penicillium pinophilum*. WO 2011/039319 discloses an isolated GH61 polypeptide having cellulolytic enhancing activity and the polynucleotide thereof from *Thermoascus* sp. WO 2011/041397 discloses an isolated GH61 polypeptide having cellulolytic enhancing activity and the polynucleotide thereof from *Penicillium* sp. WO 2011/041504 discloses isolated GH61 polypeptides having cellulolytic enhancing activity and the polynucleotides thereof from *Thermoascus crustaceus*. WO 2012/030799 discloses isolated GH61 polypeptides having cellulolytic enhancing activity and the polynucleotides thereof from *Aspergillus aculeatus*. WO 2012/113340 discloses isolated GH61 polypeptides having cellulolytic enhancing activity and the polynucleotides thereof from *Thermomyces lanuginosus*. WO 2012/122477 discloses isolated GH61 polypeptides having cellulolytic enhancing activity and the polynucleotides thereof from *Aurantiporus alborubescens*, *Trichophaea saccata*, and *Penicillium thomii*. WO 2012/135659 discloses an isolated GH61 polypeptide having cellulolytic enhancing activity and the polynucleotide thereof from *Talaromyces stipitatus*. WO 2012/146171 discloses isolated GH61 polypeptides having cellulolytic enhancing activity and the polynucleotides thereof from *Humicola insolens*. WO 2012/101206 discloses isolated GH61 polypeptides having cellulolytic enhancing activity and the polynucleotides thereof from *Malbranchea cinnamomea*, *Talaromyces leycettanus*, and *Chaetomium thermophilum*. WO 2013/043910 discloses isolated GH61 polypeptides having cellulolytic enhancing activity and the polynucleotides thereof from *Acrophialophora fusispora* and *Corynascus sepedonium*.

WO 2012/044835 and WO 2012/044836 disclose GH61 polypeptide variants having cellulolytic enhancing activity with improved thermal activity and thermostability.

There is a need in the art for GH61 polypeptides having cellulolytic enhancing activity with increased thermostability as a component of enzyme compositions for use in the degradation of lignocellulose at high temperatures.

The present invention provides GH61 polypeptide variants with increased thermostability.

SUMMARY OF THE INVENTION

The present invention relates to isolated GH61 polypeptide variants, comprising a substitution at one or more (e.g., several) positions corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250 of the mature polypeptide of SEQ ID NO: 30, wherein the variants have cellulolytic enhancing activity.

The present invention also relates to isolated polynucleotides encoding the variants; nucleic acid constructs, vectors, and host cells comprising the polynucleotides; and methods of producing the variants.

The present invention also relates to processes for degrading or converting a cellulosic material, comprising: treating the cellulosic material with an enzyme composition in the presence of a GH61 polypeptide variant of the present invention. In one aspect, the processes further comprise recovering the degraded or converted cellulosic material.

The present invention also relates to processes of producing a fermentation product, comprising: (a) saccharifying a cellulosic material with an enzyme composition in the presence of a GH61 polypeptide variant of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a GH61 polypeptide variant of the present invention. In one aspect, the fermenting of the cellulosic material produces a fermentation product. In another aspect, the processes further comprise recovering the fermentation product from the fermentation.

BRIEF DESCRIPTION OF THE FIGURES

FIG. 1 shows the genomic DNA sequence (SEQ ID NO: 29) and the deduced amino acid sequence (SEQ ID NO: 30) of an *Aspergillus fumigatus* gene encoding a GH61B polypeptide having cellulolytic enhancing activity.

DEFINITIONS

Figure 2:
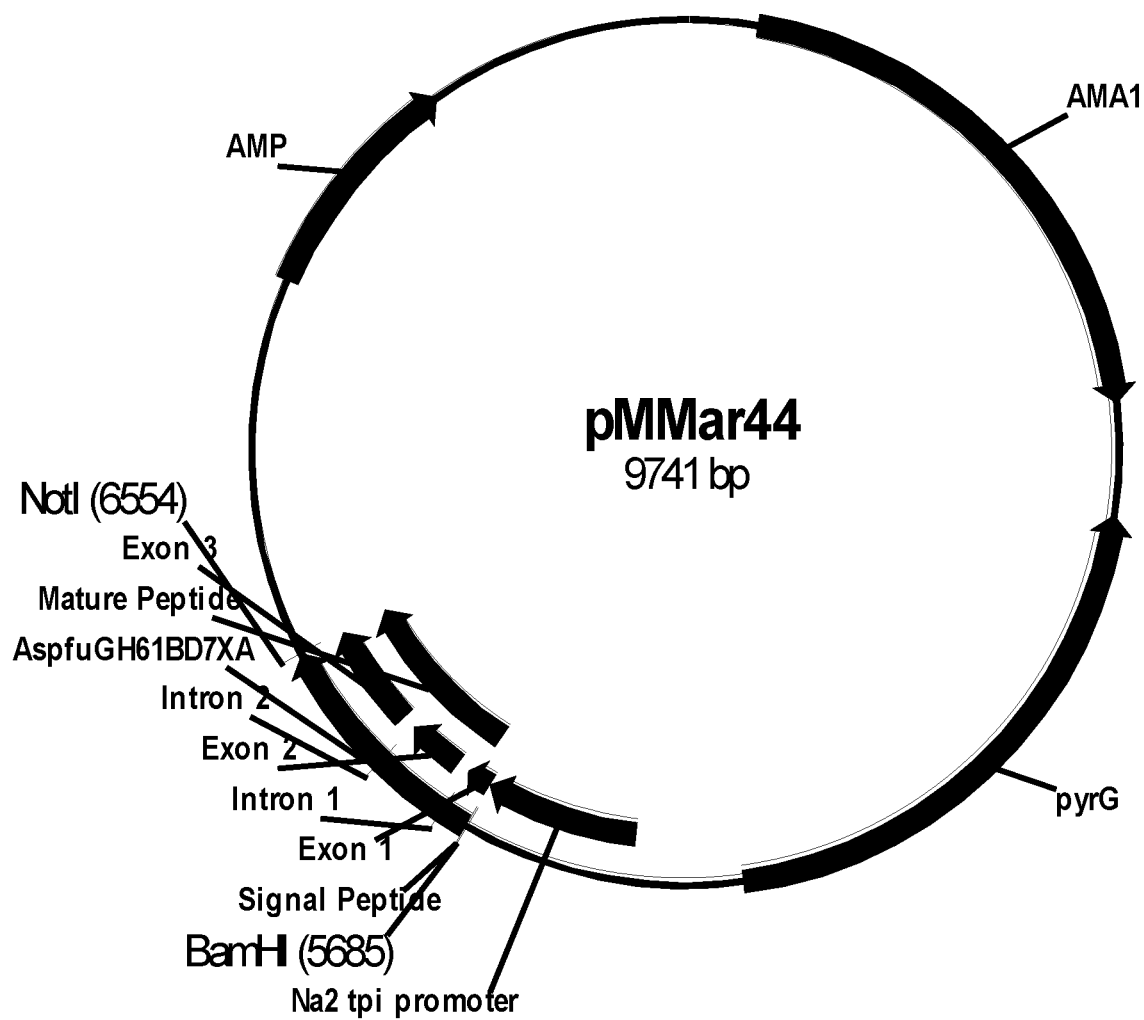
FIG. 2 shows a restriction map of pMMar44.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 µmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, CA, USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, beta-xylosidase activity is preferably determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity is preferably determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters,* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed pretreated corn stover (PCS), 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, CA, USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology,* T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is *arundo*. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is *miscanthus*. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is *eucalyptus*. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat, 1991, *Biochem. J.* 280: 309-316, and Henrissat, and Bairoch, 1996, *Biochem. J.* 316: 695-696. The enzymes in this family were originally classified as a glycoside hydrolase family based on measurement of very weak endo-1,4-beta-D-glucanase activity in one family member. The GH61s have recently been classified as lytic polysaccharide monooxygenases (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061).

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 µmole of p-nitrophenolate anion per minute at pH 5, 25° C.

Fragment: The term "fragment" means a polypeptide having one or more (e.g., several) amino acids absent from the amino and/or carboxyl terminus of the mature polypeptide thereof, wherein the fragment has cellulolytic enhancing activity. In one aspect, a fragment contains at least 85% of the amino acid residues, e.g., at least 90% of the amino acid residues or at least 95% of the amino acid residues of the mature polypeptide of a GH61 polypeptide.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure &Appl. Chem.* 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such an improved property includes, but is not limited to, increased thermostability.

Increased thermostability: The term "increased thermostability" means a higher retention of cellulolytic enhancing activity of a GH61 polypeptide variant after a period of incubation at a temperature relative to the parent. The increased thermostability of the variant relative to the parent can be assessed, for example, under conditions of one or more (e.g., several) temperatures. For example, the one or more (e.g., several) temperatures can be any temperature or temperatures in the range of 45° C. to 95° C., e.g., 45, 50, 55, 60, 65, 70, 75, 80, 85, or 95° C. (or in between, e.g., 62° C., 68° C., 72° C., etc.) at one or more (e.g., several) pHs in the range of 3 to 9, e.g., 3.0, 3.5, 4.0, 4.5, 5.0, 5.5, 6.0, 6.5, 7.0, 7.5, 8.0, 8.5, or 9.0 (or in between) for a suitable period (time) of incubation, e.g., 1 minute, 5 minutes, 10 minutes, 15 minutes, 20 minutes, 25 minutes, 30 minutes, 45 minutes, or 60 minutes (or in between, e.g., 23 minutes, 37 minutes, etc.), such that the variant retains residual activity. However, longer periods of incubation can also be used. The term "increased thermostability" can be used interchangeably with "improved thermostability".

The increased thermostability of the variant relative to the parent can be determined by differential scanning calorimetry (DSC) using methods standard in the art (see, for example, Sturtevant, 1987, *Annual Review of Physical Chemistry* 38: 463-488; Example 9). The increased thermostability of the variant relative to the parent can also be determined using protein thermal unfolding analysis (see, for example, Example 10 herein). The increased thermostability of the variant relative to the parent can also be determined using any enzyme assay known in the art for GH61 polypeptides having cellulolytic enhancing activity to measure residual activity after a temperature treatment. See for example, WO 2005/074647, WO 2008/148131 WO 2005/074656, WO 2010/065830, WO 2007/089290, WO 2009/085935, WO 2009/085859, WO 2009/085864, WO 2009/085868, and WO 2008/151043, which are incorporated herein by reference. Alternatively, the increased thermostability of the variant relative to the parent can be determined using any application assay for the variant where the performance of the variant is compared to the parent. For example, the application assays described in Example 5 can be used.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 326 of SEQ ID NO: 2 based on the SignalP 3.0 program (Bendtsen et al., 2004, *J. Mol. Biol.* 340: 783-795) that predicts amino acids 1 to 19 of SEQ ID NO: 2 are a signal peptide. In another aspect, the mature polypeptide is amino acids 18 to 239 of SEQ ID NO: 4 based on the SignalP program that predicts amino acids 1 to 17 of SEQ ID NO: 4 are a signal peptide. In another aspect, the mature polypeptide is amino acids 20 to 258 of SEQ ID NO: 6 based on the SignalP program that predicts amino acids 1 to 19 of SEQ ID NO: 6 are a signal peptide. In another aspect, the mature polypeptide is amino acids 19 to 226 of SEQ ID NO: 8 based on the SignalP program that predicts amino acids 1 to 18 of SEQ ID NO: 8 are a signal peptide. In another aspect, the mature polypeptide is amino acids 20 to 304 of SEQ ID NO: 10 based on the SignalP program that predicts amino acids 1 to 19 of SEQ ID NO: 10 are a signal peptide. In another aspect, the mature polypeptide is amino acids 16 to 317 of SEQ ID NO: 12 based on the SignalP program that predicts amino acids 1 to 15 of SEQ ID NO: 12 are a signal peptide. In another aspect, the mature polypeptide is amino acids 22 to 249 of SEQ ID NO: 14 based on the SignalP program that predicts amino acids 1 to 21 of SEQ ID NO: 14 are a signal peptide. In another aspect, the mature polypeptide is amino acids 20 to 249 of SEQ ID NO: 16 based on the SignalP program that predicts amino acids 1 to 19 of SEQ ID NO: 16 are a signal peptide. In another aspect, the mature polypeptide is amino acids 18 to 232 of SEQ ID NO: 18 based on the SignalP program that predicts amino acids 1 to 17 of SEQ ID NO: 18 are a signal peptide. In another aspect, the mature polypeptide is amino acids 16 to 235 of SEQ ID NO: 20 based on the SignalP program that predicts amino acids 1 to 15 of SEQ ID NO: 20 are a signal peptide. In another aspect, the mature polypeptide is amino acids 19 to 323 of SEQ ID NO: 22 based on the SignalP program that predicts amino acids 1 to 18 of SEQ ID NO: 22 are a signal peptide. In another aspect, the mature polypeptide is amino acids 16 to 310 of SEQ ID NO: 24 based on the SignalP program that predicts amino acids 1 to 15 of SEQ ID NO: 24 are a signal peptide. In another aspect, the mature polypeptide is amino acids 20 to 246 of SEQ ID NO: 26 based on the SignalP program that predicts amino acids 1 to 19 of SEQ ID NO: 26 are a signal peptide. In another aspect, the mature polypeptide is amino acids 22 to 354 of SEQ ID NO: 28 based on the SignalP program that predicts amino acids 1 to 21 of SEQ ID NO: 28 are a signal peptide. In another aspect, the mature polypeptide is amino acids 22 to 250 of SEQ ID NO: 30 based on the SignalP program that predicts amino acids 1 to 21 of SEQ ID NO: 30 are a signal peptide. In another aspect, the mature polypeptide is amino acids 22 to 322 of SEQ ID NO: 32 based on the SignalP program that predicts amino acids 1 to 21 of SEQ ID NO: 32 are a signal peptide. In another aspect, the mature polypeptide is amino acids 24 to 444 of SEQ ID NO: 34 based on the SignalP program that predicts amino acids 1 to 23 of SEQ ID NO: 34 are a signal peptide. In another aspect, the mature polypeptide is amino acids 26 to 253 of SEQ ID NO: 36 based on the SignalP program that predicts amino acids 1 to 25 of SEQ ID NO: 36 are a signal peptide. In another aspect, the mature polypeptide is amino acids 18 to 246 of SEQ ID NO: 38 based on the SignalP program that predicts amino acids 1 to 17 of SEQ ID NO: 38 are a signal peptide. In another aspect, the mature polypeptide is amino acids 20 to 334 of SEQ ID NO: 40 based on the SignalP program that predicts amino acids 1 to 19 of SEQ ID NO: 40 are a signal peptide. In another aspect, the mature polypeptide is amino acids 18 to 227 of SEQ ID NO: 42 based on the SignalP program that predicts amino acids 1 to 17 of SEQ ID NO: 42 are a signal peptide. In another aspect, the mature polypeptide is amino acids 20 to 223 of SEQ ID NO: 44 based on the SignalP program that predicts amino acids 1 to 19 of SEQ ID NO: 44 are a signal peptide. In another aspect, the mature polypeptide is amino acids 22 to 368 of SEQ ID NO: 46 based on the SignalP program that predicts amino acids 1 to 21 of SEQ ID NO: 46 are a signal peptide. In another aspect, the mature polypeptide is amino acids 25 to 330 of SEQ ID NO: 48 based on the SignalP program that predicts amino acids 1 to 24 of SEQ ID NO: 48 are a signal peptide. In another aspect, the mature polypeptide is amino acids 17 to 236 of SEQ ID NO: 50 based on the SignalP program that predicts amino acids 1 to 16 of SEQ ID NO: 50 are a signal peptide. In another aspect, the mature polypeptide is amino acids 19 to 250 of SEQ ID NO: 52 based on the SignalP program that predicts amino acids 1 to 18 of SEQ ID NO: 52 are a signal peptide. In another aspect, the mature polypeptide is amino acids 23 to 478 of SEQ ID NO: 54 based on the SignalP program that predicts amino acids 1 to 22 of SEQ ID NO: 54 are a signal peptide. In another aspect, the mature polypeptide is amino acids 17 to 230 of SEQ ID NO: 56 based on the SignalP program that predicts amino acids 1 to 16 of SEQ ID NO: 56 are a signal peptide. In another aspect, the mature polypeptide is amino acids 20 to 257 of SEQ ID NO: 58 based on the SignalP program that predicts amino acids 1 to 19 of SEQ ID NO: 58 are a signal peptide. In another aspect, the mature polypeptide is amino acids 23 to 251 of SEQ ID NO: 60 based on the SignalP program that predicts amino acids 1 to 22 of SEQ ID NO: 60 are a signal peptide. In another aspect, the mature polypeptide is amino acids 19 to 349 of SEQ ID NO: 62 based on the SignalP program that predicts amino acids 1 to 18 of SEQ ID NO: 62 are a signal peptide. In another aspect, the mature polypeptide is amino acids 24 to 436 of SEQ ID NO: 64 based on the SignalP program that predicts amino acids 1 to 23 of SEQ ID NO: 64 are a signal peptide. In another aspect, the mature polypeptide is amino acids 21 to 344 of SEQ ID NO: 66 based on the SignalP program that predicts amino acids 1 to 23 of SEQ ID NO: 66 are a signal peptide. In another aspect, the mature polypeptide is amino acids 26 to 400 of SEQ ID NO: 68 based on the SignalP program that predicts amino acids 1 to 25 of SEQ ID NO: 68 are a signal peptide. In another aspect, the mature polypeptide is amino acids 21 to 389 of SEQ ID NO: 70 based on the SignalP program that predicts amino acids 1 to 20 of SEQ ID NO: 70 are a signal peptide. In another aspect, the mature polypeptide is amino acids 22 to 406 of SEQ ID NO: 72 based on the SignalP program that predicts amino acids 1 to 21 of SEQ ID NO: 72 are a signal peptide. In another aspect, the mature polypeptide is amino acids 20 to 427 of SEQ ID NO: 74 based on the SignalP program that predicts amino acids 1 to 19 of SEQ ID NO: 74 are a signal peptide. In another aspect, the mature polypeptide is amino acids 18 to 267 of SEQ ID NO: 76 based on the SignalP program that predicts amino acids 1 to 17 of SEQ ID NO: 76 are a signal peptide. In another aspect, the mature polypeptide is amino acids 21 to 273 of SEQ ID NO: 78 based on the SignalP program that predicts amino acids 1 to 20 of SEQ ID NO: 78 are a signal peptide. In another aspect, the mature polypeptide is amino acids 21 to 322 of SEQ ID NO: 80 based on the SignalP program that predicts amino acids 1 to 20 of SEQ ID NO: 80 are a signal peptide. In another aspect, the mature polypeptide is amino acids 18 to 234 of SEQ ID NO: 82 based on the SignalP program that predicts amino acids 1 to 17 of SEQ ID NO: 82 are a signal peptide. In another aspect, the mature polypeptide is amino acids 24 to 233 of SEQ ID NO: 84 based on the SignalP program that predicts amino acids 1 to 23 of SEQ ID NO: 84 are a signal peptide. In another aspect, the mature polypeptide is amino acids 17 to 237 of SEQ ID NO: 86 based on the SignalP program that predicts amino acids 1 to 16 of SEQ ID NO: 86 are a signal peptide. In another aspect, the mature polypeptide is amino acids 20 to 484 of SEQ ID NO: 88 based on the SignalP program that predicts amino acids 1 to 19 of SEQ ID NO: 88 are a signal peptide. In another aspect, the mature polypeptide is amino acids 22 to 320 of SEQ ID NO: 90 based on the SignalP program that predicts amino acids 1 to 21 of SEQ ID NO: 90 are a signal peptide. In another aspect, the mature polypeptide is amino acids 23 to 272 of SEQ ID NO: 92 based on the SignalP program that predicts amino acids 1 to 22 of SEQ ID NO: 92 are a signal peptide. In another aspect, the mature polypeptide is amino acids 22 to 327 of SEQ ID NO: 94 based on the SignalP program that predicts amino acids 1 to 21 of SEQ ID NO: 94 are a signal peptide. In another aspect, the mature polypeptide is amino acids 23 to 274 of SEQ ID NO: 96 based on the SignalP program that predicts amino acids 1 to 22 of SEQ ID NO: 96 are a signal peptide. In another aspect, the mature polypeptide is amino acids 18 to 227 of SEQ ID NO: 98 based on the SignalP program that predicts amino acids 1 to 17 of SEQ ID NO: 98 are a signal peptide. In another aspect, the mature polypeptide is amino acids 17 to 257 of SEQ ID NO: 100 based on the SignalP program that predicts amino acids 1 to 16 of SEQ ID NO: 100 are a signal peptide. In another aspect, the mature polypeptide is amino acids 20 to 246 of SEQ ID NO: 102 based on the SignalP program that predicts amino acids 1 to 19 of SEQ ID NO: 102 are a signal peptide. In another aspect, the mature polypeptide is amino acids 28 to 265 of SEQ ID NO: 104 based on the SignalP program that predicts amino acids 1 to 27 of SEQ ID NO: 104 are a signal peptide. In another aspect, the mature polypeptide is amino acids 16 to 310 of SEQ ID NO: 106 based on the SignalP program that predicts amino acids 1 to 15 of SEQ ID NO: 106 are a signal peptide. In another aspect, the mature polypeptide is amino acids 21 to 354 of SEQ ID NO: 108 based on the SignalP program that predicts amino acids 1 to 20 of SEQ ID NO: 108 are a signal peptide. In another aspect, the mature polypeptide is amino acids 22 to 267 of SEQ ID NO: 110 based on the SignalP program that predicts amino acids 1 to 21 of SEQ ID NO: 110 are a signal peptide. In another aspect, the mature polypeptide is amino acids 16 to 237 of SEQ ID NO: 112 based on the SignalP program that predicts amino acids 1 to 15 of SEQ ID NO: 112 are a signal peptide. In another aspect, the mature polypeptide is amino acids 20 to 234 of SEQ ID NO: 114 based on the SignalP program that predicts amino acids 1 to 19 of SEQ ID NO: 114 are a signal peptide. In another aspect, the mature polypeptide is amino acids 18 to 226 of SEQ ID NO: 116 based on the SignalP program that predicts amino acids 1 to 17 of SEQ ID NO: 116 are a signal peptide. In another aspect, the mature polypeptide is amino acids 17 to 231 of SEQ ID NO: 118 based on the SignalP program that predicts amino acids 1 to 16 of SEQ ID NO: 118 are a signal peptide. In another aspect, the mature polypeptide is amino acids 22 to 248 of SEQ ID NO: 120 based on the SignalP program that predicts amino acids 1 to 21 of SEQ ID NO: 120 are a signal peptide. In another aspect, the mature polypeptide is amino acids 18 to 233 of SEQ ID NO: 122 based on the SignalP program that predicts amino acids 1 to 17 of SEQ ID NO: 122 are a signal peptide. In another aspect, the mature polypeptide is amino acids 21 to 243 of SEQ ID NO: 124 based on the SignalP program that predicts amino acids 1 to 20 of SEQ ID NO: 124 are a signal peptide. In another aspect, the mature polypeptide is amino acids 21 to 363 of SEQ ID NO: 126 based on the SignalP program that predicts amino acids 1 to 20 of SEQ ID NO: 126 are a signal peptide. In another aspect, the mature polypeptide is amino acids 20 to 296 of SEQ ID NO: 128 based on the SignalP program that predicts amino acids 1 to 19 of SEQ ID NO: 128 are a signal peptide. In another aspect, the mature polypeptide is amino acids 16 to 318 of SEQ ID NO: 130 based on the SignalP program that predicts amino acids 1 to 15 of SEQ ID NO: 130 are a signal peptide. In another aspect, the mature polypeptide is amino acids 19 to 259 of SEQ ID NO: 132 based on the SignalP program that predicts amino acids 1 to 18 of SEQ ID NO: 132 are a signal peptide. In another aspect, the mature polypeptide is amino acids 20 to 325 of SEQ ID NO: 134 based on the SignalP program that predicts amino acids 1 to 19 of SEQ ID NO: 134 are a signal peptide. In another aspect, the mature polypeptide is amino acids 19 to 298 of SEQ ID NO: 136 based on the SignalP program that predicts amino acids 1 to 18 of SEQ ID NO: 136 are a signal peptide. In another aspect, the mature polypeptide is amino acids 20 to 298 of SEQ ID NO: 138 based on the SignalP program that predicts amino acids 1 to 19 of SEQ ID NO: 138 are a signal peptide. In another aspect, the mature polypeptide is amino acids 22 to 344 of SEQ ID NO: 140 based on the SignalP program that predicts amino acids 1 to 21 of SEQ ID NO: 140 are a signal peptide. In another aspect, the mature polypeptide is amino acids 20 to 330 of SEQ ID NO: 142 based on the SignalP program that predicts amino acids 1 to 19 of SEQ ID NO: 142 are a signal peptide. In another aspect, the mature polypeptide is amino acids 19 to 216 of SEQ ID NO: 144 based on the SignalP program that predicts amino acids 1 to 18 of SEQ ID NO: 144 are a signal peptide. In another aspect, the mature polypeptide is amino acids 18 to 490 of SEQ ID NO: 146 based on the SignalP program that predicts amino acids 1 to 17 of SEQ ID NO: 146 are a signal peptide. In another aspect, the mature polypeptide is amino acids 21 to 306 of SEQ ID NO: 148 based on the SignalP program that predicts amino acids 1 to 20 of SEQ ID NO: 148 are a signal peptide. In another aspect, the mature polypeptide is amino acids 22 to 339 of SEQ ID NO: 150 based on the SignalP program that predicts amino acids 1 to 21 of SEQ ID NO: 150 are a signal peptide. In another aspect, the mature polypeptide is amino acids 23 to 334 of SEQ ID NO: 152 based on the SignalP program that predicts amino acids 1 to 22 of SEQ ID NO: 152 are a signal peptide. In another aspect, the mature polypeptide is amino acids 24 to 366 of SEQ ID NO: 154 based on the SignalP program that predicts amino acids 1 to 23 of SEQ ID NO: 154 are a signal peptide. In another aspect, the mature polypeptide is amino acids 21 to 364 of SEQ ID NO: 156 based on the SignalP program that predicts amino acids 1 to 20 of SEQ ID NO: 156 are a signal peptide. In another aspect, the mature polypeptide is amino acids 22 to 344 of SEQ ID NO: 158 based on the SignalP program that predicts amino acids 1 to 21 of SEQ ID NO: 158 are a signal peptide. In another aspect, the mature polypeptide is amino acids 20 to 252 of SEQ ID NO: 160 based on the SignalP program that predicts amino acids 1 to 19 of SEQ ID NO: 160 are a signal peptide. In another aspect, the mature polypeptide is amino acids 20 to 344 of SEQ ID NO: 162 based on the SignalP program that predicts amino acids 1 to 19 of SEQ ID NO: 162 are a signal peptide. In another aspect, the mature polypeptide is amino acids 22 to 347 of SEQ ID NO: 164 based on the SignalP program that predicts amino acids 1 to 21 of SEQ ID NO: 164 are a signal peptide. In another aspect, the mature polypeptide is amino acids 20 to 342 of SEQ ID NO: 166 based on the SignalP program that predicts amino acids 1 to 19 of SEQ ID NO: 166 are a signal peptide. In another aspect, the mature polypeptide is amino acids 27 to 254 of SEQ ID NO: 168 based on the SignalP program that predicts amino acids 1 to 26 of SEQ ID NO: 168 are a signal peptide. In another aspect, the mature polypeptide is amino acids 23 to 272 of SEQ ID NO: 409 based on the SignalP program that predicts amino acids 1 to 22 of SEQ ID NO: 409 are a signal peptide. In another aspect, the mature polypeptide is amino acids 23 to 272 of SEQ ID NO: 411 based on the SignalP program that predicts amino acids 1 to 22 of SEQ ID NO: 411 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellulolytic enhancing activity. In one aspect, the mature polypeptide coding sequence is nucleotides 388 to 1332 of SEQ ID NO: 1 based on the SignalP 3.0 program (Bendtsen et al., 2004, supra) that predicts nucleotides 330 to 387 of SEQ ID NO: 1 encode a signal peptide. In another aspect, the mature polypeptide coding sequence is nucleotides 98 to 821 of SEQ ID NO: 3 based on the SignalP program that predicts nucleotides 47 to 97 of SEQ ID NO: 3 encode a signal peptide. In another aspect, the mature polypeptide coding sequence is nucleotides 126 to 978 of SEQ ID NO: 5 based on the SignalP program that predicts nucleotides 69 to 125 of SEQ ID NO: 5 encode a signal peptide. In another aspect, the mature polypeptide coding sequence is nucleotides 55 to 678 of SEQ ID NO: 7 or the genomic DNA sequence thereof based on the SignalP program that predicts nucleotides 1 to 54 of SEQ ID NO: 7 encode a signal peptide. In another aspect, the mature polypeptide coding sequence is nucleotides 58 to 912 of SEQ ID NO: 9 or the genomic DNA sequence thereof based on the SignalP program that predicts nucleotides 1 to 57 of SEQ ID NO: 9 encode a signal peptide. In another aspect, the mature polypeptide coding sequence is nucleotides 46 to 951 of SEQ ID NO: 11 or the genomic DNA sequence thereof based on the SignalP program that predicts nucleotides 1 to 45 of SEQ ID NO: 11 encode a signal peptide. In another aspect, the mature polypeptide coding sequence is nucleotides 64 to 796 of SEQ ID NO: 13 based on the SignalP program that predicts nucleotides 1 to 63 of SEQ ID NO: 13 encode a signal peptide. In another aspect, the mature polypeptide coding sequence is nucleotides 77 to 766 of SEQ ID NO: 15 based on the SignalP program that predicts nucleotides 20 to 76 of SEQ ID NO: 15 or the genomic DNA sequence thereof encode a signal peptide. In another aspect, the mature polypeptide coding sequence is nucleotides 52 to 921 of SEQ ID NO: 17 based on the SignalP program that predicts nucleotides 1 to 51 of SEQ ID NO: 17 encode a signal peptide. In another aspect, the mature polypeptide coding sequence is nucleotides 46 to 851 of SEQ ID NO: 19 based on the SignalP program that predicts nucleotides 1 to 45 of SEQ ID NO: 19 encode a signal peptide. In another aspect, the mature polypeptide coding sequence is nucleotides 55 to 1239 of SEQ ID NO: 21 based on the SignalP program that predicts nucleotides 1 to 54 of SEQ ID NO: 21 encode a signal peptide. In another aspect, the mature polypeptide coding sequence is nucleotides 46 to 1250 of SEQ ID NO: 23 based on the SignalP program that predicts nucleotides 1 to 45 of SEQ ID NO: 23 encode a signal peptide. In another aspect, the mature polypeptide coding sequence is nucleotides 58 to 811 of SEQ ID NO: 25 based on the SignalP program that predicts nucleotides 1 to 57 of SEQ ID NO: 25 encode a signal peptide. In another aspect, the mature polypeptide coding sequence is nucleotides 64 to 1112 of SEQ ID NO: 27 based on the SignalP program that predicts nucleotides 1 to 63 of SEQ ID NO: 27 encode a signal peptide. In another aspect, the mature polypeptide coding sequence is nucleotides 64 to 859 of SEQ ID NO: 29 based on the SignalP program that predicts nucleotides 1 to 63 of SEQ ID NO: 29 encode a signal peptide. In another aspect, the mature polypeptide coding sequence is nucleotides 64 to 1018 of SEQ ID NO: 31 based on the SignalP program that predicts nucleotides 1 to 63 of SEQ ID NO: 31 encode a signal peptide. In another aspect, the mature polypeptide coding sequence is nucleotides 70 to 1483 of SEQ ID NO: 33 based on the SignalP program that predicts nucleotides 1 to 69 of SEQ ID NO: 33 encode a signal peptide. In another aspect, the mature polypeptide coding sequence is nucleotides 76 to 832 of SEQ ID NO: 35 based on the SignalP program that predicts nucleotides 1 to 75 of SEQ ID NO: 35 encode a signal peptide. In another aspect, the mature polypeptide coding sequence is nucleotides 52 to 875 of SEQ ID NO: 37 based on the SignalP program that predicts nucleotides 1 to 51 of SEQ ID NO: 37 encode a signal peptide. In another aspect, the mature polypeptide coding sequence is nucleotides 58 to 1250 of SEQ ID NO: 39 based on the SignalP program that predicts nucleotides 1 to 57 of SEQ ID NO: 39 encode a signal peptide. In another aspect, the mature polypeptide coding sequence is nucleotides 52 to 795 of SEQ ID NO: 41 based on the SignalP program that predicts nucleotides 1 to 51 of SEQ ID NO: 41 encode a signal peptide. In another aspect, the mature polypeptide coding sequence is nucleotides 58 to 974 of SEQ ID NO: 43 based on the SignalP program that predicts nucleotides 1 to 57 of SEQ ID NO: 43 encode a signal peptide. In another aspect, the mature polypeptide coding sequence is nucleotides 64 to 1104 of SEQ ID NO: 45 based on the SignalP program that predicts nucleotides 1 to 63 of SEQ ID NO: 45 encode a signal peptide. In another aspect, the mature polypeptide coding sequence is nucleotides 73 to 990 of SEQ ID NO: 47 based on the SignalP program that predicts nucleotides 1 to 72 of SEQ ID NO: 47 encode a signal peptide. In another aspect, the mature polypeptide coding sequence is nucleotides 49 to 1218 of SEQ ID NO: 49 based on the SignalP program that predicts nucleotides 1 to 48 of SEQ ID NO: 49 encode a signal peptide. In another aspect, the mature polypeptide coding sequence is nucleotides 55 to 930 of SEQ ID NO: 51 based on the SignalP program that predicts nucleotides 1 to 54 of SEQ ID NO: 51 encode a signal peptide. In another aspect, the mature polypeptide coding sequence is nucleotides 67 to 1581 of SEQ ID NO: 53 based on the SignalP program that predicts nucleotides 1 to 66 of SEQ ID NO: 53 encode a signal peptide. In another aspect, the mature polypeptide coding sequence is nucleotides 49 to 865 of SEQ ID NO: 55 based on the SignalP program that predicts nucleotides 1 to 48 of SEQ ID NO: 55 encode a signal peptide. In another aspect, the mature polypeptide coding sequence is nucleotides 58 to 1065 of SEQ ID NO: 57 based on the SignalP program that predicts nucleotides 1 to 57 of SEQ ID NO: 57 encode a signal peptide. In another aspect, the mature polypeptide coding sequence is nucleotides 67 to 868 of SEQ ID NO: 59 based on the SignalP program that predicts nucleotides 1 to 66 of SEQ ID NO: 59 encode a signal peptide. In another aspect, the mature polypeptide coding sequence is nucleotides 55 to 1099 of SEQ ID NO: 61 based on the SignalP program that predicts nucleotides 1 to 54 of SEQ ID NO: 61 encode a signal peptide. In another aspect, the mature polypeptide coding sequence is nucleotides 70 to 1483 of SEQ ID NO: 63 based on the SignalP program that predicts nucleotides 1 to 69 of SEQ ID NO: 63 encode a signal peptide. In another aspect, the mature polypeptide coding sequence is nucleotides 61 to 1032 of SEQ ID NO: 65 based on the SignalP program that predicts nucleotides 1 to 60 of SEQ ID NO: 65 encode a signal peptide. In another aspect, the mature polypeptide coding sequence is nucleotides 76 to 1200 of SEQ ID NO: 67 based on the SignalP program that predicts nucleotides 1 to 75 of SEQ ID NO: 67 encode a signal peptide. In another aspect, the mature polypeptide coding sequence is nucleotides 61 to 1167 of SEQ ID NO: 69 based on the SignalP program that predicts nucleotides 1 to 60 of SEQ ID NO: 69 encode a signal peptide. In another aspect, the mature polypeptide coding sequence is nucleotides 64 to 1218 of SEQ ID NO: 71 based on the SignalP program that predicts nucleotides 1 to 63 of SEQ ID NO: 71 encode a signal peptide. In another aspect, the mature polypeptide coding sequence is nucleotides 58 to 1281 of SEQ ID NO: 73 based on the SignalP program that predicts nucleotides 1 to 57 of SEQ ID NO: 73 encode a signal peptide. In another aspect, the mature polypeptide coding sequence is nucleotides 52 to 801 of SEQ ID NO: 75 based on the SignalP program that predicts nucleotides 1 to 51 of SEQ ID NO: 75 encode a signal peptide. In another aspect, the mature polypeptide coding sequence is nucleotides 61 to 819 of SEQ ID NO: 77 based on the SignalP program that predicts nucleotides 1 to 60 of SEQ ID NO: 77 encode a signal peptide. In another aspect, the mature polypeptide coding sequence is nucleotides 61 to 966 of SEQ ID NO: 79 based on the SignalP program that predicts nucleotides 1 to 60 of SEQ ID NO: 79 encode a signal peptide. In another aspect, the mature polypeptide coding sequence is nucleotides 52 to 702 of SEQ ID NO: 81 or the genomic DNA sequence thereof based on the SignalP program that predicts nucleotides 1 to 51 of SEQ ID NO: 81 encode a signal peptide. In another aspect, the mature polypeptide coding sequence is nucleotides 70 to 699 of SEQ ID NO: 83 or the genomic DNA sequence thereof based on the SignalP program that predicts nucleotides 1 to 69 of SEQ ID NO: 83 encode a signal peptide. In another aspect, the mature polypeptide coding sequence is nucleotides 49 to 711 of SEQ ID NO: 85 or the genomic DNA sequence thereof based on the SignalP program that predicts nucleotides 1 to 48 of SEQ ID NO: 85 encode a signal peptide. In another aspect, the mature polypeptide coding sequence is nucleotides 76 to 1452 of SEQ ID NO: 87 based on the SignalP program that predicts nucleotides 1 to 75 of SEQ ID NO: 87 encode a signal peptide. or In another aspect, the mature polypeptide coding sequence is nucleotides 64 to 1018 of SEQ ID NO: 89 based on the SignalP program that predicts nucleotides 1 to 63 of SEQ ID NO: 89 encode a signal peptide. In another aspect, the mature polypeptide coding sequence is nucleotides 67 to 869 of SEQ ID NO: 91 based on the SignalP program that predicts nucleotides 1 to 66 of SEQ ID NO: 91 encode a signal peptide. In another aspect, the mature polypeptide coding sequence is nucleotides 64 to 1036 of SEQ ID NO: 93 based on the SignalP program that predicts nucleotides 1 to 63 of SEQ ID NO: 93 encode a signal peptide. In another aspect, the mature polypeptide coding sequence is nucleotides 67 to 878 of SEQ ID NO: 95 based on the SignalP program that predicts nucleotides 1 to 66 of SEQ ID NO: 95 encode a signal peptide. In another aspect, the mature polypeptide coding sequence is nucleotides 52 to 818 of SEQ ID NO: 97 based on the SignalP program that predicts nucleotides 1 to 51 of SEQ ID NO: 97 encode a signal peptide. In another aspect, the mature polypeptide coding sequence is nucleotides 49 to 1117 of SEQ ID NO: 99 based on the SignalP program that predicts nucleotides 1 to 48 of SEQ ID NO: 99 encode a signal peptide. In another aspect, the mature polypeptide coding sequence is nucleotides 58 to 875 of SEQ ID NO: 101 based on the SignalP program that predicts nucleotides 1 to 57 of SEQ ID NO: 101 encode a signal peptide. In another aspect, the mature polypeptide coding sequence is nucleotides 82 to 1064 of SEQ ID NO: 103 based on the SignalP program that predicts nucleotides 1 to 81 of SEQ ID NO: 103 encode a signal peptide. In another aspect, the mature polypeptide coding sequence is nucleotides 46 to 1032 of SEQ ID NO: 105 based on the SignalP program that predicts nucleotides 1 to 45 of SEQ ID NO: 105 encode a signal peptide. In another aspect, the mature polypeptide coding sequence is nucleotides 61 to 1062 of SEQ ID NO: 107 based on the SignalP program that predicts nucleotides 1 to 60 of SEQ ID NO: 107 encode a signal peptide. In another aspect, the mature polypeptide coding sequence is nucleotides 64 to 801 of SEQ ID NO: 109 based on the SignalP program that predicts nucleotides 1 to 63 of SEQ ID NO: 109 encode a signal peptide. In another aspect, the mature polypeptide coding sequence is nucleotides 46 to 840 of SEQ ID NO: 111 based on the SignalP program that predicts nucleotides 1 to 45 of SEQ ID NO: 111 encode a signal peptide. In another aspect, the mature polypeptide coding sequence is nucleotides 58 to 702 of SEQ ID NO: 113 based on the SignalP program that predicts nucleotides 1 to 57 of SEQ ID NO: 113 encode a signal peptide. In another aspect, the mature polypeptide coding sequence is nucleotides 52 to 750 of SEQ ID NO: 115 based on the SignalP program that predicts nucleotides 1 to 51 of SEQ ID NO: 115 encode a signal peptide. In another aspect, the mature polypeptide coding sequence is nucleotides 49 to 851 of SEQ ID NO: 117 based on the SignalP program that predicts nucleotides 1 to 48 of SEQ ID NO: 117 encode a signal peptide. In another aspect, the mature polypeptide coding sequence is nucleotides 64 to 860 of SEQ ID NO: 119 based on the SignalP program that predicts nucleotides 1 to 63 of SEQ ID NO: 119 encode a signal peptide. In another aspect, the mature polypeptide coding sequence is nucleotides 52 to 830 of SEQ ID NO: 121 based on the SignalP program that predicts nucleotides 1 to 51 of SEQ ID NO: 121 encode a signal peptide. In another aspect, the mature polypeptide coding sequence is nucleotides 61 to 925 of SEQ ID NO: 123 based on the SignalP program that predicts nucleotides 1 to 60 of SEQ ID NO: 123 encode a signal peptide. In another aspect, the mature polypeptide coding sequence is nucleotides 61 to 1089 of SEQ ID NO: 125 based on the SignalP program that predicts nucleotides 1 to 60 of SEQ ID NO: 125 encode a signal peptide. In another aspect, the mature polypeptide coding sequence is nucleotides 58 to 1083 of SEQ ID NO: 127 based on the SignalP program (that predicts nucleotides 1 to 57 of SEQ ID NO: 127 encode a signal peptide. In another aspect, the mature polypeptide coding sequence is nucleotides 46 to 1029 of SEQ ID NO: 129 based on the SignalP program that predicts nucleotides 1 to 45 of SEQ ID NO: 129 encode a signal peptide. In another aspect, the mature polypeptide coding sequence is nucleotides 55 to 1110 of SEQ ID NO: 131 based on the SignalP program that predicts nucleotides 1 to 54 of SEQ ID NO: 131 encode a signal peptide. In another aspect, the mature polypeptide coding sequence is nucleotides 58 to 1100 of SEQ ID NO: 133 based on the SignalP program that predicts nucleotides 1 to 57 of SEQ ID NO: 133 encode a signal peptide. In another aspect, the mature polypeptide coding sequence is nucleotides 55 to 1036 of SEQ ID NO: 135 based on the SignalP program that predicts nucleotides 1 to 54 of SEQ ID NO: 135 encode a signal peptide. In another aspect, the mature polypeptide coding sequence is nucleotides 58 to 1022 of SEQ ID NO: 137 based on the SignalP program that predicts nucleotides 1 to 57 of SEQ ID NO: 137 encode a signal peptide. In another aspect, the mature polypeptide coding sequence is nucleotides 64 to 1032 of SEQ ID NO: 139 based on the SignalP program that predicts nucleotides 1 to 63 of SEQ ID NO: 139 encode a signal peptide. In another aspect, the mature polypeptide coding sequence is nucleotides 58 to 1054 of SEQ ID NO: 141 based on the SignalP program that predicts nucleotides 1 to 57 of SEQ ID NO: 141 encode a signal peptide. In another aspect, the mature polypeptide coding sequence is nucleotides 55 to 769 of SEQ ID NO: 143 based on the SignalP program that predicts nucleotides 1 to 54 of SEQ ID NO: 143 encode a signal peptide. In another aspect, the mature polypeptide coding sequence is nucleotides 52 to 1533 of SEQ ID NO: 145 based on the SignalP program that predicts nucleotides 1 to 51 of SEQ ID NO: 145 encode a signal peptide. In another aspect, the mature polypeptide coding sequence is nucleotides 61 to 918 of SEQ ID NO: 147 based on the SignalP program that predicts nucleotides 1 to 60 of SEQ ID NO: 147 encode a signal peptide. In another aspect, the mature polypeptide coding sequence is nucleotides 64 to 1089 of SEQ ID NO: 149 based on the SignalP program that predicts nucleotides 1 to 63 of SEQ ID NO: 149 encode a signal peptide. In another aspect, the mature polypeptide coding sequence is nucleotides 67 to 1002 of SEQ ID NO: 151 based on the SignalP program that predicts nucleotides 1 to 66 of SEQ ID NO: 151 encode a signal peptide. In another aspect, the mature polypeptide coding sequence is nucleotides 70 to 1098 of SEQ ID NO: 153 based on the SignalP program that predicts nucleotides 1 to 69 of SEQ ID NO: 153 encode a signal peptide. In another aspect, the mature polypeptide coding sequence is nucleotides 61 to 1088 of SEQ ID NO: 155 based on the SignalP program that predicts nucleotides 1 to 60 of SEQ ID NO: 155 encode a signal peptide. In another aspect, the mature polypeptide coding sequence is nucleotides 64 to 1086 of SEQ ID NO: 157 based on the SignalP program that predicts nucleotides 1 to 63 of SEQ ID NO: 157 encode a signal peptide. In another aspect, the mature polypeptide coding sequence is nucleotides 58 to 756 of SEQ ID NO: 159 based on the SignalP program that predicts nucleotides 1 to 57 of SEQ ID NO: 159 encode a signal peptide. In another aspect, the mature polypeptide coding sequence is nucleotides 58 to 1032 of SEQ ID NO: 161 based on the SignalP program that predicts nucleotides 1 to 57 of SEQ ID NO: 161 encode a signal peptide. In another aspect, the mature polypeptide coding sequence is nucleotides 64 to 1041 of SEQ ID NO: 163 based on the SignalP program that predicts nucleotides 1 to 63 of SEQ ID NO: 163 encode a signal peptide. In another aspect, the mature polypeptide coding sequence is nucleotides 58 to 1026 of SEQ ID NO: 165 based on the SignalP program that predicts nucleotides 1 to 57 of SEQ ID NO: 165 encode a signal peptide. In another aspect, the mature polypeptide coding sequence is nucleotides 79 to 762 of SEQ ID NO: 167 based on the SignalP program that predicts nucleotides 1 to 78 of SEQ ID NO: 167 encode a signal peptide. In another aspect, the mature polypeptide coding sequence is nucleotides 67 to 881 of SEQ ID NO: 408 based on the SignalP program that predicts nucleotides 1 to 66 of SEQ ID NO: 408 encode a signal peptide. In another aspect, the mature polypeptide coding sequence is nucleotides 67 to 882 of SEQ ID NO: 410 based on the SignalP program that predicts nucleotides 1 to 66 of SEQ ID NO: 410 encode a signal peptide. The term "mature polypeptide coding sequence" herein shall be understood to include the cDNA sequence of the genomic DNA sequence or the genomic DNA sequence of the cDNA sequence.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent GH61 polypeptide: The term "parent" or "parent GH61 polypeptide" means a GH61 polypeptide to which an alteration, i.e., a substitution, insertion, and/or deletion, at one or more (e.g., several) positions, is made to produce the GH61 polypeptide variants of the present invention. The parent may be a naturally occurring (wild-type) polypeptide or a variant or fragment thereof.

Polypeptide having cellulolytic enhancing activity: The term "polypeptide having cellulolytic enhancing activity" means a GH61 polypeptide or variant thereof that catalyzes the enhancement of the hydrolysis of a cellulosic material by enzyme having cellulolytic activity, i.e., a cellulase. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of a GH61 polypeptide or variant thereof for 1-7 days at a suitable temperature, such as 40° C.-80° C., e.g., 50° C., 55° C., 60° C., 65° C., or 70° C., and a suitable pH, such as 4-9, e.g., 4.5, 5.0, 5.5, 6.0, 6.5, 7.0, 7.5, 8.0, or 8.5, compared to a control hydrolysis with equal total protein loading without cellulolytic enhancing activity (1-50 mg of cellulolytic protein/g of cellulose in PCS) In one aspect, GH61 polypeptide enhancing activity is determined using a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 02/095014) of cellulase protein loading is used as the source of the cellulolytic activity.

Another assay for determining the cellulolytic enhancing activity of a GH61 polypeptide or variant thereof is to incubate the GH61 polypeptide or variant with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X100 for 24-96 hours at 40° C. followed by determination of the glucose released from the PASC.

The GH61 polypeptides or variants thereof having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the-nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the-nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence, wherein the subsequence encodes a fragment having cellulolytic enhancing activity. In one aspect, a subsequence contains at least 85% of the nucleotides, e.g., at least 90% of the nucleotides or at least 95% of the nucleotides of the mature polypeptide coding sequence of a GH61 polypeptide.

Variant: The term "variant" means a polypeptide having cellulolytic enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the cellulolytic enhancing activity of their parent GH61 polypeptides.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Wild-type GH61 polypeptide: The term "wild-type" GH61 polypeptide means a GH61 polypeptide naturally produced by a microorganism, such as a bacterium, yeast, or filamentous fungus found in nature.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrmann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

For purposes of the present invention, xylan degrading activity is determined by measuring the increase in hydrolysis of birchwood xylan (Sigma Chemical Co., Inc., St. Louis, MO, USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Conventions for Designation of Variants

For purposes of the present invention, the mature polypeptide disclosed in SEQ ID NO: 30 is used to determine the corresponding amino acid residue in another GH61 polypeptide. The amino acid sequence of another GH61 polypeptide is aligned with the mature polypeptide disclosed in SEQ ID NO: 30, and based on the alignment, the amino acid position number corresponding to any amino acid residue in the mature polypeptide disclosed in SEQ ID NO: 30 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. Numbering of the amino acid positions is based on the full-length polypeptide (e.g., including the signal peptide) of SEQ ID NO: 30 wherein position 1 is the first amino acid of the signal peptide (i.e., Met) and position 22 is His of SEQ ID NO: 30.

For example, the position corresponding to position 105 of the *Aspergillus fumigatus* GH61 polypeptide (SEQ ID NO: 30) is position 109 in the *Penicillium emersonii* GH61 polypeptide (SEQ ID NO: 36), position 105 in the *Thermoascus aurantiacus* GH61 polypeptide (SEQ ID NO: 14), and position 103 in the *Aspergillus aculeatus* GH61 polypeptide (SEQ ID NO: 68); the position corresponding to position 188 of the *Aspergillus fumigatus* GH61 polypeptide is position 192 in the *Penicillium emersonii* GH61 polypeptide, position 188 in the *Thermoascus aurantiacus* GH61 polypeptide, and position 186 in the *Aspergillus aculeatus* GH61 polypeptide; the position corresponding to position 154 of the *Aspergillus fumigatus* GH61 polypeptide is position 152 in the *Aspergillus aculeatus* GH61 polypeptide; and the position corresponding to position 189 of the *Aspergillus fumigatus* GH61 polypeptide is position 193 in the *Penicillium emersonii* GH61 polypeptide and position 187 in the *Aspergillus aculeatus* GH61 polypeptide.

Identification of the corresponding amino acid residue in another GH61 polypeptide can be determined by an alignment of multiple polypeptide sequences using several computer programs including, but not limited to MUSCLE (multiple sequence comparison by log-expectation; version 3.5 or later; Edgar, 2004, *Nucleic Acids Research* 32: 1792-1797); MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When another GH61 polypeptide has diverged from the mature polypeptide of SEQ ID NO: 30 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the GH61 polypeptide variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G-K-A |

Multiple substitutions. Variants comprising multiple substitutions are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different substitutions. Where different substitutions can be introduced at a position, the different substitutions are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to isolated GH61 polypeptide variants, comprising a substitution at one or more (e.g., several) positions corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250 of the mature polypeptide of SEQ ID NO: 30, wherein the variants have cellulolytic enhancing activity.

Variants

In an embodiment, the variant has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent GH61 polypeptide.

In another embodiment, the variant has at least 60%, e.g., at least 65%, at least 70%, at least 75%, at least 80%, 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

In one aspect, the number of substitutions in the variants of the present invention is 1-28, e.g., 1, 2, 3, 4, 5, 6, 7, 8, 9, 10, 11, 12, 13, 14, 15, 16, 17, 18, 19, 20, 21, 22, 23, 24, 25, 26, 27, and 28 substitutions.

In another aspect, a variant comprises a substitution at one or more (e.g., several) positions corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at two positions corresponding to any of positions 26, 32, 34, 40, 234, 246, 249, and 250. In another aspect, a variant comprises a substitution at three positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at four positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at five positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at six positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at seven positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at eight positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at nine positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at ten positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at eleven positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twelve positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at thirteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at fourteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at fifteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at sixteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at seventeen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at eighteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at nineteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-one positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-two positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-three positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-four positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-five positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-six positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-seven positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at each position corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250.

In another aspect, the variant comprises or consists of a substitution at a position corresponding to position 26. In another aspect, the amino acid at a position corresponding to position 26 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant comprises or consists of the substitution S26I of the mature polypeptide of SEQ ID NO: 30.

In another aspect, the variant comprises or consists of a substitution at a position corresponding to position 32. In another aspect, the amino acid at a position corresponding to position 32 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu or Ser. In another aspect, the variant comprises or consists of the substitution G32E or G32S of the mature polypeptide of SEQ ID NO: 30.

In another aspect, the variant comprises or consists of a substitution at a position corresponding to position 34. In another aspect, the amino acid at a position corresponding to position 34 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe. In another aspect, the variant comprises or consists of the substitution Y34F of the mature polypeptide of SEQ ID NO: 30.

In another aspect, the variant comprises or consists of a substitution at a position corresponding to position 40. In another aspect, the amino acid at a position corresponding to position 40 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises or consists of the substitution V40A of the mature polypeptide of SEQ ID NO: 30.

In another aspect, the variant comprises or consists of a substitution at a position corresponding to position 41. In another aspect, the amino acid at a position corresponding to position 41 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr. In another aspect, the variant comprises or consists of the substitution N41T of the mature polypeptide of SEQ ID NO: 30.

In another aspect, the variant comprises or consists of a substitution at a position corresponding to position 42. In another aspect, the amino acid at a position corresponding to position 42 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile, Glu, or Val. In another aspect, the variant comprises or consists of the substitution Q42I, Q42E, or Q42V of the mature polypeptide of SEQ ID NO: 30.

In another aspect, the variant comprises or consists of a substitution at a position corresponding to position 47. In another aspect, the amino acid at a position corresponding to position 47 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Leu, or Arg. In another aspect, the variant comprises or consists of the substitution S47E, S47L, or S47R of the mature polypeptide of SEQ ID NO: 30.

In another aspect, the variant comprises or consists of a substitution at a position corresponding to position 56. In another aspect, the amino acid at a position corresponding to position 56 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys, Glu, or Thr. In another aspect, the variant comprises or consists of the substitution S56C, S56E, or S56T of the mature polypeptide of SEQ ID NO: 30.

In another aspect, the variant comprises or consists of a substitution at a position corresponding to position 72. In another aspect, the amino acid at a position corresponding to position 72 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln or Thr. In another aspect, the variant comprises or consists of the substitution S72Q or S72T of the mature polypeptide of SEQ ID NO: 30.

In another aspect, the variant comprises or consists of a substitution at a position corresponding to position 102. In another aspect, the amino acid at a position corresponding to position 102 is substituted with Ala, Arg, Asn, Asp, Cys, Gln, Glu, Gly, His, Ile, Leu, Lys, Met, Phe, Pro, Ser, Thr, Trp, Tyr, or Val, preferably with Lys or Pro. In another aspect, the variant comprises or consists of the substitution T102K or T102P of the mature polypeptide of SEQ ID NO: 30.

In another aspect, the variant comprises or consists of a substitution at a position corresponding to position 123. In another aspect, the amino acid at a position corresponding to position 123 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg. In another aspect, the variant comprises or consists of the substitution A123R of the mature polypeptide of SEQ ID NO: 30.

In another aspect, the variant comprises or consists of a substitution at a position corresponding to position 138. In another aspect, the amino acid at a position corresponding to position 138 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys, Glu, Gly, Lys, Leu, or Met. In another aspect, the variant comprises or consists of the substitution Q138C, Q138E, Q138G, Q138K, Q138L, or Q138M of the mature polypeptide of SEQ ID NO: 30.

In another aspect, the variant comprises or consists of a substitution at a position corresponding to position 149. In another aspect, the amino acid at a position corresponding to position 149 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant comprises or consists of the substitution V149I of the mature polypeptide of SEQ ID NO: 30.

In another aspect, the variant comprises or consists of a substitution at a position corresponding to position 152. In another aspect, the amino acid at a position corresponding to position 152 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser. In another aspect, the variant comprises or consists of the substitution D152S of the mature polypeptide of SEQ ID NO: 30.

In another aspect, the variant comprises or consists of a substitution at a position corresponding to position 163. In another aspect, the amino acid at a position corresponding to position 163 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Phe, or Val. In another aspect, the variant comprises or consists of the substitution T163E, T163F, or T163V of the mature polypeptide of SEQ ID NO: 30.

In another aspect, the variant comprises or consists of a substitution at a position corresponding to position 164. In another aspect, the amino acid at a position corresponding to position 164 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys or Leu. In another aspect, the variant comprises or consists of the substitution V164C or V164L of the mature polypeptide of SEQ ID NO: 30.

In another aspect, the variant comprises or consists of a substitution at a position corresponding to position 166. In another aspect, the amino acid at a position corresponding to position 166 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant comprises or consists of the substitution I166L of the mature polypeptide of SEQ ID NO: 30.

In another aspect, the variant comprises or consists of a substitution at a position corresponding to position 169. In another aspect, the amino acid at a position corresponding to position 169 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg or Cys. In another aspect, the variant comprises or consists of the substitution S169R or S169C of the mature polypeptide of SEQ ID NO: 30. In another aspect, the variant comprises or consists of the substitution S173C of the mature polypeptide of SEQ ID NO: 36. The position in the *Penicillium* sp. (*emersonii*) GH61 mature polypeptide corresponding to position 169 in the *A. fumigatus* GH61 mature polypeptide is position 173.

In another aspect, the variant comprises or consists of a substitution at a position corresponding to position 186. In another aspect, the amino acid at a position corresponding to position 186 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe, Lys, Thr, or Tyr. In another aspect, the variant comprises or consists of the substitution S186F, S186K, S186T, or S186Y of the mature polypeptide of SEQ ID NO: 30.

In another aspect, the variant comprises or consists of a substitution at a position corresponding to position 200. In another aspect, the amino acid at a position corresponding to position 200 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile or Val. In another aspect, the variant comprises or consists of the substitution F200I or F200V of the mature polypeptide of SEQ ID NO: 30.

In another aspect, the variant comprises or consists of a substitution at a position corresponding to position 207. In another aspect, the amino acid at a position corresponding to position 207 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro. In another aspect, the variant comprises or consists of the substitution G207P of the mature polypeptide of SEQ ID NO: 30.

In another aspect, the variant comprises or consists of a substitution at a position corresponding to position 213. In another aspect, the amino acid at a position corresponding to position 213 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu. In another aspect, the variant comprises or consists of the substitution S213E of the mature polypeptide of SEQ ID NO: 30.

In another aspect, the variant comprises or consists of a substitution at a position corresponding to position 219. In another aspect, the amino acid at a position corresponding to position 219 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Met, Gln, or Cys. In another aspect, the variant comprises or consists of the substitution S219E, S219M, S219Q, or S219C of the mature polypeptide of SEQ ID NO: 30.

In another aspect, the variant comprises or consists of a substitution at a position corresponding to position 222. In another aspect, the amino acid at a position corresponding to position 222 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg. In another aspect, the variant comprises or consists of the substitution K222R of the mature polypeptide of SEQ ID NO: 30.

In another aspect, the variant comprises or consists of a substitution at a position corresponding to position 234. In another aspect, the amino acid at a position corresponding to position 234 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly or Lys. In another aspect, the variant comprises or consists of the substitution S234G or S234K of the mature polypeptide of SEQ ID NO: 30.

In another aspect, the variant comprises or consists of a substitution at a position corresponding to position 246. In another aspect, the amino acid at a position corresponding to position 246 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro. In another aspect, the variant comprises or consists of the substitution A246P of the mature polypeptide of SEQ ID NO: 30.

In another aspect, the variant comprises or consists of a substitution at a position corresponding to position 249. In another aspect, the amino acid at a position corresponding to position 249 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln, Arg, or Cys. In another aspect, the variant comprises or consists of the substitution N249Q, N249R, or N249O of the mature polypeptide of SEQ ID NO: 30. In another aspect, the variant comprises or consists of the substitution F253C of the mature polypeptide of SEQ ID NO: 36. The position in the *Penicillium* sp. (*emersonii*) GH61 mature polypeptide corresponding to position 249 in the *A. fumigatus* GH61 mature polypeptide is position 253.

In another aspect, the variant comprises or consists of a substitution at a position corresponding to position 250. In another aspect, the amino acid at a position corresponding to position 250 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys. In another aspect, the variant comprises or consists of the substitution A250C of the mature polypeptide of SEQ ID NO: 30.

In another aspect, the variant comprises or consists of one or more (e.g., several) substitutions selected from the group consisting of S26I; G32E,S; Y34F; V40A; N41T; Q42I,E,V; S47E,L,R; S56C,E,T; S72Q,T; T102K,P; A123R; Q138C, E,G,K,L,M; V149I; D152S; T163E,F,V; V164C,L; I166L; S169R,C; S186F,K,T,Y; F200I,V; G207P; S213E; S219E, M,Q,C; K222R; S234G,K; A246P; N249Q,R,C; and A250C; or the one or more (e.g., several) substitutions selected from the group consisting of S26I; G32E,S; Y34F; V40A; N41T; Q42I,E,V; S47E,L,R; S56C,E,T; S72Q,T; T102K,P; A123R; Q138C,E,G,K,L,M; V149I; D152S; T163E,F,V; V164C,L; I166L; S169R,C; S186F,K,T,Y; F200I,V; G207P; S213E; S219E,M,Q,C; K222R; S234G,K; A246P; N249Q,R,C; and A250C at positions corresponding to the mature polypeptide of SEQ ID NO: 30 in other GH61 polypeptides described herein.

In each of the aspects below, the variant comprises or consists of the one or more (e.g., several) substitutions described below at positions corresponding to SEQ ID NO: 30 in other GH61 polypeptides described herein.

In another aspect, the variant comprises or consists of the substitutions S173C+F253C of the mature polypeptide of SEQ ID NO: 36. In another aspect, the variant comprises or consists of the substitutions L111V+D152S+M155L+ A162W+Q138K+K229W of the mature polypeptide of SEQ ID NO: 30. In another aspect, the variant comprises or consists of the substitutions L111V+D152S+M155L+ A162W+547E+K229W of the mature polypeptide of SEQ ID NO: 30. In another aspect, the variant comprises or consists of the substitutions L111V+D152S+M155L+ A162W+S56A+K229W of the mature polypeptide of SEQ ID NO: 30. In another aspect, the variant comprises or consists of the substitutions L111V+D152S+M155L+ A162W+T102K+K229W of the mature polypeptide of SEQ ID NO: 30. In another aspect, the variant comprises or consists of the substitutions L111V+D152S+M155L+ A162W+S186T+K229W of the mature polypeptide of SEQ ID NO: 30. In another aspect, the variant comprises or consists of the substitutions L111V+D152S+M155L+ A162W+K229W+S234G of the mature polypeptide of SEQ ID NO: 30. In another aspect, the variant comprises or consists of the substitutions L111V+D152S+M155L+ A162W+T102K+E105K+K229W of the mature polypeptide of SEQ ID NO: 30. In another aspect, the variant comprises or consists of the substitutions L111V+D152S+M155L+ A162W+Q138K+G188F+K229W of the mature polypeptide of SEQ ID NO: 30. In another aspect, the variant comprises or consists of the substitutions L111V+D152S+ M155L+A162W+Q138K+V149I+G188F+K229W of the mature polypeptide of SEQ ID NO: 30. In another aspect, the variant comprises or consists of the substitutions L111V+D152S+M155L+A162W+S169C+G188F+ K229W+A250C of the mature polypeptide of SEQ ID NO: 30. In another aspect, the variant comprises or consists of the substitutions L111V+D152S+M155L+A162W+S72T+ Q138K+V149I+G188F+K229W of the mature polypeptide of SEQ ID NO: 30. In another aspect, the variant comprises or consists of the substitutions L111V+D152S+M155L+ A162W+Q138K+V149I+G188F+G207P+K229W of the mature polypeptide of SEQ ID NO: 30.

The variants may further comprise one or more additional alterations, e.g., substitutions, insertions, or deletions at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/ Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

The variants of the present invention may further or even further comprise a substitution at one or more (e.g., several) positions corresponding to positions 111, 152, 155, and 162 of the mature polypeptide of SEQ ID NO: 30, wherein the variants have cellulolytic enhancing activity (WO 2012/ 044835).

In one aspect, the number of additional substitutions above in the variants of the present invention is 1-4, such as 1, 2, 3, or 4 substitutions.

In another aspect, the variant further or even further comprises a substitution at one or more (e.g., several) positions corresponding to positions 111, 152, 155, and 162. In another aspect, the variant further or even further comprises a substitution at two positions corresponding to any of positions 111, 152, 155, and 162. In another aspect, the variant further or even further comprises a substitution at three positions corresponding to any of positions 111, 152, 155, and 162. In another aspect, the variant further or even further comprises a substitution at each position corresponding to positions 111, 152, 155, and 162.

In another aspect, the variant further or even further comprises a substitution at a position corresponding to position 111. In another aspect, the amino acid at a position corresponding to position 111 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the variant further or even further comprises the substitution L111V of the mature polypeptide of SEQ ID NO: 30.

In another aspect, the variant further or even further comprises a substitution at a position corresponding to position 152. In another aspect, the amino acid at a position corresponding to position 152 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser. In another aspect, the variant further or even further comprises the substitution D152S of the mature polypeptide of SEQ ID NO: 30.

In another aspect, the variant further or even further comprises a substitution at a position corresponding to position 155. In another aspect, the amino acid at a position corresponding to position 155 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant further or even further comprises the substitution M155L of the mature polypeptide of SEQ ID NO: 30.

In another aspect, the variant further or even further comprises a substitution at a position corresponding to position 162. In another aspect, the amino acid at a position corresponding to position 162 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp. In another aspect, the variant further or even further comprises the substitution A162W of the mature polypeptide of SEQ ID NO: 30.

In another aspect, the variant further or even further comprises one or more (e.g., several) substitutions selected from the group consisting of L111V, D152S, M155L, and A162W of the mature polypeptide of SEQ ID NO: 30, or the one or more (e.g., several) substitutions selected from the group consisting of L111V, D152S, M155L, and A162W at positions corresponding to the mature polypeptide of SEQ ID NO: 30 in other GH61 polypeptides described herein.

The variants of the present invention may further or even further comprise a substitution at one or more (e.g., several) positions corresponding to positions 96, 98, 200, 202, and 204 of the mature polypeptide of SEQ ID NO: 30, wherein the variants have cellulolytic enhancing activity (WO 2012/ 044836).

In one aspect, the number of additional substitutions above in the variants of the present invention is 1-5, such as 1, 2, 3, 4, or 5 substitutions.

In another aspect, the variant further or even further comprises a substitution at one or more (e.g., several) positions corresponding to positions 96, 98, 200, 202, and 204. In another aspect, the variant further or even further comprises a substitution at two positions corresponding to any of positions 96, 98, 200, 202, and 204. In another aspect, the variant further or even further comprises a substitution at three positions corresponding to any of positions 96, 98, 200, 202, and 204. In another aspect, the variant further or even further comprises a substitution at four positions corresponding to any of positions 96, 98, 200, 202, and 204. In another aspect, the variant further or even further comprises a substitution at each position corresponding to positions 96, 98, 200, 202, and 204.

In another aspect, the variant further or even further comprises a substitution at a position corresponding to position 96. In another aspect, the amino acid at a position corresponding to position 96 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the variant further or even further comprises the substitution I96V of the mature polypeptide of SEQ ID NO: 30.

In another aspect, the variant further or even further comprises a substitution at a position corresponding to position 98. In another aspect, the amino acid at a position corresponding to position 98 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant further or even further comprises the substitution F98L of the mature polypeptide of SEQ ID NO: 30.

In another aspect, the variant further or even further comprises a substitution at a position corresponding to position 200. In another aspect, the amino acid at a position corresponding to position 200 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant further or even further comprises the substitution F200I of the mature polypeptide of SEQ ID NO: 30.

In another aspect, the variant further or even further comprises a substitution at a position corresponding to position 202. In another aspect, the amino acid at a position corresponding to position 202 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant further or even further comprises the substitution I202L of the mature polypeptide of SEQ ID NO: 30.

In another aspect, the variant further or even further comprises a substitution at a position corresponding to position 204. In another aspect, the amino acid at a position corresponding to position 204 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the variant further or even further comprises the substitution I204V of the mature polypeptide of SEQ ID NO: 30.

In another aspect, the variant further or even further comprises one or more (e.g., several) substitutions selected from the group consisting of I96V, F98L, F200I, I202L, and I204V, or the one or more (e.g., several) substitutions selected from the group consisting of I96V, F98L, F200I, I202L, and I204V at positions corresponding to SEQ ID NO: 30 in other GH61 polypeptides described herein.

The variants of the present invention may further or even further comprise a substitution at one or more (e.g., several) positions corresponding to positions 105, 154, 188, 189, 216, and 229 of the mature polypeptide of SEQ ID NO: 30, wherein the variants have cellulolytic enhancing activity.

In one aspect, the number of additional substitutions above in the variants of the present invention is 1-6, e.g., 1, 2, 3, 4, 5, or 6 substitutions.

In another aspect, a variant further or even further comprises a substitution at one or more (e.g., several) positions corresponding to positions 105, 154, 188, 189, 216, and 229. In another aspect, a variant further or even further comprises a substitution at two positions corresponding to any of positions 105, 154, 188, 189, 216, and 229. In another aspect, a variant further or even further comprises a substitution at three positions corresponding to any of positions 105, 154, 188, 189, 216, and 229. In another aspect, a variant further or even further comprises a substitution at four positions corresponding to any of positions 105, 154, 188, 189, 216, and 229. In another aspect, a variant further or even further comprises a substitution at five positions corresponding to any of positions 105, 154, 188, 189, 216, and 229. In another aspect, a variant further or even further comprises a substitution at each position corresponding to positions 105, 154, 188, 189, 216, and 229.

In another aspect, the variant further or even further comprises a substitution at a position corresponding to position 105. In another aspect, the amino acid at a position corresponding to position 105 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro or Lys. In another aspect, the variant further or even further comprises of the substitution E105P or E105K of the mature polypeptide of SEQ ID NO: 30.

In another aspect, the variant further or even further comprises a substitution at a position corresponding to position 154. In another aspect, the amino acid at a position corresponding to position 154 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant further or even further comprises the substitution E154L of the mature polypeptide of SEQ ID NO: 30.

In another aspect, the variant further or even further comprises a substitution at a position corresponding to position 188. In another aspect, the amino acid at a position corresponding to position 188 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala or Trp. In another aspect, the variant further or even further comprises the substitution G188A or G188W of the mature polypeptide of SEQ ID NO: 30.

In another aspect, the variant further or even further comprises a substitution at a position corresponding to position 189. In another aspect, the amino acid at a position corresponding to position 189 is substituted with Ala, Arg, Asn, Asp, Cys, Gln, Glu, Gly, His, Ile, Leu, Lys, Met, Phe, Pro, Ser, Thr, Trp, Tyr, or Val, preferably with Lys. In another aspect, the variant further or even further comprises the substitution N189K of the mature polypeptide of SEQ ID NO: 30.

In another aspect, the variant further or even further comprises a substitution at a position corresponding to position 216. In another aspect, the amino acid at a position corresponding to position 216 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu or Tyr. In another aspect, the variant further or even further comprises the substitution A216L or A216Y of the mature polypeptide of SEQ ID NO: 30.

In another aspect, the variant further or even further comprises a substitution at a position corresponding to position 229. In another aspect, the amino acid at a position corresponding to position 229 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp, His, Ile, or Tyr. In another aspect, the variant further or even further comprises the substitution A229W, A229H, A229I, or A229Y of the mature polypeptide of SEQ ID NO: 30.

In another aspect, the variant further or even further comprises one or more (e.g., several) substitutions selected from the group consisting of E105P,K; E154L; G188A,W; N189K; A216L,Y; and A229W,H,I,Y, of the mature polypeptide of SEQ ID NO: 30, or the one or more (e.g., several) substitutions selected from the group consisting of E105P,K; E154L; G188A,W; N189K; A216L,Y; and A229W,H,I,Y at positions corresponding to the mature polypeptide of SEQ ID NO: 30 in other GH61 polypeptides described herein.

The variants may consist of at least 85% of the amino acid residues, e.g., at least 90% of the amino acid residues or at least 95% of the amino acid residues of the mature polypeptides of the corresponding parent GH61 polypeptides.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellulolytic enhancing activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. Essential amino acids in GH61 polypeptides correspond to positions 22, 107, 194, and/or 196 of the mature polypeptide of SEQ ID NO: 30.

In an embodiment, the variants have increased thermostability compared to their parent GH61 polypeptides.

In one aspect, the thermostability of the variant relative to the parent is determined at pH 3.0 and 45° C. In another aspect, the thermostability of the variant relative to the parent is determined at pH 3.0 and 50° C. In another aspect, the thermostability of the variant relative to the parent is determined at pH 3.0 and 55° C. In another aspect, the thermostability of the variant relative to the parent is determined at pH 3.0 and 60° C. In another aspect, the thermostability of the variant relative to the parent is determined at pH 3.0 and 62° C. In another aspect, the thermostability of the variant relative to the parent is determined at pH 3.0 and 65° C. In another aspect, the thermostability of the variant relative to the parent is determined at pH 3.0 and 68° C. In another aspect, the thermostability of the variant relative to the parent is determined at pH 3.0 and 70° C. In another aspect, the thermostability of the variant relative to the parent is determined at pH 3.0 and 72° C. In another aspect, the thermostability of the variant relative to the parent is determined at pH 3.0 and 75° C. In another aspect, the thermostability of the variant relative to the parent is determined at pH 3.0 and 80° C. In another aspect, the thermostability of the variant relative to the parent is determined at pH 3.0 and 85° C. In another aspect, the thermostability of the variant relative to the parent is determined at pH 3.0 and 90° C. In another aspect, the thermostability of the variant relative to the parent is determined at pH 3.0 and 95° C.

In another aspect, the thermostability of the variant relative to the parent is determined at pH 3.5 and 45° C. In another aspect, the thermostability of the variant relative to the parent is determined at pH 3.5 and 50° C. In another aspect, the thermostability of the variant relative to the parent is determined at pH 3.5 and 55° C. In another aspect, the thermostability of the variant relative to the parent is determined at pH 3.5 and 60° C. In another aspect, the thermostability of the variant relative to the parent is determined at pH 3.5 and 62° C. In another aspect, the thermostability of the variant relative to the parent is determined at pH 3.5 and 65° C. In another aspect, the thermostability of the variant relative to the parent is determined at pH 3.5 and 68° C. In another aspect, the thermostability of the variant relative to the parent is determined at pH 3.5 and 70° C. In another aspect, the thermostability of the variant relative to the parent is determined at pH 3.5 and 72° C. In another aspect, the thermostability of the variant relative to the parent is determined at pH 3.5 and 75° C. In another aspect, the thermostability of the variant relative to the parent is determined at pH 3.5 and 80° C. In another aspect, the thermostability of the variant relative to the parent is determined at pH 3.5 and 85° C. In another aspect, the thermostability of the variant relative to the parent is determined at pH 3.5 and 90° C. In another aspect, the thermostability of the variant relative to the parent is determined at pH 3.5 and 95° C.

In another aspect, the thermostability of the variant relative to the parent is determined at pH 4.0 and 45° C. In another aspect, the thermostability of the variant relative to the parent is determined at pH 4.0 and 50° C. In another aspect, the thermostability of the variant relative to the parent is determined at pH 4.0 and 55° C. In another aspect, the thermostability of the variant relative to the parent is determined at pH 4.0 and 60° C. In another aspect, the thermostability of the variant relative to the parent is determined at pH 4.0 and 62° C. In another aspect, the thermostability of the variant relative to the parent is determined at pH 4.0 and 65° C. In another aspect, the thermostability of the variant relative to the parent is determined at pH 4.0 and 68° C. In another aspect, the thermostability of the variant relative to the parent is determined at pH 4.0 and 70° C. In another aspect, the thermostability of the variant relative to the parent is determined at pH 4.0 and 72° C. In another aspect, the thermostability of the variant relative to the parent is determined at pH 4.0 and 75° C. In another aspect, the thermostability of the variant relative to the parent is determined at pH 4.0 and 80° C. In another aspect, the thermostability of the variant relative to the parent is determined at pH 4.0 and 85° C. In another aspect, the thermostability of the variant relative to the parent is determined at pH 4.0 and 90° C. In another aspect, the thermostability of the variant relative to the parent is determined at pH 4.0 and 95° C.

In another aspect, the thermostability of the variant relative to the parent is determined at pH 4.5 and 45° C. In another aspect, the thermostability of the variant relative to the parent is determined at pH 4.5 and 50° C. In another aspect, the thermostability of the variant relative to the parent is determined at pH 4.5 and 55° C. In another aspect, the thermostability of the variant relative to the parent is determined at pH 4.5 and 60° C. In another aspect, the thermostability of the variant relative to the parent is determined at pH 4.5 and 62° C. In another aspect, the thermostability of the variant relative to the parent is determined at pH 4.5 and 65° C. In another aspect, the thermostability of the variant relative to the parent is determined at pH 4.5 and 68° C. In another aspect, the thermostability of the variant relative to the parent is determined at pH 4.5 and 70° C. In another aspect, the thermostability of the variant relative to the parent is determined at pH 4.5 and 72° C. In another aspect, the thermostability of the variant relative to the parent is determined at pH 4.5 and 75° C. In another aspect, the thermostability of the variant relative to the parent is determined at pH 4.5 and 80° C. In another aspect, the thermostability of the variant relative to the parent is determined at pH 4.5 and 85° C. In another aspect, the thermostability of the variant relative to the parent is determined at pH 4.5 and 90° C. In another aspect, the thermostability of the variant relative to the parent is determined at pH 4.5 and 95° C.

In another aspect, the thermostability of the variant relative to the parent is determined at pH 5.0 and 45° C. In another aspect, the thermostability of the variant relative to the parent is determined at pH 5.0 and 50° C. In another aspect, the thermostability of the variant relative to the parent is determined at pH 5.0 and 55° C. In another aspect, the thermostability of the variant relative to the parent is determined at pH 5.0 and 60° C. In another aspect, the thermostability of the variant relative to the parent is determined at pH 5.0 and 62° C. In another aspect, the thermostability of the variant relative to the parent is determined at pH 5.0 and 65° C. In another aspect, the thermostability of the variant relative to the parent is determined at pH 5.0 and 68° C. In another aspect, the thermostability of the variant relative to the parent is determined at pH 5.0 and 70° C. In another aspect, the thermostability of the variant relative to the parent is determined at pH 5.0 and 72° C. In another aspect, the thermostability of the variant relative to the parent is determined at pH 5.0 and 75° C. In another aspect, the thermostability of the variant relative to the parent is determined at pH 5.0 and 80° C. In another aspect, the thermostability of the variant relative to the parent is determined at pH 5.0 and 85° C. In another aspect, the thermostability of the variant relative to the parent is determined at pH 5.0 and 90° C. In another aspect, the thermostability of the variant relative to the parent is determined at pH 5.0 and 95° C.

In another aspect, the thermostability of the variant relative to the parent is determined at pH 5.5 and 45° C. In another aspect, the thermostability of the variant relative to the parent is determined at pH 5.5 and 50° C. In another aspect, the thermostability of the variant relative to the parent is determined at pH 5.5 and 55° C. In another aspect, the thermostability of the variant relative to the parent is determined at pH 5.5 and 60° C. In another aspect, the thermostability of the variant relative to the parent is determined at pH 5.5 and 62° C. In another aspect, the thermostability of the variant relative to the parent is determined at pH 5.5 and 65° C. In another aspect, the thermostability of the variant relative to the parent is determined at pH 5.5 and 68° C. In another aspect, the thermostability of the variant relative to the parent is determined at pH 5.5 and 70° C. In another aspect, the thermostability of the variant relative to the parent is determined at pH 5.5 and 72° C. In another aspect, the thermostability of the variant relative to the parent is determined at pH 5.5 and 75° C. In another aspect, the thermostability of the variant relative to the parent is determined at pH 5.5 and 80° C. In another aspect, the thermostability of the variant relative to the parent is determined at pH 5.5 and 85° C. In another aspect, the thermostability of the variant relative to the parent is determined at pH 5.5 and 90° C. In another aspect, the thermostability of the variant relative to the parent is determined at pH 5.5 and 95° C.

In another aspect, the thermostability of the variant relative to the parent is determined at pH 6.0 and 45° C. In another aspect, the thermostability of the variant relative to the parent is determined at pH 6.0 and 50° C. In another aspect, the thermostability of the variant relative to the parent is determined at pH 6.0 and 55° C. In another aspect, the thermostability of the variant relative to the parent is determined at pH 6.0 and 60° C. In another aspect, the thermostability of the variant relative to the parent is determined at pH 6.0 and 62° C. In another aspect, the thermostability of the variant relative to the parent is determined at pH 6.0 and 65° C. In another aspect, the thermostability of the variant relative to the parent is determined at pH 6.0 and 68° C. In another aspect, the thermostability of the variant relative to the parent is determined at pH 6.0 and 70° C. In another aspect, the thermostability of the variant relative to the parent is determined at pH 6.0 and 72° C. In another aspect, the thermostability of the variant relative to the parent is determined at pH 6.0 and 75° C. In another aspect, the thermostability of the variant relative to the parent is determined at pH 6.0 and 80° C. In another aspect, the thermostability of the variant relative to the parent is determined at pH 6.0 and 85° C. In another aspect, the thermostability of the variant relative to the parent is determined at pH 6.0 and 90° C. In another aspect, the thermostability of the variant relative to the parent is determined at pH 6.0 and 95° C.

In another aspect, the thermostability of the variant relative to the parent is determined at pH 6.5 and 45° C. In another aspect, the thermostability of the variant relative to the parent is determined at pH 6.5 and 50° C. In another aspect, the thermostability of the variant relative to the parent is determined at pH 6.5 and 55° C. In another aspect, the thermostability of the variant relative to the parent is determined at pH 6.5 and 60° C. In another aspect, the thermostability of the variant relative to the parent is determined at pH 6.5 and 62° C. In another aspect, the thermostability of the variant relative to the parent is determined at pH 6.5 and 65° C. In another aspect, the thermostability of the variant relative to the parent is determined at pH 6.5 and 68° C. In another aspect, the thermostability of the variant relative to the parent is determined at pH 6.5 and 70° C. In another aspect, the thermostability of the variant relative to the parent is determined at pH 6.5 and 72° C. In another aspect, the thermostability of the variant relative to the parent is determined at pH 6.5 and 75° C. In another aspect, the thermostability of the variant relative to the parent is determined at pH 6.5 and 80° C. In another aspect, the thermostability of the variant relative to the parent is determined at pH 6.5 and 85° C. In another aspect, the thermostability of the variant relative to the parent is determined at pH 6.5 and 90° C. In another aspect, the thermostability of the variant relative to the parent is determined at pH 6.5 and 95° C.

In another aspect, the thermostability of the variant relative to the parent is determined at pH 7.0 and 45° C. In another aspect, the thermostability of the variant relative to the parent is determined at pH 7.0 and 50° C. In another aspect, the thermostability of the variant relative to the parent is determined at pH 7.0 and 55° C. In another aspect, the thermostability of the variant relative to the parent is determined at pH 7.0 and 60° C. In another aspect, the thermostability of the variant relative to the parent is determined at pH 7.0 and 62° C. In another aspect, the thermostability of the variant relative to the parent is determined at pH 7.0 and 65° C. In another aspect, the thermostability of the variant relative to the parent is determined at pH 7.0 and 68° C. In another aspect, the thermostability of the variant relative to the parent is determined at pH 7.0 and 70° C. In another aspect, the thermostability of the variant relative to the parent is determined at pH 7.0 and 72° C. In another aspect, the thermostability of the variant relative to the parent is determined at pH 7.0 and 75° C. In another aspect, the thermostability of the variant relative to the parent is determined at pH 7.0 and 80° C. In another aspect, the thermostability of the variant relative to the parent is determined at pH 7.0 and 85° C. In another aspect, the thermostability of the variant relative to the parent is determined at pH 7.0 and 90° C. In another aspect, the thermostability of the variant relative to the parent is determined at pH 7.0 and 95° C.

In another aspect, the thermostability of the variant relative to the parent is determined at pH 7.5 and 45° C. In another aspect, the thermostability of the variant relative to the parent is determined at pH 7.5 and 50° C. In another aspect, the thermostability of the variant relative to the parent is determined at pH 7.5 and 55° C. In another aspect, the thermostability of the variant relative to the parent is determined at pH 7.5 and 60° C. In another aspect, the thermostability of the variant relative to the parent is determined at pH 7.5 and 62° C. In another aspect, the thermostability of the variant relative to the parent is determined at pH 7.5 and 65° C. In another aspect, the thermostability of the variant relative to the parent is determined at pH 7.5 and 68° C. In another aspect, the thermostability of the variant relative to the parent is determined at pH 7.5 and 70° C. In another aspect, the thermostability of the variant relative to the parent is determined at pH 7.5 and 72° C. In another aspect, the thermostability of the variant relative to the parent is determined at pH 7.5 and 75° C. In another aspect, the thermostability of the variant relative to the parent is determined at pH 7.5 and 80° C. In another aspect, the thermostability of the variant relative to the parent is determined at pH 7.5 and 85° C. In another aspect, the thermostability of the variant relative to the parent is determined at pH 7.5 and 90° C. In another aspect, the thermostability of the variant relative to the parent is determined at pH 7.5 and 95° C.

In another aspect, the thermostability of the variant relative to the parent is determined at pH 8.0 and 45° C. In another aspect, the thermostability of the variant relative to the parent is determined at pH 8.0 and 50° C. In another aspect, the thermostability of the variant relative to the parent is determined at pH 8.0 and 55° C. In another aspect, the thermostability of the variant relative to the parent is determined at pH 8.0 and 60° C. In another aspect, the thermostability of the variant relative to the parent is determined at pH 8.0 and 62° C. In another aspect, the thermostability of the variant relative to the parent is determined at pH 8.0 and 65° C. In another aspect, the thermostability of the variant relative to the parent is determined at pH 8.0 and 68° C. In another aspect, the thermostability of the variant relative to the parent is determined at pH 8.0 and 70° C. In another aspect, the thermostability of the variant relative to the parent is determined at pH 8.0 and 72° C. In another aspect, the thermostability of the variant relative to the parent is determined at pH 8.0 and 75° C. In another aspect, the thermostability of the variant relative to the parent is determined at pH 8.0 and 80° C. In another aspect, the thermostability of the variant relative to the parent is determined at pH 8.0 and 85° C. In another aspect, the thermostability of the variant relative to the parent is determined at pH 8.0 and 90° C. In another aspect, the thermostability of the variant relative to the parent is determined at pH 8.0 and 95° C.

In another aspect, the thermostability of the variant relative to the parent is determined at pH 8.5 and 45° C. In another aspect, the thermostability of the variant relative to the parent is determined at pH 8.5 and 50° C. In another aspect, the thermostability of the variant relative to the parent is determined at pH 8.5 and 55° C. In another aspect, the thermostability of the variant relative to the parent is determined at pH 8.5 and 60° C. In another aspect, the thermostability of the variant relative to the parent is determined at pH 8.5 and 62° C. In another aspect, the thermostability of the variant relative to the parent is determined at pH 8.5 and 65° C. In another aspect, the thermostability of the variant relative to the parent is determined at pH 8.5 and 68° C. In another aspect, the thermostability of the variant relative to the parent is determined at pH 8.5 and 70° C. In another aspect, the thermostability of the variant relative to the parent is determined at pH 8.5 and 72° C. In another aspect, the thermostability of the variant relative to the parent is determined at pH 8.5 and 75° C. In another aspect, the thermostability of the variant relative to the parent is determined at pH 8.5 and 80° C. In another aspect, the thermostability of the variant relative to the parent is determined at pH 8.5 and 85° C. In another aspect, the thermostability of the variant relative to the parent is determined at pH 8.5 and 90° C. In another aspect, the thermostability of the variant relative to the parent is determined at pH 8.5 and 95° C.

In another aspect, the thermostability of the variant relative to the parent is determined at pH 9.0 and 45° C. In another aspect, the thermostability of the variant relative to the parent is determined at pH 9.0 and 50° C. In another aspect, the thermostability of the variant relative to the parent is determined at pH 9.0 and 55° C. In another aspect, the thermostability of the variant relative to the parent is determined at pH 9.0 and 60° C. In another aspect, the thermostability of the variant relative to the parent is determined at pH 9.0 and 62° C. In another aspect, the thermostability of the variant relative to the parent is determined at pH 9.0 and 65° C. In another aspect, the thermostability of the variant relative to the parent is determined at pH 9.0 and 68° C. In another aspect, the thermostability of the variant relative to the parent is determined at pH 9.0 and 70° C. In another aspect, the thermostability of the variant relative to the parent is determined at pH 9.0 and 72° C. In another aspect, the thermostability of the variant relative to the parent is determined at pH 9.0 and 75° C. In another aspect, the thermostability of the variant relative to the parent is determined at pH 9.0 and 80° C. In another aspect, the thermostability of the variant relative to the parent is determined at pH 9.0 and 85° C. In another aspect, the thermostability of the variant relative to the parent is determined at pH 9.0 and 90° C. In another aspect, the thermostability of the variant relative to the parent is determined at pH 9.0 and 95° C.

In each of the aspects above, the thermostability of the variant relative to the parent can be determined by incubating the variant and parent for 1 minute. In each of the aspects above, the thermostability of the variant relative to the parent can be determined by incubating the variant and parent for 5 minutes. In each of the aspects above, the thermostability of the variant relative to the parent can be determined by incubating the variant and parent for 10 minutes. In each of the aspects above, the thermostability of the variant relative to the parent can be determined by incubating the variant and parent for 15 minutes. In each of the aspects above, the thermostability of the variant relative to the parent can be determined by incubating the variant and parent for 20 minutes. In each of the aspects above, the thermostability of the variant relative to the parent can be determined by incubating the variant and parent for 25 minutes. In each of the aspects above, the thermostability of the variant relative to the parent can be determined by incubating the variant and parent for 30 minutes. In each of the aspects above, the thermostability of the variant relative to the parent can be determined by incubating the variant and parent for 45 minutes. In each of the aspects above, the thermostability of the variant relative to the parent can be determined by incubating the variant and parent for 60 minutes. A time period longer than 60 minutes can also be used.

In one aspect, the thermostability of the variant having cellulolytic enhancing activity is increased at least 1.01-fold, e.g., at least 1.05-fold, at least 1.1-fold, at least 1.2-fold, at least 1.3-fold, at least 1.4-fold, at least 1.5-fold, at least 1.8-fold, at least 2-fold, at least 5-fold, at least 10-fold, at least 15-fold, at least 20-fold, at least 25-fold, at least 30-fold, at least 50-fold, at least 75-fold, or at least 100-fold compared to more thermostable than the parent.

Parent GH61 Polypeptides

The parent GH61 polypeptide may be any GH61 polypeptide having cellulolytic enhancing activity.

The parent GH61 polypeptide may be (a) a polypeptide having at least 60% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411; (b) a polypeptide encoded by a polynucleotide that hybridizes under at least low stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410, or (ii) the full-length complement of (i); or (c) a polypeptide encoded by a polynucleotide having at least 60% sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410.

In one aspect, the parent has a sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellulolytic enhancing activity.

In one embodiment, the amino acid sequence of the parent differs by up to 10 amino acids, e.g., 1, 2, 3, 4, 5, 6, 7, 8, 9, or 10 from the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

In another embodiment, the parent comprises or consists of the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

In another embodiment, the parent comprises or consists of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

In another embodiment, the parent is a fragment containing at least 85% of the amino acid residues, e.g., at least 90% of the amino acid residues or at least 95% of the amino acid residues of the mature polypeptide of a GH61 polypeptide.

In another embodiment, the parent is an allelic variant of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410, or the full-length complements thereof (Sambrook et al., 1989, *Molecular Cloning, A Laboratory Manual*, 2d edition, Cold Spring Harbor, New York).

The polynucleotide of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410, or subsequences thereof, as well as the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411, or fragments thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410, or subsequences thereof, the carrier material is used in a Southern blot.

For purposes of the present invention, hybridization indicates that the polynucleotide hybridizes to a labeled nucleic acid probe corresponding to (i) SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410; (ii) the mature polypeptide coding sequence thereof; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410.

In another embodiment, the nucleic acid probe is a polynucleotide that encodes the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411; the mature polypeptide thereof; or a fragment thereof.

In another embodiment, the nucleic acid probe is SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410.

In another aspect, the parent is encoded by a polynucleotide having a sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The parent may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one embodiment, the parent is secreted extracellularly.

The parent may be a bacterial GH61 polypeptide. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* GH61 polypeptide, or a Gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* GH61 polypeptide.

In one embodiment, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* GH61 polypeptide.

The parent may be a fungal GH61 polypeptide. For example, the parent may be a yeast GH61 polypeptide such as a *Candida, Kluyveromyces, Pichia, Saccharomyces, Schizosaccharomyces,* or *Yarrowia* GH61 polypeptide; or a filamentous fungal GH61 polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptosphaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* GH61 polypeptide.

In another embodiment, the parent is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* GH61 polypeptide.

In another embodiment, the parent is an *Acremonium cellulolyticus, Aspergillus aculeatus, Aspergillus awamori, Aspergillus foetidus, Aspergillus fumigatus, Aspergillus japonicus, Aspergillus lentulus, Aspergillus nidulans, Aspergillus niger, Aspergillus oryzae, Aspergillus terreus, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fennellia nivea, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium emersonii, Penicillium funiculosum, Penicillium pinophilum, Penicillium purpurogenum, Phanerochaete chrysosporium, Talaromyces leycettanus, Thermoascus aurantiacus, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* GH61 polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a GH61 polypeptide variant having cellulolytic enhancing activity, comprising: (a) introducing into a parent GH61 polypeptide a substitution at one or more (e.g., several) positions corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250 of the mature polypeptide of SEQ ID NO: 30, wherein the variant has cellulolytic enhancing activity; and optionally (b) recovering the variant. In one aspect, the methods further or even further comprise introducing into the parent GH61 polypeptide a substitution at one or more (e.g., several) positions corresponding to positions 111, 152, 155, and 162 of the mature polypeptide of SEQ ID NO: 30, wherein the variant has cellulolytic enhancing activity. In another aspect, the methods further or even further comprise introducing into the parent GH61 polypeptide a substitution at one or more (e.g., several) positions corresponding to positions 96, 98, 200, 202, and 204 of the mature polypeptide of SEQ ID NO: 30, wherein the variant has cellulolytic enhancing activity. In another aspect, the methods further or even further comprise introducing into the parent GH61 polypeptide a substitution at one or more (e.g., several) positions corresponding to positions 105, 154, 188, 189, 216, and 229 of the mature polypeptide of SEQ ID NO: 30, wherein the variant has cellulolytic enhancing activity, The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent. Any site-directed mutagenesis procedure can be used in the present invention. There are many commercial kits available that can be used to prepare variants.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Site-saturation mutagenesis systematically replaces a polypeptide coding sequence with sequences encoding all 19 amino acids at one or more (e.g., several) specific positions (Parikh and Matsumura, 2005, *J. Mol. Biol.* 352: 621-628).

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding GH61 polypeptide variants of the present invention.

Nucleic Acid Constructs

The present invention also relates to nucleic acid constructs comprising a polynucleotide encoding a GH61 polypeptide variant of the present invention operably linked to one or more control sequences that direct the expression of the coding sequence in a suitable host cell under conditions compatible with the control sequences.

The polynucleotide may be manipulated in a variety of ways to provide for expression of a GH61 polypeptide variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide recognized by a host cell for expression of a polynucleotide encoding a variant of the present invention. The promoter contains transcriptional control sequences that mediate the expression of the GH61 polypeptide variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the GH61 polypeptide variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the GH61 polypeptide variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the GH61 polypeptide variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a GH61 polypeptide variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCI B 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a GH61 polypeptide variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the GH61 polypeptide variant and the signal peptide sequence is positioned next to the N-terminus of the propeptide sequence.

It may also be desirable to add regulatory sequences that regulate expression of the GH61 polypeptide variant relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a GH61 polypeptide variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system. The vector preferably contains an element(s) that permits integration of the vector into the host cell's genome or autonomous replication of the vector in the cell independent of the genome.

For integration into the host cell genome, the vector may rely on the polynucleotide's sequence encoding the GH61 polypeptide variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a GH61 polypeptide variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a GH61 polypeptide variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a GH61 polypeptide variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*. The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, J. Mol. Biol. 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Talaromyces emersonii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp. 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a GH61 polypeptide variant, comprising: (a) cultivating a recombinant host cell of the present invention under conditions conducive for production of the variant; and optionally (b) recovering the variant.

The host cells are cultivated in a nutrient medium suitable for production of the GH61 polypeptide variant using methods known in the art. For example, the cells may be cultivated by multi-well plates such as 24, 48, or 96 well plates, shake flask cultivation, or small-scale or large-scale fermentation (including continuous, batch, fed-batch, or solid state fermentations) in laboratory or industrial fermentors in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The GH61 polypeptide variant may be detected using methods known in the art that are specific for the variant. These detection methods include, but are not limited to, use of specific antibodies, formation of an enzyme product, or disappearance of an enzyme substrate. For example, an enzyme assay may be used to determine the activity of the variant. A specific assay for GH61 proteins is to incubate the GH61 polypeptide variants with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X100 for 24-96 hours at 40° C. followed by an assay of this reaction to determine the glucose released from the PASC. See the assay described in Example 5.

The GH61 polypeptide variants may be recovered using methods known in the art. For example, the variant may be recovered from the nutrient medium by conventional procedures including, but not limited to, collection, centrifugation, filtration, extraction, spray-drying, evaporation, or precipitation. In one aspect, a whole fermentation broth comprising a variant of the present invention is recovered.

The GH61 polypeptide variants may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the GH61 polypeptide variant is not recovered, but rather a host cell of the present invention expressing the variant is used as a source of the variant.

Fermentation Broth Formulations or Cell Compositions

The present invention also relates to a fermentation broth formulation or a cell composition comprising a variant of the present invention. The fermentation broth product further comprises additional ingredients used in the fermentation process, such as, for example, cells (including, the host cells containing the gene encoding the variant of the present invention which are used to produce the variant), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a variant of the present invention. Preferably, the compositions are enriched in such a variant. The term "enriched" indicates that the cellulolytic enhancing activity of the composition has been increased, e.g., with an enrichment factor of at least 1.1.

The compositions may comprise a variant of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, a GH61 polypeptide, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following processes for using the GH61 polypeptide variants having cellulolytic enhancing activity, or compositions thereof.

The present invention also relates to processes for degrading or converting a cellulosic material, comprising: treating the cellulosic material with an enzyme composition in the presence of a GH61 polypeptide variant of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a GH61 polypeptide variant of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a GH61 polypeptide variant of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel (ethanol, n-butanol, isobutanol, biodiesel, jet fuel) and/or platform chemicals (e.g., acids, alcohols, ketones, gases, oils, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, DC, 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd et al., 2002, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

Pretreatment. In practicing the processes of the present invention, any pretreatment process known in the art can be used to disrupt plant cell wall components of the cellulosic material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technol.* 100: 10-18; Mosier et al., 2005, *Bioresource Technol.* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, countercurrent reactors, or continuous counter-current shrinking bed reactors (Duff and Murray, 1996, supra; Schell et al., 2004, *Bioresource Technology* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, DC, 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, DC, chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification. In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a GH61 polypeptide variant of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a ligninolytic enzyme, an oxidoreductase, a pectinase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another aspect, the oxidoreductase is preferably one or more (e.g., several) enzymes selected from the group consisting of a catalase, a laccase, and a peroxidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a GH61 polypeptide having cellulolytic enhancing activity. In another aspect, the enzyme composition comprises an endoglucanase and a GH61 polypeptide having cellulolytic enhancing activity. In another aspect, the enzyme composition comprises a cellobiohydrolase and a GH61 polypeptide having cellulolytic enhancing activity. In another aspect, the enzyme composition comprises a beta-glucosidase and a GH61 polypeptide having cellulolytic enhancing activity. In another aspect, the enzyme composition comprises an endoglucanase and a cellobiohydrolase. In another aspect, the enzyme composition comprises an endoglucanase and a cellobiohydrolase I, a cellobiohydrolase II, or a combination of a cellobiohydrolase I and a cellobiohydrolase II. In another aspect, the enzyme composition comprises an endoglucanase and a beta-glucosidase. In another aspect, the enzyme composition comprises a beta-glucosidase and a cellobiohydrolase. In another aspect, the enzyme composition comprises a beta-glucosidase and a cellobiohydrolase I, a cellobiohydrolase II, or a combination of a cellobiohydrolase I and a cellobiohydrolase II In another aspect, the enzyme composition comprises an endoglucanase, a GH61 polypeptide having cellulolytic enhancing activity, and a cellobiohydrolase. In another aspect, the enzyme composition comprises an endoglucanase, a GH61 polypeptide having cellulolytic enhancing activity, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and a GH61 polypeptide having cellulolytic enhancing activity. In another aspect, the enzyme composition comprises a beta-glucosidase, a GH61 polypeptide having cellulolytic enhancing activity, and a cellobiohydrolase. In another aspect, the enzyme composition comprises a beta-glucosidase, a GH61 polypeptide having cellulolytic enhancing activity, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and a cellobiohydrolase. In another aspect, the enzyme composition comprises an endoglucanase, a beta-glucosidase, and a cellobiohydrolase I, a cellobiohydrolase II, or a combination of a cellobiohydrolase I and a cellobiohydrolase II. In another aspect, the enzyme composition comprises an endoglucanase, a cellobiohydrolase, a beta-glucosidase, and a GH61 polypeptide having cellulolytic enhancing activity. In another aspect, the enzyme composition comprises an endoglucanase, a beta-glucosidase, a GH61 polypeptide having cellulolytic enhancing activity, and a cellobiohydrolase I, a cellobiohydrolase II, or a combination of a cellobiohydrolase I and a cellobiohydrolase II.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family xylanase. In another preferred aspect, the xylanase is a Family 11 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises an oxidoreductase. In another preferred aspect, the oxidoreductase is a catalase. In another preferred aspect, the oxidoreductase is a laccase. In another preferred aspect, the oxidoreductase is a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be native proteins, recombinant proteins, or a combination of native proteins and recombinant proteins. For example, one or more (e.g., several) components may be native proteins of a cell, which is used as a host cell to express recombinantly one or more (e.g., several) other components of the enzyme composition. It is understood herein that the recombinant proteins may be heterologous (e.g., foreign) and native to the host cell. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and the GH61 polypeptide variants depend on several factors including, but not limited to, the mixture of cellulolytic enzymes and/or hemicellulolytic enzymes, the cellulosic material, the concentration of cellulosic material, the pretreatment(s) of the cellulosic material, temperature, time, pH, and inclusion of a fermenting organism (e.g., for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a GH61 polypeptide variant to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a GH61 polypeptide variant to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material (collectively hereinafter "polypeptides having enzyme activity") can be derived or obtained from any suitable origin, including, archaeal, bacterial, fungal, yeast, plant, or animal origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by, for example, site-directed mutagenesis or shuffling.

A polypeptide having enzyme activity may be a bacterial polypeptide. For example, the polypeptide may be a Gram-positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia*, or *Oceanobacillus* polypeptide having enzyme activity, or a Gram-negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having enzyme activity.

The polypeptide having enzyme activity may also be a fungal polypeptide, and more preferably a yeast polypeptide such as a *Candida, Kluyveromyces, Pichia, Saccharomyces,*

*Schizosaccharomyces*, or *Yarrowia* polypeptide having enzyme activity; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptosphaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), SPEZYME™ CP (Genencor Int.), ACCELERASE™ TRIO (DuPont), FILTRASE® NL (DSM); METHAPLUS® S/L 100 (DSM), ROHAMENT™ 7069 W (Rohm GmbH), or ALTERNAFUEL® CMAX3™ (Dyadic International, Inc.). The cellulase enzymes are added in amounts effective from about 0.001 to about 5.0 wt. % of solids, e.g., about 0.025 to about 4.0 wt. % of solids or about 0.005 to about 2.0 wt. % of solids.

Examples of bacterial endoglucanases that can be used in the processes of the present invention, include, but are not limited to, Acidothermus *cellulolyticus* endoglucanase (WO 91/05039; WO 93/15186; U.S. Pat. No. 5,275,944; WO 96/02551; U.S. Pat. No. 5,536,655; WO 00/70031; WO 05/093050), *Erwinia carotovora* endoglucanase (Saarilahti et al., 1990, *Gene* 90: 9-14), *Thermobifida fusca* endoglucanase III (WO 05/093050), and *Thermobifida fusca* endoglucanase V (WO 05/093050).

Examples of fungal endoglucanases that can be used in the present invention, include, but are not limited to, *Trichoderma reesei* endoglucanase I (Penttila et al., 1986, *Gene* 45: 253-263, *Trichoderma reesei* Cel7B endoglucanase I (GenBank: M15665), *Trichoderma reesei* endoglucanase II (Saloheimo et al., 1988, *Gene* 63:11-22), *Trichoderma reesei* Cel5A endoglucanase II (GenBank: M19373), *Trichoderma reesei* endoglucanase III (Okada et al., 1988, *Appl. Environ. Microbiol.* 64: 555-563, GenBank: AB003694), *Trichoderma reesei* endoglucanase V (Saloheimo et al., 1994, *Molecular Microbiology* 13: 219-228, GenBank: Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Fusarium oxysporum* endoglucanase (GenBank: L29381), *Humicola grisea* var. thermoidea endoglucanase (Gen Bank:AB003107), *Melanocarpus albomyces* endoglucanase (GenBank: MAL515703), *Neurospora crassa* endoglucanase (GenBank: XM_324477), *Humicola insolens* endoglucanase V, *Myceliophthora thermophila* CBS 117.65 endoglucanase, *Thermoascus aurantiacus* endoglucanase I (GenBank: AF487830), and *Trichoderma reesei* strain No. VTT-D-80133 endoglucanase (GenBank: M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Penicillium* occitanis cellobiohydrolase I (GenBank: AY690482), *Talaromyces emersonii* cellobiohydrolase I (GenBank: AF439936), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 02/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat, 1991, *Biochem. J.* 280: 309-316, and Henrissat and Bairoch, 1996, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593.

In the processes of the present invention, any GH61 polypeptide having cellulolytic enhancing activity can be used as a component of the enzyme composition.

Examples of GH61 polypeptides useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, and WO 2009/085868), *Aspergillus fumigatus* (WO 2010/138754), *Penicillium pinophilum* (WO 2011/005867), *Thermoascus* sp. (WO 2011/039319), *Penicillium* sp. (WO 2011/041397), *Thermoascus* crustaceous (WO 2011/041504), *Aspergillus aculeatus* (WO 2012/125925), *Thermomyces lanuginosus* (WO 2012/113340, WO 12/129699, and WO 2012/130964), *Aurantiporus alborubescens* (WO 2012/122477), *Trichophaea saccata* (WO 2012/122477), *Penicillium thomii* (WO 2012/122477), *Talaromyces stipitatus* (WO 2012/135659), *Humicola insolens* (WO 2012/146171), *Malbranchea cinnamomea* (WO 2012/101206), *Talaromyces* leycettanus (WO 2012/101206), and *Chaetomium thermophilum* (WO 2012/101206).

In one aspect, the GH61 polypeptide variant and GH61 polypeptide having cellulolytic enhancing activity is used in the presence of a soluble activating divalent metal cation according to WO 2008/151043, e.g., manganese or copper.

In another aspect, the GH61 polypeptide variant and GH61 polypeptide having cellulolytic enhancing activity is used in the presence of a dioxy compound, a bicyclic compound, a heterocyclic compound, a nitrogen-containing compound, a quinone compound, a sulfur-containing compound, or a liquor obtained from a pretreated cellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

In one aspect, such a compound is added at a molar ratio of the compound to glucosyl units of cellulose of about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK), ALTERNA FUEL 100P (Dyadic), and ALTERNA FUEL 200P (Dyadic).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Talaromyces lanuginosus* GH11 (WO 2012/130965), *Talaromyces thermophilus* GH11 (WO 2012/13095), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt:Q7SOW4), *Trichoderma reesei* (UniProtKB/TrEMBL:Q92458), *Talaromyces emersonii* (SwissProt:Q8X212), and *Talaromyces thermophilus* GH11 (WO 2012/13095).

Examples of acetylxylan esterases useful in the processes of the present invention include, but are not limited to, acetylxylan esterases from *Aspergillus aculeatus* (WO 2010/108918), *Chaetomium globosum* (UniProt:Q2GWX4), *Chaetomium gracile* (GeneSeqP:AAB82124), *Humicola*

*insolens* DSM 1800 (WO 2009/073709), *Hypocrea jecorina* (WO 2005/001036), Myceliophtera *thermophila* (WO 2010/014880), *Neurospora crassa* (UniProt: q7s259), *Phaeosphaeria nodorum* (UniProt:Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), Neosartorya *fischeri* (UniProt:A1D9T4), *Neurospora crassa* (UniProt:Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP: AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt: alcc12), *Aspergillus fumigatus* (SwissProt:Q4WW45), *Aspergillus niger* (UniProt:Q96WX9), *Aspergillus terreus* (Swiss Prot: Q0CJP9), *Humicola insolens* (WO 2010/014706), *Penicillium aurantiogriseum* (WO 2009/068565), *Talaromyces emersonii* (UniProt:Q8X211), and *Trichoderma reesei* (UniProt:Q99024).

Examples of oxidoreductases useful in the processes of the present invention include, but are not limited to, *Aspergillus fumigatus* catalase, *Aspergillus lentilus* catalase, *Aspergillus niger* catalase, *Aspergillus oryzae* catalase, *Humicola insolens* catalase, *Neurospora crassa* catalase, *Penicillium emersonii* catalase, *Scytalidium thermophilum* catalase, *Talaromyces stipitatus* catalase, *Thermoascus aurantiacus* catalase, *Coprinus cinereus* laccase, *Myceliophthora thermophila* laccase, *Polyporus pinsitus* laccase, *Pycnoporus cinnabarinus* laccase, *Rhizoctonia solani* laccase, *Streptomyces coelicolor* laccase, *Coprinus cinereus* peroxidase, Soy peroxidase, and Royal palm peroxidase.

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), More Gene Manipulations in Fungi, Academic Press, C A, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., Biochemical Engineering Fundamentals, McGraw-Hill Book Company, N Y, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation. The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous.

Any suitable hydrolyzed cellulosic material can be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Yeast include strains of *Candida, Kluyveromyces,* and *Saccharomyces*, e.g., *Candida sonorensis, Kluyveromyces marxianus,* and *Saccharomyces cerevisiae*.

Examples of fermenting organisms that can ferment pentose sugars in their native state include bacterial and fungal organisms, such as some yeast. Xylose fermenting yeast include strains of *Candida*, preferably *C. sheatae* or *C. sonorensis*; and strains of *Pichia*, e.g., *P. stipitis*, such as *P. stipitis* CBS 5773. Pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum,* and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis,* and *C. scehatae; Clostridium*, such as *C. acetobutylicum, C. thermocellum,* and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus*, *K. lactis*, *K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In an aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, *Appl. Biochem. Biotechnol.* 39-40: 135-147; Ho et al., 1998, *Appl. Environ. Microbiol.* 64: 1852-1859; Kotter and Ciriacy, 1993, *Appl. Microbiol. Biotechnol.* 38: 776-783; Walfridsson et al., 1995, *Appl. Environ. Microbiol.* 61: 4184-4190; Kuyper et al., 2004, *FEMS Yeast Research* 4: 655-664; Beall et al., 1991, *Biotech. Bioeng.* 38: 296-303; Ingram et al., 1998, *Biotechnol. Bioeng.* 58: 204-214; Zhang et al., 1995, *Science* 267: 240-243; Deanda et al., 1996, *Appl. Environ. Microbiol.* 62: 4465-4470; WO 03/062430).

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603.

In another preferred aspect, the fermentation product is an alkane. The alkane may be an unbranched or a branched alkane. The alkane can be, but is not limited to, pentane, hexane, heptane, octane, nonane, decane, undecane, or dodecane.

In another preferred aspect, the fermentation product is a cycloalkane. The cycloalkane can be, but is not limited to, cyclopentane, cyclohexane, cycloheptane, or cyclooctane.

In another preferred aspect, the fermentation product is an alkene. The alkene may be an unbranched or a branched alkene. The alkene can be, but is not limited to, pentene, hexene, heptene, or octene.

In another preferred aspect, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another preferred aspect, the fermentation product is a gas. The gas can be, but is not limited to, methane, $H_2$, $CO_2$, or CO. See, for example, Kataoka et al., 1997, *Water Science* and *Technology* 36(6-7): 41-47; and Gunaseelan, 1997, *Biomass and Bioenergy* 13(1-2): 83-114.

In another preferred aspect, the fermentation product is isoprene.

In another preferred aspect, the fermentation product is a ketone. It will be understood that the term "ketone" encompasses a substance that contains one or more ketone moieties. The ketone can be, but is not limited to, acetone.

In another preferred aspect, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another preferred aspect, the fermentation product is polyketide.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Detergent Compositions

The present invention also relates to detergent compositions comprising a GH61 polypeptide variant of the present invention and a surfactant. A GH61 polypeptide variant of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In one aspect, the present invention also relates to methods for cleaning or washing a hard surface or laundry, the method comprising contacting the hard surface or the laundry with a detergent composition of the present invention.

In a specific aspect, the present invention provides a detergent additive comprising a GH61 polypeptide variant of the invention. The detergent additive as well as the detergent composition may comprise one or more (e.g., several) enzymes selected from the group consisting of an amylase, arabinase, cutinase, carbohydrase, cellulase, galactanase, laccase, lipase, mannanase, oxidase, pectinase, peroxidase, protease, and xylanase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include CELLUZYME™, and CAREZYME™ (Novozymes A/S), CLAZINASE™, and PURADAX HA™ (Genencor International Inc.), and KAC-500(B)™ (Kao Corporation).

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include ALCALASE™, SAVINASE™ PRIMASE™, DURALASE™, ESPERASE™, and KANNASE™ (Novozymes A/S), MAXATASE™, MAXACAL™, MAXAPEM™, PROPERASE™, PURAFECT™, PURAFECT OXP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™ (Novozymes A/S).

Amylases: Suitable amylases (a and/or β) include those of bacterial or fungal origin.

Chemically modified or protein engineered mutants are included. Amylases include, for example, α-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™ and BAN™ (Novozymes A/S), RAPIDASE™ and PURASTAR™ (from Genencor International Inc.).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME™ (Novozymes A/S).

The detergent enzyme(s) may be included in a detergent composition by adding separate additives containing one or more (e.g., several) enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste, or a liquid. A liquid detergent may be aqueous, typically containing up to 70% water and 0-30% organic solvent, or non-aqueous.

The detergent composition comprises one or more (e.g., several) surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more (e.g., several) polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a GH61 polypeptide variant of the present invention having cellulolytic enhancing activity may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A GH61 polypeptide variant having cellulolytic enhancing activity of the present invention may also be incorporated in the detergent formulations disclosed in WO 97/07202, which is hereby incorporated by reference.

Plants

The present invention also relates to isolated plants, e.g., a transgenic plant, plant part, or plant cell, comprising a polynucleotide of the present invention so as to express and produce a GH61 polypeptide variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences (Sticklen, 2008, *Nature Reviews* 9: 433-443), is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and optionally (b) recovering the variant.

The present invention is further described by the following examples that should not be construed as limiting the scope of the invention.

EXAMPLES

Strains

*Aspergillus oryzae* strain PFJO218 (amy$^-$, alp$^-$, Npl$^-$, CPA$^-$, KA$^-$, pyrG$^-$, ku70$^-$; U.S. Patent Application 20100221783) was used as an expression host for the GH61 polypeptide variants.

*Aspergillus oryzae* strain COLs1300 was also used as an expression host for GH61 polypeptide variants. *A. niger* COLs1300 (amyA, amyB, amyC, alpA, nprA, kusA, niiA, amdS+) was created from *A. oryzae* PFJ0220 (EP 2 147 107 B1) by deleting the promoter and 5' part of both the nitrite reductase (niiA) gene and nitrate reductase (niaD) gene.

Media and Reagents

AMG trace metals solution was composed of 14.3 g of $ZnSO_4 \cdot 7H_2O$, 2.5 g of $CuSO_4 \cdot 5H_2O$, 0.5 g of $NiCl_2 \cdot 6H_2O$, 13.8 g of $FeSO_4 \cdot 7H_2O$, 8.5 g of $MnSO_4 \cdot H_2O$, 3 g of citric acid, and deionized water to 1 liter.

COLs1300 protoplasting cultivating medium was composed of 100 ml of sucrose medium and 1 ml of 1 M urea.

COLs1300 protoplasting solution was composed of 80 mg of GLUCANEX® (Novozymes A/S, Bagsvaerd, Denmark), 0.5 mg/ml of chitinase (Sigma Chemical Co., Inc., St. Louis, MO, USA), 10 ml of 1.2 M $MgSO_4$, and 100 µl of 1 M $NaH_2PO_4$ pH 5.8.

COVE-N-Gly plates were composed of 50 ml of COVE salt solution, 218 g of sorbitol, 10 g of glycerol, 2.02 g of $KNO_3$, 25 g of Noble agar, and deionized water to 1 liter.

COVE-N-Gly plates with 10 mM uridine were composed of 50 ml of COVE salt solution, 218 g of sorbitol, 10 g of glycerol, 2.02 g of $KNO_3$, 25 g of Noble agar, and deionized water to 1 liter; uridine was then added at a concentration of 10 mM to individual plates.

COVE salt solution was composed of 26 g of KCl, 26 g of $MgSO_4 \cdot 7H_2O$, 76 g of $KH_2PO_4$, 50 ml of COVE trace elements solution, and deionized water to 1 liter.

COVE trace elements solution was composed of 40 mg of $Na_2B_4O_7 \cdot 10H_2O$, 0.4 g of $CuSO_4 \cdot 5H_2O$, 1.2 g of $FeSO_4 \cdot 7H_2O$, 0.7 g of $MnSO_4 \cdot H_2O$, 0.8 g of $Na_2MoO_2 \cdot 2H_2O$, 10 g of $ZnSO_4 \cdot 7H_2O$, and deionized water to 1 liter.

LB agar were composed of 5 g of starch (Merck, Whitehouse Station, NJ, USA), 37 g of LB agar (Sigma Chemical Co., Inc., St. Louis, MO, USA), and deionized water to 1 liter.

LB+Amp agar plates were composed of LB agar supplemented with 150 µg of ampicillin per ml.

M400 medium was composed of 50 g of maltodextrin, 2 g of $MgSO_4 \cdot 7H_2O$, 2 g of $KH_2PO_4$, 4 g of citric acid, 8 g of yeast extract, 2 g of urea, 0.5 ml of AMG trace metals solution, 0.5 g of $CaCl_2$, and deionized water to 1 liter; adjusted with NaOH to pH 6. After pH adjustment 0.7 ml of antifoam was added.

Magnificent broth was composed of 50 g of Magnificent Broth powder (MacConnell Research Corp. San Diego, CA, USA) and deionized water to 1 liter.

MaltV1 medium was composed of 20 g of maltose, 10 g of Bacto Peptone, 1 g of yeast extract, 1.45 g of $(NH_4)_2SO_4$, 2.08 g of $KH_2PO_4$, 0.28 g of $CaCl_2$, 0.42 g of $MgSO_4 \cdot 7H_2O$, 0.42 ml of *Trichoderma* trace metals solution, 0.48 g of citric acid, 19.52 g of 2-(N-morpholino)ethanesulfonic acid (MES), and deionized water to 1 liter; adjusted with NaOH to pH 5.5.

MDU2BP medium (pH 5.0) was composed of 135 g of maltose, 3 g of $MgSO_4 \cdot 7H_2O$, 3 g of NaCl, 6 g of $K_2SO_4$, 36 g of $KH_2PO_4$, 21 g of yeast extract, 6 g of urea, 1.5 ml of AMG trace metals solution, and deionized water up to 1 liter.

PEG solution was composed of 6 g of polyethylene glycol 4000 (PEG 4000), 100 µl of 1 M Tris pH 7.5, 100 µl of 1 M $CaCl_2$, and deionized water to 10 ml.

Protoplasting cultivation medium was composed of 92 ml of transformation sucrose medium, 2 ml of 1 M uridine, 1 ml of 1 M $NaNO_3$, and 10 ml of YP medium.

Protoplasting solution was composed of 15 ml of 1.2 M $MgSO_4$, 150 µl of 1 M $NaH_2PO_4$ (pH 5.8), 100 mg of GLUCANEX® (Novozymes A/S, Bagsvaerd, Denmark), and 10 mg of chitinase (Sigma Chemical Co., Inc., St. Louis, MO, USA).

ST solution was composed of 1.5 ml of 2 M sorbitol, 500 µl of 1 M Tris pH 7.5, and deionized water to 5 ml.

STC solution was composed of 60 ml of 2 M sorbitol, 1 ml of 1 M Tris pH 7.5, 1 ml of 1 M $CaCl_2$, and deionized water to 100 ml.

Sucrose medium was composed of 20 ml of COVE salt solution, 342 g of sucrose, and deionized water to 1 liter.

Sucrose agar plates were composed of 20 ml of *Trichoderma* trace metals solution, 20 g of Noble agar, 342 g of sucrose, and deionized water to 1 liter.

TAE buffer was composed of 40 mM 2-amino-2-hydroxymethyl-propane-1,3-diol, 20 mM glacial acetic acid, and 2 mM ethylenediaminetetraacetic acid at pH 8.0.

TBE buffer was composed of 10.8 g of Tris base, 5.5 g of boric acid, and 0.74 g of EDTA (pH 8) in deionized water to 1 liter.

TE buffer was composed of 10 mM Tris-0.1 mM EDTA pH 8.

Top agar was composed of 500 ml of sucrose medium, 5 g of low melting agarose, and 10 ml of 20 mM Tris pH 7.5.

Transformation sucrose medium was composed of 70 ml of 1 M sucrose and 20 ml of COVE salt solution.

*Trichoderma* trace metals solution was composed of 216 g of FeCl$_3$·6H$_2$O, 58 g of ZnSO$_4$·7H$_2$O, 27 g of MnSO$_4$·H$_2$O, 10 g of CuSO$_4$·5H$_2$O, 2.4 g of H$_3$BO$_3$, 336 g of citric acid, and deionized water to 1 liter.

2XYT agar plates were composed of 16 g of tryptone, 10 g of yeast extract, 5 g of NaCl, 15 g of Bacto agar, and deionized water to 1 liter.

sequence (WO 2012/044835), *Penicillium emersonii* GH61A polypeptide coding sequence (SEQ ID NO: 35 [genomic DNA sequence] and SEQ ID NO: 36 [deduced amino acid sequence]), and *Thermoascus aurantiacus* GH61A polypeptide coding sequence (SEQ ID NO: 13 [genomic DNA sequence] and SEQ ID NO: 14 [deduced amino acid sequence]) were amplified from source plasmids described below using the primers shown in Table 1. Bold letters represent coding sequence. The remaining sequences are homologous to insertion sites of pENI2376 for expression of the GH61 polypeptide coding sequences.

TABLE 1

| GH61 Polypeptide origin | Source Template | Plasmid | Primer ID | Primer Sequence |
|---|---|---|---|---|
| *Aspergillus fumigatus* GH61B | pAG43 (WO 2010/138754) | pMMar44 | AspfuGH61Bp ENI2376F_2 | CACAACTGGGGATCCATGACT TTGTCCAAGATCACTTCCA (SEQ ID NO: 171) |
| | | | AspfuGH61Bp ENI2376R_2 | GGCCTCCGCGGCCGCTTAAG CGTTGAACAGTGCAGGACCA (SEQ ID NO: 172) |
| Mutated *Aspergillus fumigatus* GH61B | pTH230 (WO 2012/044835) | pMMar49 | AfumGH61SD MB3pENI3376 F | CACAACTGGGGATCCATGACT TTGTCCAAGATCACTTCCA (SEQ ID NO: 173) |
| | | | AfumGH61SD MB3pENI3376 R | GGCCTCCGCGGCCGCTTAAG CGTTGAACAGTGCAGGACCA (SEQ ID NO: 174) |
| *Penicillium emersonii* GH61A | pDM286 | pMMar45 | PenemGH61p ENI2376F | CACAACTGGGGATCCATGCTG TCTTCGACGACTCGCACCC (SEQ ID NO: 175) |
| | | | PenemGH61p ENI2376R | GGCCTCCGCGGCCGCCTAGA ACGTCGGCTCAGGCGGCCCC (SEQ ID NO: 176) |
| *Thermoascus aurantiacus* GH61A | pDZA2 (WO 2005/074656) | pDFng113 | TaGH61aBaM HItagF | CTGGGGATCCATGTCCTTTTC CAAGAT (SEQ ID NO: 177) |
| | | | TaGH61aNcoI tagR | CTCCGCGGCCGCTTAACCAGT ATACAGAG (SEQ ID NO: 178) |

2XYT+Amp agar plates were composed of 2XYT agar supplemented with 100 μg of ampicillin per ml.

YP medium was composed of 10 g of Bacto yeast extract, 20 g of Bacto peptone, and deionized water to 1 liter.

Example 1: Construction of Expression Vectors pMMar44, pMMar49, pMMar45, and pDFng113

Plasmid pMMar44 was constructed as described below for expression of the *Aspergillus fumigatus* GH61B polypeptide, and generation of mutant gene libraries. Additionally, plasmids pMMar49, pMMar45, and pDFng113 were constructed as described below for expression of the *Aspergillus fumigatus* GH61B polypeptide variants (WO 2012/044835), *Penicillium* sp. (*emersonii*) GH61A polypeptide (hereinafter *Penicillium emersonii* GH61A polypeptide), and *Thermoascus aurantiacus* GH61A polypeptide, respectively, and generation of variants.

Plasmid pENI2376 (U.S. Patent Application 20060234340) containing the AMA sequence for autonomous maintenance in *Aspergillus* was digested with Bam HI and Not I to linearize the plasmid and remove an 8 bp fragment. The digested plasmid was purified using a PCR Purification Kit (QIAGEN Inc., Valencia, CA, USA).

The *Aspergillus fumigatus* GH61B polypeptide coding sequence (FIG. 1; SEQ ID NO: 29 [genomic DNA sequence] and SEQ ID NO: 30 [deduced amino acid sequence]), mutated *Aspergillus fumigatus* GH61B polypeptide coding Construction of plasmid pMMar44 containing the *Aspergillus fumigatus* GH61B polypeptide coding sequence is described below. The *Aspergillus fumigatus* GH61B polypeptide coding sequence was amplified from plasmid pAG43 (WO 2010/138754) using the primers shown in Table 1 with overhangs designed for cloning into plasmid pENI2376.

Fifty picomoles of each of the primers listed in Table 1 were used in a PCR composed of 90 ng of pAG43, 1× ADVANTAGE® 2 PCR Buffer (Clontech Laboratories, Inc., Mountain View, CA, USA), 1 μl of a blend of dATP, dTTP, dGTP, and dCTP, each at 10 mM, and 1× ADVANTAGE® 2 DNA Polymerase Mix (Clontech Laboratories, Inc., Mountain View, CA, USA) in a final volume of 50 μl. The amplification was performed using an EPPENDORF® MASTERCYCLER® 5333 (Eppendorf Scientific, Inc., Westbury, NY, USA) programmed for 1 cycle at 95° C. for 1 minute; 30 cycles each at 95° C. for 30 seconds, 60° C. for 30 seconds, and 72° C. for 1 minute; and a final elongation at 72° C. for 10 minutes. The heat block then went to a 4° C. soak cycle.

The reaction product was isolated by 1.0% agarose gel electrophoresis using TBE buffer where an approximately 862 bp PCR product band was excised from the gel and extracted using a QIAQUICK® Gel Extraction Kit (QIAGEN Inc., Valencia, CA, USA).

The homologous ends of the 862 bp PCR product and the digested pENI2376 were joined together using an IN-FU- SION™ ADVANTAGE® PCR Cloning Kit (Clontech Laboratories, Inc., Mountain View, CA, USA). A total of 63 ng of the 862 bp PCR product and 200 ng of the Bam HI/NotI digested pENI2376 were used in a reaction composed of 4 µl of 5× IN-FUSION™ reaction buffer (Clontech Laboratories, Inc., Mountain View, CA, USA) and 2 µl of IN-FUSION™ enzyme (Clontech Laboratories, Inc., Mountain View, CA, USA) in a final volume of 20 µl. The reaction was incubated for 15 minutes at 37° C., followed by 15 minutes at 50° C., and then placed on ice. The reaction volume was increased to 100 µl with TE buffer and 2 µl of the reaction were transformed into *E. coli* XL10-GOLD® Super Competent Cells (Stratagene, La Jolla, CA, USA) according to the manufacturer's instructions. *E. coli* transformants were selected on 2XYT+Amp agar plates. Plasmid DNA from several of the resulting *E. coli* transformants was prepared using a BIOROBOT® 9600 (QIAGEN Inc., Valencia, CA, USA). The *Aspergillus fumigatus* GH61B polypeptide coding sequence insert was confirmed by DNA sequencing using a Model 3130xL Genetic Analyzer (Applied Biosystems®, Life Technologies, Grand Island, NY, USA) and dye-terminator chemistry from a BigDye® Terminator v3.1 Cycle Sequencing Kit (Applied Biosystems®, Life Technologies). Sequencing primers used for verification of the gene insert and sequence are shown below.

```
Primer 996271:
                                      (SEQ ID NO: 179)
ACTCAATTTACCTCTATCCACACTT Primer pALLO2 3':
                                      (SEQ ID NO: 180)
GAATTGTGAGCGGATAACAATTTCA
```

A plasmid containing the correct *A. fumigatus* GH61B polypeptide coding sequence was selected and designated pMMar44 (FIG. 2).

Construction of plasmid pMMar49 containing eight base-pair changes resulted in four amino acid mutations of the *Aspergillus fumigatus* GH61B polypeptide (WO 2012/044835) is described below. The mutated *Aspergillus fumigatus* GH61B polypeptide coding sequence (WO 2012/044835) was amplified from plasmid pTH230 using the primers shown in Table 1 with overhangs designed for cloning into plasmid pENI2376.

Fifty picomoles of each of the primers listed in Table 1 were used in a PCR composed of 100 ng of pTH230, 1× ADVANTAGE® 2 PCR Buffer (Clontech Laboratories, Inc., Mountain View, CA, USA), 1 µl of a blend of dATP, dTTP, dGTP, and dCTP, each at 10 mM, and 1× ADVANTAGE® 2 DNA Polymerase Mix (Clontech Laboratories, Inc., Mountain View, CA, USA) in a final volume of 50 µl. The amplification was performed using an EPPENDORF® MASTERCYCLER® 5333 programmed for 1 cycle at 95° C. for 1 minute; 30 cycles each at 95° C. for 30 seconds, 60° C. for 30 seconds, and 72° C. for 1 minute; and a final elongation at 72° C. for 7 minutes. The heat block then went to a 4° C. soak cycle.

The reaction product was isolated by 1.0% agarose gel electrophoresis using TBE buffer where an approximately 862 bp PCR product band was excised from the gel and extracted using a QIAQUICK® Gel Extraction Kit.

The homologous ends of the 862 bp PCR product and the digested pENI2376 were joined together using an IN-FUSION™ ADVANTAGE® PCR Cloning Kit. A total of 90 ng of the 862 bp PCR product and 220 ng of the Bam HI/Not I digested pENI2376 were used in a reaction composed of 4 µl of 5× IN-FUSION™ reaction buffer and 2 µl of IN-FUSION™ enzyme in a final volume of 20 µl. The reaction was incubated for 15 minutes at 37° C., followed by 15 minutes at 50° C., and then placed on ice. The reaction volume was increased to 100 µl with TE buffer and 2 µl of the reaction were transformed into *E. coli* XL10-GOLD® Super Competent Cells according to the manufacturer's instructions. *E. coli* transformants were selected on 2XYT+Amp agar plates. Plasmid DNA from several of the resulting *E. coli* transformants was prepared using a BIOROBOT® 9600. The mutated *Aspergillus fumigatus* GH61B polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers 996271 and pALLO2 3' were used for verification of the gene insert and sequence.

Figure 3:
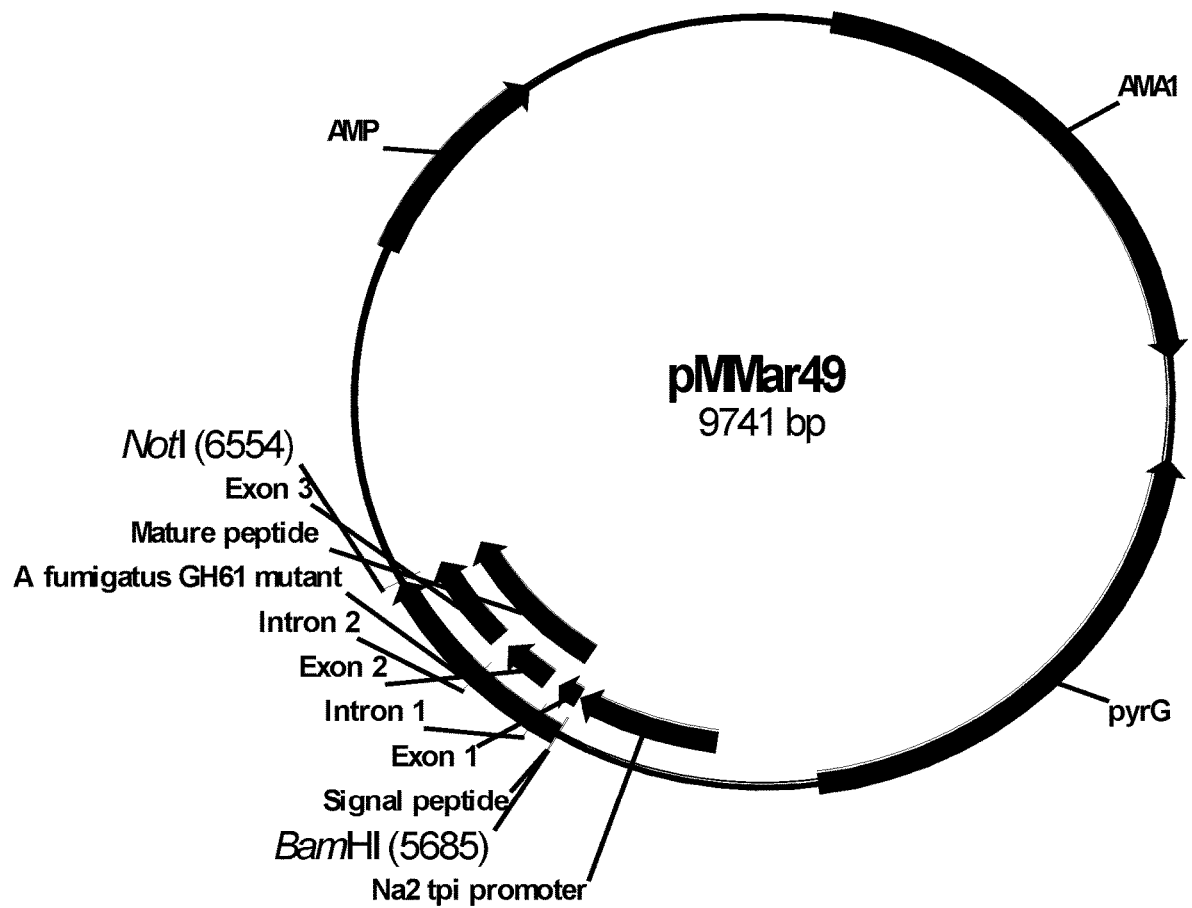
FIG. 3 shows a restriction map of pMMar49.

A plasmid containing the correct mutated *A. fumigatus* GH61B polypeptide coding sequence was selected and designated pMMar49 (FIG. 3).

Construction of plasmid pMMar45 containing the *Penicillium emersonii* GH61A polypeptide coding sequence is described below. The *Penicillium emersonii* GH61A polypeptide coding sequence was amplified from plasmid pDM286 containing the *Penicillium emersonii* GH61A polypeptide coding sequence using the primers shown in Table 1 with overhangs designed for cloning into plasmid pENI2376.

Plasmid pDM286 was constructed according to the following protocol. The *P. emersonii* GH61A polypeptide gene was amplified from plasmid pGH61D23Y4 (WO 2011/041397) using PHUSION™ High-Fidelity Hot Start DNA Polymerase (Finnzymes Oy, Espoo, Finland) and gene-specific forward and reverse primers shown below. The region in italics represents vector homology to the site of insertion.

```
Forward primer:
                                      (SEQ ID NO: 181)
5'-CGGACTGCGCACCATGCTGTCTTCGACGACTCGCAC-3'

Reverse primer:
                                      (SEQ ID NO: 182)
5'-TCGCCACGGAGCTTATCGACTTCTTCTAGAACGTC-3'
```

The amplification reaction contained 30 ng of plasmid pGH61D23Y4, 50 pmoles of each of the primers listed above, 1 µl of a 10 mM blend of dATP, dTTP, dGTP, and dCTP, 1× PHUSION™ High-Fidelity Hot Start DNA Polymerase buffer (Finnzymes Oy, Espoo, Finland) and 1 unit of PHUSION™ High-Fidelity Hot Start DNA Polymerase in a final volume of 50 µl.

The amplification reaction was incubated in an EPPENDORF® MASTERCYCLER® 5333 epgradient S (Eppendorf Scientific, Inc., Westbury, NY, USA) programmed for 1 cycle at 98° C. for 30 seconds; 35 cycles each at 98° C. for 10 seconds, 60° C. for 30 seconds, and 72° C. for 30 seconds, and 1 cycle at 72° C. for 10 minutes.

PCR products were separated by 1% agarose gel electrophoresis using TAE buffer. A 0.87 kb fragment was excised from the gel and extracted using a NUCLEOSPIN® Extract II Kit (Macherey-Nagel, Inc., Bethlehem, PA, USA).

Plasmid pMJ09 (US 2005/0214920 A1) was digested with Nco I and Pac I, and after digestion, the digested vector was isolated by 1.0% agarose gel electrophoresis using TBE buffer where an approximately 7.1 kb fragment was excised from the gel and extracted using a QIAQUICK® Gel Extraction Kit. The 0.87 kb PCR product was inserted into Nco I/Pac I-digested pMJ09 using an IN-FUSION™ ADVANTAGE® PCR Cloning Kit according to the manufacturer's protocol. The IN-FUSION™ reaction was composed of 1× IN-FUSION™ Reaction buffer, 180 ng of Not I/Pac I digested plasmid pMJ09, 108 ng of the 0.87 kb PCR product, and 1 µl of IN-FUSION™ Enzyme in a 10 µl reaction volume. The reaction was incubated for 15 minutes at 37° C. and then for 15 minutes at 50° C. To the reaction 40 µl of TE were added and 2 µl were used to transform ONE SHOT® TOP10 competent cells (Invitrogen, Carlsbad, CA, USA) according to the manufacturer's protocol. E. coli transformants were selected on 2XYT+Amp agar plates. Plasmid DNA from several of the resulting E. coli transformants was prepared using a BIOROBOT® 9600. The insert was confirmed by DNA sequencing using a Model 3130xL Genetic Analyzer and dye-terminator chemistry from a BigDye® Terminator v3.1 Cycle Sequencing Kit. One clone containing the insert with no PCR errors was identified and designated plasmid pDM286. Plasmid pDM286 can be digested with Pme I to generate an approximately 5.4 kb fragment for T. reesei transformation. This 5.4 kb fragment contains the expression cassette [T. reesei Cel7A cellobiohydrolase (CBHI) promoter, P. emersonii glycosyl hydrolase 61A (GH61A) gene, T. reesei Cel7A cellobiohydrolase (CBHI) terminator], and Aspergillus nidulans acetamidase (amdS) gene.

For construction of pMMar45, 50 picomoles of each of the primers listed in Table 1 were used in a PCR composed of 120 ng of pDM286, 1× EXPAND® PCR Buffer (Roche Diagnostics, Inc., Indianapolis, IN, USA), 1 µl of a blend of dATP, dTTP, dGTP, and dCTP, each at 10 mM, and 1× EXPAND® DNA Polymerase Mix (Roche Diagnostics, Inc., Indianapolis, IN, USA) in a final volume of 50 µl. The amplification was performed using an EPPENDORF® MASTERCYCLER® 5333 programmed for 1 cycle at 95° C. for 1 minute; 30 cycles each at 95° C. for 30 seconds, 60° C. for 30 seconds, and 72° C. for 1 minute; and a final elongation at 72° C. for 10 minutes. The heat block then went to a 4° C. soak cycle.

The reaction product was isolated by 1.0% agarose gel electrophoresis using TBE buffer where an approximately 762 bp PCR product band was excised from the gel and extracted using a QIAQUICK® Gel Extraction Kit.

The homologous ends of the 762 bp PCR product and the Bam HI/Not I digested pENI2376 were joined together using an IN-FUSION™ ADVANTAGE® PCR Cloning Kit. A total of 90 ng of the 762 bp PCR product and 200 ng of the digested pENI2376 were used in a reaction composed of 4 µl of 5× IN-FUSION™ reaction buffer and 2 µl of IN-FUSION™ enzyme in a final volume of 20 µl. The reaction was incubated for 15 minutes at 37° C., followed by 15 minutes at 50° C., and then placed on ice. The reaction volume was increased to 100 µl with TE buffer and 2 µl of the reaction were transformed into E. coli XL10-GOLD® Super Competent Cells according to the manufacturer's instructions. E. coli transformants were selected on 2XYT+Amp agar plates. Plasmid DNA from several of the resulting E. coli transformants was prepared using a BIOROBOT® 9600. The P. emersonii GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers 996271 and pALLO2 3' were used for verification of the gene insert and sequence.

Figure 4:
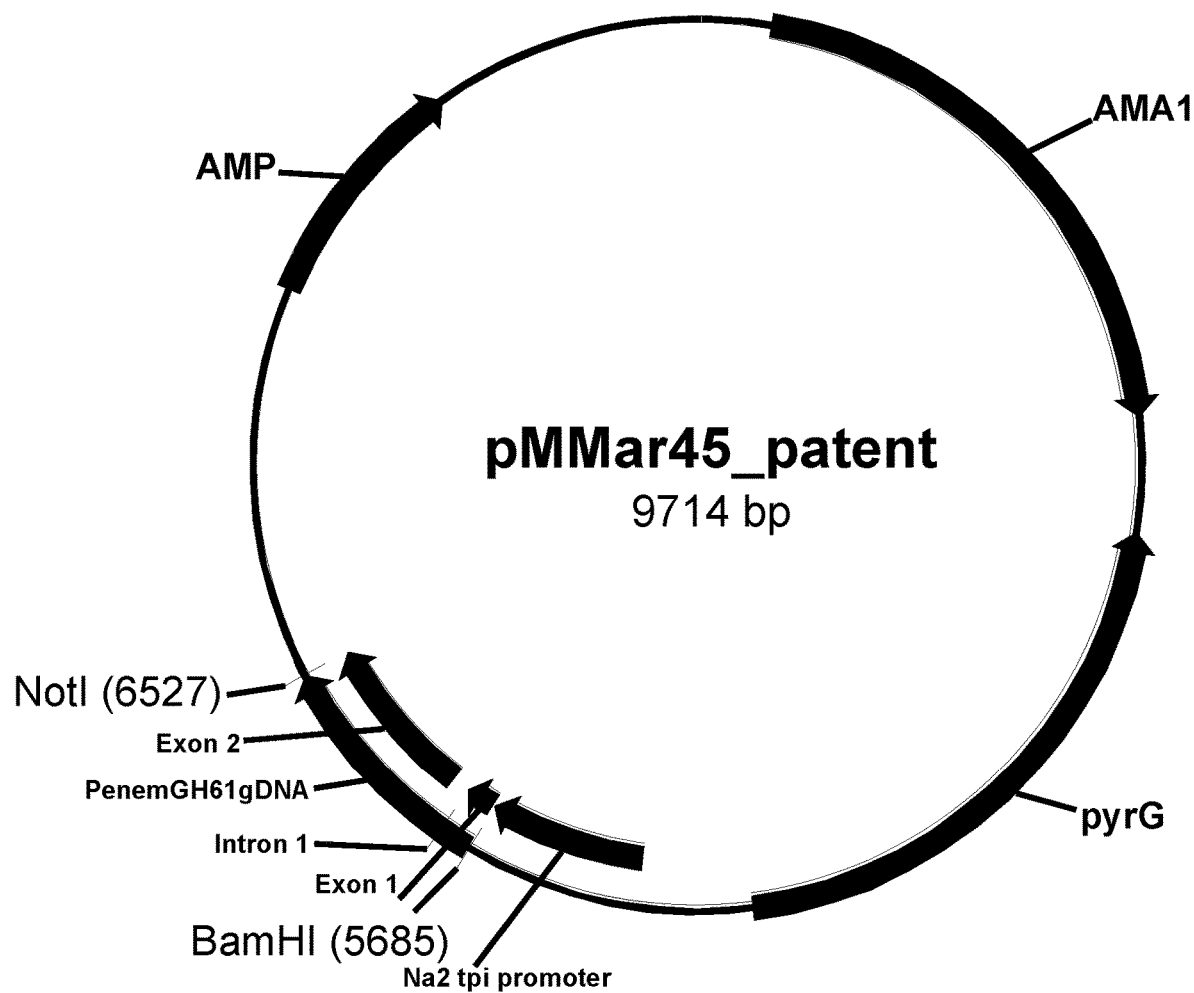
FIG. 4 shows a restriction map of pMMar45.

A plasmid containing the correct P. emersonii GH61A polypeptide coding sequence was selected and designated pMMar45 (FIG. 4).

Construction of plasmid pDFng113 containing the Thermoascus aurantiacus GH61A polypeptide coding sequence is described below. The Thermoascus aurantiacus GH61A polypeptide coding sequence was amplified from plasmid pDZA2 (WO 2005/074656) using the primers shown in Table 1 with overhangs designed for cloning into plasmid pENI2376.

Fifty picomoles of each of the primers listed in Table 1 were used in a PCR composed of 100 ng of pDZA2, 1× EXPAND® PCR Buffer, 1 µl of a blend of dATP, dTTP, dGTP, and dCTP, each at 10 mM, and 1× EXPAND® DNA Polymerase Mix in a final volume of 50 µl. The amplification reaction was performed using an EPPENDORF® MASTERCYCLER® 5333 programmed for 1 cycle at 94° C. for 2 minutes; 30 cycles each at 94° C. for 15 seconds, 59.9° C. for seconds, and 72° C. for 1 minute; and a final elongation at 72° C. for 7 minutes. The heat block then went to a 4° C. soak cycle.

The reaction product was isolated by 1.0% agarose gel electrophoresis using TBE buffer where an approximately 822 bp PCR product band was excised from the gel and extracted using a QIAQUICK® Gel Extraction Kit.

The homologous ends of the 822 bp PCR product and the Bam HI/Not I digested pENI2376 were joined together using an IN-FUSION™ ADVANTAGE® PCR Cloning Kit. A total of 37 ng of the 799 bp PCR product and 200 ng of the digested pENI2376 were used in a reaction composed of 4 µl of 5× IN-FUSION™ reaction buffer and 2 µl of IN-FUSION™ enzyme in a final volume of 20 µl. The reaction was incubated for 15 minutes at 37° C., followed by 15 minutes at 50° C., and then placed on ice. The reaction volume was increased to 50 µl with TE buffer and 2 µl of the reaction were transformed into E. coli XL10-GOLD® Ultracompetent Cells (Stratagene, La Jolla, CA, USA) according to the manufacturer's instructions. E. coli transformants were selected on 2XYT+Amp agar plates. Plasmid DNA from several of the resulting E. coli transformants was prepared using a BIOROBOT® 9600. The T. aurantiacus GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers 996271 and pALLO2 3' were used for verification of the gene insert and sequence.

Figure 5:
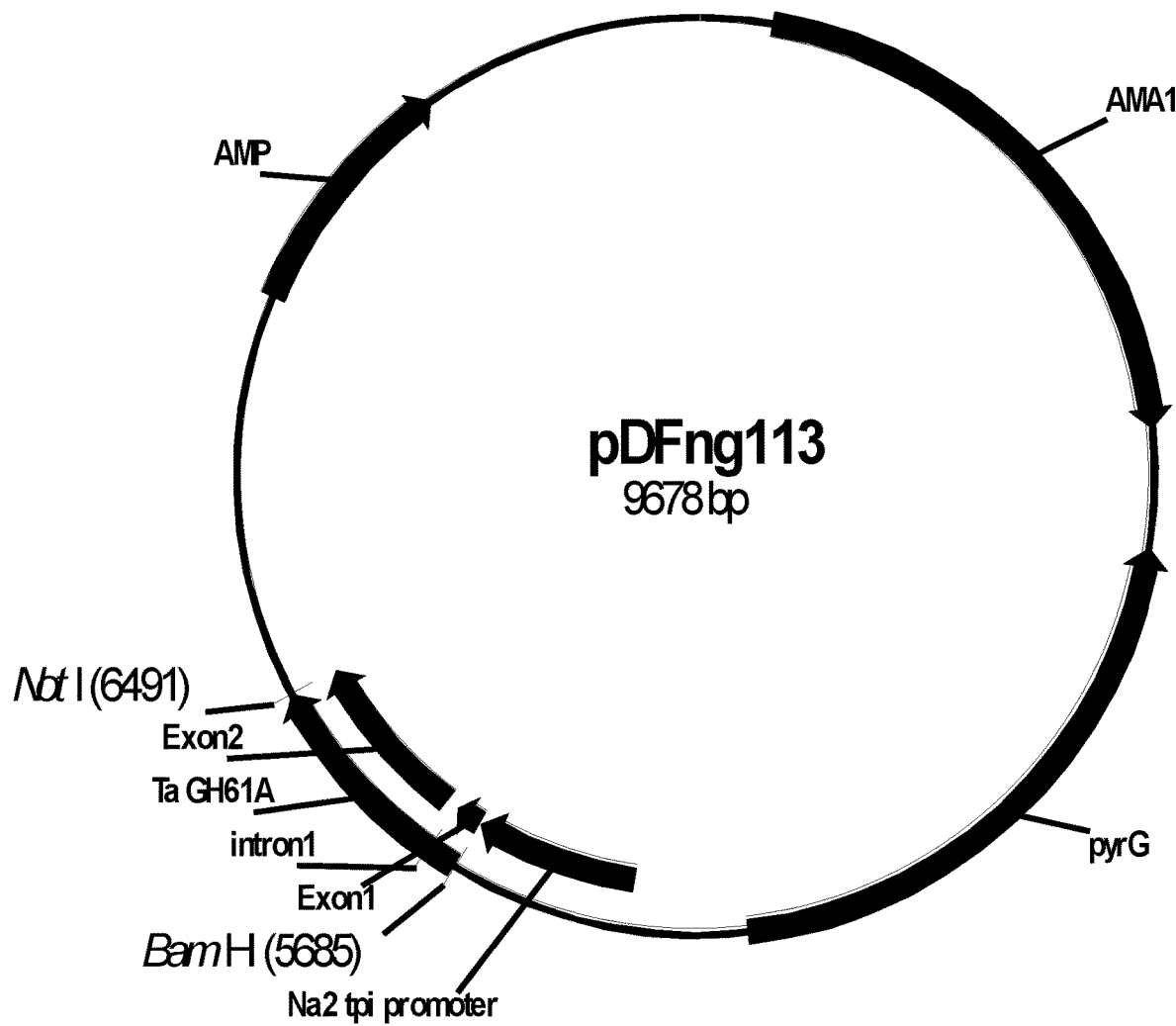
FIG. 5 shows a restriction map of pDFng113.

A plasmid containing the correct T. aurantiacus GH61A polypeptide coding sequence was selected and designated pDFng113 (FIG. 5).

Example 2: Construction of an Aspergillus fumigatus GH61B Polypeptide Site Saturation Library A site saturation library of the Aspergillus fumigatus GH61B polypeptide coding sequence was synthesized by GeneArt AG (Regensburg, Germany). An average of 16.8 mutations per position was synthesized for a total of 165 residues, excluding the most conserved residues, resulting in a total of 2768 mutants. E. coli DH10B (Invitrogen, Carlsbad, CA, USA) strains containing mutant plasmids with known mutations were arrayed in 96 well plates as 50 µl glycerol stocks, and stored at −80° C.

DNA was generated from a thawed GeneArt plate by using a sterile 96 well replicator to stamp the GeneArt plate onto a 2XYT agar plate containing 100 µg/ml of ampicillin.

The agar plate was incubated overnight at 37° C. Resulting colonies from the agar plate were used to inoculate a 96 deep well block with each well containing 1 ml of Magnificent broth supplemented with 400 µg of ampicillin per ml. The block was covered with an airpore breathable lid and then incubated in a humidified box at 37° C. overnight at 350 rpm. The block was centrifuged at 1100×g for 10 minutes and the supernatant discarded. Plasmids were extracted from the cell pellets using a BIOROBOT® 9600.

Example 3: Expression of the Wild-Type and Variants of the *A. fumigatus* GH61B Polypeptide and *P. emersonii* GH61A Polypeptide in *Aspergillus oryzae* PFJO218

*Aspergillus oryzae* PFJO218 was inoculated onto a COVE-N-Gly plate with 10 mM uridine and incubated at 34° C. until confluent. Spores were collected from the plate by washing with 8 ml of 0.01% TWEEN® 20. One ml of the spore suspension was used to inoculate 103 ml of the Protoplasting cultivation medium in a 500 ml polycarbonate shake flask. The shake flask was incubated at 30° C. with agitation at 180 rpm for 17-20 hours. Mycelia were filtered through a funnel lined with MIRACLOTH® (Calbiochem, La Jolla, CA, USA) and washed with 200 ml of 0.6 M $MgSO_4$. Washed mycelia were resuspended in 15 ml of Protoplasting solution in a 125 ml sterile polycarbonate shake flask and incubated on ice for 5 minutes. One ml of a solution of 12 mg of bovine serum albumin per ml of deionized water was added to the shake flask and the shake flask was then incubated at 37° C. with mixing at 70 rpm for 1-3 hours until protoplasting was complete. The mycelia/protoplast mixture was filtered through a funnel lined with MIRACLOTH® into a 50 ml conical tube and overlayed with 5 ml of ST solution. The 50 ml conical tube was centrifuged at 1050×g for 15 minutes with slow acceleration/deceleration. After centrifugation, the liquid was separated into 3 phases. The interphase which contained the protoplasts was transferred to a new 50 ml conical tube. Two volumes of STC solution were added to the protoplasts followed by a brief centrifugation at 1050×g for 5 minutes. The supernatant was discarded. The protoplasts were washed twice with 20 ml of STC with resuspension of the protoplast pellet, centrifugation at 1050×g for 10 minutes, and decanting of the supernatant each time. After the final decanting, the protoplast pellet was resuspended in STC at a concentration of $1\times10^8$/ml. Protoplasts were frozen at −80° C. until transformation.

A 1.3 µl volume of each mutant plasmid was used to transform 3.5 µl of *A. oryzae* PFJO218 protoplasts with 3.5 µl of PEG solution per well in a 24 well plate. Plasmid pMMar44 or pMMar45 (Table 1) was also transformed as above into *A. oryzae* PFJO218 protoplasts to provide broth comprising the *A. fumigatus* or *P. emersonii* wild-type GH61 polypeptides. The 24 well plate was incubated at 37° C. stationary for 30 minutes followed by addition of 28.6 µl of Transformation sucrose medium containing 10 mM $NaNO_3$ and 14.3 µl of STC. The 24 well plate was then placed in a humidified box at 37° C. stationary for 7 days. On day 7, 1 ml of MaltV1 medium was added to each well. The plate was returned to the humidified box at 39° C. stationary and incubated for an additional 5 days. At least 550 µl of broth for each variant or the wild-type *A. fumigatus* or *P. emersonii* GH61 polypeptide were harvested using a pipette to remove the mycelia mat and aspirate the liquid, for assay using PASC as a substrate. Mutant plasmids resulting in variants with improved thermostability using a PASC assay (Example 5) were transformed again and retested using the protocols described above.

Some of the variants were spore-purified for further characterization. After a 7 day incubation of the transformation and prior to the addition of 1 ml of MaltV1 expression medium, a loop was swiped over the initial growth from the transformation to collect spores in the well. The spores were then streaked onto a COVE-N-Gly plate and incubated at 37° C. for approximately 36 hours. Single individual transformants were excised from the plate and transferred onto fresh COVE-N-Gly plates. The plates were stored at 34° C. until confluent. Once confluent, a loop dipped in 0.01% TWEEN® 20 was swiped over the spores which was then used to inoculate a 24 well plate with each well containing 1 ml of MaltV1 expression medium. The 24 well plate was placed in a humidified box at 39° C. Samples were harvested on the fifth day by removing the mycelia mat and pipetting up the broth.

Example 4: Preparation of *Aspergillus fumigatus* Beta-Glucosidase

*Aspergillus fumigatus* NN055679 Cel3A beta-glucosidase (SEQ ID NO: 169 [DNA sequence] and SEQ ID NO: 170 [deduced amino acid sequence]) was recombinantly prepared according to WO 2005/047499 using *Aspergillus oryzae* as a host.

The filtered broth was adjusted to pH 8.0 with 20% sodium acetate, which made the solution turbid. To remove the turbidity, the solution was centrifuged (20000×g for 20 minutes), and the supernatant was filtered through a 0.2 µm filtration unit (Nalgene, Rochester, NY, USA). The filtrate was diluted with deionized water to reach the same conductivity as 50 mM Tris/HCl, pH 8.0. The adjusted enzyme solution was applied to a Q SEPHAROSE® Fast Flow column (GE Healthcare, Piscataway, NJ, USA) equilibrated with 50 mM Tris-HCl pH 8.0 and eluted with a linear gradient from 0 to 500 mM sodium chloride. Fractions were pooled and treated with 1% (w/v) activated charcoal to remove color from the beta-glucosidase pool. The charcoal was removed by filtration of the suspension through a 0.2 µm filtration unit (Nalgene, Rochester, NY, USA). The filtrate was adjusted to pH 5.0 with 20% acetic acid and diluted 10 times with deionized water. The adjusted filtrate was applied to a SP SEPHAROSE® Fast Flow column (GE Healthcare, Piscataway, NJ, USA) equilibrated with 10 mM succinic acid pH 5.0 and eluted with a linear gradient from 0 to 500 mM sodium chloride. Protein concentration was determined using a Microplate BCA™ Protein Assay Kit (Thermo Fischer Scientific, Waltham, MA, USA) in which bovine serum albumin was used as a protein standard.

Example 5: Screening of *Aspergillus fumigatus* GH61B and *Penicillium emersonii* GH61A Polypeptide Variant Libraries Using a BIOMEK® FX Laboratory Automation Workstation (Beckman Coulter, Fullerton, CA, USA) with a DYAD® Thermal Cycler (Bio-Rad Laboratories, Inc., Richmond, CA, USA), 80 µl of each broth sample from the library plates of the *Aspergillus fumigatus* GH61B variants and parent (wild-type) polypeptide grown in MaltV1 medium (Example 3) were mixed with 20 µl of 1 M sodium acetate-10 mM $MnSO_4$ pH 5.0 buffer. Depending on the library, the samples were then heat challenged at 62° C., 65° C., 68° C., 72° C., or 75° C. for 20 minutes and compared to ambient temperature controls. After the heat challenge, the broth samples were diluted 1.25, 2.5, 6.25, and 15.625-fold in 2 mM MnSO$_4$-200 mM sodium acetate pH 5 and 12.5 µl of the dilutions were then transferred to 384-well polypropylene assay plates containing 25 µl of 1% phosphoric acid swollen cellulose (PASC) and 12.5 µl of a cofactor solution (400 mM sodium acetate pH 5, 4 mM MnSO$_4$, 0.4% gallic acid, 0.1 mg/ml of *Aspergillus fumigatus* beta-glucosidase, and 0.04% TRITON® X100). The plates were heat-sealed using an ALPS-300™ (Abgene, Epsom, United Kingdom) with a plastic sheet and incubated at 40° C. for 4 days.

Background glucose concentration of the buffer-treated broth samples was determined prior to incubation by performing a glucose assay using the following reagents per liter: 0.9951 g of ATP, 0.5176 g of NAD, 0.5511 g of MgSO$_4$·7H$_2$O, 20.9 g of MOPS, 1000 units of hexokinase, 1000 units of glucose-6-phosphate dehydrogenase, and 0.01% TRITON® X-100, pH 7.5. The BIOMEK® FX Laboratory Automation Workstation was used for this assay. Four 2-fold serial dilutions were performed in 384-well polystyrene plates using water as diluent. Five µl of the dilutions were added to a new 384-well polystyrene plate, followed by addition of 60 µl of the above reagents. The plate was incubated at ambient temperature (22° C.±2° C.) for 30 to 45 minutes. Relative fluorescent units (RFU) were determined using a DTX 880 plate reader (Beckman Coulter, Fullerton, CA, USA) with excitation at 360 nm and emission at 465 nm and compared to glucose standards (1 mg/ml and 0.125 mg/ml) diluted in the same plate as the samples. At the end of four days, the 40° C. incubated PASC plates were analyzed for glucose concentration using the glucose assay described above. Any background glucose was subtracted from the appropriate samples and then residual activity was calculated by comparing the glucose released in the PASC assay of the ambient sample treatment to the glucose released in the PASC assay of the heat challenged sample. Only data that fits in the linear part of the curve (defined as less than or equal to 1 mg/ml glucose produced in an assay containing 5 mg/ml PASC) was used in the calculation. The formula for calculating the residual activity of the heat treatment was as follows: (mg/ml glucose produced for heat treated sample/mg/ml glucose produced for ambient treated sample)×100%. Improved variants were those having a higher % residual activity as compared to wild-type *A. fumigatus* GH61A polypeptide broth from MaltV1 medium in at least one heat treatment condition. MICROSOFT® EXCEL® (Microsoft Corporation, Redmond, WA, USA) was used for all calculations.

Example 6: Thermostability of *Aspergillus fumigatus* GH61B Variants Measured by Residual Activity after Heat Treatment Based on the residual activity ratios as described in Example 5, screening of libraries constructed in the previous Examples generated the results listed in Table 2.

Table 2 shows average % Residual Activity (from 3-5 samples of each variant and the wild-type control) after treatment at 62, 65, or 68° C. The parent *Aspergillus fumigatus* GH61B polypeptide showed decreased residual activity of 56%, 35%, and 12% when the temperature was increased from 62° C. to 65° C. to 68° C., respectively. The increase in thermostability of the *Aspergillus fumigatus* GH61B polypeptide variants ranged from 1.02- to 1.3-fold increase when treated at 62° C., 1.06- to 1.7-fold increase when treated at 65° C., and 1.3- to 3.8-fold increase when treated at 68° C. compared to the wild-type *A. fumigatus* GH61 polypeptide. The results showed that improvements were most significant when treated at 68° C.

TABLE 2

Variants with improved thermostability at 62, 65, or 68° C. treatment

| Variant | Avg % Res. Act. 62° C. treatment | Standard Deviation | Avg % Res. Act. 65° C. treatment | Standard Deviation | Avg % Res. Act. 68° C. treatment | Standard Deviation |
|---|---|---|---|---|---|---|
| Parent (Wild-Type) | 56% | 13% | 35% | 16% | 12% | 10% |
| S26I | 71% | 8% | 59% | 15% | 36% | 17% |
| G32E | 64% | 21% | 50% | 24% | 28% | 20% |
| G32S | 67% | 17% | 50% | 20% | 33% | 15% |
| Y34F | 50% | 6% | 38% | 9% | 25% | 21% |
| V40A | 46% | 10% | 35% | 7% | 22% | 7% |
| N41T | 59% | 21% | 56% | 22% | 41% | 30% |
| Q42E | 60% | 20% | 43% | 15% | 27% | 19% |
| Q42I | 48% | 7% | 50% | 16% | 41% | 33% |
| Q42V | 62% | 22% | 47% | 14% | 28% | 14% |
| S47R | 58% | 13% | 41% | 17% | 18% | 11% |
| S47E | 58% | 11% | 47% | 11% | 22% | 4% |
| S47L | 52% | 13% | 42% | 7% | 18% | 6% |
| S56T | 53% | 8% | 41% | 15% | 19% | 15% |
| S56E | 59% | 9% | 40% | 12% | 22% | 16% |
| S56C | 55% | 10% | 38% | 15% | 16% | 14% |
| S72Q | 57% | 6% | 45% | 8% | 31% | 21% |
| S72T | 60% | 13% | 45% | 7% | 25% | 12% |
| T102K | 60% | 2% | 44% | 10% | 26% | 7% |
| T102P | 55% | 7% | 42% | 9% | 33% | 18% |
| A123R | 52% | 7% | 39% | 9% | 17% | 15% |
| Q138C | 67% | 13% | 51% | 16% | 35% | 15% |
| Q138E | 63% | 15% | 58% | 10% | 46% | 11% |
| Q138K | 69% | 11% | 58% | 8% | 46% | 13% |
| Q138L | 69% | 11% | 56% | 16% | 39% | 17% |
| Q138M | 62% | 12% | 55% | 11% | 34% | 21% |
| Q138G | 53% | 11% | 47% | 13% | 29% | 21% |

TABLE 2-continued

Variants with improved thermostability at 62, 65, or 68° C. treatment

| Variant | Avg % Res. Act. 62° C. treatment | Standard Deviation | Avg % Res. Act. 65° C. treatment | Standard Deviation | Avg % Res. Act. 68° C. treatment | Standard Deviation |
|---|---|---|---|---|---|---|
| V149I | 53% | 2% | 43% | 4% | 28% | 11% |
| D152S | 64% | 7% | 59% | 8% | 39% | 17% |
| T163V | 60% | 13% | 50% | 5% | 24% | 3% |
| T163F | 61% | 15% | 47% | 8% | 20% | 5% |
| T163E | 59% | 13% | 43% | 8% | 21% | 4% |
| V164C | 58% | 12% | 48% | 7% | 24% | 3% |
| V164L | 56% | 9% | 40% | 5% | 16% | 1% |
| I166L | 59% | 16% | 45% | 11% | 17% | 3% |
| S169R | 45% | 9% | 48% | 14% | 38% | 29% |
| S186K | 47% | 8% | 41% | 9% | 38% | 22% |
| S186F | 46% | 11% | 38% | 11% | 28% | 15% |
| S186T | 46% | 23% | 35% | 25% | 31% | 29% |
| S186Y | 45% | 19% | 37% | 16% | 32% | 20% |
| F200I | 42% | 13% | 40% | 13% | 32% | 15% |
| F200V | 48% | 14% | 45% | 19% | 32% | 31% |
| G207P | 60% | 12% | 40% | 17% | 20% | 14% |
| S213E | 50% | 12% | 35% | 11% | 18% | 8% |
| S219C | 45% | 9% | 35% | 4% | 27% | 6% |
| S219E | 47% | 12% | 39% | 7% | 28% | 8% |
| S219M | 48% | 9% | 42% | 13% | 31% | 18% |
| S219Q | 49% | 12% | 41% | 30% | 31% | 31% |
| K222R | 61% | 14% | 50% | 24% | 35% | 35% |
| S234K | 52% | 22% | 36% | 21% | 17% | 26% |
| S234G | 68% | 13% | 45% | 18% | 27% | 27% |
| A246P | 56% | 7% | 43% | 11% | 26% | 15% |
| N249Q | 67% | 14% | 52% | 16% | 36% | 20% |
| N249R | 61% | 19% | 46% | 20% | 32% | 22% |

Example 7: Thermostability of *Aspergillus fumigatus* GH61B Polypeptide Combinatorial Variants Plasmid pLSBF09-3 was constructed as a template for subsequent *Aspergillus fumigatus* GH61B combinatorial variants. This plasmid was constructed by performing a single site-directed mutagenesis reaction on pMMar49 (Example 1) using a QUIKCHANGE® II XL Site-Directed Mutagenesis Kit (Stratagene, La Jolla, CA, USA). Two mutagenic primers were designed to insert the desired mutation. The PCR was composed of 125 ng of each primer, approximately 25 ng of template plasmid, 1× QUIKCHANGE® reaction buffer (Stratagene, La Jolla, CA, USA), 3 μl of QUIKSOLUTION® (Stratagene, La Jolla, CA, USA), 1 μl of XL dNTP mix, and 1 μl of 2.5 U/μl Pfu ULTRA™ enzyme (Stratagene, La Jolla, CA, USA) in a final volume of 50 μl. The amplification reaction was performed using an EPPENDORF® MASTERCYCLER® thermocycler programmed for a 95° C. hot start; 1 cycle at 95° C. for 1 minute; 18 cycles each at 95° C. for 50 seconds, 60° C. for 50 seconds, and 68° C. for 10 minutes; and a 4° C. hold. One microliter of Dpn I was directly added to the amplification reaction and incubated at 37° C. for 1 hour. A 2 μl volume of the Dpn I digested reaction was used to transform *E. coli* XL10-GOLD® Ultracompetent Cells according to the manufacturer's instructions. *E. coli* transformants were selected on 2XYT+Amp agar plates. One of the clones with the desired mutation was designated pLSBF09-3. Using pLSBF09-3 as a template, two additional combinatorial plasmids were constructed. Plasmids pDFng146 and pDFng148 were each mutagenized as described above. The primers used in these reactions are shown in Table 3.

TABLE 3

| Plasmid | Mutations | Parent Plasmid | Oligo ID # | Sequence |
|---|---|---|---|---|
| pLSBF09-3 | L111V, D152S, M155L, A162W, K229W | pMMar49 | 615628 | ACAAGAATACTGATCCTGGCATCT GGTTTGACATCTACTCGGATCTGA G (SEQ ID NO: 183) |
| | | | 615632 | CTCAGATCCGAGTAGATGTCAAAC CAGATGCCAGGATCAGTATTCTTG T (SEQ ID NO: 184) |
| pDFng146 | L111V, D152S, M155L, A162W, G188F, K229W | pLSBF09-3 | 1200378 | ATCATCGCCCTTCACTCTGCGTTT AACCTGAACGGCGCGCAGAAC (SEQ ID NO: 185) |
| | | | 1200379 | GTTCTGCGCGCCGTTCAGGTTAA ACGCAGAGTGAAGGGCGATGAT (SEQ ID NO: 186) |

TABLE 3-continued

| Plasmid | Mutations | Parent Plasmid | Oligo ID # | Sequence |
|---|---|---|---|---|
| pDFng148 | L111V, D152S, M155L, A162W, Q138K, K229W | pLSBF09-3 | 1200382 | GAAGTTTGTCAAGATCGCCGCTAA GGGCTTGATCGACGGCTCCAAC (SEQ ID NO: 187) |
|  |  |  | 1200383 | GTTGGAGCCGTCGATCAAGCCCT TAGCGGCGATCTTGACAAACTTC (SEQ ID NO: 188) |

Seven variants (pLSBF15, 17, 18, 20, 22, 53, and pDFNG145) of the *Aspergillus fumigatus* GH61B polypeptide were constructed by adding a single amino acid mutation on top of pLSBF09-3 or pDFng148 using a QUIKCHANGE® II XL Site-Directed Mutagenesis Kit). The site directed mutagenesis method described above was used in the construction of these mutants as well. Primers used in these reactions are shown in Table 4.

Four additional variants (pLSBF47, 48, 49, and 54) of *Aspergillus fumigatus* GH61B were constructed via multi-site-directed mutagenesis of pDFng146 or pDFng148 using a QUIKCHANGE® Lightning Multi Site-Directed Mutagenesis Kit (Stratagene, La Jolla, CA, USA). One mutagenic primer was designed for each desired mutation. One hundred ng of each primer (Table 4) were used in a PCR containing approximately 100 ng of template plasmid, 1× QUIKCHANGE® Lightning Multi Buffer (Stratagene, La Jolla, CA, USA), 0.5 µl of QUIKSOLUTION® (Stratagene, La Jolla, CA, USA), 1 µl of dNTP mix, and 1 µl of QUIKCHANGE® Lightning Multi enzyme blend (Stratagene, La Jolla, CA, USA) in a final volume of 25 µl. The amplification reaction was performed using an EPPENDORF® MASTERCYCLER® thermocycler programmed for a 95° C. hot start; 1 cycle at 95° C. for 2 minutes; 30 cycles each at 95° C. for 20 seconds, 55° C. for 30 seconds, and 65° C. for 5 minutes; 1 cycle at 65° C. for 5 minutes, and a 4° C. hold. One microliter of Dpn I was directly added to the amplification reaction and incubated at 37° C. for 5 minutes. A 1.5 µl volume of the Dpn I digested reaction was transformed into *E. coli* XL10-GOLD® Ultracompetent Cells according to the manufacturer's instructions. *E. coli* transformants were selected on 2XYT+Amp agar plates. Plasmid DNA from several of the resulting *E. coli* transformants was prepared using a BIOROBOT® 9600. The insert was confirmed by DNA sequencing using a Model 3130xL Genetic Analyzer and dye-terminator chemistry from a BigDye® Terminator v3.1 Cycle Sequencing Kit. One of the clones with the desired mutations was designated as each plasmid listed below. The *A. fumigatus* GH61A polypeptide variants were expressed using *Aspergillus oryzae* PFJO218 as host was performed according to the procedure described in Example 3.

TABLE 4

| Plasmid | Mutations | Parent Plasmid | Oligo ID # | Sequence |
|---|---|---|---|---|
| pLSBF15 | L111V, D152S, M155L, A162W, S47E, K229W | pLSBF09-3 | 1200265 | CTTGTTAACCAATACCCCTACATGGAA AACCCTCCCGACACCATTGCC (SEQ ID NO: 189) |
|  |  |  | 1200266 | GGCAATGGTGTCGGGAGGGTTTTCCA TGTAGGGGTATTGGTTAACAAG (SEQ ID NO: 190) |
| pLSBF17 | L111V, D152S, M155L, A162W, S56A, K229W | pLSBF09-3 | 1200269 | CTCCCGACACCATTGCCTGGGCCACC ACCGCCACCGACCTCG (SEQ ID NO: 191) |
|  |  |  | 1200270 | CGAGGTCGGTGGCGGTGGTGGCCCA GGCAATGGTGTCGGGAG (SEQ ID NO: 192) |
| pLSBF18 | L111V, D152S, M155L, A162W, T102K, K229W | pLSBF09-3 | 1200271 | ACAGATCGAATTCCAGTGGACGAAGT GGCCAGAGTCTCACCATGGA (SEQ ID NO: 193) |
|  |  |  | 1200272 | ACAGATCGAATTCCAGTGGACGAAGT GGCCAGAGTCTCACCATGGA (SEQ ID NO: 194) |
| pLSBF20 | L111V, D152S, M155L, A162W, T102K, E105K, K229W | pLSBF09-3 | 1200275 | CCAGTGGACGAAGTGGCCAAAGTCTC ACCATGGACCG (SEQ ID NO: 195) |
|  |  |  | 1200276 | CGGTCCATGGTGAGACTTTGGCCACT TCGTCCACTGG (SEQ ID NO: 196) |
| pLSBF22 | L111V, D152S, M155L, A162W, K229W, S234G | pLSBF09-3 | 1200279 | CTGGCATCTGGTTTGACATCTACGGC GATCTGAGCGGTGGATACCCT (SEQ ID NO: 197) |
|  |  |  | 1200280 | AGGGTATCCACCGCTCAGATCGCCGT AGATGTCAAACCAGATGCCAG (SEQ ID NO: 198) |

TABLE 4-continued

| Plasmid | Mutations | Parent Plasmid | Oligo ID # | Sequence |
|---|---|---|---|---|
| pLSBF53 | L111V, D152S, M155L, A162W, Q138K, G188F, K229W | pDFng148 | 1200378 | ATCATCGCCCTTCACTCTGCGTTTAAC CTGAACGGCGCGCAGAAC (SEQ ID NO: 199) |
| | | | 1200379 | GTTCTGCGCGCCGTTCAGGTTAAACG CAGAGTGAAGGGCGATGAT (SEQ ID NO: 200) |
| pDFng145 | L111V, D152S, M155L, A162W, S186T, K229W | pLSBF09-3 | 1200376 | CACGAGATCATCGCCCTTCACACCGC GGGTAACCTGAACGGCGC (SEQ ID NO: 201) |
| | | | 1200377 | GCGCCGTTCAGGTTACCCGCGGTGTG AAGGGCGATGATCTCGTG (SEQ ID NO: 202) |
| pLSBF47 | L111V, D152S, M155L, A162W Q138K, V149I, G188F, K229W | pDFng148 | 1200378 | ATCATCGCCCTTCACTCTGCGTTTAAC CTGAACGGCGCGCAGAAC (SEQ ID NO: 203) |
| | | | 1201840 | CGGCTCCAACCCACCTGGTATCTGGG CTTCCGATGAACTGATCG (SEQ ID NO: 204) |
| pLSBF48 | L111V, D152S, M155L, A162W, S72T, Q138K, V149I, G188F, K229W | pDFng148 | 1200378 | ATCATCGCCCTTCACTCTGCGTTTAAC CTGAACGGCGCGCAGAAC (SEQ ID NO: 205) |
| | | | 1201840 | CGGCTCCAACCCACCTGGTATCTGGG CTTCCGATGAACTGATCG (SEQ ID NO: 206) |
| | | | 1201841 | CGGCACCGGCTACCAGACCCCGGATA TTATCTGCCACAGAGACGC (SEQ ID NO: 207) |
| pLSBF49 | L111V, D152S, M155L, A162W, Q138K, V149I, G188F, G207P, K229W | pDFng148 | 1200378 | ATCATCGCCCTTCACTCTGCGTTTAAC CTGAACGGCGCGCAGAAC (SEQ ID NO: 208) |
| | | | 1201840 | CGGCTCCAACCCACCTGGTATCTGGG CTTCCGATGAACTGATCG (SEQ ID NO: 209) |
| | | | 1201842 | CCAGTGTTTCAACATCCAAATCACCGG TCCTGGCAGTGCTCAGGG (SEQ ID NO: 210) |
| pLSBF54 | L111V, D152S, M155L, A162W S169C, G188F, K229W, A250C | pDFng146 | 1201386 | CCATTCCTGCCTGCTATGCCCCCGGA AACTACGTCC (SEQ ID NO: 211) |
| | | | 1201390 | CCTGGTCCTGCACTGTTCAACTGCTAA GCGGCC (SEQ ID NO: 212) |

Based on the residual activity ratios determined according to Example 5, screening of libraries constructed in the previous Examples generated the results listed in Table 5. Table 5 shows an average % Residual Activity (2-199 samples for each of the combinatorial variants and 34-179 samples for the wild-type GH61 polypeptide after treatment at any of 65° C., 68° C., 72° C., or 75° C.

The parent wild-type *A. fumigatus* GH61 polypeptide showed decreased residual activity of 40%, 24%, 0% and 0% when the temperature of treatment was increased from 65° C. to 68° C. to 72° C. to 75° C., respectively. The thermostability of the *Aspergillus fumigatus* GH61B polypeptide combinatorial variants ranged from 0.8-fold (decrease) to 1.4-fold increase at 65° C., no increase to 2-fold increase at 68° C. compared to the wild-type *A. fumigatus* GH61 polypeptide. Since wild-type GH61 polypeptide has no residual activity at 72° C., the other variant (L111V, D152S, M155L, A162W) was used for comparison at 72° C. and 75° C. In these cases, the variants ranged from no increase to 4.4-fold increase at 72° C., and 4-fold to 33-fold increase at 75° C. The results showed that improvements were most significant at the 75° C. treatment for those measured at 75° C., otherwise they were most significant at 72° C. where the wild-type had no measurable residual activity.

TABLE 5

*Aspergillus fumigatus* GH61B polypeptide variants with improved thermostability at 65° C., 68° C., 72° C. or 75° C. treatment

| Mutations | Avg % Res. Act. 65° C. | Standard Deviation | Avg % Res. Act. 68° C. | Standard Deviation | Avg % Res. Act. 72° C. | Standard Deviation | Avg % Res. Act. 75° C. | Standard Deviation |
|---|---|---|---|---|---|---|---|---|
| L111V, D152S, M155L, A162W | 55% | 16% | 49% | 21% | 10% | 7% | 1% | 7% |
| L111V, D152S, M155L, A162W, Q138K, G188F, K229W | 51% | 7% | NA | NA | 44% | 1% | 30% | 5% |
| L111V, D152S, M155L, A162W, Q138K, V149I, G188F, G207P, K229W | 47% | 9% | NA | NA | 42% | 9% | 32% | 12% |
| L111V, D152S, M155L, A162W, S72T, Q138K, V149I, G188F, K229W | 50% | 4% | NA | NA | 41% | 6% | 31% | 8% |
| L111V, D152S, M155L, A162W, S169C, G188F, K229W, A250C | 39% | 12% | NA | NA | 37% | 14% | 33% | 12% |
| L111V, D152S, M155L, A162W, Q138K, V149I, G188F, K229W | 49% | 6% | NA | NA | 36% | 19% | 28% | 14% |
| L111V, D152S, M155L, A162W, Q138K, K229W | 49% | 12% | 35% | 11% | 26% | 8% | 4% | 5% |
| L111V, D152S, M155L, A162W, K229W, S234G | 34% | 15% | 32% | 9% | 20% | 4% | NA | NA |
| L111V, D152S, M155L, A162W, T102K, E105K, K229W | 37% | 24% | 33% | 21% | 19% | 10% | NA | NA |
| L111V, D152S, M155L, A162W, S186T, K229W | 33% | 14% | 32% | 11% | 18% | 3% | NA | NA |
| L111V, D152S, M155L, A162W, T102K, K229W | 36% | 16% | 33% | 16% | 18% | 11% | NA | NA |
| L111V, D152S, M155L, A162W, S47E, K229W | 32% | 21% | 27% | 24% | 11% | 13% | NA | NA |
| L111V, D152S, M155L, A162W, S56A, K229W | 34% | 28% | 25% | 18% | 11% | 3% | NA | NA |
| Wild-Type | 40% | 18% | 24% | 21% | 0% | 0% | 0% | 0% |

Example 8: Purification of Aspergillus fumigatus GH61B and Penicillium emersonii GH61 Polypeptide Variants Expression and purification of the wild-type Aspergillus fumigatus GH61B and Penicillium emersonii GH61 polypeptides was conducted as previously described in WO 2012/044835.

Strains expressing Aspergillus fumigatus GH61B and Penicillium emersonii GH61 polypeptide variants, generated as described in Examples 7 and 11, were cultured in shake flasks to generate material as described below for purification Following isolation of single colonies, the Aspergillus oryzae PFJO218 transformants were cultured for 4 days at 34° C. on COVE-N-Gly plates in preparation for larger scale fermentation. Spores were recovered from each plate using 0.01% TWEEN® 20. Each spore suspension (500 µl) was inoculated into 25 ml of M400 medium in 125 ml plastic shake flasks. The transformants were fermented for 3 days at 39° C. with agitation at 150 rpm and the broths were collected and filtered using 0.22 µm filters. The filtered culture broths were then concentrated by centrifugal ultrafiltration using VIVACELL® 100 5 kDa MWCO centrifugal concentration devices (Sartorius Stedim, Goettingen, Germany) and then buffer exchanged into 20 mM Tris-HCl pH 8.0.

The concentrated and buffer exchanged Aspergillus fumigatus GH61B and Penicillium emersonii GH61 polypeptide variants were further purified by one of two chromatographic methods. In one method, the concentrated and buffer exchanged broths were then each applied to a MONO Q® HR 16/10 column (GE Healthcare, Piscataway, NJ, USA) equilibrated with 20 mM Tris-HCl pH 8.0. Bound proteins were eluted with a linear gradient of 0-500 mM sodium chloride in 20 mM Tris-HCl pH 8.0. Fractions were analyzed by SDS-PAGE using a CRITERION® Stain-Free Tris-HCl 8-16% SDS-PAGE gel (Bio-Rad Laboratories, Inc., Hercules, CA, USA), pooled based on the abundance of an approximately 25 kDa band, and concentrated using VIVASPIN® kDa MWCO centrifugal concentration devices (GE Healthcare, Buckinghamshire, United Kingdom). Alternatively, the concentrated and desalted broths were then each applied to a HI LOAD® 26/60 SUPERDEX® 75 (GE Healthcare, Piscataway, NJ, USA) size exclusion column equilibrated with 20 mM Tris-HCl pH 8.0 and 150 mM NaCl. Applied proteins were eluted isocratically using 20 mM Tris-HCl pH 8.0 and 150 mM NaCl as the mobile phase. Fractions were analyzed by SDS-PAGE using a CRITERION® Stain-Free Tris-HCl 8-16% SDS-PAGE gel, pooled based on the abundance of an approximately 25 kDa band, and concentrated using VIVASPIN® 5 kDa MWCO centrifugal concentration devices and then buffer exchanged into 20 mM MES pH 6.0.

Protein concentrations were determined using a Microplate BCA™ Protein Assay Kit in which bovine serum albumin was used as a protein standard.

Example 9: Determination of Tm (Melting Temperature) of the Aspergillus fumigatus Wild-Type GH61B Polypeptide and Aspergillus fumigatus GH61B Polypeptide Variants by Differential Scanning Calorimetry The thermostabilities of the A. fumigatus wild-type GH61B polypeptide and the Aspergillus fumigatus GH61B polypeptide variants, which were purified as described in Example 8, were determined by Differential Scanning calorimetry (DSC) using a VP Differential Scanning calorimeter (MicroCal Inc., GE Healthcare, Piscataway, NJ, USA). The melting temperature, Tm (° C.), was taken as the top of denaturation peak (major endothermic peak) in thermograms (Cp vs. T) obtained after heating a 1 mg protein per ml solution of the enzyme in 50 mM sodium acetate pH 5.0, 100 µM $CuSO_4$, or a 1 mg protein per ml solution of the enzyme in 50 mM sodium acetate pH 5.0, 10 mM EDTA pH 5.0, at a constant programmed heating rate. One ml of sample and reference-solutions were degassed at 25° C. using a ThermoVac (MicroCal Inc., GE Healthcare, Piscataway, NJ, USA) prior to loading of sample and reference cells of the calorimeter. Sample and reference (reference: degassed water) solutions were manually loaded into the DSC and thermally pre-equilibrated to 25° C. before the DSC scan was performed from 25° C. to 95° C. at a scan rate of 90 K/hour. Denaturation temperatures were determined at an accuracy of approximately +/−1° C. The results of the thermostability determinations of the A. fumigatus GH61B polypeptide variants are shown in Table 6.

TABLE 6

Melting temperatures (° C.) of the A. fumigatus GH61B polypeptide and variants of the A. fumigatus GH61B polypeptide, as determined by differential scanning calorimetry

| Mutations | Tm + 100 µm $CuSO_4$ | Tm + 10 mM EDTA pH 5 |
| --- | --- | --- |
| WT | 69 | 59 |
| S186K | 77 | n.d. |
| S234K | 73 | n.d. |
| L111V, D152S, M155L, A162W, Q138K, K229W | n.d. | 69 |

Example 10: Determination of Tm (Melting Temperature) of the Aspergillus fumigatus Wild-Type GH61B Polypeptide and Aspergillus fumigatus GH61B Polypeptide Variants by Protein Thermal Unfolding Analysis Protein thermal unfolding of the Aspergillus fumigatus GH61B polypeptide variants was monitored using SYPRO® Orange Protein Stain (Invitrogen, Naerum, Denmark) using a StepOnePlus™ Real-Time PCR System (Applied Biosystems Inc., Foster City, CA, USA). In a 96-well white PCR-plate, 15 µl of a protein sample (prepared as described in Example 8) in 100 mM sodium acetate pH 5.0 was mixed (1:1) with Sypro Orange (resulting concentration=10×; stock solution=5000× in DMSO) in 20 mM EDTA. The plate was sealed with an optical PCR seal. The PCR instrument was set at a scan-rate of 76° C. per hour, starting at 25° C. and finishing at 96° C. Fluorescence was monitored every 20 seconds using a built-in LED blue light for excitation and ROX-filter (610 nm, emission). Tm-values were calculated as the maximum value of the first derivative (dF/dK) (Gregory et al., 2009, J. Biomol. Screen. 14: 700). The results of the thermostability determinations are shown in Table 7.

TABLE 7

Melting temperatures (° C.) of the
A. fumigatus GH61B polypeptide
and variants determined
by thermal unfolding analysis

| Mutations | Tm |
|---|---|
| Wild-Type | 59 |
| Q138E | 61 |
| Q138L | 62 |
| D152S | 65 | and dye-terminator chemistry from a BigDye® Terminator v3.1 Cycle Sequencing Kit. One of the clones with the desired 2 mutations was designated as pLSBF10. The primers used in this reaction can be found below in Table 8.

A summary of the primers used for the site-directed mutagenesis and the variant (S173C, F253C) obtained are shown in Table 8.

The resulting mutant plasmid DNA was prepared using a BIOROBOT® 9600. Each mutant plasmid was sequenced using a 3130xl Genetic Analyzer to verify the substitutions. The sequencing primers 996271 and pALLO2 3' were used for verification.

TABLE 8

| Plasmid | Mutation(s) | Parent Plasmid | Oligo ID # | Sequence |
|---|---|---|---|---|
| pLSBF10 | S173C, F253C | pMMar45 | 615942 | TGGACCGTCACCATTCCCAA CTGCGTCGCCCCCGGCAAC TACG (SEQ ID NO: 213) |
| | | | 615943 | CGTAGTTGCCGGGGGCGAC GCAGTTGGGAATGGTGACG GTCCA (SEQ ID NO: 214) |
| | | | 615944 | CCGGGGCCGCCTGAGCCGA CGTGCTAGGCGGCCGCGGA GGCCACC (SEQ ID NO: 215) |
| | | | 615945 | GGTGGCCTCCGCGGCCGCC TAGCACGTCGGCTCAGGCG GCCCCGG (SEQ ID NO: 216) |

Example 11: Construction of *Penicillium emersonii* GH61A Polypeptide Variants

Variant plasmid pLSBF10 was constructed through two sequential single site-directed mutagenesis reactions on pMMar45 (Example 1) using a QUIKCHANGE® 11 XL Site-Directed Mutagenesis Kit. Two mutagenic primers were designed to insert each desired mutation. A total of 125 ng of each primer was used in a PCR containing approximately 25 ng of template plasmid, 1× QUIKCHANGE® reaction buffer, 3 µl of QUIKSOLUTION®, 1 µl of XL dNTP mix (provided in the QUIKCHANGE® 11 XL Site-Directed Mutagenesis Kit), and 1 µl of 2.5 U/µl Pfu Ultra enzyme in a final volume of 50 µl. The PCR was performed using an EPPENDORF® MASTERCYCLER® thermocycler programmed for a 95° C. hot start; 1 cycle at 95° C. for 1 minute; 18 cycles each at 95° C. for 50 seconds, 60° C. for 50 seconds, and 68° C. for 10 minutes; and a 4° C. hold. One microliter of Dpn I was directly added to the amplification reaction and incubated at 37° C. for 1 hour. A 2 µl volume of the Dpn I digested reaction was used to transform *E. coli* XL10-GOLD® Ultracompetent Cells according to the manufacturer's instructions. *E. coli* transformants were selected on 2XYT+Amp agar plates. Plasmid DNA from several of the resulting *E. coli* transformants was prepared using a BIOROBOT® 9600. The insert was confirmed by DNA sequencing using a Model 3130xL Genetic Analyzer The *P. emersonii* GH61A polypeptide variants were expressed using *Aspergillus oryzae* PFJO218 as host was performed according to the procedure described in Example 3.

Example 12: Thermostability of the *P. emersonii* Wild-Type GH61A Polypeptide and *P. emersonii* GH61A Polypeptide Variant Based on the residual activity ratios determined according to Example 5, screening of libraries constructed in the previous Examples generated the results listed in Table 9. Table 9 shows an average % Residual Activity (from 2-14 samples each for the combinatorial variants and 14 samples of wild-type after treatment at any of 65° C., 68° C., 72° C. or, 75° C.

The parent wild-type *P. emersonii* GH61A polypeptide showed decreased residual activity of 45%, 18% and 1% when the temperature of treatment was increased from 65° C. to 72° C. to 75° C., respectively (68° C. was not tested). The thermostability of the *P. emersonii* GH61A polypeptide combinatorial variant (S173C, F253C) ranged from 0.8-fold (decrease) to 2.2-fold increase at 72° C., and 30-fold compared to the wild-type *P. emersonii* GH61A polypeptide at 75° C.

TABLE 9

Penicillium emersonii GH61A polypeptide variants with improved thermostability at 65° C., 68° C., 72° C. or 75° C. treatment

| Mutations | Avg % Res. Act. 65° C. | Standard Deviation | Avg % Res. Act. 68° C. | Standard Deviation | Avg % Res. Act. 72° C. | Standard Deviation | Avg % Res. Act. 75° C. | Standard Deviation |
|---|---|---|---|---|---|---|---|---|
| Wild-Type | 45% | 7% | NA | NA | 18% | 7% | 1% | 5% |
| S173C, F253C | 38% | 6% | 49% | 8% | 40% | 19% | 30% | 6% |

Example 13: Determination of Tm (Melting Temperature) of the P. emersonii Wild-Type GH61A Polypeptide and P. emersonii GH61A Polypeptide Variant by Differential Scanning Calorimetry The thermostabilities of the P. emersonii wild-type GH61A polypeptide and the P. emersonii GH61A polypeptide variant (S173C, F253C), purified as described in Example 8, were determined by Differential Scanning calorimetry (DSC) using a VP Differential Scanning calorimeter as described in Example 9. The results of the thermostability determination of the P. emersonii GH61A polypeptide variant are shown in Table 10.

TABLE 10

Melting temperatures (° C.) of the P. emersonii wild-type GH61A polypeptide and P. emersonii GH61A polypeptide and variant of P. emersonii GH61A polypeptide, as determined by differential scanning calorimetry

| Enzyme Sample | Tm + 100 um CuSO4 pH 5 | Tm + 10 mM EDTA pH 5 |
|---|---|---|
| Wild-Type | 82 | 74 |
| S173C, F253C | 87 | 77 |

Example 14: Determination of Tm (Melting Temperature) of the P. emersonii Wild-Type GH61A Polypeptide and P. emersonii GH61A Polypeptide Variant by Protein Thermal Unfolding Analysis Protein thermal unfolding of the Penicillium emersonii GH61A polypeptide variant (S173C, F253C) was monitored using SYPRO® Orange Protein Stain and was performed using a StepOnePlus™ Real-Time PCR System as described as Example 10. The culture broths of P. emersonii GH61A wild-type polypeptide and P. emersonii GH61A polypeptide variant were prepared as described in Example 11. The results of the thermostability determination are shown in Table 11.

TABLE 11

Melting temperature (° C.) of Penicillium emersonii GH61A polypeptide variants by protein thermal unfolding analysis

| Mutations | Tm |
|---|---|
| Wild-Type | 64 |
| S173C, F253C | 69 |

Example 15: Construction of Expression Vectors pDFng153-4, pDFng154-17, pDFng155-33, pDFng156-37, and pDFng157-51

Figure 6:
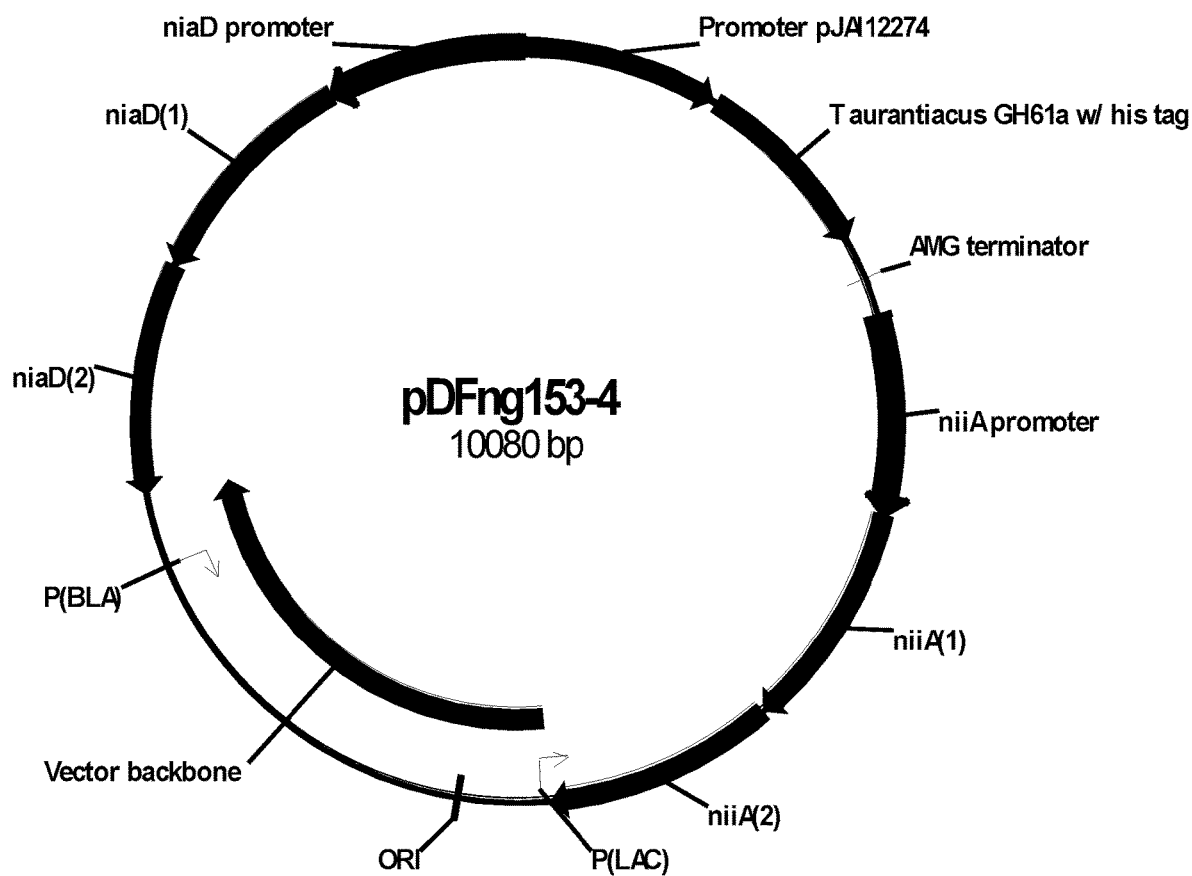
FIG. 6 shows a restriction map of pDFng153-4.
Figure 7:
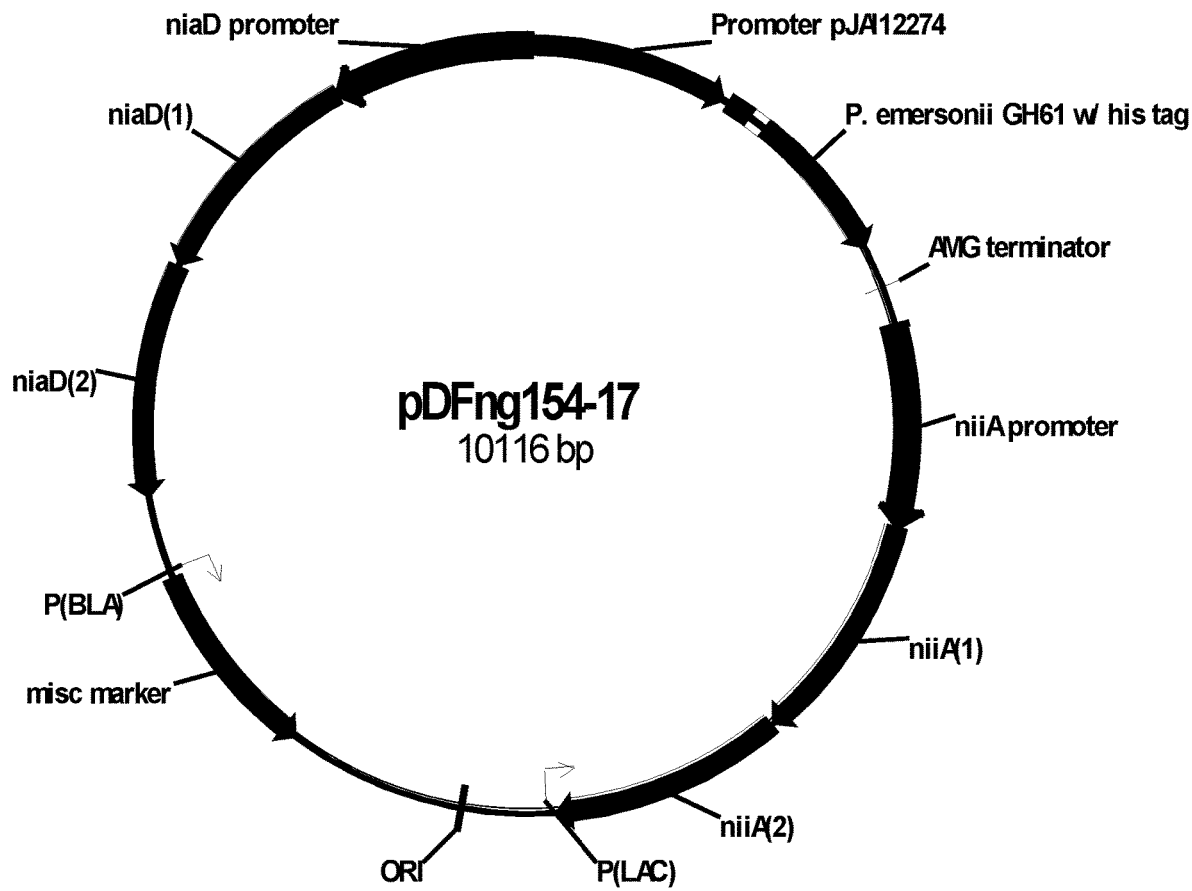
FIG. 7 shows a restriction map of pDFng154-17.
Figure 8:
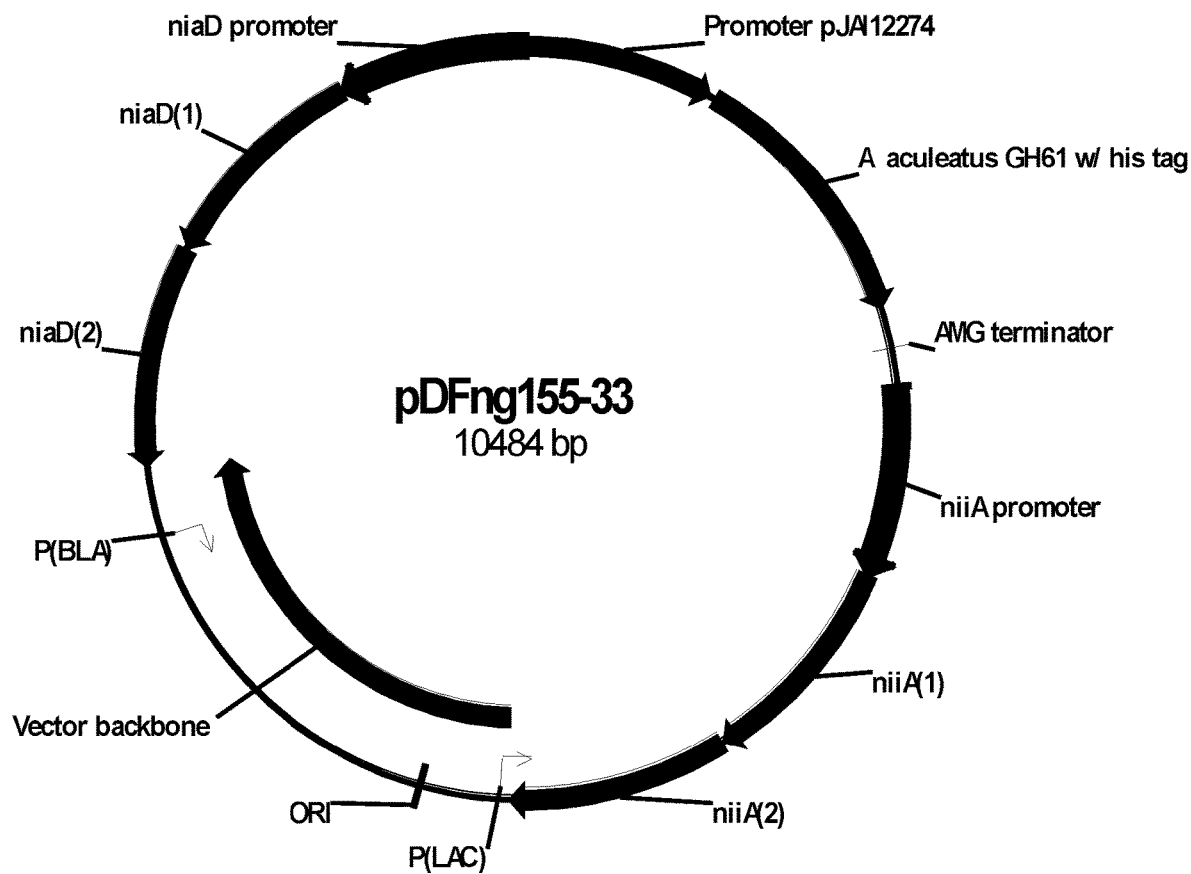
FIG. 8 shows a restriction map of pDFng155-33.
Figure 9:
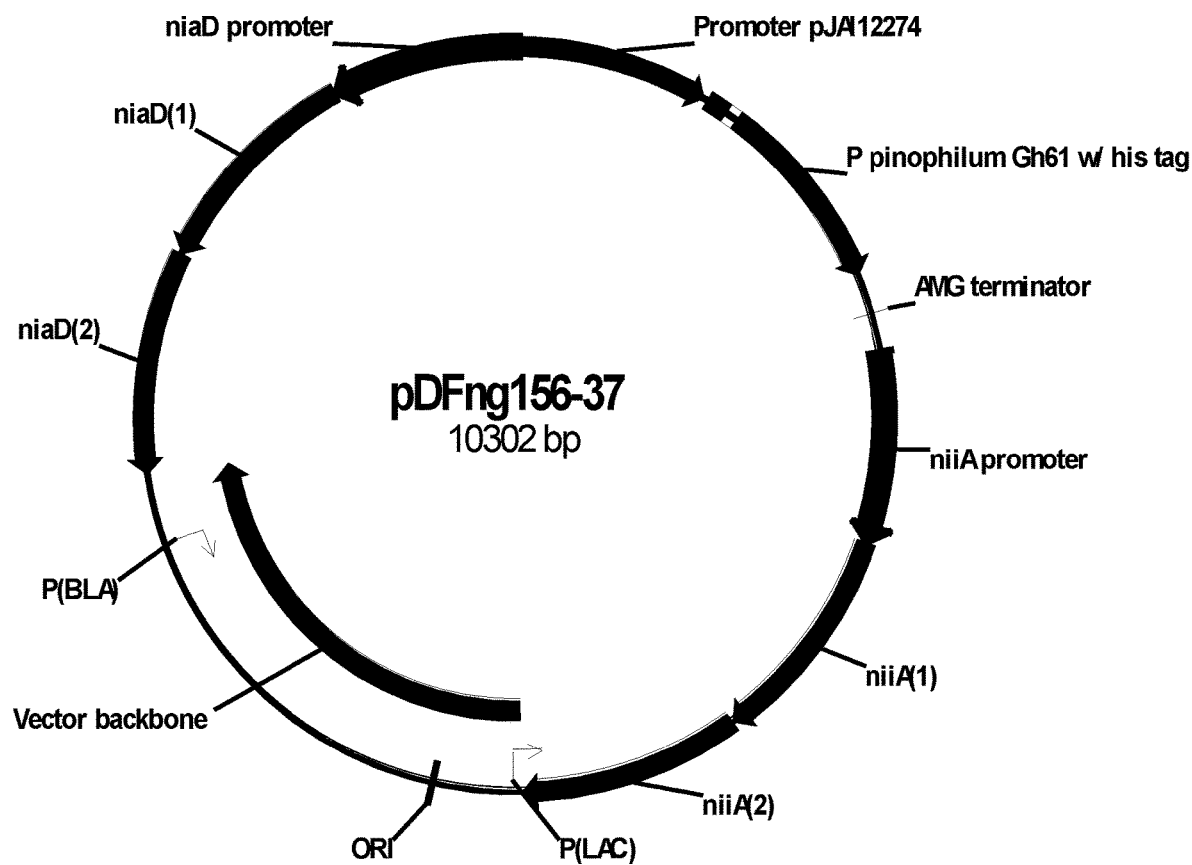
FIG. 9 shows a restriction map of pDFng156-37.
Figure 10:
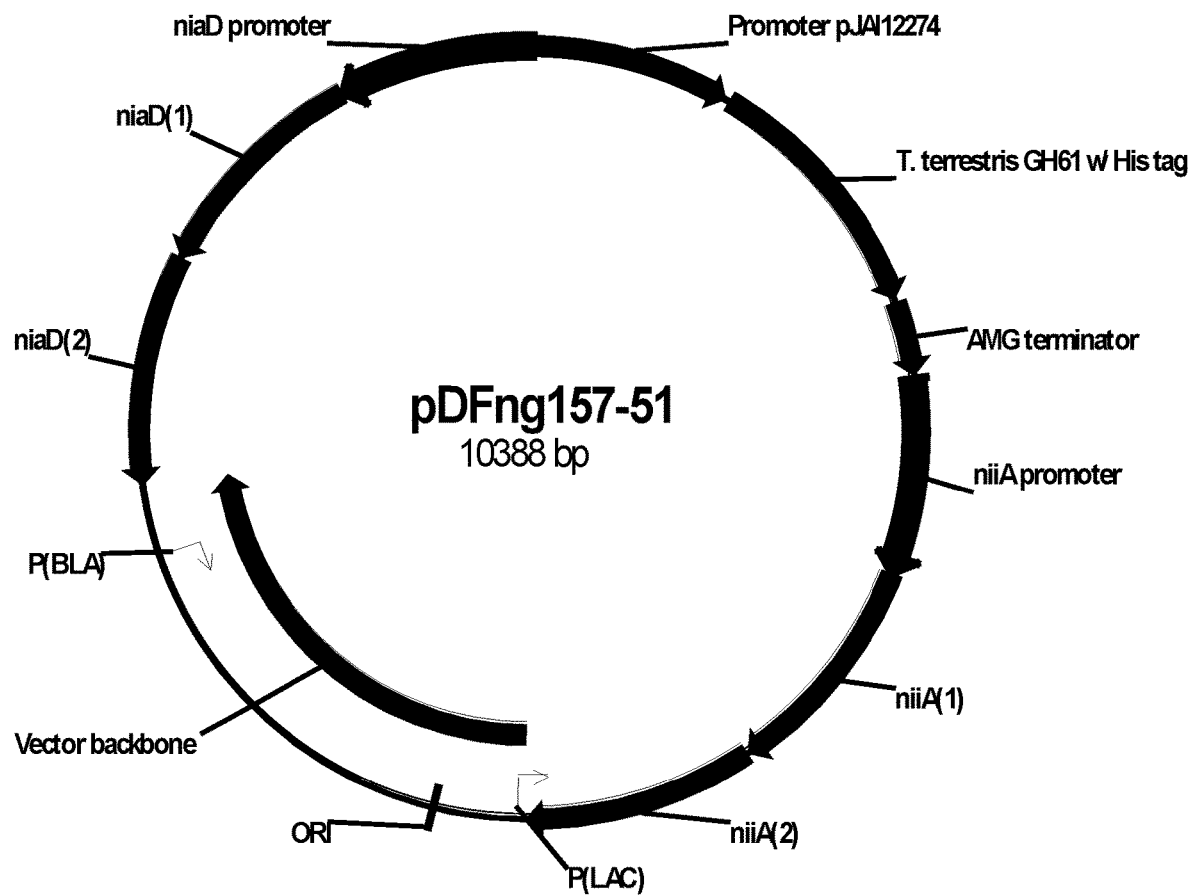
FIG. 10 shows a restriction map of pDFng157-51.
Figure 11:
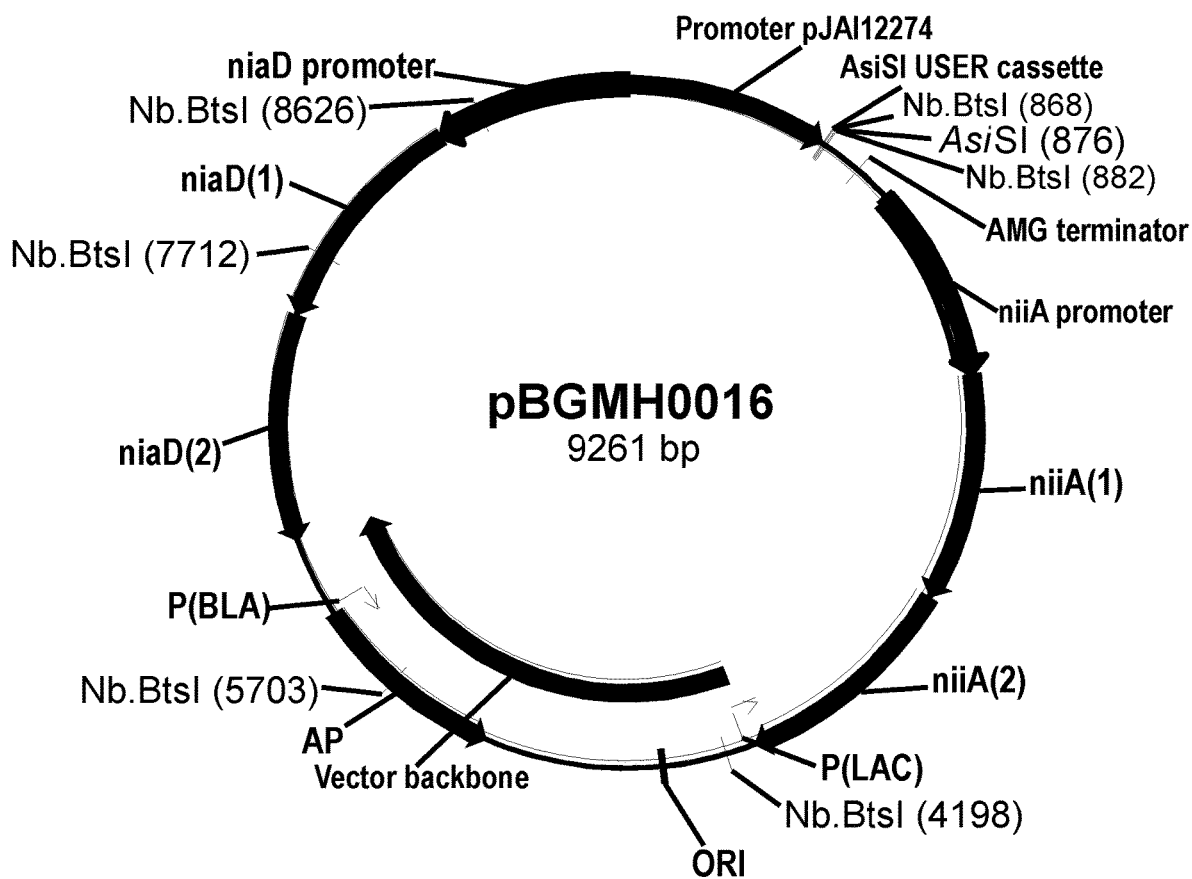
FIG. 11 shows a restriction map of pBGMH16.

Plasmids pDFng153-4 (FIG. 6), pDFng154-17 (FIG. 7), pDFng155-33 (FIG. 8), and pDFng156-37 (FIG. 9), and pDFng157-51 (FIG. 10) were constructed as described below for expression of the Thermoascus aurantiacus GH61A polypeptide, Penicillium emersonii GH61A polypeptide, Aspergillus aculeatus GH61 polypeptide, Penicillium pinophilum GH61 polypeptide, and Thielavia terrestris GH61 polypeptide, respectively, and generation of the variants listed in Table 12. The plasmids were constructed using plasmid pBGMH16 (FIG. 11).

Plasmid pBGMH16 was constructed according to the protocol described below. A Nb.BtsI recognition site in pUC19 was removed by PCR using the primer pair BGMH24 and BGMH25 shown below followed by the uracil-specific excision reagent USER™ based cloning (New England BioLabs, Ipswich, MA, USA). Plasmid pUC19 is described in Yanisch-Perron et al., 1985, Gene 33(1): 103-19.

```
Primer BGM H24:
                                (SEQ ID NO: 217)
ATGCAGCGCUGCCATAACCATGAGTGA Primer BGMH25:
                                (SEQ ID NO: 218)
AGCGCTGCAUAATTCTCTTACTGTCATG
```

Underlined sequence is used in the USER™ assisted fusion of the PCR fragment creating pBGMH13. USER™ (Uracil-Specific Excision Reagent) Enzyme (New England Biolabs, Ipswich, MA, USA) generates a single nucleotide gap at the location of a uracil. USER™ Enzyme is a mixture of Uracil DNA glycosylase (UDG) and the DNA glycosylase-lyase endonuclease VIII. UDG catalyzes the excision of a uracil base, forming an abasic (apyrimidinic) site while leaving the phosphodiester backbone intact. The lyase activity of endonuclease VIII cleaves the phosphodiester backbone at the 3' and 5' sides of the basic site so that base-free deoxyribose is released.

The amplification reaction was composed of 100 ng of each primer, 10 ng of pUC19, 1× PfuTurbo® C$_x$ Reaction Buffer (Stratagene, La Jolla, CA, USA), 2.5 µl of a blend of dATP, dTTP, dGTP, and dCTP, each at 10 mM, and 2.5 units of PfuTurbo® C$_x$ Hot Start DNA Polymerase (Stratagene, La Jolla, CA, USA) in a final volume of 50 µl. The reaction was performed using a EPPENDORF® MASTERCYCLER® 5333 programmed for 1 cycle at 95° C. for 2 minutes; 32 cycles each at 95° C. for 30 seconds, 55° C. for 30 seconds, and 72° C. for 3 minutes; and a final elongation at 72° C. for 7 minutes. Five µl of 10× NEBuffer 4 (New England Biolabs, Inc., Ipswich, MA, USA) and 20 units of Dpn I were added and incubated at 37° C. for 1 hour. The Dpn I was inactivated at 80° C. for 20 minutes. A total of 100 ng of the PCR product and 1 unit of USER™ enzyme in a total volume of 10 µl were incubated 20 minutes at 37° C. followed by 20 minutes at 25° C. Ten µl were transformed into ONE SHOT® TOP10 competent cells. E. coli transformants were selected on LB+Amp agar plates and plasmid DNA was prepared using QIAPREP® Spin Miniprep Kit (QIAGEN Inc., Valencia, CA, USA). The resulting plasmid pBGMH13 was confirmed by sequencing using an Applied Biosystems Model 3730XL Automated DNA Sequencer using version 3.1 BIG-DYE™ terminator chemistry (Applied Biosystems, Inc., Foster City, CA, USA).

Plasmid pBGMH14 contains part of pBGMH13 as vector backbone and a Pac I/Nt.BbvCI USER™ cassette (Hansen et al., 2011, Appl. Environ. Microbiol. 77(9): 3044-51) which is flanked by part of the A. oryzae niaD gene on one side and part of the A. oryzae niiA gene on the other side. The Pac I/Nt.BbvCI USER™ cassette can be linearized with Pac I and Nt.BbvCI and a PCR product with compatible overhangs can be cloned into this site (New England Biolabs, Ipswich, MA, USA).

An Aspergillus oryzae niiA fragment was generated using primers BGMH27 and BGMH29 shown below. The primer pair BGMH28 and BGMH32 shown below was used to amplify the Aspergillus oryzae niaD gene region and primer pair BGMH30 and BGMH31 shown below was used to amplify the plasmid backbone region.

```
Primer BGMH 27:
                                   (SEQ ID NO: 219)
AATTAAGUCCTCAGCGTGATTTAAAACGCCATTGCT Primer BGMH 28:
                                   (SEQ ID NO: 220)
ACTTAATUAAACCCTCAGCGCAGTTAGGTTGGTGTTCTTCT Primer BGMH 29:
                                   (SEQ ID NO: 221)
AGCTCAAGGAUACCTACAGTTATTCGAAA Primer BGMH 30:
                                   (SEQ ID NO: 222)
ATCCTTGAGCUGTTTCCTGTGTGAAATTGTTATCC Primer BGMH 31:
                                   (SEQ ID NO: 223)
ATCTCCTCUGCTGGTCTGGTTAAGCCAGCCCCGACAC Primer BGMH 32:
                                   (SEQ ID NO: 224)
AGAGGAGAUAATACTCTGCGCTCCGCC
```

Underlined sequence was used in the USER™ assisted fusion of the three fragments. The sequence marked in bold was used to introduce a PacI/Nt.BbvCI USER™ cassette (Hansen et al., 2011, supra) between the niiA and niaD fragments.

Genomic DNA from A. oryzae BECH2 (WO 00/39322) was purified using a FASTDNA™ 2 ml SPIN Kit for Soil (MP Biomedicals, Santa Ana, California, USA).

Each PCR was composed of 100 ng of each primer, template DNA (pBGMH13 or A. oryzae BECH2 genomic DNA), 1× PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase in a final volume of 50 µl. The PCRs were performed using a EPPENDORF® MASTERCYCLER® 5333 programmed for 1 cycle at 95° C. for 2 minutes; 32 cycles each at 95° C. for 30 seconds, 55° C. for 30 seconds, and 72° C. for 4 minutes; and a final elongation at 72° C. for 10 minutes. Where template DNA was a plasmid, 5 µl of 10× NEBuffer 4 and 20 units of Dpn I were added and incubated at 37° C. for 1 hour. The Dpn I was inactivated at 80° C. for 20 minutes. Fifty ng of each of the PCR products and 1 unit of USER™ enzyme in a total volume of 10 µl were incubated for 20 minutes at 37° C. followed by 20 minutes at 25° C. Then 10 µl were transformed into ONE SHOT® TOP10 competent cells. The three fragments were fused by uracil-specific excision reagent based cloning (Nour-Eldin et al., 2010, Methods Mol. Biol. 643: 185-200). E. coli transformants were selected on LB+Amp agar plates and plasmid DNA was prepared using QIAPREP® Spin Miniprep Kit. Plasmid pBGMH14 was confirmed by sequencing using an Applied Biosystems Model 3730XL Automated DNA Sequencer using version 3.1 BIG-DYE™ terminator chemistry. Promoter P13amy is a derivative of the NA2-tpi promoter from pJaL676 (WO 2003/008575). The A. niger AMG terminator used is described by Christensen et al., 1988, Nature Biotechnology 6: 141-1422. The P13amy promoter and AMG terminator were cloned into the Pac I/Nt.BbvCI USER™ cassette in pBGMH14. The primers shown below were designed so that an Asi SI/Nb.BtsI USER™ cassette (Hansen et al., 2011, supra) was introduced between the promoter and terminator.

```
Primer BGMH 49:
                                   (SEQ ID NO: 225)
GGGTTTAAUCCTCACACAGGAAACAGCTATGA Primer BGMH 50:
                                   (SEQ ID NO: 226)
AGTGTCTGCGAUCGCTCTCACTGCCCCCAGTTGTGTATATAGAGGA Primer BGMH 51:
                                   (SEQ ID NO: 227)
ATCGCAGACACUGCTGGCGGTAGACAATCAATCCAT Primer BGMH 52:
                                   (SEQ ID NO: 228)
GGACTTAAUGGATCTAAGATGAGCTCATGGCT
```

Underlined sequence was used in the USER™ assisted fusion of the two fragments into a Pac I/Nt.BbvCI digested pBGMH14. The sequence marked in bold was used to introduce a AsiSI/Nb.BtsI USER™ cassette (Hansen et al., 2011, supra) between the promoter and terminator.

The primer pair BGMH49 and BGMH50 was used to amplify promoter P13amy and the primer pair BGMH51 and BGMH52 was used to amplify the AMG terminator. The PCR was composed of 100 ng of each primer, template DNA, 1× PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase in a final volume of 50 µl. The reaction was performed using a EPPENDORF® MASTERCYCLER® 5333 programmed for 1 cycle at 95° C. for 2 minutes; 32 cycles each at 95° C. for 30 seconds, 55° C. for 30 seconds, and 72° C. for 45 seconds; and a final elongation at 72° C. for 3 minutes. Then 5 µl of 10× NEBuffer 4 and 20 units of Dpn I were added and incubated at 37° C. for 1 hour. The Dpn I was inactivated at 80° C. for 20 minutes.

The two fragments were fused into Pac I/Nt.BbvCI digested pBGMH14 by USER™ based cloning method in a reaction composed of 10 ng of Pac I/Nt.BbvCI digested pBGMH14, 50 ng of each of the two PCR products, and 1 unit of USER™ enzyme in a total volume of 10 µl. The reaction was incubated at 37° C. for 20 minutes followed by 20 minutes at 25° C. Then 10 µl were transformed into ONE SHOT® TOP10 competent cells. *E. coli* transformants were selected on LB+Amp agar plates and plasmid DNA was prepared using QIAPREP® Spin Miniprep Kit. Plasmid pBGMH16 was confirmed by sequencing.

DNA sequence was verified by Sanger sequencing with an Applied Biosystems Model 3730XL Automated DNA Sequencer using version 3.1 BIG-DYE™ terminator chemistry. Sequencing primers used for verification of niiA, niaD, the P13amy promoter, AsiSI/Nb.BtsI USER™ cassette, and AMG terminator sequence in BGMH16 are shown below.

```
BGMH 36
                              (SEQ ID NO: 229)
ACGCCATTGCTATGATGCTTGAAG

BGMH 37
                              (SEQ ID NO: 230)
TGGTGAGGTGCTATCGTCCTT

BGMH 38
                              (SEQ ID NO: 231)
CTTCCTGTAGGTGCACCGAAG

BGMH 39
                              (SEQ ID NO: 232)
ACAGAACGATATCGGACCTCG

BGMH 40
                              (SEQ ID NO: 233)
TCGTTATGTTAAGTCTTCTATCA

BGMH 41
                              (SEQ ID NO: 234)
AGAGCTCGAAGTTCCTCCGAG

BGMH 42
                              (SEQ ID NO: 235)
TATCACGAGGCCCTTTCGTCTC

BGMH 43
                              (SEQ ID NO: 236)
TCCGTCGGCTCCTCTCCTTCGT

BGMH 44
                              (SEQ ID NO: 237)
TGCATATCCTCTGACAGTATGA

BGMH 45
                              (SEQ ID NO: 238)
CAGTGAAGAGGGCAGTCGATAGT

BGMH 46
                              (SEQ ID NO: 239)
ACGAGGAACATGGCTATCTGGA

BGMH 47
                              (SEQ ID NO: 240)
TCAGCTCATTCTGGGAGGTGGGA

BGMH 48
                              (SEQ ID NO: 241)
ACTCCAGGATCCTTTAAATCCA

BGMH 53
                              (SEQ ID NO: 242)
ACTGGCAAGGGATGCCATGCT

BGMH 54
                              (SEQ ID NO: 243)
TGATCATATAACCAATTGCCCT

BGMH 55
                              (SEQ ID NO: 244)
AGTTGTGTATATAGAGGATTGA

BGMH 56
                              (SEQ ID NO: 245)
TGGTCCTTCGCTCGTGATGTGGA

BGMH 57
                              (SEQ ID NO: 246)
AGTCCTCAGCGTTACCGGCA

BGMH 58
                              (SEQ ID NO: 247)
ACCCTCAGCTGTGTCCGGGA

BGMH 59
                              (SEQ ID NO: 248)
TGGTATGTGAACGCCAGTCTG
```

Plasmid pBGMH16 contains flanking regions designed to repair the niiA gene and niaD gene in *Aspergillus oryzae* COLs1300. Plasmid pBGMH16 was digested with Asi Si and Nb. Bts I to linearize the plasmid and create single stranded overhangs so that a PCR product with compatible overhangs can be cloned into this site by USER™ cloning (New England Biolabs, Inc., Ipswich, MA, USA). The digested plasmid was purified using a DNA Purification Kit (QIAGEN Inc., Valencia, CA, USA) according to the manufacturer's instructions.

The *T. aurantiacus* GH61A polypeptide coding sequence (SEQ ID NO: 13 [genomic DNA sequence] and SEQ ID NO: 14 [deduced amino acid sequence]), *P. emersonii* GH61A polypeptide coding sequence (SEQ ID NO: 35 [genomic DNA sequence] and SEQ ID NO: 36 [deduced amino acid sequence]), *A. aculeatus* GH61 polypeptide coding sequence (SEQ ID NO: 67 [genomic DNA sequence] and SEQ ID NO: 68 [deduced amino acid sequence]), *P. pinophilum* GH61 polypeptide coding sequence (SEQ ID NO: 31 [genomic DNA sequence] and SEQ ID NO: 32 [deduced amino acid sequence]), and *T. terrestris* GH61 polypeptide coding sequence (SEQ ID NO: 45 [genomic DNA sequence; cDNA was used herein] and SEQ ID NO: 46 [deduced amino acid sequence]) were amplified from source plasmids described below using the primers shown in Table 12. Bold letters represent coding sequence. The single deoxyuridine (U) residue inserted into each primer is the U that is excised from the PCR products using the USER™ enzyme (New England Biolabs, Inc., Ipswich, MA, USA) to obtain overhangs for the insertion site. The underline letters represent a His tag. The remaining sequences are homologous to insertion sites of pBGMH16 for expression of the GH61 polypeptides.

TABLE 12

| GH61 origin | Source Template | Plasmid | Primer ID | Primer Sequence |
|---|---|---|---|---|
| *Thermoascus aurantiacus* GH61A | pDFng113 Example 1 | pDFng153-4 | TaGH61_US ERtagF | AGAGCGA(U)ATGTCCTTTTCA AGATAAT (SEQ ID NO: 249) |
| | | | TaGH61_US ER_HIStagR | TCTGCGA(U)TTAGTGATGGTG GTGATGATG<u>ACCAGTATACAG AGGAGGAC</u> (SEQ ID NO: 250) |
| *Penicillium emersonii* GH61A | pMMar45 Example 1 | pDFng154-17 | PeGH61_US ERtagF | AGAGCGA(U)ATGCTGTCTTCG ACGACTCG (SEQ ID NO: 251) |
| | | | PeGH61_US ER_HIStagR | TCTGCGA(U)CTAGTGATGGTG GTGATGATG<u>GAACGTCGGCTC AGGCGGCC</u> (SEQ ID NO: 252) |
| *Aspergillus aculeatus* GH61 | Xyz1566 (WO2012/030799) | pDFng155-33 | AaGH61_US ERtagF | AGAGCGA(U)ATGTCTGTTGCT AAGTTTGCTGGTG (SEQ ID NO: 253) |
| | | | AaGH61_US ER_HIStagR | TCTGCGA(U)TTAGTGATGGTG GTGATGATG<u>GGGCGGAGAGGTC ACGGGCGT</u> (SEQ ID NO: 254) |
| *Penicillium pinophilum* GH61 | pSMai215 (Example 15) | pDFng156-37 | PpGH61_US ERtagF | AGAGCGA(U)ATGCCTTCTACT AAAGTCGCTGCC (SEQ ID NO: 255) |
| | | | PpGH61_US ER_HIStagR | TCTGCGA(U)TCAGTGATGGTG GTGATGATG<u>AAGGACAGTAGT GGTGATGA</u> (SEQ ID NO: 256) |
| *Thielavia terrestris* GH61 | pAG68 (WO2011/035027) | pDFng157-51 | TtGH61_USE RtagF | AGAGCGA(U)ATGCCTTCTTTCG CCTCCAAGACTCTCCTTTC (SEQ ID NO: 257) |
| | | | TtGH61_USE R_HIStagR | TCTGCGA(U)TCAGTGATGGTG GTGATGATG<u>GTTTGCCTCCTCA GCCCCTC</u> (SEQ ID NO: 258 ID NO) |

Construction of plasmid pDFng153-4 containing the *Thermoascus aurantiacus* GH61A polypeptide coding sequence is described below. The *T. aurantiacus* GH61A polypeptide coding sequence was amplified from plasmid pDFng113 using the primers shown in Table 12 with overhangs designed for cloning into plasmid pBGMH16. The amplification was composed of 100 ng of each primer listed in Table 12, 30 ng of pDFng113, 1× PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase in a final volume of 50 µl. The PCR was performed using an EPPENDORF® MASTERCYCLER® 5333 programmed for 1 cycle at 95° C. for 2 minutes; 30 cycles each at 95° C. for 30 seconds, 57.7° C. for 30 seconds, and 72° C. for 1.5 minutes; and a final elongation at 72° C. for 10 minutes. The heat block then went to a 10° C. soak cycle.

The PCR solution was analyzed by 0.7% agarose gel electrophoresis using TBE buffer where an approximately 894 bp PCR product band was observed. The PCR solution was then digested with 1 µl of Dpn I and 4.5 µl of NEBuffer 4 at 37° C. overnight and purified using a QIAGEN® Purification Kit according to the manufacturer's instructions.

The homologous ends of the 894 bp PCR product and the Asi SI and Nb.BtsI digested pBGMH16 were joined together in a reaction composed of 10 µl of the PCR containing the 894 bp PCR product, 1 µl of the Asi SI and Nb.BtsI digested plasmid pBGMH16, and 1 µl of USER™ enzyme. The reaction was incubated for 15 minutes at 37° C., followed by 15 minutes at 25° C. Ten µl of the reaction were transformed into *E. coli* XL10-GOLD® Super Competent Cells according to the manufacturer's instructions. *E. coli* transformants were selected on 2XYT+Amp agar plates.

Plasmid DNA from several of the resulting *E. coli* transformants was prepared using a BIOROBOT® 9600. The *T. aurantiacus* GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers shown below were used for verification of the gene insert and sequence.

```
Primer TaGH61seqF:
                                   (SEQ ID NO: 259)
CCCAGTTATCAACTACCTTG Primer pBGMH16seqF:
                                   (SEQ ID NO: 260)
CTCAATTTACCTCTATCCAC Primer pBGMH16seqR:
                                   (SEQ ID NO: 261)
TATAACCAATTGCCCTCATC
```

A plasmid containing the correct *T. aurantiacus* GH61A polypeptide coding sequence was selected and designated pDFng153-4.

Construction of plasmid pDFng154-17 containing the *Penicillium emersonii* GH61A polypeptide coding sequence is described below. The *P. emersonii* GH61A polypeptide coding sequence was amplified from plasmid pMMar45 using the primers shown in Table 12 with overhangs designed for cloning into plasmid pBGMH16. The amplification was composed of 100 ng of each primer listed in Table 12, 30 ng of pMMar45, 1× PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase in a final volume of 50 µl. The amplification was performed using an EPPENDORF® MASTERCYCLER® 5333 programmed for 1 cycle at 95° C. for 2 minutes; 30 cycles each at 95° C. for 30 seconds, 64.1° C. for 30 seconds, and 72° C. for 1.5 minutes; and a final elongation at 72° C. for 10 minutes. The heat block then went to a 10° C. soak cycle.

The PCR solution was analyzed by 0.7% agarose gel electrophoresis using TBE buffer where an approximately 930 bp PCR product band was observed. The PCR solution was then digested with 1 µl of Dpn I and 4.5 µl of NEBuffer 4 at 37° C. overnight and purified using a QIAGEN® Purification Kit according to the manufacturer's instructions.

The homologous ends of the 930 bp PCR product and the Asi SI and Nb.BtsI digested pBGMH16 were joined together in a reaction composed of 10 µl of the PCR solution containing the 930 bp PCR product, 1 µl of the Asi SI and Nb.BtsI digested pBGMH16, and 1 µl of USER™ enzyme. The reaction was incubated for 15 minutes at 37° C., followed by 15 minutes at 25° C. Ten µl of the reaction were transformed into *E. coli* XL10-GOLD® Super Competent Cells according to the manufacturer's instructions. *E. coli* transformants were selected on 2XYT+Amp agar plates. Plasmid DNA from several of the resulting *E. coli* transformants was prepared using a BIOROBOT® 9600. The *P. emersonii* GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers pBGMH16seqF and pBGMH16seqR and primer PeGH61seqF shown below were used for verification of the gene insert and sequence.

```
PeGH61seqF:
                               (SEQ ID NO: 261)
GCACCGTCGAGCTGCAGTGG
```

A plasmid containing the correct *P. emersonii* GH61A polypeptide coding sequence was selected and designated pDFng154-17.

Construction of plasmid pDFng155-33 containing the *Aspergillus aculeatus* GH61A polypeptide coding sequence is described below. The *A. aculeatus* GH61A polypeptide coding sequence was amplified from plasmid Xyz1566 (WO 2012/030799 Example 3) using primers shown in Table 12 with overhangs designed for cloning into plasmid pBGMH16. The amplification reaction was composed of 100 ng of each primer listed in Table 12, 30 ng of plasmid Xyz1566, 1× PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase in a final volume of 50 µl. The amplification was performed using an EPPENDORF® MASTERCYCLER® 5333 programmed for 1 cycle at 95° C. for 2 minutes; 30 cycles each at 95° C. for 30 seconds, 63.4° C. for 30 seconds, and 72° C. for 1.5 minutes; and a final elongation at 72° C. for 10 minutes. The heat block then went to a 10° C. soak cycle.

The PCR product solution was analyzed by 0.7% agarose gel electrophoresis using TBE buffer where an approximately 1.3 kb PCR product band was observed. The PCR product solution was then digested with 1 µl of Dpn I and 4.5 µl of NEBuffer 4 at 37° C. overnight and purified using a QIAGEN® Purification Kit according to the manufacturer's instructions.

The homologous ends of the 1.3 kb PCR product and the digested pBGMH16 were joined together in a reaction composed of 10 µl of the PCR containing the 1.3 kb PCR product, 1 µl of the digested pBGMH16, and 1 µl of USER™ enzyme. The reaction was incubated for 15 minutes at 37° C., followed by 15 minutes at 25° C. Ten µl of the reaction were transformed into *E. coli* XL10-GOLD® Super Competent Cells according to the manufacturer's instructions. *E. coli* transformants were selected on 2XYT+Amp agar plates. Plasmid DNA from several of the resulting *E. coli* transformants was prepared using a BIOROBOT® 9600. The *A. aculeatus* GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers pBGMH16seqF and pBGMH16seqR and primer AaGH61seqF shown below were used for verification of the gene insert and sequence.

```
Primer AaGH61seqF:
                               (SEQ ID NO: 263)
CCTTGCCAACTGCAATGGTG
```

A plasmid containing the correct *A. aculeatus* GH61A polypeptide coding sequence was selected and designated pDFng155-33.

Plasmid pSMai215 was used to provide the DNA template of the *Penicillium pinophilum* GH61A gene for construction of pDFng156-37. Plasmid pSMai215 was constructed as described below. Two synthetic oligonucleotide primers shown below were designed to PCR amplify the *Penicillium pinophilum* GH61A polypeptide gene. An IN-FUSION™ PCR Cloning Kit was used to clone the fragment directly into the expression vector pMJ09 (WO 2005/047499). Bold letters represent coding sequence. The remaining sequence is homologous to the insertion sites of pMJ09.

```
Forward primer:
                               (SEQ ID NO: 264)
5'-GGACTGCGCACCATGCCTTCTACTAAAG-3'

Reverse primer:
                               (SEQ ID NO: 265)
5'-GCCACGGAGCTTAATTAATCAAAGGACAGTAGTG-3'
```

Fifty picomoles of each of the primers above were used in a PCR composed of 10 ng of pPin7, 1× EXPAND® High Fidelity PCR buffer with $MgCl_2$ (Roche Diagnostics Corporation, Indianapolis, IN, USA), 0.25 mM each of dATP, dTTP, dGTP, and dCTP, and 2.6 units of EXPAND® High Fidelity Enzyme Mix (Roche Diagnostics Corporation, Indianapolis, IN, USA), in a final volume of 50 µl. The amplification was performed using an EPPENDORF® MASTERCYCLER® 5333 epgradient S programmed for 1 cycle at 98° C. for 3 minute; 30 cycles each at 98° C. for 30 seconds, 59° C. for 30 seconds, and 72° C. for 1 minute; and a final elongation at 72° C. for 15 minutes. The heat block then went to a 4° C. soak cycle. The reaction products were isolated by 1% agarose gel electrophoresis in TAE buffer where an approximately 1.05 kb product band was observed on the gel. The PCR product solution was purified using a MINELUTE® Gel Extraction Kit.

Plasmid pMJ09 (WO 2005/047499) was digested with Nco I and Pac I, isolated by 1.0% agarose gel electrophoresis in TAE buffer, excised from the gel, and extracted using a QIAQUICK® Gel Extraction Kit (QIAGEN Inc., Valencia, CA, USA) according to the manufacturer's instructions.

The 1.05 kb gene fragment and the digested vector were ligated together using an IN-FUSION™ PCR Cloning Kit (Clontech Laboratories Inc., Mountain View, CA, USA)

resulting in pSMai215. The ligation reaction (20 µl) was composed of 1× IN-FUSION™ Buffer, 1×BSA, 1 µl of IN-FUSION™ enzyme (diluted 1:10), 100 ng of the gel-purified Nco I/Pac I digested pMJ09, and 42 ng of the purified 1.05 kb PCR product. The reaction was incubated at 37° C. for 15 minutes follow by 50° C. for 15 minutes. After diluting the reaction mix with 50 µl of TE buffer (pH 8), 2.5 µl of the reaction were transformed into *E. coli* XL10 SOLOPACK® Gold Supercompetent cells. The *E. coli* transformation reactions were spread onto 2XYTamp agar plates. An *E. coli* transformant containing pSMai215 was detected by restriction digestion and plasmid DNA was prepared using a BIOROBOT® 9600. The *Penicillium pinophilum* GH61A insert in pSMai215 was confirmed by DNA sequencing.

Construction of plasmid pDFng156-37 containing the *Penicillium pinophilum* GH61A polypeptide coding sequence is described below. The *P. pinophilum* GH61A polypeptide coding sequence was amplified from plasmid pSMai215 using the primers shown in Table 12 with overhangs designed for cloning into plasmid pBGMH16. The amplification reaction was composed of 100 ng of each primer listed in Table 12, 30 ng of plasmid pSMai215, 1× PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase in a final volume of 50 µl. The PCR was performed using an EPPENDORF® MASTERCYCLER® 5333 programmed for 1 cycle at 95° C. for 2 minutes; 30 cycles each at 95° C. for 30 seconds, 61.2° C. for 30 seconds, and 72° C. for 1.5 minutes; and a final elongation at 72° C. for 10 minutes. The heat block then went to a 10° C. soak cycle.

The PCR product solution was analyzed by 0.7% agarose gel electrophoresis using TBE buffer where an approximately 1.1 kb PCR product band was observed. The PCR product solution was then digested with 1 µl of Dpn I and 4.5 µl of NEB4 buffer at 37° C. overnight and purified using a QIAGEN® Purification Kit.

The homologous ends of the 1.1 kb PCR product and the digested pBGMH16 were joined together in a reaction composed of 10 µl of the PCR containing the 1.1 kb PCR product, 1 µl of the digested pBGMH16, and 1 µl of USER™ enzyme. The reaction was incubated at 37° C. for 15 minutes, followed by 15 minutes at 25° C. Ten µl of the reaction were transformed into *E. coli* XL10-GOLD® Super Competent Cells according to the manufacturer's instructions. *E. coli* transformants were selected on 2XYT+Amp agar plates. Plasmid DNA from several of the resulting *E. coli* transformants was prepared using a BIOROBOT® 9600. The *P. pinophilum* GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers pBGMH16seqF and pBGMH16seqR and primer PpGH61seqF shown below were used for verification of the gene insert and sequence.

```
Primer PpGH61seqF:
                            (SEQ ID NO: 266)
CAATGGCAATTGTTCTACCG
```

A plasmid containing the correct *P. pinophilum* GH61A polypeptide coding sequence was selected and designated pDFng156-37.

Construction of plasmid pDFng157-51 containing the *Thielavia terrestris* GH61 polypeptide coding sequence is described below. The *T. terrestris* GH61 polypeptide coding sequence was amplified from plasmid pAG68 using the primers shown in Table 12 with overhangs designed for cloning into plasmid pBGMH16. The amplification reaction was composed of 100 ng of each primer listed in Table 12, 30 ng of plasmid pAG68, 1× PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase in a final volume of 50 µl. The PCR was performed using an EPPENDORF® MASTERCYCLER® 5333 programmed for 1 cycle at 95° C. for 2 minutes; 30 cycles each at 95° C. for 30 seconds, 61.2° C. for 30 seconds, and 72° C. for 1.5 minutes; and a final elongation at 72° C. for 10 minutes. The heat block then went to a 10° C. soak cycle.

The PCR product solution was analyzed by 0.7% agarose gel electrophoresis using TBE buffer where an approximately 1.2 kb PCR product band was observed. The PCR product solution was then digested with 1 µl of Dpn I and 4.5 µl of NEB4 buffer at 37° C. overnight and purified using a QIAGEN® Purification Kit according to the manufacturer's instructions The homologous ends of the 1.2 kb PCR product and the digested pBGMH16 were joined together in a reaction composed of 10 µl of the PCR containing the 1.1 kb PCR product, 1 µl of the digested pBGMH16, and 1 µl of USER™ enzyme. The reaction was incubated at 37° C. for 15 minutes, followed by 15 minutes at 25° C. Ten µl of the reaction were transformed into *E. coli* XL10-GOLD® Super Competent Cells according to the manufacturer's instructions. *E. coli* transformants were selected on 2XYT+Amp agar plates. Plasmid DNA from several of the resulting *E. coli* transformants was prepared using a BIOROBOT® 9600. The *T. terrestris* GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers pBGMH16seqF and pBGMH16seqR and primer TtGH61seqF shown below were used for verification of the gene insert and sequence.

```
Primer TtGH61seqF:
                            (SEQ ID NO: 267)
CGACGGCAGCTCGGCGCCCG
```

A plasmid containing the correct *T. terrestris* GH61 polypeptide coding sequence was selected and designated pDFng157-51.

Example 16: Construction of *Thermoascus aurantiacus* GH61 Polypeptide Variants

The *Thermoascus aurantiacus* GH61 polypeptide variants were constructed by SOE-PCR (Splicing by Overhang Extension Polymerase Chain Reaction) with plasmid pDFng153-4. In brief, the first PCR used forward primer EbZn NiaD Fwd and a mutation specific reverse primer (Table 13). The second PCR used reverse primer EbZn NiiA Rev and a mutation specific forward primer (Table 13) containing the sequence coding for the altered amino acid. The mutation specific forward and reverse primers contained 15-20 overlapping nucleotides. The third PCR used the overlapping nucleotides to splice together the fragments produced in the first and second reaction. Finally, using a nested forward primer BGMH110V2F and a nested reverse primer BGMH109V2R, the spliced fragment was amplified by PCR.

Primer EbZn NiaD Fwd:
(SEQ ID NO: 268)
5'-GCATTTATCAGGGTTATTGTCTCATGAGCGG-3'

Primer EbZn NiiA Rev:
(SEQ ID NO: 269)
5'-GCTGATAAATCTGGAGCCGGTGAGCG-3'

Primer BGMH110V2F:
(SEQ ID NO: 270)
5'-CCAGACCAGCAGAGGAGATAATACTCTGCG-3'

Primer BGMH109V2R:
(SEQ ID NO: 271)
5'-CAAGGATACCTACAGTTATTCGAAACCTCCTG-3'

The first PCRs for the *T. aurantiacus* GH61 polypeptide variants contained 0.2 picomole of the EbZn NiaD Fwd primer, 0.2 picomole of the reverse primer listed in Table 13, 10 ng of template (pDFng153-4), 1 nanomole each dATP, dTTP, dGTP, and dCTP, 1x PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient (Eppendorf Scientific, Inc., Westbury, NY, USA) programmed for 1 cycle at 98° C. for 2 minutes; 35 cycles each at 98° C. for 25 seconds, 66° C. for 30 seconds, and 72° C. for 5 minute; and a final elongation at 72° C. for 10 minutes. The heat block then went to a 10° C. hold stage.

The second SOE-PCRs for the *T. aurantiacus* GH61 variants contained 0.2 picomole of the forward primer listed in Table 13, 0.2 picomole of the EbZn NiiA Rev primer, 10 ng of template (pDFng153-4), 1 nanomole each dATP, dTTP, dGTP, and dCTP, 1x PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 25 seconds, 66° C. for seconds, and 72° C. for 5 minutes; and a final elongation at 72° C. for 10 minutes. The heat block then went to a 10° C. hold stage.

Each PCR product was analyzed by 1.0% agarose electrophoresis using TAE buffer where a 4.1 to 5.3 kb (as specified in Table 13) PCR product band was observed indicating proper amplification. The remaining 45 microliters were then treated with 10 units of Dpn I and 1x NEB4 to remove the remaining wild-type template. The reaction was incubated for 4 hours at 37° C. and then purified using a MINELUTE® 96 UF Purification Kit (QIAGEN Inc., Valencia, CA, USA). The purified PCR products were resuspended in deionized water to a final volume equal to 20 µl. The concentration of each fragment was measured using a NanoDrop 2000 (Thermo Scientific, Wilmington, DE, USA).

The third SOE-PCR for the *T. aurantiacus* GH61 variants contained 50 to 100 ng of each fragment produced in the first and second PCRs, 1 nanomole each dATP, dTTP, dGTP, and dCTP, 1x PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage. Primer BGMH110V2F primer (0.2 picomole) and primer BGMH109V2R (0.2 picomole) were added during the annealing/elongation step of the fifth cycle to allow the overlapping nucleotides to splice before amplification.

The wild-type fragment was produced using conditions similar to the third PCR. The reaction was composed of 10 ng of template (pDFng153-4), 0.2 picomole of primer BGMH110V2F, 0.2 picomole of primer BGMH109V2R, 1 nanomole each dATP, dTTP, dGTP, and dCTP, 1x PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage.

Each SOE-PCR product was analyzed by 1.0% agarose electrophoresis using TAE buffer where an approximately 8 kb PCR product band was observed indicating proper amplification. The remaining 45 µl of each SOE-PCR product was then purified using a MINELUTE® 96 UF Purification Kit. The purified PCR products were resuspended in deionized water to a final volume equal to 20 µl. The concentration of each fragment was measured using a NanoDrop 2000. The entire volume was then transformed into the *Aspergillus oryzae* COLs1300 strain as described in Example 21.

TABLE 13

| Template Backbone | Amino Acid Substitution | Primer ID | Primer Direction | Primer Sequence | PCR fragment size (kb) |
|---|---|---|---|---|---|
| *Thermoascus aurantiacus* GH61 | Q26I | 1203249 | Fwd | GTGGCTGGCCATGGCTTCGT TATCAACATCGTGATTGATG GTAAAAGT (SEQ ID NO: 272) | 5.3 |
| | | 1203250 | Rev | AACGAAGCCATGGCCAGCC ACTAGAGAAGCAGA (SEQ ID NO: 273) | 4.1 |
| *Thermoascus aurantiacus* GH61 | Q42I | 1203262 | Fwd | GTTATGGCGGGTATCTAGTG AACATCTATCCATACATGTCC AATCCTCC (SEQ ID NO: 274) | 5.2 |
| | | 1203261 | Rev | GTTCACTAGATACCCGCCAT AACTGTCGATTGTCA (SEQ ID NO: 275) | 4.2 |

TABLE 13-continued

| Template Backbone | Amino Acid Substitution | Primer ID | Primer Direction | Primer Sequence | PCR fragment size (kb) |
|---|---|---|---|---|---|
| Thermoascus aurantiacus GH61 | Q42V | 1203263 | Fwd | GTTATGGCGGGTATCTAGTG AACGTCTATCCATACATGTC CAATCCTCC (SEQ ID NO: 277) | 5.2 |
| | | 1203261 | Rev | GTTCACTAGATACCCGCCAT AACTGTCGATTGTCA (SEQ ID NO: 278) | 4.2 |
| Thermoascus aurantiacus GH61 | S123R | 1203276 | Fwd | TGCTCCGTGCAATGGTGATT GTAGGACTGTGGATAAGACC CAATTAGAA (SEQ ID NO: 279) | 4.9 |
| | | 1203277 | Rev | ACAATCACCATTGCACGGAG CAAGGTAGTTGATAA (SEQ ID NO: 280) | |
| Thermoascus aurantiacus GH61 | S138E | 1203280 | Fwd | ATTAGAATTCTTCAAAATTGC CGAGGAGGGTCTCATCAATG ATGACAATCC (SEQ ID NO: 281) | 4.9 |
| | | 1203279 | Rev | CTCGGCAATTTTGAAGAATT CTAATTGGGTCTTATCC (SEQ ID NO: 282) | 4.5 |
| Thermoascus aurantiacus GH61 | S138K | 1203281 | Fwd | ATTAGAATTCTTCAAAATTGC CGAGAAAGGTCTCATCAATG ATGACAATCC (SEQ ID NO: 283) | 4.9 |
| | | 1203279 | Rev | CTCGGCAATTTTGAAGAATT CTAATTGGGTCTTATCC (SEQ ID NO: 284) | 4.5 |
| Thermoascus aurantiacus GH61 | S138L | 1203282 | Fwd | ATTAGAATTCTTCAAAATTGC CGAGCTGGGTCTCATCAATG ATGACAATCC (SEQ ID NO: 285) | 4.9 |
| | | 1203279 | Rev | CTCGGCAATTTTGAAGAATT CTAATTGGGTCTTATCC (SEQ ID NO: 286) | 4.5 |
| Thermoascus aurantiacus GH61 | T163V | 1203285 | Fwd | GATAGCAGCCAACAACAGCT GGGTCGTCACCATTCCAACC ACAATTGC (SEQ ID NO: 287) | 4.8 |
| | | 1203286 | Rev | CCAGCTGTTGTTGGCTGCTA TCAGATTGTCTGAAG (SEQ ID NO: 288) | 4.6 |
| Thermoascus aurantiacus GH61 | T163E | 1203288 | Fwd | GATAGCAGCCAACAACAGCT GGGAGGTCACCATTCCAACC ACAATTGC (SEQ ID NO: 289) | 4.8 |
| | | 1203289 | Rev | CCAGCTGTTGTTGGCTGCTA TCAGATTGTCTGAAG (SEQ ID NO: 290) | 4.6 |
| Thermoascus aurantiacus GH61 | S186K | 1203297 | Fwd | GGCATGAGATTATTGCTCTT CACAAAGCTCAGAACCAGGA TGGTGCC (SEQ ID NO: 291) | 4.8 |
| | | 1203298 | Rev | GTGAAGAGCAATAATCTCAT GCCTCAGAACATAGTT (SEQ ID NO: 292) | 4.6 |
| Thermoascus aurantiacus GH61 | S186F | 1203299 | Fwd | GGCATGAGATTATTGCTCTT CACTTCGCTCAGAACCAGGA TGGTGCC (SEQ ID NO: 293) | 4.8 |
| | | 1203298 | Rev | GTGAAGAGCAATAATCTCAT GCCTCAGAACATAGTT (SEQ ID NO: 294) | 4.6 |
| Thermoascus aurantiacus GH61 | S186T | 1203300 | Fwd | GGCATGAGATTATTGCTCTT CACACTGCTCAGAACCAGGA TGGTGCC (SEQ ID NO: 295) | 4.8 |
| | | 1203298 | Rev | GTGAAGAGCAATAATCTCAT GCCTCAGAACATAGTT (SEQ ID NO: 296) | 4.6 |

TABLE 13-continued

| Template Backbone | Amino Acid Substitution | Primer ID | Primer Direction | Primer Sequence | PCR fragment size (kb) |
|---|---|---|---|---|---|
| Thermoascus aurantiacus GH61 | S186Y | 1203301 | Fwd | GGCATGAGATTATTGCTCTT CACTATGCTCAGAACCAGGA TGGTGCC (SEQ ID NO: 297) | 4.8 |
| | | 1203298 | Rev | GTGAAGAGCAATAATCTCAT GCCTCAGAACATAGTT (SEQ ID NO: 298) | 4.6 |
| Thermoascus aurantiacus GH61 | I200V | 1203302 | Fwd | GCCCAGAACTATCCCCAGTG CGTCAATCTGCAGGTCACTG GAGGTG (SEQ ID NO: 299) | 4.7 |
| | | 1203303 | Rev | GCACTGGGGATAGTTCTGG GCACCATCCTGGT (SEQ ID NO: 300) | 4.7 |
| Thermoascus aurantiacus GH61 | A213E | 1203306 | Fwd | TGGAGGTGGTTCTGATAACC CTGAGGGAACTCTTGGAACG GCACTC (SEQ ID NO: 301) | 4.7 |
| | | 1203307 | Rev | AGGGTTATCAGAACCACCTC CAGTGACCTGCAG (SEQ ID NO: 302) | 4.7 |
| Thermoascus aurantiacus GH61 | A219C | 1203308 | Fwd | CCTGCTGGAACTCTTGGAAC GTGCCTCTACCACGATACCG ATCCTG (SEQ ID NO: 303) | 4.7 |
| | | 1203309 | Rev | CGTTCCAAGAGTTCCAGCAG GGTTATCAGAACC (SEQ ID NO: 304) | 4.7 |
| Thermoascus aurantiacus GH61 | A219E | 1203310 | Fwd | CCTGCTGGAACTCTTGGAAC GGAGCTCTACCACGATACCG ATCCTG (SEQ ID NO: 305) | 4.7 |
| | | 1203309 | Rev | CGTTCCAAGAGTTCCAGCAG GGTTATCAGAACC (SEQ ID NO: 306) | 4.7 |
| Thermoascus aurantiacus GH61 | A219Q | 1203312 | Fwd | CCTGCTGGAACTCTTGGAAC GCAGCTCTACCACGATACCG ATCCTG (SEQ ID NO: 307) | 4.7 |
| | | 1203309 | Rev | CGTTCCAAGAGTTCCAGCAG GGTTATCAGAACC (SEQ ID NO: 308) | 4.7 |
| Thermoascus aurantiacus GH61 | T248R | 1203320 | Fwd | CATCCCTGGTCCTCCTCTGT ATAGGGGTCATCATCACCAC CATCACT (SEQ ID NO: 309) | 4.6 |
| | | 1203319 | Rev | ATACAGAGGAGGACCAGGG ATGATATAGCTGGAAA (SEQ ID NO: 310) | 4.8 |

Example 17: Construction of *Penicillium emersonii* GH61 Polypeptide Variants

The *Penicillium emersonii* GH61 polypeptide variants were constructed by SOE-PCR (Splicing by Overhang Extension Polymerase Chain Reaction) with plasmid pDFng154-17. In brief, the first PCR used forward primer EbZn NiaD Fwd and a mutation specific reverse primer (Table 14). The second PCR used reverse primer EbZn NiiA Rev and a mutation specific forward primer (Table 14) containing the sequence coding for the altered amino acid. The mutation specific forward and reverse primers contained 15-20 overlapping nucleotides. The third PCR used the overlapping nucleotides to splice together the fragments produced in the first and second reaction. Finally, using a nested forward primer BGMH110V2F and a nested reverse primer BGMH109V2R, the spliced fragment was amplified by PCR.

The first PCRs for the *P. emersonii* GH61 polypeptide variants contained 0.2 picomole of the EbZn NiaD Fwd primer, 0.2 picomole of the reverse primer listed in Table 14, 10 ng of template (pDFng154-17), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 25 seconds, 66° C. for seconds, and 72° C. for 5 minute; and a final elongation at 72° C. for 10 minutes. The heat block then went to a 10° C. hold stage.

The second PCRs for the *P. emersonii* GH61 variants contained 0.2 picomole of the forward primer listed in Table 14, 0.2 picomole of the EbZn NiiA Rev primer, 10 ng of template (pDFng154-17), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 25 seconds, 66° C. for seconds, and 72° C. for 5 minutes; and a final elongation at 72° C. for 10 minutes. The heat block then went to a 10° C. hold stage.

Each PCR product was analyzed by 1.0% agarose electrophoresis using TAE buffer where a 4.2 to 5.2 kb (as specified in Table 14) PCR product band was observed indicating proper amplification. The remaining 45 microliters were then treated with 10 units of Dpn I and 1× NEB4 to remove the remaining wild-type template. The reaction was incubated for 4 hours at 37° C. and then purified using a MINELUTE® 96 UF Purification Kit. The purified PCR products were resuspended in deionized water to a final volume equal to 20 μl. The concentration of each fragment was measured using a NanoDrop 2000.

The third SOE-PCR for the *P. emersonii* GH61 variants contained 50 to 100 ng of each fragment produced in the first and second PCRs, 4 nanomoles each dATP, dTTP, dGTP, and dCTP, 1× ADVANTAGE® GC-Melt Buffer (Clontech Laboratories, Inc., Mountain View, CA, USA), and 2.5 units of ADVANTAGE® GC Genomic LA Polymerase (Clontech Laboratories, Inc., Mountain View, CA, USA) in a final reaction volume of 50 μl. The amplification was performed using an EPPENDORF® MASTERCYCLER® Gradient programmed for 1 cycle at 94° C. for 1 minutes; 35 cycles each at 94° C. for 30 seconds, 66° C. for 30 seconds, and 72° C. for 10 minutes; and a final elongation at 72° C. for 10 minutes. The heat block then went to a 10° C. hold stage. Primer BGMH110V2F primer (0.4 picomole) and primer BGMH109V2R (0.4 picomole) were added during the annealing/elongation step of the fifth cycle to allow for the overlapping nucleotides to splice before amplification.

The wild-type fragment was produced using conditions similar to the third PCR. The reaction was composed of 10 ng of template (pDFng154-17), 0.4 picomole of primer BGMH110V2F, 0.4 picomole of primer BGMH109V2R, 1 nanomole each dATP, dTTP, dGTP, and dCTP, 1× ADVANTAGE® GC-Melt Buffer, and 2.5 units of ADVANTAGE® GC Genomic LA Polymerase in a final reaction volume of 50 μl. The amplification was performed using an EPPENDORF® MASTERCYCLER® Gradient programmed for 1 cycle at 94° C. for 1 minutes; 35 cycles each at 94° C. for 30 seconds, 66° C. for 30 seconds, and 72° C. for 10 minutes; and a final elongation at 72° C. for 10 minutes. The heat block then went to a 10° C. hold stage.

Each SOE-PCR product was analyzed by 1.0% agarose electrophoresis using TAE buffer where an approximately 8 kb PCR product band was observed indicating proper amplification. The remaining 45 μl of each SOE-PCR product was then purified using a MINELUTE® 96 UF Purification Kit. The purified PCR products were resuspended in deionized water to a final volume equal to 20 μl. The concentration of each fragment was measured using a NanoDrop 2000. The entire volume was then transformed into the *Aspergillus oryzae* COLs1300 strain as described in Example 21.

TABLE 14

| Template Backbone | Amino Acid Substitution | Primer ID | Primer Direction | Primer Sequence | PCR fragment size (kb) |
|---|---|---|---|---|---|
| *Penicillium emersonii* GH61 | S46V | 1203486 | Fwd | CTACAGCGGGTACATCGTCAA CGTCTTCCCCTACGAATCCAA CCCAC (SEQ ID NO: 311) | 5.2 |
|  |  | 1203484 | Rev | GTTGACGATGTACCCGCTGTA GCTGTTGGGAGT (SEQ ID NO: 312) | 4.2 |
| *Penicillium emersonii* GH61 | G76Q | 1203493 | Fwd | GTCGACGGCACAGGATACCA ACAGCCGGACATCATCTGCC ACCG (SEQ ID NO: 313) | 5.1 |
|  |  | 1203494 | Rev | TTGGTATCCTGTGCCGTCGAC GAAGCCCAGG (SEQ ID NO: 314) | 4.3 |
| *Penicillium emersonii* GH61 | S127R | 1203496 | Fwd | CGCCGTGCAACGGCAACTGC CGCACCGTCGACAAGACGAC GCTG (SEQ ID NO: 315) | 4.9 |
|  |  | 1203497 | Rev | GCAGTTGCCGTTGCACGGCG CCAGGTAGGTG (SEQ ID NO: 316) | 4.5 |

Example 18: Construction of *Aspergillus aculeatus* GH61 Polypeptide Variants

The *Aspergillus aculeatus* GH61 polypeptide variants were constructed by SOE-PCR (Splicing by Overhang Extension Polymerase Chain Reaction) with plasmid pDFng155-33. In brief, the first PCR used forward primer EbZn NiaD Fwd and a mutation specific reverse primer (Table 15). The second PCR used reverse primer EbZn NiiA Rev and a mutation specific forward primer (Table 15) containing the sequence coding for the altered amino acid. The mutation specific forward and reverse primers contained 15-20 overlapping nucleotides. The third PCR used the overlapping nucleotides to splice together the fragments produced in the first and second reaction. Finally, using a nested forward primer BGMH110V2F and a nested reverse primer BGMH109V2R, the spliced fragment was amplified by PCR.

The first PCRs for the *A. aculeatus* GH61 polypeptide variants contained 0.2 picomole of the EbZn NiaD Fwd primer, 0.2 picomole of the reverse primer listed in Table 15, 10 ng of template (pDFng155-33), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 μl. The amplification was performed using an EPPENDORF® MASTERCYCLER® Gradient programmed for 1 cycle at 98° C. for 2 minutes; 35 cycles each at 98° C. for 25 seconds, 66° C. for seconds, and 72° C. for 5 minutes; and a final elongation at 72° C. for 10 minutes. The heat block then went to a 10° C. hold stage.

The second PCRs for the *A. aculeatus* GH61 variants contained 0.2 picomole of the forward primer listed in Table 15, 0.2 picomole of the EbZn NiiA Rev primer, 10 ng of template (pDFng155-33), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 25 seconds, 66° C. for seconds, and 72° C. for 5 minutes; and a final elongation at 72° C. for 10 minutes. The heat block then went to a 10° C. hold stage.

Each PCR product was analyzed by 1.0% agarose electrophoresis using TAE buffer where a 4.6 to 5.1 kb (as specified in Table 15) PCR product band was observed indicating proper amplification. The remaining 45 microliters were then treated with 10 units of Dpn I and 1× NEB4 to remove the remaining wild-type template. The reaction was incubated for 4 hours at 37° C. and then purified using a MINELUTE® 96 UF Purification Kit. The purified PCR products were resuspended in deionized water to a final volume equal to 20 µl. The concentration of each fragment was measured using a NanoDrop 2000.

The third SOE-PCR for the *A. aculeatus* GH61 variants contained 50 to 100 ng of each fragment produced in the first and second PCRs, 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage. Primer BGMH110V2F primer (0.2 picomole) and primer BGMH109V2R (0.2 picomole) were added during the annealing/elongation step of the fifth cycle to allow for the overlapping nucleotides to splice before amplification.

The wild-type fragment was produced using conditions similar to the third PCR. The reaction was composed of 10 ng of template (pDFng155-33), 0.2 picomole of primer BGMH110V2F, 0.2 picomole of primer BGMH109V2R, 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage.

Each SOE-PCR product was analyzed by 1.0% agarose electrophoresis using TAE buffer where an approximately 8 kb PCR product band was observed indicating proper amplification. The remaining 45 µl of each SOE-PCR product was then purified using a MINELUTE® 96 UF Purification Kit. The purified PCR products were resuspended in deionized water to a final volume equal to 20 µl. The concentration of each fragment was measured using a NanoDrop 2000. The entire volume was then transformed into the *Aspergillus oryzae* COLs1300 strain as described in Example 21.

TABLE 15

| Template Backbone | Amino Acid Substitution | Primer ID | Primer Direction | Primer Sequence | PCR fragment size (kb) |
|---|---|---|---|---|---|
| *Aspergillus aculeatus* GH61 | D70Q | 1203194 | Fwd | CGTCGATGGTAGCGAGTATG CTCAGGCCGACATCATTTGCC ACAAGA (SEQ ID NO: 317) | 5.6 |
| | | 1203195 | Rev | AGCATACTCGCTACCATCGAC GAAACCCAAGTCG (SEQ ID NO: 318) | 4.1 |
| *Aspergillus aculeatus* GH61 | D70T | 1203196 | Fwd | CGTCGATGGTAGCGAGTATG CTACCGCCGACATCATTTGCC ACAAGA (SEQ ID NO: 319) | 5.6 |
| | | 1203195 | Rev | AGCATACTCGCTACCATCGAC GAAACCCAAGTCG (SEQ ID NO: 320) | 4.1 |
| *Aspergillus aculeatus* GH61 | S136C | 1203202 | Fwd | CTCGAGTTTTTCAAGATTGAC GAGTGCGGTCTCATCAACGA CGACGAC (SEQ ID NO: 321) | 5.4 |
| | | 1203203 | Rev | CTCGTCAATCTTGAAAAACTC GAGGTCGGTCTTGG (SEQ ID NO: 322) | 4.3 |
| *Aspergillus aculeatus* GH61 | S136G | 1203208 | Fwd | CTCGAGTTTTTCAAGATTGAC GAGGGTGGTCTCATCAACGA CGACGAC (SEQ ID NO: 323) | 5.4 |
| | | 1203203 | Rev | CTCGTCAATCTTGAAAAACTC GAGGTCGGTCTTGG (SEQ ID NO: 324) | 4.3 |
| *Aspergillus aculeatus* GH61 | T147I | 1203209 | Fwd | ACGACGACGACGTCCCCGGT ATCTGGGCCAGTGATAACTTG ATCG (SEQ ID NO: 325) | 5.3 |
| | | 1203210 | Rev | ACCGGGGACGTCGTCGTCGT TGATGAGACCG (SEQ ID NO: 326) | 4.4 |

TABLE 15-continued

| Template Backbone | Amino Acid Substitution | Primer ID | Primer Direction | Primer Sequence | PCR fragment size (kb) |
|---|---|---|---|---|---|
| Aspergillus aculeatus GH61 | T161V | 1203211 | Fwd | GATCGCCAACAACAACAGCT GGGTCGTGACCATCCCCTCT GACATTG (SEQ ID NO: 327) | 5.3 |
| | | 1203212 | Rev | CCAGCTGTTGTTGTTGGCGAT CAAGTTATCACTGG (SEQ ID NO: 328) | 4.4 |
| Aspergillus aculeatus GH61 | T161F | 1203213 | Fwd | GATCGCCAACAACAACAGCT GGTTCGTGACCATCCCCTCTG ACATTG (SEQ ID NO: 329) | 5.3 |
| | | 1203212 | Rev | CCAGCTGTTGTTGTTGGCGAT CAAGTTATCACTGG (SEQ ID NO: 330) | 4.4 |
| Aspergillus aculeatus GH61 | D167R | 1203220 | Fwd | TGGACTGTGACCATCCCCTCT CGTATTGCGGCTGGCAACTA CGTC (SEQ ID NO: 331) | 5.3 |
| | | 1203221 | Rev | AGAGGGGATGGTCACAGTCC AGCTGTTGTTGTT (SEQ ID NO: 332) | 4.4 |
| Aspergillus aculeatus GH61 | S184K | 1203222 | Fwd | GTCACGAAATCATTGCCCTTC ACAAGGCTGGTAACAAGGAT GGTGCTC (SEQ ID NO: 333) | 5.2 |
| | | 1203223 | Rev | GTGAAGGGCAATGATTTCGTG ACGGAGGACGTAG (SEQ ID NO: 334) | 4.5 |
| Aspergillus aculeatus GH61 | S184T | 1203225 | Fwd | GTCACGAAATCATTGCCCTTC ACACCGCTGGTAACAAGGAT GGTGCTC (SEQ ID NO: 335) | 5.2 |
| | | 1203223 | Rev | GTGAAGGGCAATGATTTCGTG ACGGAGGACGTAG (SEQ ID NO: 336) | 4.5 |
| Aspergillus aculeatus GH61 | S184Y | 1203226 | Fwd | GTCACGAAATCATTGCCCTTC ACTACGCTGGTAACAAGGAT GTGCTC (SEQ ID NO: 337) | 5.2 |
| | | 1203223 | Rev | GTGAAGGGCAATGATTTCGTG ACGGAGGACGTAG (SEQ ID NO: 338) | 4.5 |
| Aspergillus aculeatus GH61 | L198I | 1203227 | Fwd | GCTCAGAACTACCCTCAGTGC ATCAACTTGAAGGTCACTGGC GGC (SEQ ID NO: 339) | 5.2 |
| | | 1203228 | Rev | GCACTGAGGGTAGTTCTGAG CACCATCCTTGTT (SEQ ID NO: 340) | 4.5 |
| Aspergillus aculeatus GH61 | L198V | 1203229 | Fwd | GCTCAGAACTACCCTCAGTGC GTCAACTTGAAGGTCACTGGC GGC (SEQ ID NO: 341) | 5.2 |
| | | 1203228 | Rev | GCACTGAGGGTAGTTCTGAG CACCATCCTTGTT (SEQ ID NO: 342) | 4.5 |
| Aspergillus aculeatus GH61 | S217M | 1203237 | Fwd | CCTTCTGGCACTGCTGGTGA GATGCTGTACAAGGACACCG ATGCTG (SEQ ID NO: 343) | 5.1 |
| | | 1203235 | Rev | CTCACCAGCAGTGCCAGAAG GAGCGAGATCAC (SEQ ID NO: 344) | 4.6 |
| Aspergillus aculeatus GH61 | S217Q | 1203238 | Fwd | CCTTCTGGCACTGCTGGTGA GCAGCTGTACAAGGACACCG ATGCTG (SEQ ID NO: 345) | 5.1 |
| | | 1203235 | Rev | CTCACCAGCAGTGCCAGAAG GAGCGAGATCAC (SEQ ID NO: 346) | 4.6 |

TABLE 15-continued

| Template Backbone | Amino Acid Substitution | Primer ID | Primer Direction | Primer Sequence | PCR fragment size (kb) |
|---|---|---|---|---|---|
| Aspergillus aculeatus GH61 | K220R | 1203239 | Fwd | ACTGCTGGTGAGAGCCTGTA CCGTGACACCGATGCTGGTA TCCTC (SEQ ID NO: 347) | 5.1 |
| | | 1203240 | Rev | GTACAGGCTCTCACCAGCAG TGCCAGAAGGAG (SEQ ID NO: 348) | 4.6 |
| Aspergillus aculeatus GH61 | A243P | 1203244 | Fwd | CTCCTACGATATTCCCGGACC TCCCATGTACAACGCTACCTC CAGCT (SEQ ID NO: 349) | 5.0 |
| | | 1203245 | Rev | AGGTCCGGGAATATCGTAGG AGGAAAGAGACTGG (SEQ ID NO: 350) | 4.7 |

Example 19: Construction of *Penicillium pinophilum* GH61 Polypeptide Variants

The *Penicillium pinophilum* GH61 polypeptide variants were constructed by SOE-PCR (Splicing by Overhang Extension Polymerase Chain Reaction) with plasmid pDFng156-37. In brief, the first PCR used forward primer EbZn NiaD Fwd and a mutation specific reverse primer (Table 16). The second PCR used reverse primer EbZn NiiA Rev and a mutation specific forward primer (Table 16) containing the sequence coding for the altered amino acid. The mutation specific forward and reverse primers contained 15-20 overlapping nucleotides. The third PCR used the overlapping nucleotides to splice together the fragments produced in the first and second reaction. Finally, using a nested forward primer BGMH110V2F and a nested reverse primer BGMH109V2R, the spliced fragment was amplified by PCR.

The first PCRs for the *P. pinophilum* GH61 polypeptide variants contained 0.2 picomole of the EbZn NiaD Fwd primer, 0.2 picomole of the reverse primer listed in Table 16, 10 ng of template (pDFng156-37), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 25 seconds, 66° C. for 30 seconds, and 72° C. for 5 minutes; and a final elongation at 72° C. for 10 minutes. The heat block then went to a 10° C. hold stage.

The second PCRs for the *P. pinophilum* GH61 variants contained 0.2 picomole of the forward primer listed in Table 16, 0.2 picomole of the EbZn NiiA Rev primer, 10 ng of template (pDFng156-37), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 25 seconds, 66° C. for seconds, and 72° C. for 5 minutes; and a final elongation at 72° C. for 10 minutes. The heat block then went to a 10° C. hold stage.

Each PCR product was analyzed by 1.0% agarose electrophoresis using TAE buffer where a 4.1 to 5.5 kb (as specified in Table 16) PCR product band was observed indicating proper amplification. The remaining 45 microliters were then treated with 10 units of Dpn I and 1× NEB4 to remove the remaining wild-type template. The reaction was incubated for 4 hours at 37° C. and then purified using a MINELUTE® 96 UF Purification Kit. The purified PCR products were resuspended in deionized water to a final volume equal to 20 µl. The concentration of each fragment was measured using a NanoDrop 2000.

The third SOE-PCR for the *P. pinophilum* GH61 variants contained 50 to 100 ng of each fragment produced in the first and second PCRs, 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage. Primer BGMH110V2F primer (0.2 picomole) and primer BGMH109V2R (0.2 picomole) were added during the annealing/elongation step of the fifth cycle to allow for the overlapping nucleotides to splice before amplification.

The wild-type fragment was produced using conditions similar to the third PCR. The reaction was composed of 10 ng of template (pDFng156-37), 0.2 picomole of primer BGMH110V2F, 0.2 picomole of primer BGMH109V2R, 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage.

Each SOE-PCR product was analyzed by 1.0% agarose electrophoresis using TAE buffer where an approximately 8 kb PCR product band was observed indicating proper amplification. The remaining 45 µl of each SOE-PCR product was then purified using a MINELUTE® 96 UF Purification Kit. The purified PCR products were resuspended in deionized water to a final volume equal to 20 µl. The concentration of each fragment was measured using a NanoDrop 2000. The entire volume was then transformed into the *Aspergillus oryzae* COLs1300 strain as described in Example 21.

TABLE 16

| Template Backbone | Amino Acid Substitution | Primer ID | Primer Direction | Primer Sequence | PCR fragment size (kb) |
|---|---|---|---|---|---|
| *Penicillium pinophilum* GH61 | S34F | 1203326 | Fwd | CAAAACATCGTTATCGACG GTAAATTTTAAGCAGTGAT GCATCCATTATTAA (SEQ ID NO: 351) | 5.5 |
| | | 1203327 | Rev | TTTACCGTCGATAACGATG TTTTGCACAAAACCATG (SEQ ID NO: 352) | 4.1 |
| *Penicillium pinophilum* GH61 | Q42I | 1203334 | Fwd | AGTTACTCTGGATACCTTG TGAATATCTTCCCCTACGA GTCCAACCCA (SEQ ID NO: 353) | 5.4 |
| | | 1203333 | Rev | ATTCACAAGGTATCCAGAG TAACTGATTTTTTTGTAAG (SEQ ID NO: 354) | 4.2 |
| *Penicillium pinophilum* GH61 | Q42V | 1203335 | Fwd | AGTTACTCTGGATACCTTG TGAATGTCTTCCCCTACGA GTCCAACCCA (SEQ ID NO: 355) | 5.4 |
| | | 1203333 | Rev | ATTCACAAGGTATCCAGAG TAACTGATTTTTTTGTAAG (SEQ ID NO: 356) | 4.2 |
| Penicillium pinophilum GH61 | S47L | 1203338 | Fwd | TGTGAATCAGTTCCCCTAC GAGCTTAACCCACCAGCT GTTATTGGGT (SEQ ID NO: 357) | 5.4 |
| | | 1203337 | Rev | CTCGTAGGGGAACTGATTC ACAAGGTATCCAGAG (SEQ ID NO: 358) | 4.2 |
| *Penicillium pinophilum* GH61 | A56C | 1203340 | Fwd | CCACCAGCTGTTATTGGGT GGTGCACAACTGCAACCG ACCTGGGA (SEQ ID NO: 359) | 5.4 |
| | | 1203341 | Rev | CCACCCAATAACAGCTGGT GGGTTGGACTCGT (SEQ ID NO: 360) | 4.2 |
| *Penicillium pinophilum* GH61 | A56E | 1203342 | Fwd | CCACCAGCTGTTATTGGGT GGGAGACAACTGCAACCG ACCTGGGA (SEQ ID NO: 361 | 5.4 |
| | | 1203341 | Rev | CCACCCAATAACAGCTGGT GGGTTGGACTCGT (SEQ ID NO: 362) | 4.2 |
| *Penicillium pinophilum* GH61 | G138C | 1203353 | Fwd | CTAGACTTTGTCAAGATTG ACCAATGCGGTTTGATCGA CGATACTACCC (SEQ ID NO: 363) | 5.1 |
| | | 1203354 | Rev | TTGGTCAATCTTGACAAAG TCTAGCTTAGTCTTATCC (SEQ ID NO: 364) | 4.5 |
| *Penicillium pinophilum* GH61 | T149I | 1203359 | Fwd | ACGATACTACCCCCCGG GTATCTGGGCTTCCGACAA ACTTATCG (SEQ ID NO: 365) | 5.1 |
| | | 1203360 | Rev | ACCCGGGGGGTAGTATC GTCGATCAAACCAC (SEQ ID NO: 366) | 4.5 |
| *Penicillium pinophilum* GH61 | V164C | 1203365 | Fwd | GCTGCCAACAACAGCTGG ACTTGCACTATCCCCTCCA CCATCGCG (SEQ ID NO: 367) | 5.1 |
| | | 1203366 | Rev | AGTCCAGCTGTTGTTGGCA GCGATAAGTTTGTCG (SEQ ID NO: 368) | 4.5 |
| *Penicillium pinophilum* GH61 | V164L | 1203367 | Fwd | GCTGCCAACAACAGCTGG ACTCTTACTATCCCCTCCA CCATCGCG (SEQ ID NO: 369) | 5.1 |

TABLE 16-continued

| Template Backbone | Amino Acid Substitution | Primer ID | Primer Direction | Primer Sequence | PCR fragment size (kb) |
|---|---|---|---|---|---|
| | | 1203366 | Rev | AGTCCAGCTGTTGTTGGCA GCGATAAGTTTGTCG (SEQ ID NO: 370) | 4.5 |
| Penicillium pinophilum GH61 | I166L | 1203368 | Fwd | CCAACAACAGCTGGACTGT AACTCTTCCCTCCACCATC GCGCCTGG (SEQ ID NO: 372) | 5.0 |
| | | 1203369 | Rev | AGTTACAGTCCAGCTGTTG TTGGCAGCGATAAGTT (SEQ ID NO: 372) | 4.6 |
| Penicillium pinophilum GH61 | T169R | 1203370 | Fwd | CTGGACTGTAACTATCCCC TCCCGCATCGCGCCTGGA AACTACGTTT (SEQ ID NO: 373) | 5.0 |
| | | 1203371 | Rev | GGAGGGGATAGTTACAGT CCAGCTGTTGTTGGC (SEQ ID NO: 374) | 4.6 |
| Penicillium pinophilum GH61 | S186K | 1203372 | Fwd | GCCACGAAATCATTGCTCT TCACAAGGCTGGAAACGC AGACGGTGC (SEQ ID NO: 375) | 5.0 |
| | | 1203373 | Rev | GTGAAGAGCAATGATTTCG TGGCGCAAAACGTAGT (SEQ ID NO: 376) | 4.6 |
| Penicillium pinophilum GH61 | S186F | 1203374 | Fwd | GCCACGAAATCATTGCTCT TCACTTTGCTGGAAACGCA GACGGTGC (SEQ ID NO: 377) | 5.0 |
| | | 1203373 | Rev | GTGAAGAGCAATGATTTCG TGGCGCAAAACGTAGT (SEQ ID NO: 378) | 4.6 |
| Penicillium pinophilum GH61 | S186T | 1203375 | Fwd | GCCACGAAATCATTGCTCT TCACACCGCTGGAAACGC AGACGGTGC (SEQ ID NO: 379) | 5.0 |
| | | 1203373 | Rev | GTGAAGAGCAATGATTTCG TGGCGCAAAACGTAGT (SEQ ID NO: 380) | 4.6 |
| Penicillium pinophilum GH61 | S186Y | 1203376 | Fwd | GCCACGAAATCATTGCTCT TCACTACGCTGGAAACGCA GACGGTGC (SEQ ID NO: 381) | 5.0 |
| | | 1203373 | Rev | GTGAAGAGCAATGATTTCG TGGCGCAAAACGTAGT (SEQ ID NO: 382) | 4.6 |
| Penicillium pinophilum GH61 | I200V | 1203377 | Fwd | TGCCCAAAACTACCCTCAA TGCGTCAACTTGGAGATCA CCGGCAGC (SEQ ID NO: 383) | 4.9 |
| | | 1203378 | Rev | GCATTGAGGGTAGTTTTGG GCACCGTCTGCGT (SEQ ID NO: 384) | 4.7 |
| Penicillium pinophilum GH61 | S213E | 1203381 | Fwd | GCAGCGGAACCGCCGCTC CCGAGGGTACCGCTGGCG AAAAGCTC (SEQ ID NO: 385) | 4.9 |
| | | 1203382 | Rev | GGGAGCGGCGGTTCCGCT GCCGGTGATCTC (SEQ ID NO: 386) | 4.7 |

TABLE 16-continued

| Template Backbone | Amino Acid Substitution | Primer ID | Primer Direction | Primer Sequence | PCR fragment size (kb) |
|---|---|---|---|---|---|
| Penicillium pinophilum GH61 | T222R | 1203388 | Fwd | ACCGCTGGCGAAAAGCTC TACCGCTCTACTGACCCCG GTATCTTGG (SEQ ID NO: 387) | 4.9 |
| | | 1203389 | Rev | GTAGAGCTTTTCGCCAGC GGTACCAGAGGGAG (SEQ ID NO: 388) | 4.7 |
| Penicillium pinophilum GH61 | T245P | 1203393 | Fwd | GACCTACGTTATTCCCGGA CCACCCCTGTGGAGCGGT GCTGCCAA (SEQ ID NO: 389) | 4.8 |
| | | 1203394 | Rev | TGGTCCGGGAATAACGTA GGTCGACAAGGATTGG (SEQ ID NO: 390) | 4.8 |

Example 20: Construction of *Thielavia terrestris* GH61 Polypeptide Variants

The *Thielavia terrestris* GH61 polypeptide variants were constructed by SOE-PCR (Splicing by Overhang Extension Polymerase Chain Reaction) with plasmid pDFng157-51. In brief, the first PCR used forward primer EbZn NiaD Fwd and a mutation specific reverse primer (Table 17). The second PCR used reverse primer EbZn NiiA Rev and a mutation specific forward primer (Table 17) containing the sequence coding for the altered amino acid. The mutation specific forward and reverse primers contained 15-20 overlapping nucleotides. The third PCR used the overlapping nucleotides to splice together the fragments produced in the first and second reaction. Finally, using a nested forward primer BGMH110V2F and a nested reverse primer BGMH109V2R, the spliced fragment was amplified by PCR.

The first PCRs for the *T. terrestris* GH61 polypeptide variants contained 0.2 picomole of the EbZn NiaD Fwd primer, 0.4 picomole of the reverse primer listed in Table 17, 10 ng of template (pDFng157-51), 4 nanomoles each dATP, dTTP, dGTP, and dCTP, 1× ADVANTAGE® GC-Melt Buffer, and 2.5 units of ADVANTAGE® GC Genomic LA Polymerase in a final reaction volume of 50 µl. The amplification was performed using an EPPENDORF® MASTERCYCLER® Gradient programmed for 1 cycle at 94° C. for 1 minute; 35 cycles each at 94° C. for 30 seconds, 66° C. for 30 seconds, and 72° C. for 5 minutes; and a final elongation at 72° C. for 10 minutes. The heat block then went to a 10° C. hold stage.

The second PCRs for the *T. terrestris* GH61 variants contained 0.2 picomole of the forward primer listed in Table 17, 0.4 picomole of the EbZn NiiA Rev primer, 10 ng of template (pDFng157-51), 4 nanomoles each dATP, dTTP, dGTP, and dCTP, 1x Advantage® GC-Melt Buffer, and 2.5 units of Advantage® GC Genomic LA Polymerase in a final reaction volume of 50 µl. The amplification was performed using an EPPENDORF® MASTERCYCLER® Gradient programmed for 1 cycle at 94° C. for 1 minute; 35 cycles each at 94° C. for 30 seconds, 66° C. for 30 seconds, and 72° C. for 5 minutes; and a final elongation at 72° C. for 10 minutes. The heat block then went to a 10° C. hold stage.

Each PCR product was analyzed by 1.0% agarose electrophoresis using TAE buffer where a 4.1 to 5.6 kb (as specified in Table 17) PCR product band was observed indicating proper amplification. The remaining 45 microliters were then treated with 10 units of Dpn I and 1× NEB4 to remove the remaining wild-type template. The reaction was incubated for 4 hours at 37° C. and then purified using a MINELUTE® 96 UF Purification Kit. The purified PCR products were resuspended in deionized water to a final volume equal to 20 µl. The concentration of each fragment was measured using a NanoDrop 2000.

The third SOE-PCR for the *T. terrestris* GH61 variants contained 50 to 100 ng of each fragment produced in the first and second PCRs, 4 nanomoles each dATP, dTTP, dGTP, and dCTP, 1× Advantage® GC-Melt Buffer, and 2.5 units of Advantage® GC Genomic LA Polymerase in a final reaction volume of 50 µl. The amplification was performed using an EPPENDORF® MASTERCYCLER® Gradient programmed for 1 cycle at 94° C. for 1 minute; 35 cycles each at 94° C. for 30 seconds, 66° C. for 30 seconds, and 72° C. for 10 minutes; and a final elongation at 72° C. for 10 minutes. The heat block then went to a 10° C. hold stage. Primer BGMH110V2F primer (0.4 picomole) and primer BGMH109V2R (0.4 picomole) were added during the annealing/elongation step of the fifth cycle to allow for the overlapping nucleotides to splice before amplification.

The wild-type fragment was produced using conditions similar to the third PCR. The reaction was composed of 10 ng of template (pDFng157-51), 0.4 picomole of primer BGMH110V2F, 0.4 picomole of primer BGMH109V2R, 1 nanomole each dATP, dTTP, dGTP, and dCTP, 1× Advantage® GC-Melt Buffer, and 2.5 units of Advantage® GC Genomic LA Polymerase in a final reaction volume of 50 µl. The amplification was performed using an EPPENDORF® MASTERCYCLER® Gradient programmed for 1 cycle at 94° C. for 1 minute; 35 cycles each at 94° C. for 30 seconds, 66° C. for 30 seconds, and 72° C. for 10 minutes; and a final elongation at 72° C. for 10 minutes. The heat block then went to a 10° C. hold stage.

Each SOE-PCR product solution was analyzed by 1.0% agarose electrophoresis using TAE buffer where an approximately 8 kb PCR product band was observed indicating proper amplification. The remaining 45 µl of each SOE-PCR product was then purified using a MINELUTE® 96 UF Purification Kit. The purified PCR products were resuspended in deionized water to a final volume equal to 20 µl. The concentration of each fragment was measured using a NanoDrop 2000. The entire volume was then transformed into the *Aspergillus oryzae* COLs1300 strain as described in Example 21.

TABLE 17

| Template Backbone | Amino Acid Substitution | Primer ID | Primer Direction | Primer Sequence | PCR fragment size (kb) |
|---|---|---|---|---|---|
| Thielavia terrestris GH61 | S42I | 1203409 | Fwd | TACCAGGGTTACGATCCGACCAT CTTCCCTTACATGCAGAACCCGC (SEQ ID NO: 391) | 5.6 |
| | | 1203408 | Rev | GGTCGGATCGTAACCCTGGTACG AGACCCCG (SEQ ID NO: 392) | 4.1 |
| Thielavia terrestris GH61 | S42V | 1203410 | Fwd | TACCAGGGTTACGATCCGACCGT CTTCCCTTACATGCAGAACCCGC (SEQ ID NO: 393) | 5.6 |
| | | 1203408 | Rev | GGTCGGATCGTAACCCTGGTACG AGACCCCG (SEQ ID NO: 394) | 4.1 |
| Thielavia terrestris GH61 | Q47L | 1203413 | Fwd | CCGACCTCCTTCCCTTACATGCT CAACCCGCCCATCGTGGTCGG (SEQ ID NO: 395) | 5.5 |
| | | 1203412 | Rev | CATGTAAGGGAAGGAGGTCGGAT CGTAACCCTG (SEQ ID NO: 396) | 4.2 |
| Thielavia terrestris GH61 | S72T | 1203421 | Fwd | TTGCCCCGGATGCCTTCGCCACC GGCGATATCATCTGCCACAAGA (SEQ ID NO: 397) | 5.4 |
| | | 1203420 | Rev | GGCGAAGGCATCCGGGGCAACA AAGCCGTTG (SEQ ID NO: 398) | 4.3 |
| Thielavia terrestris GH61 | V139C | 1203427 | Fwd | CGAGTTCTTCAAGATCGACGAGT GCGGCCTGGTCGACGGCAGCTC (SEQ ID NO: 399) | 5.3 |
| | | 1203428 | Rev | CTCGTCGATCTTGAAGAACTCGA GCTTGGTCTTG (SEQ ID NO: 400) | 4.4 |
| Thielavia terrestris GH61 | V139G | 1203433 | Fwd | CGAGTTCTTCAAGATCGACGAGG GCGGCCTGGTCGACGGCAGCTC (SEQ ID NO: 401) | 5.3 |
| | | 1203428 | Rev | CTCGTCGATCTTGAAGAACTCGA GCTTGGTCTTG (SEQ ID NO: 402) | 4.4 |
| Thielavia terrestris GH61 | V150I | 1203434 | Fwd | ACGGCAGCTCGGCGCCCGGTAT CTGGGGCTCCGACCAGCTCAT (SEQ ID NO: 403) | 5.2 |
| | | 1203435 | Rev | ACCGGGCGCCGAGCTGCCGTCG ACCAGG (SEQ ID NO: 404) | 4.5 |
| Thielavia terrestris GH61 | V165L | 1203442 | Fwd | GCCAACAACAACTCGTGGCTCCT CGAGATCCCGCCCACCATCGC (SEQ ID NO: 405) | 5.2 |
| | | 1203441 | Rev | GAGCCACGAGTTGTTGTTGGCGA TGAGCTGGT (SEQ ID NO: 406) | 4.5 |
| Thielavia terrestris GH61 | A246P | 1203469 | Fwd | CCTACACCGTCCCGGGGCCGCC GCTCATCTCCGGCGCCGTCAG (SEQ ID NO: 407) | 4.9 |
| | | 1203470 | Rev | CGGCCCCGGGACGGTGTAGGTG ATCGGGG (SEQ ID NO: 408) | 4.8 |

Example 21: Expression of the *T. aurantiacus* GH61A, *P. emersonii* GH61A, *A. aculeatus* GH61, *Penicillium pinophilum* GH61, and *Thielavia terrestris* GH61 Polypeptides Variants in *Aspergillus oryzae* COLs1300

*Aspergillus oryzae* COLs1300 was inoculated onto a COVE-N-Gly plate containing 10 mM urea and incubated at 34° C. until confluent. Spores were collected from the plate by washing with 10 ml of YP medium. The whole spore suspension was used to inoculate 100 ml of COL1300 protoplasting cultivation medium in a 500 ml polycarbonate shake flask. The shake flask was incubated at 30° C. with agitation at 200 rpm for 16-20 hours. Mycelia were filtered through a funnel lined with MIRACLOTH® and washed with 200 ml of 0.6 M $MgSO_4$. Washed mycelia were resuspended in 20 ml of COLs1300 protoplasting solution in a 125 ml sterile polycarbonate shake flask and incubated at room temperature for 3 minutes. One ml of a solution of 12 mg of BSA per ml of deionized water was added to the shake flask and the shake flask was then incubated at 37° C. with mixing at 65 rpm for 100-150 minutes until protoplasting was complete. The mycelia/protoplast mixture was filtered through a funnel lined with MIRACLOTH® in to a 50 ml conical tube and overlayed with 5 ml of ST solution. The 50 ml conical tube was centrifuged at 1050×g for 15 minutes with slow acceleration/deceleration. After centrifugation, the liquid was separated in 3 phases. The interphase which contained the protoplasts was transferred to a new 50 ml conical tube. Two volumes of STC solution were added to the protoplasts followed by centrifugation at 1050×g for 5 minutes. The supernatant was discarded and the protoplasts were washed twice with 5 ml of STC solution with resuspension of the protoplast pellet, centrifugation at 1050×g for 5 minutes, and decanting of the supernatant each time. After the final decanting, the protoplast pellet was resuspended in STC solution at a concentration of 5×10 7/ml. Protoplasts were frozen at −80° C. until transformation.

A 15 µl volume of each mutant fragment, as described in Examples 16-20, was used to transform 100 µl of *A. oryzae* COLs1300 protoplasts in a 15 ml round bottom tube. After an initial incubation at room temperature for 15 minutes, 300 µl of PEG solution was added to the 15 ml round bottom tube containing the transformation mixture. The reaction was incubated for an additional 15 minutes at room temperature. Six ml of melted top agar was added to the reaction and the whole mixture was poured evenly onto a sucrose agar plate supplemented with 10 mM $NaNO_3$ and left at room temperature until the top agar was set. The plates were incubated at 37° C. for 4-6 days. Resulting transformants were picked using sterile inoculating loops and transferred to plates containing COVE-N-gly medium and incubated at 34° C. for approximately 4 days (until sporulation). Spores were inoculated into a deep well 48 well plate containing 0.5 ml of MDU2BP medium incubated at 34° C. for 3 days, stationary in a humidified box. Samples were harvested on the third day by removing the mycelia mat.

Example 22: Determination of Tm (Melting Temperature) of *T. aurantiacus* GH61A, *P. emersonii* GH61A, *A. aculeatus* GH61, *Penicillium pinophilum* GH61, and *Thielavia terrestris* GH61 Variants by Protein Thermal Unfolding Analysis Protein thermal unfolding of the *Thermoascus aurantiacus* GH61A, *Penicillium emersonii* GH61A, *Aspergillus aculeatus* GH61, *Penicillium pinophilum* GH61, *Thielavia terrestris* GH61 variants was determined by protein thermal unfolding analysis described according to Example 10. The broths of the variants, and wild-type polypeptides thereof were prepared as described in Example 21. Average reading of triplicate broths from one to five transformants for each variant was determined, and the increase in Tm for each variant is shown in Table 18.

TABLE 18

Increase of melting temperatures (° C.) of *T. aurantiacus* GH61A, *P. emersonii* GH61A, *A. aculeatus* GH61, *P. pinophilum* GH61, and *T. terrestris* GH61 polypeptides variants comparing to wild-type polypeptide as determined by protein thermal unfolding analysis

| Wild-Type *T. aurantiacus* GH61A | Wild-Type Tm (° C.) 73.0 |
|---|---|
| Mutation | Δ° C. |
| *T. aurantiacus* GH61A Q26I | 3 |
| *T. aurantiacus* GH61A Q42I | 2 |
| *T. aurantiacus* GH61A Q42V | 2 |
| *T. aurantiacus* GH61A S123R | 2 |
| *T. aurantiacus* GH61A S138E | 3 |
| *T. aurantiacus* GH61A S138K | 3 |
| *T. aurantiacus* GH61A S138L | 3 |
| *T. aurantiacus* GH61A T163V | 3 |
| *T. aurantiacus* GH61A T163E | 3 |
| *T. aurantiacus* GH61A S186K | 3 |
| *T. aurantiacus* GH61A S186F | 3 |
| *T. aurantiacus* GH61A S186T | 3 |
| *T. aurantiacus* GH61A S186Y | 3 |
| *T. aurantiacus* GH61A I200V | 3 |
| *T. aurantiacus* GH61A A213E | 3 |

TABLE 18-continued

Increase of melting temperatures (° C.) of *T. aurantiacus* GH61A, *P. emersonii* GH61A, *A. aculeatus* GH61, *P. pinophilum* GH61, and *T. terrestris* GH61 polypeptides variants comparing to wild-type polypeptide as determined by protein thermal unfolding analysis

| *T. aurantiacus* GH61A | A219C | 3 |
|---|---|---|
| *T. aurantiacus* GH61A | A219E | 3 |
| *T. aurantiacus* GH61A | A219Q | 3 |
| *T. aurantiacus* GH61A | T248R | 3 |

| Wild-Type *P. emersonii* GH61A | Wild-Type Tm (° C.) 67.2 |
|---|---|
| Mutation | Δ° C. |
| *P. emersonii* GH61A S46V | 2 |
| *P. emersonii* GH61A G76Q | 1 |
| *P. emersonii* GH61A S127R | 1 |

| Wild-Type *A. aculeatus* GH61 | Wild-Type Tm (° C.) 44.8 |
|---|---|
| Mutation | Δ° C. |
| *A. aculeatus* GH61 D70Q | 1 |
| *A. aculeatus* GH61 D70T | 2 |
| *A. aculeatus* GH61 S136C | 2 |
| *A. aculeatus* GH61 S136G | 1 |
| *A. aculeatus* GH61 T147I | 3 |
| *A. aculeatus* GH61 T161V | 2 |
| *A. aculeatus* GH61 T161F | 2 |
| *A. aculeatus* GH61 D167R | 5 |
| *A. aculeatus* GH61 S184K | 2 |
| *A. aculeatus* GH61 S184T | 2 |
| *A. aculeatus* GH61 S184Y | 3 |
| *A. aculeatus* GH61 L198I | 2 |
| *A. aculeatus* GH61 L198V | 1 |
| *A. aculeatus* GH61 S217M | 2 |
| *A. aculeatus* GH61 S217Q | 2 |
| *A. aculeatus* GH61 K220R | 2 |
| *A. aculeatus* GH61 A243P | 3 |

| Wild-Type *P. pinophilum* GH61 | Wild-Type Tm (° C.) 55.4 |
|---|---|
| Mutation | Δ° C. |
| *P. pinophilum* GH61 S34F | 2 |
| *P. pinophilum* GH61 Q42I | 4 |
| *P. pinophilum* GH61 Q42V | 4 |
| *P. pinophilum* GH61 S47L | 2 |
| *P. pinophilum* GH61 A56C | 2 |
| *P. pinophilum* GH61 A56E | 2 |
| *P. pinophilum* GH61 G138C | 5 |
| P. pinophilum GH61 T149I | 3 |
| *P. pinophilum* GH61 V164C | 4 |
| *P. pinophilum* GH61 V164L | 3 |
| *P. pinophilum* GH61 I166L | 2 |
| *P. pinophilum* GH61 T169R | 2 |
| *P. pinophilum* GH61 S186K | 5 |
| *P. pinophilum* GH61 S186F | 5 |
| *P. pinophilum* GH61 S186T | 2 |
| *P. pinophilum* GH61 S186Y | 4 |
| *P. pinophilum* GH61 I200V | 2 |
| *P. pinophilum* GH61 S213E | 2 |
| *P. pinophilum* GH61 T222R | 5 |
| *P. pinophilum* GH61 T245P | 3 |

| Wild-Type *T. terrestris* GH61 | Wild-Type Tm (° C.) 56.1 |
|---|---|
| Mutation | Δ° C. |
| *T. terrestris* GH61 S42I | 2 |
| *T. terrestris* GH61 S42V | 2 |
| *T. terrestris* GH61 Q47L | 2 |
| *T. terrestris* GH61 S72T | 2 |
| *T. terrestris* GH61 V139C | 2 |
| *T. terrestris* GH61 V139G | 2 |

TABLE 18-continued

Increase of melting temperatures (° C.) of *T. aurantiacus* GH61A, *P. emersonii* GH61A, *A. aculeatus* GH61, *P. pinophilum* GH61, and *T. terrestris* GH61 polypeptides variants comparing to wild-type polypeptide as determined by protein thermal unfolding analysis

| | | |
|---|---|---|
| *T. terrestris* GH61 | V150I | 1 |
| *T. terrestris* GH61 | V165L | 2 |
| *T. terrestris* GH61 | A246P | 3 |

The present invention is further described by the following numbered paragraphs:

[1] A GH61 polypeptide variant, comprising a substitution at one or more positions corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250 of the mature polypeptide of SEQ ID NO: 30, wherein the variant has cellulolytic enhancing activity and wherein the variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the amino acid sequence of a parent GH61 polypeptide.

[2] The variant of paragraph 1, wherein the parent GH61 polypeptide is selected from the group consisting of: (a) a polypeptide having at least 60% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411; (b) a polypeptide encoded by a polynucleotide that hybridizes under at least low stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410, or (ii) the full-length complement of (i); (c) a polypeptide encoded by a polynucleotide having at least 60% sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410; and (d) a fragment of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411, which has cellulolytic enhancing activity.

[3] The variant of paragraph 2, wherein the parent GH61 polypeptide has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99% or 100% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

[4] The variant of paragraph 2, wherein the parent GH61 polypeptide is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410 or (ii) the full-length complement of (i).

[5] The variant of paragraph 2, wherein the parent GH61 polypeptide is encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99%, or 100% sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410.

[6] The variant of paragraph 2, wherein the parent GH61 polypeptide comprises or consists of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

[7] The variant of paragraph 2, wherein the parent GH61 polypeptide is a fragment of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411, wherein the fragment has cellulolytic enhancing activity.

[8] The variant of any of paragraphs 1-7, which has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

[9] The variant of any of paragraphs 2-8, wherein the fragment of the variant consists of at least 85% of the amino acid residues, e.g., at least 90% of the amino acid residues or at least 95% of the amino acid residues of the mature polypeptide of the parent GH61 polypeptide.

[10] The variant of any of paragraphs 1-9, wherein the number of substitutions is 1-29, e.g., 1, 2, 3, 4, 5, 6, 7, 8, 9, 10, 11, 12, 13, 14, 15, 16, 17, 18, 19, 20, 21, 22, 23, 24, 25, 26, 27, and 28 substitutions

[11] The variant of any of paragraphs 1-10, which comprises a substitution at a position corresponding to position 26.

[12] The variant of paragraph 11, wherein the substitution is Ile.

[13] The variant of any of paragraphs 1-12, which comprises a substitution at a position corresponding to position 32.

[14] The variant of paragraph 13, wherein the substitution is Glu or Ser.

[15] The variant of any of paragraphs 1-14, which comprises a substitution at a position corresponding to position 34.

[16] The variant of paragraph 15, wherein the substitution is Phe.

[17] The variant of any of paragraphs 1-16, which comprises a substitution at a position corresponding to position 40.

[18] The variant of paragraph 17, wherein the substitution is Ala.

[19] The variant of any of paragraphs 1-18, which comprises a substitution at a position corresponding to position 41.

[20] The variant of paragraph 19, wherein the substitution is Thr.

[21] The variant of any of paragraphs 1-20, which comprises a substitution at a position corresponding to position 42.

[22] The variant of paragraph 21, wherein the substitution is Ile, Glu, or Val.

[23] The variant of any of paragraphs 1-22, which comprises a substitution at a position corresponding to position 47.

[24] The variant of paragraph 23, wherein the substitution is Glu, Leu, or Arg.

[25] The variant of any of paragraphs 1-24, which comprises a substitution at a position corresponding to position 56.

[26] The variant of paragraph 25, wherein the substitution is Cys, Glu, or Thr.

[27] The variant of any of paragraphs 1-26, which comprises a substitution at a position corresponding to position 72.

[28] The variant of paragraph 27, wherein the substitution is Gln or Thr.

[29] The variant of any of paragraphs 1-28, which comprises a substitution at a position corresponding to position 102.

[30] The variant of paragraph 29, wherein the substitution is Lys or Pro.

[31] The variant of any of paragraphs 1-30, which comprises a substitution at a position corresponding to position 123.

[32] The variant of paragraph 31, wherein the substitution is Arg.

[33] The variant of any of paragraphs 1-32, which comprises a substitution at a position corresponding to position 138.

[34] The variant of paragraph 33, wherein the substitution is Cys, Glu, Gly, Lys, Leu, or Met.

[35] The variant of any of paragraphs 1-34, which comprises a substitution at a position corresponding to position 149.

[36] The variant of paragraph 35, wherein the substitution is Ile.

[37] The variant of any of paragraphs 1-36, which comprises a substitution at a position corresponding to position 152.

[38] The variant of paragraph 37, wherein the substitution is Ser.

[39] The variant of any of paragraphs 1-38, which comprises a substitution at a position corresponding to position 163.

[40] The variant of paragraph 39, wherein the substitution is Glu, Phe, or Val.

[41] The variant of any of paragraphs 1-40, which comprises a substitution at a position corresponding to position 164.

[42] The variant of paragraph 41, wherein the substitution is Cys or Leu.

[43] The variant of any of paragraphs 1-42, which comprises a substitution at a position corresponding to position 166.

[44] The variant of paragraph 43, wherein the substitution is Leu.

[45] The variant of any of paragraphs 1-44, which comprises a substitution at a position corresponding to position 169.

[46] The variant of paragraph 45, wherein the substitution is Arg or Cys.

[47] The variant of any of paragraphs 1-46, which comprises a substitution at a position corresponding to position 173.

[48] The variant of paragraph 47, wherein the substitution is Cys.

[49] The variant of any of paragraphs 1-48, which comprises a substitution at a position corresponding to position 186.

[50] The variant of paragraph 49, wherein the substitution is Phe, Lys, Thr, or Tyr.

[51] The variant of any of paragraphs 1-50, which comprises a substitution at a position corresponding to position 200.

[52] The variant of paragraph 51, wherein the substitution is Ile or Val.

[53] The variant of any of paragraphs 1-52, which comprises a substitution at a position corresponding to position 207.

[54] The variant of paragraph 53, wherein the substitution is Pro.

[55] The variant of any of paragraphs 1-54, which comprises a substitution at a position corresponding to position 213.

[56] The variant of paragraph 55, wherein the substitution is Glu.

[57] The variant of any of paragraphs 1-56, which comprises a substitution at a position corresponding to position 219.

[58] The variant of paragraph 57, wherein the substitution is Glu, Met, Gin, or Cys.

[59] The variant of any of paragraphs 1-58, which comprises a substitution at a position corresponding to position 222.

[60] The variant of paragraph 59, wherein the substitution is Arg.

[61] The variant of any of paragraphs 1-60, which comprises a substitution at a position corresponding to position 234.

[62] The variant of paragraph 61, wherein the substitution is Gly or Lys.

[63] The variant of any of paragraphs 1-62, which comprises a substitution at a position corresponding to position 246.

[64] The variant of paragraph 63, wherein the substitution is Pro.

[65] The variant of any of paragraphs 1-64, which comprises a substitution at a position corresponding to position 249.

[66] The variant of paragraph 65, wherein the substitution is Gin, Arg, or Cys.

[67] The variant of any of paragraphs 1-66, which comprises a substitution at a position corresponding to position 250.

[68] The variant of paragraph 67, wherein the substitution is Cys.

[69] The variant of any of paragraphs 1-68, which comprises a substitution at two positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[70] The variant of any of paragraphs 1-68, which comprises a substitution at three positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[71] The variant of any of paragraphs 1-68, which comprises a substitution at four positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[72] The variant of any of paragraphs 1-68, which comprises a substitution at five positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[73] The variant of any of paragraphs 1-68, which comprises a substitution at six positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[74] The variant of any of paragraphs 1-68, which comprises a substitution at seven positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[75] The variant of any of paragraphs 1-68, which comprises a substitution at eight positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[76] The variant of any of paragraphs 1-68, which comprises a substitution at nine positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[77] The variant of any of paragraphs 1-68, which comprises a substitution at ten positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[78] The variant of any of paragraphs 1-68, which comprises a substitution at eleven positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[79] The variant of any of paragraphs 1-68, which comprises a substitution at twelve positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[80] The variant of any of paragraphs 1-68, which comprises a substitution at thirteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[81] The variant of any of paragraphs 1-68, which comprises a substitution at fourteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[82] The variant of any of paragraphs 1-68, which comprises a substitution at fifteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[83] The variant of any of paragraphs 1-68, which comprises a substitution at sixteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[84] The variant of any of paragraphs 1-68, which comprises a substitution at seventeen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[85] The variant of any of paragraphs 1-68, which comprises a substitution at eighteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[86] The variant of any of paragraphs 1-68, which comprises a substitution at nineteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[87] The variant of any of paragraphs 1-68, which comprises a substitution at twenty positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[88] The variant of any of paragraphs 1-68, which comprises a substitution at twenty-one positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[89] The variant of any of paragraphs 1-68, which comprises a substitution at twenty-two positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[90] The variant of any of paragraphs 1-68, which comprises a substitution at twenty-three positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[91] The variant of any of paragraphs 1-68, which comprises a substitution at twenty-four positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[92] The variant of any of paragraphs 1-68, which comprises a substitution at twenty-five positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[93] The variant of any of paragraphs 1-68, which comprises a substitution at twenty-six positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[94] The variant of any of paragraphs 1-68, which comprises a substitution at twenty-seven positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[95] The variant of any of paragraphs 1-68, which comprises a substitution at each position corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250.

[96] The variant of any of paragraphs 1-95, which comprises one or more substitutions selected from the group consisting of S26I; G32E,S; Y34F; V40A; N41T; Q42I,E,V; S47E,L,R; S56C,E,T; S72Q,T; T102K,P; A123R; Q138C,E,G,K,L,M; V149I; D152S; T163E,F,V; V164C,L; I166L; S169R,C; S186F,K,T,Y; F200I,V; G207P; S213E; S219E,M,Q,C; K222R; S234G,K; A246P; N249Q,R,C, and A250C.

[97] The variant of any of paragraphs 1-96, which comprises the substitutions S173C+F253C of the mature polypeptide of SEQ ID NO: 36.

[98] The variant of any of paragraphs 1-96, which comprises the substitutions L111V+D152S+M155L+A162W+Q138K+K229W of the mature polypeptide of SEQ ID NO: 30.

[99] The variant of any of paragraphs 1-96, which comprises the substitutions L111V+D152S+M155L+A162W+547E+K229W of the mature polypeptide of SEQ ID NO: 30.

[100] The variant of any of paragraphs 1-96, which comprises the substitutions L111V+D152S+M155L+A162W+S56A+K229W of the mature polypeptide of SEQ ID NO: 30.

[101] The variant of any of paragraphs 1-96, which comprises the substitutions L111V+D152S+M155L+A162W+T102K+K229W of the mature polypeptide of SEQ ID NO: 30.

[102] The variant of any of paragraphs 1-96, which comprises the substitutions L111V+D152S+M155L+A162W+S186T+K229W of the mature polypeptide of SEQ ID NO: 30.

[103] The variant of any of paragraphs 1-96, which comprises the substitutions L111V+D152S+M155L+A162W+K229W+S234G of the mature polypeptide of SEQ ID NO: 30.

[104] The variant of any of paragraphs 1-96, which comprises the substitutions L111V+D152S+M155L+A162W+T102K+E105K+K229W of the mature polypeptide of SEQ ID NO: 30.

[105] The variant of any of paragraphs 1-96, which comprises the substitutions L111V+D152S+M155L+A162W+Q138K+G188F+K229W of the mature polypeptide of SEQ ID NO: 30.

[106] The variant of any of paragraphs 1-96, which comprises the substitutions L111V+D152S+M155L+A162W+Q138K+V149I+G188F+K229W of the mature polypeptide of SEQ ID NO: 30.

[107] The variant of any of paragraphs 1-96, which comprises the substitutions L111V+D152S+M155L+A162W+S169C+G188F+K229W+A250C of the mature polypeptide of SEQ ID NO: 30.

[108] The variant of any of paragraphs 1-96, which comprises the substitutions L111V+D152S+M155L+A162W+S72T+Q138K+V149I+G188F+K229W of the mature polypeptide of SEQ ID NO: 30.

[109] The variant of any of paragraphs 1-96, which comprises the substitutions L111V+D152S+M155L+A162W+Q138K+V149I+G188F+G207P+K229W of the mature polypeptide of SEQ ID NO: 30

[110] The variant of any of paragraphs 1-109, which further comprises a substitution at positions corresponding to positions 111, 152, 155, and 162 of the mature polypeptide of SEQ ID NO: 30, wherein the variant has cellulolytic enhancing activity.

[111] The variant of paragraph 110, wherein the number of additional substitutions is 1-4, e.g., such as 1, 2, 3, or 4 substitutions.

[112] The variant of paragraph 110 or 111, which comprises a substitution at a position corresponding to position 111.

[113] The variant of paragraph 112, wherein the substitution is Val.

[114] The variant of any of paragraphs 110-113, which comprises a substitution at a position corresponding to position 152.

[115] The variant of paragraph 114, wherein the substitution is Ser.

[116] The variant of any of paragraphs 110-115, which comprises a substitution at a position corresponding to position 155.

[117] The variant of paragraph 116, wherein the substitution is Leu.

[118] The variant of any of paragraphs 110-117, which comprises a substitution at a position corresponding to position 162.

[119] The variant of paragraph 118, wherein the substitution is Trp.

[120] The variant of any of paragraphs 110-119, which comprises a substitution at two positions corresponding to any of positions 111, 152, 155, and 162.

[121] The variant of any of paragraphs 110-119, which comprises a substitution at three positions corresponding to any of positions 111, 152, 155, and 162.

[122] The variant of any of paragraphs 110-119, which comprises a substitution at each position corresponding to positions 111, 152, 155, and 162.

[123] The variant of any of paragraphs 110-119, which comprises one or more substitutions selected from the group consisting of L111V, D152S, M155L, and A162W.

[124] The variant of any of paragraphs 1-123, which further comprises a substitution at positions corresponding to positions 96, 98, 200, 202, and 204 of the mature polypeptide of SEQ ID NO: 30, wherein the variant has cellulolytic enhancing activity.

[125] The variant of paragraph 124, wherein the number of additional substitutions is 1-5, e.g., such as 1, 2, 3, 4, or 5 substitutions.

[126] The variant of paragraph 124 or 125, which comprises a substitution at a position corresponding to position 96.

[127] The variant of paragraph 126, wherein the substitution is Val.

[128] The variant of any of paragraphs 124-127, which comprises a substitution at a position corresponding to position 98.

[129] The variant of paragraph 128 wherein the substitution is Leu.

[130] The variant of any of paragraphs 124-129, which comprises a substitution at a position corresponding to position 200.

[131] The variant of paragraph 130, wherein the substitution is Ile.

[132] The variant of any of paragraphs 124-131, which comprises a substitution at a position corresponding to position 202.

[133] The variant of paragraph 132, wherein the substitution is Leu.

[134] The variant of any of paragraphs 124-133, which comprises a substitution at a position corresponding to position 204.

[135] The variant of paragraph 134, wherein the substitution is Val.

[136] The variant of any of paragraphs 124-135, which comprises a substitution at two positions corresponding to any of positions 96, 98, 200, 202, and 204.

[137] The variant of any of paragraphs 124-135, which comprises a substitution at three positions corresponding to any of positions 96, 98, 200, 202, and 204.

[138] The variant of any of paragraphs 124-135, which comprises a substitution at four positions corresponding to any of positions 96, 98, 200, 202, and 204.

[139] The variant of any of paragraphs 124-135, which comprises a substitution at each position corresponding to positions 96, 98, 200, 202, and 204.

[140] The variant of any of paragraphs 124-135, which comprises one or more substitutions selected from the group consisting of I96V, F98L, F200I, I202L, and I204V.

[141] The variant of any of paragraphs 1-140, which further comprises a substitution at positions corresponding to positions 105, 154, 188, 189, 216, and 229 of the mature polypeptide of SEQ ID NO: 30, wherein the variant has cellulolytic enhancing activity.

[142] The variant of paragraph 141, wherein the number of additional substitutions is 1-6, e.g., 1, 2, 3, 4, 5, or 6 substitutions.

[143] The variant of paragraph 141 or 142, which comprises a substitution at a position corresponding to position 105.

[144] The variant of paragraph 143, wherein the substitution is Pro or Lys.

[145] The variant of any of paragraphs 141-144, which comprises a substitution at a position corresponding to position 154.

[146] The variant of paragraph 145, wherein the substitution is Leu.

[147] The variant of any of paragraphs 141-146, which comprises a substitution at a position corresponding to position 188.

[148] The variant of paragraph 147, wherein the substitution is Ala or Trp.

[149] The variant of any of paragraphs 141-148, which comprises a substitution at a position corresponding to position 189.

[150] The variant of paragraph 149, wherein the substitution is Lys.

[151] The variant of any of paragraphs 141-150, which comprises a substitution at a position corresponding to position 216.

[152] The variant of paragraph 151, wherein the substitution is Leu or Tyr.

[153] The variant of any of paragraphs 141-152, which comprises a substitution at a position corresponding to position 229.

[154] The variant of paragraph 153, wherein the substitution is Trp, His, Ile, or Tyr.

[155] The variant of any of paragraphs 141-154, which comprises one or more substitutions selected from the group consisting of E105P,K; E154I, L; G188F, M, A,W; N189H, K; A216L,Y; and A229W,H,I,Y.

[156] The variant of any of paragraphs 1-155, which has an increased thermostability of at least 1.01-fold, e.g., at least 1.05-fold, at least 1.1-fold, at least 1.2-fold, at least 1.3-fold, at least 1.4-fold, at least 1.5-fold, at least 1.8-fold, at least 2-fold, at least 5-fold, at least 10-fold, at least 15-fold, at least 20-fold, at least 25-fold, at least 30-fold, at least 50-fold, at least 75-fold, or at least 100-fold compared to the parent.

[157] An isolated polynucleotide encoding the variant of any of paragraphs 1-156.

[158] A nucleic acid construct comprising the polynucleotide of paragraph 157.

[159] An expression vector comprising the polynucleotide of paragraph 157.

[160] A recombinant host cell comprising the polynucleotide of paragraph 157.

[161] A method of producing a GH61 polypeptide variant, comprising: cultivating the host cell of paragraph 160 under conditions suitable for expression of the variant.

[162] The method of paragraph 161, further comprising recovering the variant.

[163] A transgenic plant, plant part or plant cell transformed with the polynucleotide of paragraph 157.

[164] A method of producing a variant of any of paragraphs 1-156, comprising: cultivating a transgenic plant or a plant cell comprising a polynucleotide encoding the variant under conditions conducive for production of the variant.

[165] The method of paragraph 164, further comprising recovering the variant.

[166] A method for obtaining a GH61 polypeptide variant, comprising introducing into a parent GH61 polypeptide a substitution at one or more positions corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250 of the mature polypeptide of SEQ ID NO: 30, wherein the variant has cellulolytic enhancing activity; and recovering the variant.

[167] The method of paragraph 166, further comprising introducing into the parent GH61 polypeptide a substitution at one or more positions corresponding to positions 111, 152, 155, and 162 of the mature polypeptide of SEQ ID NO: 30, wherein the variant has cellulolytic enhancing activity.

[168] The method of paragraph 166 or 167, further comprising introducing into the parent GH61 polypeptide a substitution at one or more positions corresponding to positions 96, 98, 200, 202, and 204 of the mature polypeptide of SEQ ID NO: 30, wherein the variant has cellulolytic enhancing activity.

[169] The method of any of paragraphs 166-168, further comprising introducing into the parent GH61 polypeptide a substitution at one or more positions corresponding to positions 105, 154, 188, 189, 216, and 229 of the mature polypeptide of SEQ ID NO: 30, wherein the variant has cellulolytic enhancing activity.

[170] A process for degrading or converting a cellulosic material, comprising: treating the cellulosic material with an enzyme composition in the presence of the GH61 polypeptide variant having cellulolytic enhancing activity of any of paragraphs 1-156.

[171] The process of paragraph 170, wherein the cellulosic material is pretreated.

[172] The process of paragraph 170 or 171, further comprising recovering the degraded cellulosic material.

[173] The process of any of paragraphs 170-172, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[174] The process of paragraph 173, wherein the cellulase is one or more enzymes selected from the group consisting of an endoglucanase, a cellobiohydrolase, and a beta-glucosidase.

[175] The process of paragraph 173, wherein the hemicellulase is one or more enzymes selected from the group consisting of a xylanase, an acetylxylan esterase, a feruloyl esterase, an arabinofuranosidase, a xylosidase, and a glucuronidase.

[176] The process of any of paragraphs 170-175, wherein the degraded cellulosic material is a sugar.

[177] The process of paragraph 176, wherein the sugar is selected from the group consisting of glucose, xylose, mannose, galactose, and arabinose.

[178] A process for producing a fermentation product, comprising: (a) saccharifying a cellulosic material with an enzyme composition in the presence of the GH61 polypeptide variant having cellulolytic enhancing activity of any of paragraphs 1-156; (b) fermenting the saccharified cellulosic material with one or more fermenting microorganisms to produce the fermentation product; and (c) recovering the fermentation product from the fermentation.

[179] The process of paragraph 178, wherein the cellulosic material is pretreated.

[180] The process of paragraph 178 or 179, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[181] The process of paragraph 180, wherein the cellulase is one or more enzymes selected from the group consisting of an endoglucanase, a cellobiohydrolase, and a beta-glucosidase.

[182] The process of paragraph 180, wherein the hemicellulase is one or more enzymes selected from the group consisting of a xylanase, an acetylxylan esterase, a feruloyl esterase, an arabinofuranosidase, a xylosidase, and a glucuronidase.

[183] The process of any of paragraphs 178-182, wherein steps (a) and (b) are performed simultaneously in a simultaneous saccharification and fermentation.

[184] The process of any of paragraphs 178-183, wherein the fermentation product is an alcohol, an alkane, a cycloalkane, an alkene, an amino acid, a gas, isoprene, a ketone, an organic acid, or polyketide.

[185] A process of fermenting a cellulosic material, comprising: fermenting the cellulosic material with one or more fermenting microorganisms, wherein the cellulosic material is saccharified with an enzyme composition in the presence of the GH61 polypeptide variant having cellulolytic enhancing activity of any of paragraphs 1-156.

[186] The process of paragraph 185, wherein the cellulosic material is pretreated before saccharification.

[187] The process of paragraph 185 or 186, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[188] The process of paragraph 187, wherein the cellulase is one or more enzymes selected from the group consisting of an endoglucanase, a cellobiohydrolase, and a beta-glucosidase.

[189] The process of paragraph 187, wherein the hemicellulase is one or more enzymes selected from the group consisting of a xylanase, an acetylxylan esterase, a feruloyl esterase, an arabinofuranosidase, a xylosidase, and a glucuronidase.

[190] The process of any of paragraphs 185-189, wherein the fermenting of the cellulosic material produces a fermentation product.

[191] The process of paragraph 190, further comprising recovering the fermentation product from the fermentation.

[182] The process of paragraph 190 or 191, wherein the fermentation product is an alcohol, an alkane, a cycloalkane, an alkene, an amino acid, a gas, isoprene, a ketone, an organic acid, or polyketide.

[193] A composition comprising the variant of any of paragraphs 1-156.

[194] A whole broth formulation or cell culture composition, comprising the variant of any of paragraphs 1-156.

[195] A detergent composition, comprising a surfactant and the variant of any of paragraphs 1-156.

[196] The composition of paragraph 195, further comprising one or more enzymes selected from the group consisting of an amylase, arabinase, cutinase, carbohydrase, cellulase, galactanase, laccase, lipase, mannanase, oxidase, pectinase, peroxidase, protease, and xylanase.

[197] The composition of paragraph 195 or 196, which is formulated as a bar, a tablet, a powder, a granule, a paste, or a liquid.

[198] A method for cleaning or washing a hard surface or laundry, the method comprising contacting the hard surface or the laundry with the composition of any of paragraphs 195-197.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A variant of a parent GH61 polypeptide having cellulolytic enhancing activity, comprising a substitution at one or more positions corresponding to positions 138, 219, 26, 32, 34, 40, 41, 42, 47, 56, 72, 102, 123, 149, 152, 163, 164, 166, 169, 186, 200, 207, 213, 222, 234, 246, 249, and 250 of the mature polypeptide of SEQ ID NO: 30 for numbering, wherein the substitution at position 138 is with Cys, Glu, Gly, Lys, Leu, or Met, the substitution at position 219 is with Glu, Met, Gln, or Cys, the substitution at position 26 is with Ile, the substitution at position 32 is with Glu or Ser, the substitution at position 34 is with Phe, the substitution at position 40 is with Ala, the substitution at position 41 is with Thr, the substitution at position 42 is with Ile, Glu, or Val, the substitution at position 47 is with Glu, Leu, or Arg, the substitution at position 56 is with Cys, Glu, or Thr, the substitution at position 72 is with Gln or Thr, the substitution at position 102 is with Lys or Pro, the substitution at position 123 is with Arg, the substitution at position 149 is with Ile, the substitution at position 152 is with Ser, the substitution at position 163 is with Glu, Phe, or Val, the substitution at position 164 is with Cys or Leu, the substitution at position 166 is with Leu, the substitution at position 169 is with Arg or Cys, the substitution at position 186 is with Phe, Lys, Thr, or Tyr, the substitution at position 200 is with Ile or Val, the substitution at position 207 is with Pro, the substitution at position 213 is with Glu, the substitution at position 222 is with Arg, the substitution at position 234 is with Gly or Lys, the substitution at position 246 is with Pro, the substitution at position 249 is with Gln, Arg, or Cys, and the substitution at position 250 is with Cys, wherein the variant has cellulolytic enhancing activity, wherein the variant has increased thermostability relative to the parent GH61 polypeptide, and wherein the parent GH61 polypeptide is selected from the group consisting of:
   (a) a GH61 polypeptide having at least 90% sequence identity to the mature polypeptide of SEQ ID NO: 14, SEQ ID NO: 34, SEQ ID NO: 60, SEQ ID NO: 62, or SEQ ID NO: 64; and
   (b) a GH61 polypeptide encoded by a polynucleotide having at least 90% sequence identity to the mature polypeptide coding sequence of SEQ ID NO: 13, SEQ ID NO: 33, SEQ ID NO: 59, SEQ ID NO: 61 or SEQ ID NO: 63;
   wherein the variant has at least 90% but less than 100% sequence identity to the mature polypeptide of SEQ ID NO: 14, SEQ ID NO: 34, SEQ ID NO: 60, SEQ ID NO: 62, or SEQ ID NO: 64.

2. The variant of claim 1, wherein the parent GH61 polypeptide has at least 95% sequence identity to the mature polypeptide of SEQ ID NO: 14, SEQ ID NO: 34, SEQ ID NO: 60, SEQ ID NO: 62, or SEQ ID NO: 64.

3. The variant of claim 1, wherein the parent GH61 polypeptide has at least 99% sequence identity to the mature polypeptide of SEQ ID NO: 14, SEQ ID NO: 34, SEQ ID NO: 60, SEQ ID NO: 62, or SEQ ID NO: 64.

4. The variant of claim 1, wherein the parent GH61 polypeptide comprises the mature polypeptide of SEQ ID NO: 14, SEQ ID NO: 34, SEQ ID NO: 60, SEQ ID NO: 62, or SEQ ID NO: 64.

5. The variant of claim 1, wherein the parent GH61 polypeptide consists of the mature polypeptide of SEQ ID NO: 14, SEQ ID NO: 34, SEQ ID NO: 60, SEQ ID NO: 62, or SEQ ID NO: 64.

6. The variant of claim 1, which comprises one or more substitutions selected from the group consisting of S26I; G32E,S; Y34F; V40A; N41T; Q42I,E,V; S47E,L,R; S56C,E,T; S72Q,T; T102K,P; A123R; Q138C,E,G,K,L,M; V149I; D152S; T163E,F,V; V164C,L; I166L; S169R,C; S186F,K,T,Y; F200I,V; G207P; S213E; S219E,M,Q,C; K222R; S234G,K; A246P; N249Q,R,C; and A250C.

7. The variant of claim 1, which further comprises a substitution at one or more positions corresponding to positions 111, 152, 155, 162, 96, 98, 200, 202, 204, 105, 154, 188, 189, and 216 of the mature polypeptide of SEQ ID NO: 30 for numbering, wherein the variant has cellulolytic enhancing activity and wherein the substitution at position 111 is with Val, the substitution at position 152 is with Ser, the substitution at position 155 is with Leu, the substitution at position 162 is with Trp, the substitution at position 96 is with Val, the substitution at position 98 is with Leu, the substitution at position 200 is with Ile, the substitution at position 202 is with Leu, the substitution at position 204 is with Val, the substitution at position 105 is with Pro or Lys, the substitution at position 154 is with Leu, the substitution at position 188 is with Ala or Trp, the substitution at position 189 is with Lys, and the substitution at position 152 is with Leu or Tyr.

8. The variant of claim 7, which comprises one or more substitutions selected from the group consisting of L111V, D152S, M155L, A162W, I96V, F98L, F200I, I202L, I204V, E105P,K; E154L; G188A,W; N189K; and A216L,Y.

9. A composition comprising the variant of claim 1.

10. A whole broth formulation or cell culture composition, comprising the variant of claim 1.

11. A detergent composition, comprising a surfactant and the variant of claim 1.

12. An isolated polynucleotide encoding the variant of claim 1.

13. A recombinant host cell comprising the polynucleotide of claim 12.

14. A method of producing a GH61 polypeptide variant, comprising: cultivating the recombinant host cell of claim 13 under conditions suitable for expression of the variant.

15. A transgenic plant, plant part or plant cell transformed with the polynucleotide of claim 12.

16. A method of producing the variant of claim 1, comprising: cultivating a transgenic plant or a plant cell comprising a polynucleotide encoding the variant under conditions conducive for production of the variant.

17. A process for degrading or converting a cellulosic material, comprising: treating the cellulosic material with an enzyme composition comprising the GH61 polypeptide variant having cellulolytic enhancing activity of claim 1.

18. The process of claim 17, wherein the cellulosic material is pretreated.

19. The process of claim 17, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

20. The process of claim 17, further comprising recovering the degraded or converted cellulosic material.

21. The process of claim 20, wherein the degraded or converted cellulosic material is a sugar selected from the group consisting of glucose, xylose, mannose, galactose, and arabinose.

22. A process for producing a fermentation product, comprising: (a) saccharifying a cellulosic material with an enzyme composition comprising the GH61 polypeptide variant having cellulolytic enhancing activity of claim 1; (b) fermenting the saccharified cellulosic material with one or more fermenting microorganisms to produce the fermentation product; and (c) recovering the fermentation product from the fermentation.

23. The process of claim 22, wherein the cellulosic material is pretreated.

24. The process of claim 22, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

25. The process of claim 22, wherein steps (a) and (b) are performed simultaneously in a simultaneous saccharification and fermentation.

26. The process of claim 22, wherein the fermentation product is an alcohol, an alkane, a cycloalkane, an alkene, an amino acid, a gas, isoprene, a ketone, an organic acid, or polyketide.

27. A process of fermenting a cellulosic material, comprising: fermenting the cellulosic material with one or more fermenting microorganisms, wherein the cellulosic material is saccharified with an enzyme composition comprising the GH61 polypeptide variant having cellulolytic enhancing activity of claim 1.

28. The process of claim 27, wherein the cellulosic material is pretreated.

29. The process of claim 27, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

30. The process of claim 27, wherein the fermenting of the cellulosic material produces a fermentation product.

31. The process of claim 30, further comprising recovering the fermentation product from the fermentation.

32. The process of claim 30, wherein the fermentation product is an alcohol, an alkane, a cycloalkane, an alkene, an amino acid, a gas, isoprene, a ketone, an organic acid, or polyketide.

* * * * *

SEQUENCE LISTING

```
Sequence total quantity: 411
SEQ ID NO: 1            moltype = DNA  length = 1846
FEATURE                 Location/Qualifiers
source                  1..1846
                        mol_type = genomic DNA
                        organism = Thielavia terrestris
SEQUENCE: 1
aattgaagga gggagtggcg gagtggccac caagtcaggc ggctgtcaac taaccaagga  60
tgggaacagt tcggctcgcc ttgcccgagg gcagcgttcc ctgatgggga cgaaccatgg 120
gactggggtc agctgctgta taaaagttca aatcgatgat ctctcagatg gcgctgctgg 180
ggtgttctgc gcttttccat cctcgcaacc tggtatccca ctagtccagc gttcggcaac 240
atgaagtcgt tcaccattgc cgccttggca gccctatggg cccaggaggc cgccgcccac 300
gcgaccttcc aggacctctg gattgatgga gtcgactacg gctcgcaatg tgtccgcctc 360
ccggcgtcca actcccccgt caccaatgtt gcgtccgacg atatccgatg caatgtcggc 420
acctcgaggc ccaccgtcaa gtgcccggtc aaggccggct ccacggtcac gatcgagatg 480
caccaggttc gcacgcctct ctgcgtaggc ccccagcta ctatatggca ctaacacgac 540
ctccagcaac ctggcgaccg gtcttgcgcc aacgaggcta tcggcggcga ccactacggc 600
cccgtaatgg tgtacatgtc caaggtcgat gacgcggtga cagccgacgg ttcatcgggc 660
tggttcaagg tgttccagga cagctgggcc aagaacccgt cgggttcgac gggcgacgac 720
gactactggg gcaccaagga cctcaactcg tgctgcggca agatgaacgt caagatcccc 780
gaagacatcg agccgggcga ctacctgctc cgcgccgagg ttatcgcgct gcacgtggcc 840
gccagctcgg gcggcgcgca gttctacatg tcctgctacc agctgaccgt gacgggctcc 900
ggcagcgcca cccctcgac cgtgaatttc ccgggcgcct actcggccag cgaccgggc 960
atcctgatca acatccacgc gccatgtcg acctacgtcg tcccgggccc gaccgtgtac 1020
gcgggcggct cgaccaagtc ggctggcagc tcctgctccg gctgcgaggc gacctgcacg 1080
gttggttccg gcccagcgc gacactgacg cagcccacct ccaccgcgac cgcgacctcc 1140
gccctggcg gcggcggctc cggctgcacg gcggccaagt accagcagtg cggcggcacc 1200
ggctacactg ggtgcaccac ctgcgctgta agttccctcg tgatatgcag cggaacaccg 1260
tctggactgt tttgctaact cgcgtcgtag tccgggtcta cctgcagcgc cgtctcgcct 1320
ccgtactact cgcagtgcct ctaagccggg agcgcttgct cagcgggctg ctgtgaagga 1380
gctccatgtc cccatgccgc catggccgga gtaccgggct gagcgcccaa ttcttgtata 1440
tagttgagtt ttcccaatca tgaatacata tgcatctgca tggactgttg cgtcgtcagt 1500
ctacatcctt tgctccactg aactgtgaga ccccatgtca tccggaccat tcgatcggtg 1560
ctcgctctac catctcggtt gatgggtctg ggcttgagag tcactggcac gtcctcggcg 1620
gtaatgaaat gtggaggaaa gtgtgagctg tctgacgcac tcggcgctga tgagacgttg 1680
agcgcggccc acactggtgt tctgtaagcc agcacacaaa agaatactcc aggatggccc 1740
atagcggcaa atatacagta tcagggatgc aaaaagtgca aaagtaaggg gctcaatcgg 1800
ggatcgaacc cgagacctcg cacatgactt atttcaagtc aggggt           1846

SEQ ID NO: 2            moltype = AA  length = 326
FEATURE                 Location/Qualifiers
source                  1..326
                        mol_type = protein
                        organism = Thielavia terrestris
SEQUENCE: 2
MKSFTIAALA ALWAQEAAAH ATFQDLWIDG VDYGSQCVRL PASNSPVTNV ASDDIRCNVG  60
TSRPTVKCPV KAGSTVTIEM HQQPGDRSCA NEAIGGDHYG PVMVYMSKVD DAVTADGSSG 120
WFKVFQDSWA KNPSGSTGDD DYWGTKDLNS CCGKMNVKIP EDIEPGDYLL RAEVIALHVA 180
ASSGGAQFYM SCYQLTVTGS GSATPSTVNF PGAYSASDPG ILINIHAPMS TYVVPGPTVY 240
AGGSTKSAGS SCSGCEATCT VGSGPSATLT QPTSTATATS APGGGGSGCT AAKYQQCGGT 300
GYTGCTTCAS GSTCSAVSPP YYSQCL                                    326

SEQ ID NO: 3            moltype = DNA  length = 880
FEATURE                 Location/Qualifiers
source                  1..880
                        mol_type = genomic DNA
                        organism = Thielavia terrestris
SEQUENCE: 3
accccgggat cactgcccct aggaaccagc acacctcggt ccaatcatgc ggttcgacgc  60
cctctccgcc ctcgctcttg cgccgcttgt ggctggccac ggcgccgtga ccagctacat 120
catcgcggc aaaacctatc ccggctacga gggcttctcg cctgcctcga gcccgccgac 180
gatccagtac cagtggcccg actacaaccc gaccctgagc gtgaccgacc cgaagatgcg 240
ctgcaacggc ggcacctcgg cagagctcag cgcgcccgtc caggccggcg agaacgtgac 300
ggccgtctgc taagcagtgga cccaccagca aggcccgtc atggtctgga tgttcaagtg 360
ccccggcgac ttctcgtcgt gccacggcga cggcaagggc tggttcaaga tcgaccagct 420
gggcctgtgg ggcaacaacc tcaactcgaa caactggggc accgcgatcg tctacaagac 480
```

```
cctccagtgg agcaacccga tccccaagaa cctcgcgccg ggcaactacc tcatccgcca   540
cgagctgctc gccctgcacc aggccaacac gccgcagttc tacgccgagt gcgcccagct   600
ggtcgtctcc ggcagcggct ccgccctgcc cccgtccgac tacctctaca gcatccccgt   660
ctacgcgccc cagaacgacc ccggcatcac cgtgagtggg cttccgttcc gcggcgagct   720
ctgtggaaat cttgctgacg atgggctagg ttgacatcta caacggcggg cttacctcct   780
acacccgcc cggcggcccc gtctggtctg gcttcgagtt ttaggcgcat tgagtcgggg   840
gctacgaggg gaaggcatct gttcgcatga gcgtgggtac                         880
```

```
SEQ ID NO: 4              moltype = AA   length = 239
FEATURE                   Location/Qualifiers
source                    1..239
                          mol_type = protein
                          organism = Thielavia terrestris
SEQUENCE: 4
MRFDALSALA LAPLVAGHGA VTSYIIGGKT YPGYEGFSPA SSPPTIQYQW PDYNPTLSVT    60
DPKMRCNGGT SAELSAPVQA GENVTAVWKQ WTHQQGPVMV WMFKCPGDFS SSHGDGKGWF   120
KIDQLGLWGN NLNSNNWGTA IVYKTLQWSN PIPKNLAPGN YLIRHELLAL HQANTPQFYA   180
ECAQLVVSGS GSALPPSDYL YSIPVYAPQN DPGITVDIYN GGLTSYTPPG GPVWSGFEF    239

SEQ ID NO: 5              moltype = DNA   length = 1000
FEATURE                   Location/Qualifiers
source                    1..1000
                          mol_type = genomic DNA
                          organism = Thielavia terrestris
SEQUENCE: 5
ctcctgttcc tgggccaccg cttgttgcct gcactattgg tagagttggt ctattgctag    60
agttggccat gcttctcaca tcagtcctcg gctcggctgc cctgcttgct agcggcgctg   120
cggcacacgg cgccgtgacc agctacatca tcgccggcaa gaattacccg gggtgggtag   180
ctgattattg agggcgcatt caaggttcat accggtgtgc atggctgaca accggctggc   240
agataccaag gcttttctcc tgcgaactcg ccgaacgtca tccaatggca atggcatgac   300
tacaaccccg tcttgtcgtg cagcgactcg aagcttcgct gcaacggcgg cacgtcgcc   360
accctgaacg ccacggccgc accgggcgac accatcaccg ccatctgggc gcagtggacg   420
cacagccagg gccccatcct ggtgtggatg tacaagtgcc cgggctcctt cagctcctgt   480
gacggctcgg gcgctggctg gttcaagatc gacgaggccg gcttccacgg cgacggcgtc   540
aaggtcttcc tcgacaccga gaacccgtcc ggctggtaca tcgccaagct cgtcggcggc   600
aacaagcagt ggagcagcaa ggtccccgag ggcctcgccc ccggcaacta cctcgtccgc   660
cacgagttga tcgccctgca ccaggccaac aacccgcagt tctacccgga gtgcgcccag   720
gtcgtcatca ccggctccgg caccgcgcag ccggatgcct catacaaggc ggctatcccc   780
ggctactgca accagaatga cccgaacatc aaggtagat ccaggcgtaa tgcagtctac   840
tgctggaaag aaagtggtcc aagctaaacc gcgctccagg tgcccatcaa cgaccactcc   900
atccctcaga cctacaagat tcccggccct ccgtcttca agggcaccgc cagcaagaag   960
gcccgggact tcaccgcctg aagttgttga atcgatggag                        1000

SEQ ID NO: 6              moltype = AA   length = 258
FEATURE                   Location/Qualifiers
source                    1..258
                          mol_type = protein
                          organism = Thielavia terrestris
SEQUENCE: 6
MLLTSVLGSA ALLASGAAAH GAVTSYIIAG KNYPGYQGFS PANSPNVIQW QWHDYNPVLS    60
CSDSKLRCNG GTSATLNATA APGDTITAIW AQWTHSQGPI LVWMYKCPGS FSSCDGSGAG   120
WFKIDEAGFH GDGVKVFLDT ENPSGWYDIAK LVGGNKQWSS KVPEGLAPGN YLVRHELIAL   180
HQANNPQFYP ECAQVVITGS GTAQPDASYK AAIPGYCNQN DPNIKVPIND HSIPQTYKIP   240
GPPVFKGTAS KKARDFTA                                                 258

SEQ ID NO: 7              moltype = DNA   length = 681
FEATURE                   Location/Qualifiers
source                    1..681
                          mol_type = genomic DNA
                          organism = Thielavia terrestris
SEQUENCE: 7
atgctcgcaa acggtgccat cgtcttcctg gccgccgccc tcggcgtcag tggccactac    60
acctggccac gggttaacga cggcgccgac tggcaacagg tccgtaaggc ggacaactgg   120
caggacaacg gctacgtcgg ggatgtcacg tcgccaacag tccgctgttt ccaggcgacg   180
ccgtccccgg ccccatccgt cctcaacacc acggccggct cgaccgtgac ctactgggcg   240
aacccccgacg tctaccaccc cggggcctgt cagttttaca tggcccgcgt gcccgatggc   300
gaggacatca actcgtggaa cggcgacggc gccgtgtggt tcaaggtgta cgaggaccat   360
cctaccttg gcgctcagct cacatggcc agcacgggca agctcgtt cgcggttccc   420
atcccccgt gcatcaagtc cggctactac ctcctccggg ggagcaaat cggcctgcac   480
gtcgcccaga gcgtaggcgg agcgcagttc tacatctcat gcgcccagct cagcgtcacc   540
ggcggcggca gcaccgagcc gccgaacaag gtggccttcc ccggcgctta cagtgcgacg   600
gacccgggca ttctgatcaa catctactac cctgttccca gtcctacca gaaccccggc   660
ccggccgtct tcagctgctg a                                             681

SEQ ID NO: 8              moltype = AA   length = 226
FEATURE                   Location/Qualifiers
source                    1..226
                          mol_type = protein
                          organism = Thielavia terrestris
```

```
SEQUENCE: 8
MLANGAIVFL AAALGVSGHY TWPRVNDGAD WQQVRKADNW QDNGYVGDVT SPQIRCFQAT    60
PSPAPSVLNT TAGSTVTYWA NPDVYHPGPV QFYMARVPDG EDINSWNGDG AVWFKVYEDH   120
PTFGAQLTWP STGKSSFAVP IPPCIKSGYY LLRAEQIGLH VAQSVGGAQF YISCAQLSVT   180
GGGSTEPPNK VAFPGAYSAT DPGILINIYY PVPTSYQNPG PAVFSC                 226

SEQ ID NO: 9            moltype = DNA   length = 960
FEATURE                 Location/Qualifiers
source                  1..960
                        mol_type = genomic DNA
                        organism = Thielavia terrestris
SEQUENCE: 9
atgaagggac ttttcagtgc cgccgccctc tccctggccg tcggccaggc ttcggcccat    60
tacatcttcc agcaactctc catcaacggg aaccagtttc cggtgtacca atatattcgc   120
aagaacacca attataacag tcccgttacc gatctcacgt ccgacgatct tcggtgcaat   180
gtcggcgccc agggtgctgg gacagacacc gtcacggtga aggccggcga ccagttcacc   240
ttcacccttg acacccctgt ttaccaccag gggcccatct ccatctacat gtccaaggcc   300
ccggggcgcg cgtcagacta cgatggcagc ggcggctggt tcaagatcaa ggactgggga   360
ccgactttca acgccgacgg cacggccacc tgggacatgg ccggctcata cacctacaac   420
atcccgacct gcattccgga cggcgactat ctgctccgca tccagtcgct ggccatccac   480
aaccctggc cggcgggcat cccgcagttc tacatctcct cgcccagat caccgtgacc   540
ggcggcggca acggcaaccc tggcccgacg gccctcatcc cggcgcctt caaggacacc   600
gacccgggct acacggtgaa catctacacg aacttccaca actacacggt tcccggcccc   660
gaggtcttca gctgcaacgg cggcggctcg aacccgcccc cgccggtgag tagcagcacg   720
cccgcgacca cgacgctggt cacgtcgacg cgcaccacgt cctccacgtc ctccgcctcg   780
acgcccgct cgaccggcgg cgtcaccgtc gccaagtggg gccagtgcgg cggcaacggg   840
tacaccggct gcacgacctg cgcggccggg tccacctgca gcaagcagaa cgactactac   900
tcgcagtgct gtaagggag gccgcaaagc atgaggtgtt tgaagaggag gagaggggtc   960

SEQ ID NO: 10           moltype = AA    length = 304
FEATURE                 Location/Qualifiers
source                  1..304
                        mol_type = protein
                        organism = Thielavia terrestris
SEQUENCE: 10
MKGLFSAAAL SLAVGQASAH YIFQQLSING NQFPVYQYIR KNTNYNSPVT DLTSDDLRCN    60
VGAQGAGTDT VTVKAGDQFT FTLDTPVYHQ GPISIYMSKA PGAASDYDGS GGWFKIKDWG   120
PTFNADGTAT WDMAGSYTYN IPTCIPDGDY LLRIQSLAIH NPWPAGIPQF YISCAQITVT   180
GGGNGNPGPT ALIPGAFKDT DPGYTVNIYT NFHNYTVPGP EVFSCNGGGS NPPPPVSSST   240
PATTTLVTST RTTSSTSSAS TPASTGGCTV AKWGQCGGNG YTGCTTCAAG STCSKQNDYY   300
SQCL                                                               304

SEQ ID NO: 11           moltype = DNA   length = 954
FEATURE                 Location/Qualifiers
source                  1..954
                        mol_type = genomic DNA
                        organism = Thielavia terrestris
SEQUENCE: 11
atgaagggcc tcagcctcct cgccgctgcg tcggcagcga ctgctcatac catcttcgtg    60
cagctcgagt caggggggaac gacctatccg gtatcctacg gcatccggga ccctagctac   120
gacggtccca tcaccgacgt cacctccgac tcactggctt gcaatggtcc cccgaacccc   180
acgacgccgt ccccgtacat catcaacgtc accgccggca ccacggtcgc ggcgatctgg   240
aggcacaccc tcacatccgg ccccgacgat gtcatggacg ccagccacaa ggggccgacc   300
ctggcctacc tcaagaaggt cgatgatgcc ttgaccgaca cgggtatcgg cggcggctgg   360
ttcaagatcc aggaggccgg ttacgacaat ggcaattgga ctaccagcac ggtgatcacc   420
aacggtggct ccaatatat tgacatcccc gcctgcattc ccaacggcca gtatctgctc   480
cgcgccgaga tgatcgcgct ccacgccgcc agcacgcagg gtggtgccca gctctacatg   540
gagtgcgcgc agatcaacgt ggtgggcggc tccggcagcg ccagcccgca gacgtacagc   600
atcccgggca tctaccaggc aaaccgaccc ggctgctga tcaacatcta ctccatgacg   660
ccgtccagcc agtacaccat tccgggtccg cccctgttca cctgcagcgg cagcggcaac   720
aacggcggcg gcagcaaccc gtcgggcggg cagaccacga cggcgaagcc cacgacgacg   780
acggcggcga cgaccacctc ctccgccgct cctaccagca gccagggggg cagcagcggt   840
tgcaccgttc cccagtggca gcagtgcggt ggcatctcgt tcaccggctg caccacctgc   900
gcggcgggct acacctgcaa gtatctgaac gactattact cgcaatgcca gtaa         954

SEQ ID NO: 12           moltype = AA    length = 317
FEATURE                 Location/Qualifiers
source                  1..317
                        mol_type = protein
                        organism = Thielavia terrestris
SEQUENCE: 12
MKGLSLLAAA SAATAHTIFV QLESGGTTYP VSYGIRDPSY DGPITDVTSD SLACNGPPNP    60
TTPSPYIINV TAGTTVAAIW RHTLTSGPDD VMDASHKGPT LAYLKKVDDA LTDTGIGGGW   120
FKIQEAGYDN GNWATSVIT NGGFQYIDIP ACIPNGQYLL RAEMIALHAA STQGGAQLYM   180
ECAQINVVGG SGSASPQTYS IPGIYQATDP GLLINIYSMT PSSQYTIPGP PLFTCSGSGN   240
NGGGSNPSGG QTTAKPTTT TAATTTSSAA PTSSQGGSSG CTVPQWQQCG GISFTGCTTC   300
AAGYTCKYLN DYYSQCQ                                                 317

SEQ ID NO: 13           moltype = DNA   length = 799
```

```
FEATURE                   Location/Qualifiers
source                    1..799
                          mol_type = genomic DNA
                          organism = Thermoascus aurantiacus
SEQUENCE: 13
atgtcctttt ccaagataat tgctactgcc ggcgttcttg cctctgcttc tctagtggct    60
ggccatggct tcgttcagaa catcgtgatt gatggtaaaa agtatgtcat tgcaagacgc   120
acataagcgg caacagctga caatcgacag ttatggcggg tatctagtga accagtatcc   180
atacatgtcc aatcctccag aggtcatcgc ctggtctact acggcaactg atcttggatt   240
tgtggacggt actggatacc aaacccccaga tatcatctgc catagggggcg ccaagcctgg   300
agccctgact gctccagtct ctccaggagg aactgttgag cttcaatgga ctccatggcc   360
tgattctcac catggcccag ttatcaacta ccttgctccg tgcaatggtg attgttccac   420
tgtggataag acccaattag aattcttcaa aattgccgag agcggtctca tcaatgatga   480
caatcctcct gggatctggg cttcagacaa tctgatagca gccaacaaca gctggactgt   540
caccattcca accacaattg cacctggaaa ctatgttctg aggcatgaga ttattgtctc   600
tcactcagct cagaaccagg atggtgccca gaactatccc cagtgcatca atctgcaggt   660
cactggaggt ggttctgata accctgctgg aactcttgga acggcactct accacgatac   720
cgatcctgga attctgatca acatctatca gaaactttcc agctatatca tccctggtcc   780
tcctctgtat actggttaa                                                 799

SEQ ID NO: 14             moltype = AA  length = 249
FEATURE                   Location/Qualifiers
source                    1..249
                          mol_type = protein
                          organism = Thermoascus aurantiacus
SEQUENCE: 14
MSFSKIIATA GVLASASLVA GHGFVQNIVI DGKYYGGYLV NQYPYMSNPP EVIAWSTTAT    60
DLGFVDGTGY QTPDIICHRG AKPGALTAPV SPGGTVELQW TPWPDSHHGP VINYLAPCNG   120
DCSTVDKTQL EFFKIAESGL INDDNPPGIW ASDNLIAANN SWTVTIPTTI APGNYVLRHE   180
IIALHSAQNQ DGAQNYPQCI NLQVTGGGSD NPAGTLGTAL YHDTDPGILI NIYQKLSSYI   240
IPGPPLYTG                                                             249

SEQ ID NO: 15             moltype = DNA  length = 1172
FEATURE                   Location/Qualifiers
source                    1..1172
                          mol_type = genomic DNA
                          organism = Trichoderma reesei
SEQUENCE: 15
ggatctaagc cccatcgata tgaagtcctg cgccattctt gcagcccttg gctgtcttgc    60
cgggagcgtt ctcggccatg gacaagtcca aaacttcacg atcaatggac aatacaatca   120
gggtttcatt ctcgattact actatcagaa gcagaatact ggtcacttcc ccaacgttgc   180
tggctggtac gccgaggacc tagacctggg cttcatctcc cctgaccaat acaccacgcc   240
cgacattgtc tgtcacaaga acgcggcccc aggtgccatc tctgccactg cagcggccgg   300
cagcaacatc gtcttccaat ggggcccctgg cgtctggcct cacccctacg gtcccatcgt   360
tacctacgtg gctgagtgca gcggatcgtg cacgaccgtg aacaagaaca acctgcgctg   420
ggtcaagatt caggaggccg gcatcaacta taacacccaa gtctgggcgc agcaggatct   480
gatcaaccag ggcaacaagt ggactgtgaa gatcccgtcg agcctcaggc ccggaaacta   540
tgtcttccgc catgaacttc ttgctgccca tggtgcctct agtgcgaacg gcatgcagaa   600
ctatcctcag tgcgtgaaca tcgccgtcac aggctcgggc acgaaagcgc tccctgccgg   660
aactcctgca actcagctct acaagcccac tgaccctggc atcttgttca cccttacac   720
aacaatcacg agctacacca tccctggccc agccctgtgg caaggctaga tccagggcgta   780
cggtgttggc gttcgtgaag tcggagctgt tgacaaggat atctgatgat gaacggagag   840
gactgatggg cgtgactgag tgtatatatt tttgatgacc aaattgtata cgaaatccga   900
acgcatggtg atcattgttt atccctgtag tatattgtct ccaggctgct aagagcccac   960
cgggtgtatt acggcaacaa gtcaggaat ttgggtgcga atgaacggag gtctccatga  1020
atgtatatgt gaagaggcat cggctggcat gggcattacc agatatagcc cctgtgaaac  1080
atatagtact tgaacgtgct actggaacgg atcataagca agtcatcaac atgtgaaaaa  1140
acactacatg taaaaaaaaa aaaaaaaaa aa                                  1172

SEQ ID NO: 16             moltype = AA  length = 249
FEATURE                   Location/Qualifiers
source                    1..249
                          mol_type = protein
                          organism = Trichoderma reesei
SEQUENCE: 16
MKSCAILAAL GCLAGSVLGH GQVQNFTING QYNQGFILDY YYKQNTGHF PNVAGWYAED     60
LDLGFISPDQ YTTPDIVCHK NAAPGAISAT AAGSNIVFQ WGPGVWPHPY GPIVTYVVEC   120
SGSCTTVNKN NLRWVKIQEA GINYNTQVWA QQDLINQGNK WTVKIPSSLR PGNYVFRHEL   180
LAAHGASSAN GMQNYPQCVN IAVTGSGTKA LPAGTPATQL YKPTDPGILF NPYTTITSYT   240
IPGPALWQG                                                             249

SEQ ID NO: 17             moltype = DNA  length = 924
FEATURE                   Location/Qualifiers
source                    1..924
                          mol_type = genomic DNA
                          organism = Myceliophthora thermophila
SEQUENCE: 17
atgaagttca cctcgtccct cgctgtcctg gcggctgccg cgcccaggc tcactgttag    60
tcgaccctcg aacccaacac ccccctcccc cctttcctcc tccatctcct cggcctcact   120
```

```
tagtagccgc tgacaacgac tagataccct ccctagggcc ggcactggtg gctcgctctc    180
tggcgagtgg gaggtggtcc gcatgaccga gaaccattac tcgcacgcc cggtcaccga     240
tgtcaccagc cccgagatga cctgctatca gtccggcgtg cagggtgcgc cccagaccgt    300
ccaggtcaag gcgggctccc aattcacctt cagcgtggat ccctcgatcg ccacccccgg    360
ccctctccag ttctacatgg ctaaggtgcc gtcgggccag acggccgcca cctttgacgg    420
cacgggagcc gtgtggttca agatctacca agacgcccg aacggcctcg gcaccgacag    480
cattacctgg cccagcgccg gttcgtgact tcctccccac tcgctttttt tttttattt    540
tttattttt tttctttcgg aactcaagaa tctttctctc tctctcccgt ctttggcctt    600
gaacaacact aaaactcttc cttactgtat taattaggca aaaccgaggt tcggtcacc    660
atccccagct gcatcgatga tggcgagtac ctgctccggg tcgagcacat cgcgctccac    720
agcgccagca gcgtggggcgg cgctcagttc tacattgcct gcgcccagct ctccgtcacc    780
ggcggctccg gcaccctcaa cacgggctcg ctcgtctccc tgcccggcgc ctacaaggcc    840
accgaccccg gcatcctctt ccagctctac tggcccatcc cgaccgagta catcaacccc    900
ggcccggccc ccgtctcttg ctaa                                           924

SEQ ID NO: 18                 moltype = AA  length = 232
FEATURE                       Location/Qualifiers
source                        1..232
                              mol_type = protein
                              organism = Myceliophthora thermophila
SEQUENCE: 18
MKFTSSLAVL AAAGAQAHYT FPRAGTGGSL SGEWEVVRMT ENHYSHGPVT DVTSPEMTCY     60
QSGVQGAPQT VQVKAGSQFT FSVDPSIGHP GPLQFYMAKV PSGQTAATFD GTGAVWFKIY    120
QDGPNGLGTD SITWPSAGKT EVSVTIPSCI DDGEYLLRVE HIALHSASSV GGAQFYIACA    180
QLSVTGGSGT LNTGSLVSLP GAYKATDPGI LFQLYWPIPT EYINPGPAPV SC            232

SEQ ID NO: 19                 moltype = DNA  length = 854
FEATURE                       Location/Qualifiers
source                        1..854
                              mol_type = genomic DNA
                              organism = Myceliophthora thermophila
SEQUENCE: 19
atgaaggccc tctctctcct tgcggctgcc tcggcagtct ctgcgcatac catcttcgtc     60
cagctcgaag cagacggcac gaggtacccg gtctcgtacg ggatccggga cccaagctac    120
gacggcccca tcaccgacgt cacatccaac gacgttgctt gcaacggcgg gccgaacccg    180
acgacccccct ccagcgacgt catcaccgtc accgggggca ccacggtcaa ggccatctgg    240
aggcacaccc tccaatccgg cccggacgat gtcatggacg ccagccacaa gggcccgacc    300
ctggcctacc tcaagaaggt cggcgatgcc accaaggact cggcgtcgg cggtggctgg    360
ttcaagattc aggaggacgg ctacaacaac ggccagtggg gcaccagcac cgttatctcc    420
aacggcggcg agcactacat tgagccatt cctccgagag aagaccaaga ctcttgacga    480
tctcgctgac ccgtgcaaca agtgacatcc cggcctgcat ccccgagggt cagtacctcc    540
tccgcgccga gatgatcgcc ctccacgcgg ccgggtcccc cggcggtgcc cagctctacg    600
taagcctctg cccttccccc cttcctcttg atcgaatcgg actgcccacc ccccttttcg    660
actccgacta acaccgttgc cagatggaat gtgcccagat caacatcgtc ggcggcctcc    720
gctcggtgcc cagctcgacc gtcagcttcc ccggcgcgta cagcccccaac gacccggcgt    780
tcctcatcaa catctattcc atgtcgccct cgagctcgta caccatcccg ggcccgcccg    840
tcttcaagtg ctag                                                       854

SEQ ID NO: 20                 moltype = AA  length = 235
FEATURE                       Location/Qualifiers
source                        1..235
                              mol_type = protein
                              organism = Myceliophthora thermophila
SEQUENCE: 20
MKALSLLAAA SAVSAHTIFV QLEADGTRYP VSYGIRDPSY DGPITDVTSN DVACNGGPNP     60
TTPSSDVITV TAGTTVKAIW RHTLQSGPDD VMDASHKGPT LAYLKKVGDA TKDSGVGGGW    120
FKIQEDGYNN GQWGTSTVIS NGGEHYIDIP ACIPEGQYLL RAEMIALHAA GSPGGAQLYM    180
ECAQINIVGG SGSVPSSTVS FPGAYSPNDP GLLINIYSMS PSSSYTIPGP PVFKC          235

SEQ ID NO: 21                 moltype = DNA  length = 1242
FEATURE                       Location/Qualifiers
source                        1..1242
                              mol_type = genomic DNA
                              organism = Myceliophthora thermophila
SEQUENCE: 21
atgaagtcct cgccctcac cactctggcc gccctggccg gcaacgccgc cgctcacgcg     60
accttccagg ccctctgggt cgacggcgtc gactacggcg cgcagtgtgc ccgtctgccc    120
gcgtccaact cccccggtca ccgacgtgga tccaacgcga tccgctgcaa cgccaaccg    180
tcgccccgctc gggcaagtg cccggtcaag gccggctcac ccgttacgcg cgagatgcat    240
caggtacgtt ggatgaatga aggggaaag gaagcagagg cagaagggga aggcgaaggg    300
aaagaaaaag aaaaagaaat ggaaaagaaa aagaaatgga aaagaaaag aaaaatgaaa    360
aagaaagtga aaaccgtcag actaactggg gctcctcccc ccaccctc ctttgatatc    420
agcaacccgg tgaccggtcg tgcagcagcg aggcgatcc cggggcgcac tacggccccg    480
tcatggtgta catgtccaag gtgtcggacg cggcgtccgg ggtggtcg tcgggctggt    540
tcaaggtgtt cgaggacggc tgggccaaga accgtccgg cggtcgggc gacgacgact    600
actgggcac aaggacctg aactcgtgct gcgggaagat gaacgtcaag atccccgccg    660
acctgccctc gggcgactac ctgctccggg ccgaggcct cgcgctgcac acggcgggca    720
gcgcggcgg cgcccagttc tacatgacgt gctaccagct caccgtgacg ggctccggca    780
gcgccagccc gcccaccgtc tccttccgg ggcctacaa ggcaccgac ccgggcatcc    840
```

```
tcgtcaacat ccacgcccg ctgtccggct acaccgtgcc cggcccggcc gtctactccg   900
gcggctccac caagaaggcc ggcagcgcct gcaccggctg cgagtccacc tgcgccgtcg   960
gctccggccc caccgccacc gtctcccagt cgcccggttc caccgccacc tccgccccg   1020
gcggcggcgg cggctgcacc gtccagaagt accagcagtg cggcggcgag ggctacaccg  1080
gctgcaccaa ctgcgcggta cgttttcaa ccccgttttt tttttcctt ccctacctta   1140
tttggttacc taattaatta cttccggct gctgacttt tgcttagtc cggctctacc     1200
tgcagcgccg tctcgccgcc ctactactcg cagtgcgtct aa                     1242

SEQ ID NO: 22            moltype = AA   length = 323
FEATURE                  Location/Qualifiers
source                   1..323
                         mol_type = protein
                         organism = Myceliophthora thermophila
SEQUENCE: 22
MKSFALTTLA ALAGNAAAHA TFQALWVDGV DYGAQCARLP ASNSPVTDVT SNAIRCNANP   60
SPARGKCPVK AGSTVTVEMH QQPGDRSCSS EAIGGAHYGP VMVYMSKVSD AASADGSSGW  120
FKVFEDGWAK NPSGGSGDDD YWGTKDLNSC CGKMNVKIPA DLPSGDYLLR AEALALHTAG  180
SAGGAQFYMT CYQLTVTGSG SASPPTVSFP GAYKATDPGI LVNIHAPLSG YTVPGPAVYS  240
GGSTKKAGSA CTGCESTCAV GSGPTATVSQ SPGSTATSAP GGGGGCTVQK YQQCGGEGYT  300
GCTNCASGST CSAVSPPYYS QCV                                         323

SEQ ID NO: 23            moltype = DNA   length = 1253
FEATURE                  Location/Qualifiers
source                   1..1253
                         mol_type = genomic DNA
                         organism = Myceliophthora thermophila
SEQUENCE: 23
atgaagcctt ttagcctcgt cgccctggcg accgccgtga gcggccatgc catcttccag    60
cgggtgtcgg tcaacgggca ggaccagggc cagctcaagg gggtgcgggc gccgtcgagc   120
aactcccga tccagaacgt caacgatgcc aacatgtgcc gcaacgccaa cattgtgtac    180
cacgacagca ccatcatcaa ggtgcccgcg ggagcccgcg tcggcgcgtg gtggcagcac   240
gtcatcggcg gccgcagggg cgccaacgac cggacaacc cgatcgcggc ctcccacaag    300
ggtatgatga tcgatgatgc ctctctcttc ccccgttctt gatggacagg cgatggctcc   360
caggaacacg cgtgactgac caccgaatcc aggcccatc caggtctacc tggccaaggt   420
ggacaacgcg gcgacggcgt cgccgtcggg cctcaggtgg ttcaaggtgg ccgagcgcgg   480
cctgaacaac ggcgtgtggg ccgtcgatga gctcatcgcc aacaacggct ggcactactt   540
cgacctgccg tcgtgcgtgg ccccggcca gtacctgatg cgcgtcgagc tgctcgccct   600
gcacagcgcc tcaagcccg cgggcgccca gttctacatg ggctgcgcac agatcgaagg   660
tgcgtcgatc tttgttctcc ttccgtgtcc tctctgactc tttctctctt cttttcttt   720
ctttactcc ctttccttcc atcttcggag aagcaacgaa ggggggaaagg gataagaaga   780
aggaatgaga gacgacgaaa gagaggattg gggaaagaca agacagggaa aaaaagacaa   840
gaaaaaaaaa aaaaaaaaa aacagagtga gctaacaaga acaatcagtc actggctccg   900
gcaccaactc gggctccgac tttgtctcgt tccccggcca acgatccgg                960
gcatcttgct aagcatctac gacagctcgg gcaagcccac caacggcggg cgctcgtacc  1020
cgatccccgg cccgcgcccc atcctgct ccggcagcgg cgacgcggc aacaacggcg  1080
gcggcggcga cgacaacaac aataacaacg gtggtgcaa aacggcggc ggcggcgcg   1140
gcagcgtccc cctgtacggg cagtgcggcg gcatcggcta cgggcccg accacctgtg  1200
cccagggaac ttgcaaggtg tcgaacgaat actacagcca gtgcctcccc tag        1253

SEQ ID NO: 24            moltype = AA   length = 310
FEATURE                  Location/Qualifiers
source                   1..310
                         mol_type = protein
                         organism = Myceliophthora thermophila
SEQUENCE: 24
MKPFSLVALA TAVSGHAIFQ RVSVNGQDQG QLKGVRAPSS NSPIQNVNDA NMACNANIVY   60
HDSTIIKVPA GARVGAWWQH VIGGPQGAND PDNPIAASHK GPIQVYLAKV DNAATASPSG  120
LRWFKVAERG LNNGVWAVDE LIANNGWHYF DLPSCVAPGQ YLMRVELLAL HSASSPGGAQ  180
FYMGCAQIEV TGSGTNSGSD FVSFPGAYSA NDPGILLSIY DSSGKPTNGG RSYPIPGPRP  240
ISCSGSGDGG NNGGGGDDNN NNNGGGNNGG GGGGSVPLYG QCGGIGYTGP TTCAQGTCKV  300
SNEYYSQCLP                                                        310

SEQ ID NO: 25            moltype = DNA   length = 814
FEATURE                  Location/Qualifiers
source                   1..814
                         mol_type = genomic DNA
                         organism = Myceliophthora thermophila
SEQUENCE: 25
atgaagctct ccctcttctc cgtcctggcc actgccctca ccgtcgaggg gcatgccatc    60
ttccagaagg tctccgtcaa cggagcggac cagggctccc tcaccggcct ccgcgctccc   120
aacaacaaca cccccgtgca ggatgtcaac agccaggaca tgatctgcgg ccagtcggga   180
tcgacgtcga acactatcat cgaggtcaag gccggcgata ggatcggtgc ctggtatcag   240
catgtcatcg gcggtgccca gttccccaac gacccagaca accgattgc caagtcgcac   300
aagggccccg tcatgcgcta cctcgccaag gttgacaatg ccgcaacgcc cagcaagacg   360
ggcctgaagt ggtatgtatt cccgcggcc gagggacatc gggttgggca agtcgagact   420
gacggagctc gcttctccgt ataggttcaa gatttgggag gatacctta atcccagcac   480
caagacctgg ggtgtcgaca acctcatcaa taacaacggc tgggtgtact tcaacctccc   540
gcagtgcatc gccgacggca actacctcct ccgcgtcgag gtcctcgctc tgcactcggc   600
ctactctcag ggccaggctc agttctacca gtcctgcgcc cagatcaacg tatccggcgg   660
```

```
cggctccttc acaccgccgt cgactgtcag cttcccgggt gcctacacgc cagcgacccc    720
cggtatcctg atcaacatct acggcgccac cggccagccc gacaacaacg ccagccgta    780
cactgccccct gggcccgcgc ccatctcctg ctga                              814

SEQ ID NO: 26           moltype = AA  length = 246
FEATURE                 Location/Qualifiers
source                  1..246
                        mol_type = protein
                        organism = Myceliophthora thermophila
SEQUENCE: 26
MKLSLFSVLA TALTVEGHAI FQKVSVNGAD QGSLTGLRAP NNNNPVQDVN SQDMICGQSG    60
STSNTIIEVK AGDRIGAWYQ HVIGGAQFPN DPDNPIAKSH KGPVMAYLAK VDNAATASKT   120
GLKWFKIWED TFNPSTKTWG VDNLINNNGW VYFNLPQCIA DGNYLLRVEV LALHSAYSQG   180
QAQFYQSCAQ INVSGGGSFT PPSTVSFPGA YSASDPGILI NIYGATGQPD NNGQPYTAPG   240
PAPISC                                                              246

SEQ ID NO: 27           moltype = DNA  length = 1115
FEATURE                 Location/Qualifiers
source                  1..1115
                        mol_type = genomic DNA
                        organism = Thermoascus aurantiacus
SEQUENCE: 27
atgtcgttct cgaagattgc tgcgatcacc ggggccatta cctatgcgtc tctggccgcc    60
gctcacggtt atgttacagg aatcgtagcc gatggcacct agtatgtaac gctcatgcca   120
agatccgcat tgctgtacta acaattagca gctacggggg ctatatcgtg acccaatacc   180
cctacatgtc gacaccgccg gatgtcatcg cctggtctac caaagcaact gatcttggtt   240
tcgtggatcc cagtagctat gcttcgtctg atattatctg ccacaagggt gctgagcctg   300
gtgccctgag cgccaaggtg gctgctggag ggaccgtcga gctgcagtgg acggattggc   360
ctgagagtca caagggcccg gtcattgact acctcgccgc ctgtaacggg gactgctcga   420
ctgtcgacaa gaccaaacta gagttcttca agattgatga gagtggccta attgacggca   480
gcagcgcccc aggcacatgg gcctctgaca acttgattgt caataacaac agctggaccg   540
tcaccatccc gagcacgatt gctcccggca actatgtcct gagacatgaa atcattgccc   600
tccactccgc cggaaataca aatggtgctc agaactaccc cagtgtatc aaccttgagg    660
tcacaggcag tggcaccgac acccctgccg gcaccctcgg aacggagctt tataaggcaa   720
cggacctgg  cattctggtc aacatctacc agaccctgac cagctacgat attcccggcc   780
ctgctctgta caccggtggt agctctggta gctctggttc ctccaacacc gccaaggcca   840
ccacttcgac ggcttctagc tctatcgtga ccccgacgcc tgttaacaac ccaacgttaa   900
ctcagactgc cgttgttgat gtcacccaga ctgtttccca gaatgctgcc gtcgccacca   960
cgactccggc ctccactgca gttgctacag ctgtcccaac gggaaccacc tttagcttg   1020
attccgatgac ctcggatgaa ttcgtcagcc tgatgcgtgc gaccgtgaat tggctgcttt  1080
ctaacaagaa gcatgcccgg gatctttctt actaa                            1115

SEQ ID NO: 28           moltype = AA  length = 354
FEATURE                 Location/Qualifiers
source                  1..354
                        mol_type = protein
                        organism = Thermoascus aurantiacus
SEQUENCE: 28
MSFSKIAAIT GAITYASLAA AHGYVTGIVA DGTYYGGYIV TQYPYMSTPP DVIAWSTKAT    60
DLGFVDPSSY ASSDIICHKG AEPGALSAKV AAGGTVELQW TDWPESHKGP VIDYLAACNG   120
DCSTVDKTKL EFFKIDESGL IDGSSAPGTW ASDNLIANNN SWTVTIPSTI APGNYVLRHE   180
IIALHSAGNT NGAQNYPQCI NLEVTGSGTD TPAGTLGTEL YKATDPGILV NIYQTLTSYD   240
IPGPALYTGG SSGSSGSSNT AKATTSTASS SIVTPTPVNN PTVTQTAVVD VTQTVSQNAA   300
VATTTPASTA VATAVPTGTT FSFDSMTSDE FVSLMRATVN WLLSNKKHAR DLSY         354

SEQ ID NO: 29           moltype = DNA  length = 862
FEATURE                 Location/Qualifiers
source                  1..862
                        mol_type = genomic DNA
                        organism = Aspergillus fumigatus
SEQUENCE: 29
atgactttgt ccaagatcac ttccattgct ggccttctgg cctcagcgtc tctcgtggct    60
ggccacggct ttgtttctgg cattgttgct gatgggaaat agtatgtgct tgaaccacac   120
aaatgacagc tgcaacagct aacttctatt ccagttacgg agggtacctt gttaaccaat   180
acccctacat gagcaacccct cccgacacca ttgcctggtc caccaccgcc accgacctcg   240
gctttgtgga cggcaccggc taccagtctc ggatattat ctgccacaga gacgcaaaga    300
atggcaagtt gaccgcaacc gttgcagccg gttcacagat cgaattccag tggacgacgt   360
ggccagagtc tcaccatgga ccggtacgac gccgaagaga agagaacata ttgtgaccag   420
ataggctaac atagcatagt tgattactta cctcgctcca tgcaacggcg actgtgccaa   480
cgtggacaag accaccctga gtttgtcaa gatcgccgct caaggcttga tcgacggctc    540
caacccacct ggtgtttggg ctgatgatga aatgatcgcc aacaacaaca cggccacagt   600
gaccattcct gcctcctatg cccccggaaa ctacgtcctt cgccacgaga tcatcgccct   660
tcactctgcg ggtaacctga acggcgcgca gaactacccc cagtgtttca acatcccaaat  720
caccggttgg ggcagtgctc agggatctgg caccggctgc acgtccctgt acaagaatac   780
tgatcctgcc atcaagtttg acatctactc ggatctgagc ggtggatacc ctattcctgg   840
tcctgcactg ttcaacgctt aa                                            862

SEQ ID NO: 30           moltype = AA  length = 250
FEATURE                 Location/Qualifiers
```

```
source                      1..250
                            mol_type = protein
                            organism = Aspergillus fumigatus
SEQUENCE: 30
MTLSKITSIA GLLASASLVA GHGFVSGIVA DGKYYGGYLV NQYPYMSNPP DTIAWSTTAT    60
DLGFVDGTGY QSPDIICHRD AKNGKLTATV AAGSQIEFQW TTWPESHHGP LITYLAPCNG   120
DCATVDKTTL KFVKIAAQGL IDGSNPPGVW ADDEMIANNN TATVTIPASY APGNYVLRHE   180
IIALHSAGNL NGAQNYPQCF NIQITGGGSA QGSGTAGTSL YKNTDPGIKF DIYSDLSGGY   240
PIPGPALFNA                                                         250

SEQ ID NO: 31               moltype = DNA  length = 1021
FEATURE                     Location/Qualifiers
source                      1..1021
                            mol_type = genomic DNA
                            organism = Penicillium pinophilum
SEQUENCE: 31
atgccttcta ctaaagtcgc tgcccttcct gctgttctag cttttggcctc cacggttgct    60
ggccatggtt ttgtgcaaaa catcgttatc gacggtcagt cgtaagcagt gatgcatcca   120
ttattaaact agacatgctt acaaaaaaat cagttactct ggatacctttg tgaatcagtt   180
ccctacgag tccaacccac cagctgttat tgggtgggca acaactgcaa ccgacctggg    240
attcgtcgct cccagtgagt acaccaatgc agacattatc tgccacaaga acgccacacc   300
tggcgcgctt tctgctccag ttgctgcagg gggcactgtc gagctccagt ggactacatg   360
gcccgatagt catcacggtc ctgtcatcag ctacctcgcc aactgcaatg gcaattgttc   420
taccgtggat aagactaagc tagactttgt caagattgac caaggtggtt tgatcgacga   480
tactacccccc ccgggtacat gggcttccga caaacttatc gctgccaaca acagctggac   540
tgtaactatc ccctccacca tcgcgcctgg aaactacgtt ttgcgccaca aaatcattgc   600
tcttcactcc gctggaaacg cagacgtgc ccaaaactac cctcaatgca tcaacttgga    660
gatcaccggc agcggaaccg ccgctccctc tggtaccgct ggcgaaaagc tctacacctc   720
tactgacccc ggtatcttgg tcaatatcta ccaatccttg tcgacctacg ttattcccgg   780
accaactctg tgggagcggtg ctgccaatgg cgctgttgcc actggttctg ctactgcgat   840
tgctacgact gccactgctt ctgcgaccgc tactcctacc acacttgtta cctctgtcgc    900
tccagcttca tctaccttttg ccactgctgt tgtgaccact gtcgctcctg cagtaactga   960
tgtcgtgact gtcaccgatg tagttaccgt gaccaccgtc atcaccacta ctgtcctttg  1020
a                                                                 1021

SEQ ID NO: 32               moltype = AA  length = 322
FEATURE                     Location/Qualifiers
source                      1..322
                            mol_type = protein
                            organism = Penicillium pinophilum
SEQUENCE: 32
MPSTKVAALS AVLALASTVA GHGFVQNIVI DGKSYSGYLV NQFPYESNPP AVIGWATTAT    60
DLGFVAPSEY TNADIICHKN ATPGALSAPV AAGGTVELQW TTWPDSHHGP VISYLANCNG   120
NCSTVDKTKL DFVKIDQGGL IDDTTPPGTW ASDKLIAANN SWTVTIPSTI APGNYVLRHE   180
IIALHSAGNA DGAQNYPQCI NLEITGSGTA APSGTAGEKL YTSTDPGILV NIYQSLSTYV   240
IPGPTLWSGA ANGAVATGSA TAVATTATAS ATATPTTLVT SVAPASSTFA TAVVTTVAPA   300
VTDVVTVTDV VTVTTVITTT VL                                           322

SEQ ID NO: 33               moltype = DNA  length = 1486
FEATURE                     Location/Qualifiers
source                      1..1486
                            mol_type = genomic DNA
                            organism = Thermoascus sp.
SEQUENCE: 33
atgttgtcgt tcgcttctgc caagtcagct gtgctgacga ccccttctact tcttggatcc    60
gctcaggctc acactttgat gaccaccctg tttgtggatg gcgtcaatca gggagatggt   120
gtctgtattc gcatgaacaa caacggtagt actgccaaca cctatatcca gcctgtcacg   180
agcaaggata ttgcctgcgg taagtacagt accggtccag atatcatact ctatttcaat   240
ccgacaacag tcagagctgg agagcaatgc taaacatccc caggcattca aggcgaaatt   300
ggcgccgctc gagtctgtcc agcaaggctc tcatccaccc tcacgttcca attccggagag   360
cagccatcca acccgaattc cgctcctctc gatccctcgc acaaaggccc cgctgcggtg   420
tacctgaaaa aggtagactc cgccatcgcg agcaacaacg ccgctggaga cggctggttc   480
aagatctggg agtccgtcta cgacgagtcc acgggcaaat ggggtacgac caagatgatc   540
gagaacaaacg ggcacatctc tgtcaaggtc cccgacgata tcgagggtgg gtattatctc   600
gcgcgtacgg agcttctggc gctgcacgcg cgaacgaag gggatccgca gttctacgtt   660
ggctgcgcgc agctgttcat cgattcagcg gggacagcga aaccgcctac tgtctctatt   720
ggagagggga cctacgatct gagcatgcct gccatgacgt acaatatcta ccagactccg   780
ttggctctac catacccgat gtatgggcct cctgtctaca cacctggctc tggctcgggt   840
tctggggtcg gttccgggtc agcttctgca acgagatctt ctgctattcc tactgccacc   900
gctgttacgg actgttcttc gaagaggac agggaagact cagtcatggc aaccggtgtt   960
cccgttgcaa gaagcacact cagaacctgg gttgacagac tgtcatggca tggtaaggcc  1020
cgtgagaacg tgaaaccagc cgccaggaga gcgcccttg tccagaccga gggtctgaag  1080
ccggaaggct gcatcttcgt caacggcaac tggtgcggtt tcgaggtccc cgattacaac  1140
gatgcggaaa ggtgcttggg gttacgttcc cgtctaatta cttaaaacga aataaaagct  1200
aacagtactt ttcttttttct aatcccaggc ctccgacaac tgctggaaac agtccgactc  1260
gtgctgaaac cagacccagc ccaccggcta acaactgc cagatctggc aagaccagaa  1320
atgcaagccc atccaggact cgtgtagcca atccaacccg actggaccgc cgaacaaggg  1380
caaggatata actccaacgt ggccgcccct ggagggctcg atgaagacct tcaccaagcg  1440
cactgtcagt taccgtgatt ggattatgaa aaggaaagga gcataa                1486
```

```
SEQ ID NO: 34              moltype = AA   length = 444
FEATURE                    Location/Qualifiers
source                     1..444
                           mol_type = protein
                           organism = Thermoascus sp.
SEQUENCE: 34
MLSFASAKSA VLTTLLLLGS AQAHTLMTTL FVDGVNQGDG VCIRMNNNGS TANTYIQPVT   60
SKDIACGIQG EIGAARVCPA KASSTLTFQF REQPSNPNSA PLDPSHKGPA AVYLKKVDSA  120
IASNNAAGDG WFKIWESVYD ESTGKWGTTK MIENNGHISV KVPDDIEGGY YLARTELLAL  180
HAANEGDPQF YVGCAQLFID SAGTAKPPTV SIGEGTYDLS MPAMTYNIYQ TPLALPYPMY  240
GPPVYTPGSG SGSGSGSGSA SATRSSAIPT ATAVTDCSSE EDREDSVMAT GVPVARSTLR  300
TWVDRLSWHG KARENVKPAA RRSALVQTEG LKPEGCIFVN GNWCGFEVPD YNDAESCWAA  360
SDNCWKQSDS CWNQTQPTGY NNCQIWQDQK CKPIQDSCSQ SNPTGPPNKG KDITPTWPPL  420
EGSMKTFTKR TVSYRDWIMK RKGA                                        444

SEQ ID NO: 35              moltype = DNA   length = 835
FEATURE                    Location/Qualifiers
source                     1..835
                           mol_type = genomic DNA
                           organism = Penicillium sp.
SEQUENCE: 35
atgctgtctt cgacgactcg caccctcgcc tttacaggcc ttgcgggcct tctgtccgct   60
cccctggtca aggcccatgg ctttgtccag ggcattgtca tcggtgacca attgtaagtc  120
cctctcttgc agttctgtcg attaactgct ggactgcttg cttgactccc tgctgactcc  180
caacagctac agcgggtaca tcgtcaactc gttccctac gaatccaacc caccccccgt   240
catcggctgg gccacgaccg ccaccgacct gggcttcgtc gacggcacag gataccaagg  300
cccggacatc atctgccacc ggaatgcgac gcccgcgccg ctgacagccc ccgtggccgc  360
cggcggcacc gtcgagctgc agtggacgcc gtggccggac agccaccacg gacccgtcat  420
cacctacctg gcgccgtgca acggcaactg ctcgaccgtc gacaagacga cgctggagtt  480
cttcaagatc gaccagcagg gcctgatcga cgacacgagc ccgccgggca cctgggcgtc  540
ggacaacctc atcgccaaca acaatagctg gaccgtcacc attccaaaca gcgtcgcccc  600
cggcaactac gtcctgcgcc acgagatcat cgccctgcac tcggccaaca caaggacgcc  660
cgcccagaac taccccagt gcatcaacat cgaggtcacg ggcggcggct ccgacgcgcc  720
tgagggtact ctgggcgagg atctctacca tgacaccgac ccgggcattc tggtcgacat  780
ttacgagccc attgcgacgt ataccattcc ggggccgcct gagccgacgt tctag       835

SEQ ID NO: 36              moltype = AA   length = 253
FEATURE                    Location/Qualifiers
source                     1..253
                           mol_type = protein
                           organism = Penicillium sp.
SEQUENCE: 36
MLSSTTRTLA FTGLAGLLSA PLVKAHGFVQ GIVIGDQFYS GYIVNSFPYE SNPPPVIGWA   60
TTATDLGFVD GTGYQGPDII CHRNATPAPL TAPVAAGGTV ELQWTPWPDS HHGPVITYLA  120
PCNGNCSTVD KTTLEFFKID QQGLIDDTSP PGTWASDNLI ANNNSWTVTI PNSVAPGNYV  180
LRHEIIALHS ANNKDGAQNY PQCINIEVTG GGSDAPEGTL GEDLYHDTDP GILVDIYEPI  240
ATYTIPGPPE PTF                                                    253

SEQ ID NO: 37              moltype = DNA   length = 878
FEATURE                    Location/Qualifiers
source                     1..878
                           mol_type = genomic DNA
                           organism = Thielavia terrestris
SEQUENCE: 37
atgaagttct cactggtgtc tctgctggct tacggcctct cggtcgaggc cactccatc    60
ttccaggttc gtctcgcaca tcacgctcaa ctcggctcgt ggcgtaaggg caaggattaa  120
cacggccggc agagagtctc ggtcaacggc caagaccaag gcctgctcac cggcctccgc  180
gctccaagca acaacaaccc agtgcaagat gtcaacagcc agaacatgat ttgcggccag  240
tcgggctcca agtcgcagac cgttatcaac gtcaaggccg gcgacaggat cggctcgctc  300
tggcagcatg tcatcggcgg cgcccagttt tcggtgacc cggacaaccc gatcgcccac   360
tcgcacaagg cccccgtgat ggcgtaccett gctaaggtcg acaatgccgc gtccgcgagc  420
caaacgggtc tgaagtggta agtagcgggc gacgctcagg gacgggggat cggggggcctg  480
ctccatccga gactaacacc gtggacaggt tcaagatcgg aggacgggtt tcgatacca   540
gcagcaagac atgggcgtc gacaacctga tcaagaacaa cggctggtg tacttcacc    600
tgccgcagtg cctcgctccg ggccagtatc tcctgcgcgt cgaggttctg gcgctgcact  660
cggcgtacca gcagggccag gcccagttct accagtcctg cgcccagatc aacgtctccg  720
gctccgggtc cttcagcccg tcccagacgg tcagcatccc gggcgtctac agcgccaccg  780
acccgagcat cctcatcaac atctacgca gcacggggca gcccgacaac ggcggcaagg  840
cttacaaccc ccctggaccc gccccgatct cctgctga                          878

SEQ ID NO: 38              moltype = AA   length = 246
FEATURE                    Location/Qualifiers
source                     1..246
                           mol_type = protein
                           organism = Thielavia terrestris
SEQUENCE: 38
MKFSLVSLLA YGLSVEAHSI FQRVSVNGQD QGLLTGLRAP SNNNPVQDVN SQNMICGQSG   60
SKSQTVINVK AGDRIGSLWQ HVIGGAQFSG DPDNPIAHSH KGPVMAYLAK VDNAASASQT  120
```

```
GLKWFKIWQD GFDTSSKTWG VDNLIKNNGW VYFHLPQCLA PGQYLLRVEV LALHSAYQQG  180
QAQFYQSCAQ INVSGSGSFS PSQTVSIPGV YSATDPSILI NIYGSTGQPD NGGKAYNPPG  240
PAPISC                                                             246

SEQ ID NO: 39           moltype = DNA   length = 1253
FEATURE                 Location/Qualifiers
source                  1..1253
                        mol_type = genomic DNA
                        organism = Thielavia terrestris
SEQUENCE: 39
atgaggacga cattcgccgc cgcgttggca gccttcgctg cgcaggaagt ggcaggccat   60
gccatcttcc aacagctctg ggtggacggc accgactata tacgtgctcc ccttttcctt  120
ttgtgtttgc ccatcctcga ttgataaccc gaggccatcc aatgctgact cttacagcag  180
ggctcctcct gcgtccgcat gccgctgtcg aactcgcccg tcacgaacgt cggcagcagg  240
gacatgatct gcaacgccgg cacgcgcccc gtcagcggga gtgccccgt caaggccggc   300
ggcaccgtga cggttgagat gcaccaggtg ggctgatttc ctgagcgtcc tattcctccc  360
ggaagccct ttcccatcct tgccctggc taaccctcc gccctccca gcaacccggg     420
gatccgtcgt gtaacaacga agccatcggc ggcgcccact gggaccggt gcaggtgtac   480
ctcagcaagg tggaggacgc gagcacggcg gacgggtcga cgggctggtt caagatcttc  540
gcggacacgt ggtccaagaa ggcgggcagc tcggtggggg acgacgacaa ctgggggcacg  600
cgcgacctca acgcgtgctg cggcaagatg caggtcaaga tcccggcgga catcccgtcg  660
ggcgactacc tgctgcgggc ggaggcgctg gcgctgcaca cggccgggca ggtgggcggc  720
gcgcagttct acatgagctg ctaccagatc accgtgtcgg gcggcggcag cgccagcccg  780
gccaccgtca agttccccgg cgcctacagc gccaacgacc cgggcatcca catcaacatc  840
cacgcggccg tgtccaacta cgtcgcgccc ggcccggccg tctattccgg cggcacgacc  900
aaggtggccg ggtccgggt ccaaggctgc gagaacactg gcaaggtcgg ctcgtcgccg   960
acggcgacgg cgccgtcggg caagagcggc gcggttccg acggcggcgc tgggaccgac   1020
ggcgggtctt cgtcttcgag ccccgacacg ggcagcgcgt gcagcgtgca ggcctacggg  1080
cagtgcggcg ggaacgggta ctcggttgc acccagtgcg cggtaagttc ggggtcgtct   1140
gtcttttgta ggaacatccg agaggcttgg ctgacgaggc gttgttgtag cccggctata   1200
cttgcaaggc ggtctctccg ccgtactatt cgcagtgcgc cccttcttct tag          1253

SEQ ID NO: 40           moltype = AA   length = 334
FEATURE                 Location/Qualifiers
source                  1..334
                        mol_type = protein
                        organism = Thielavia terrestris
SEQUENCE: 40
MRTTFAAALA AFAAQEVAGH AIFQQLWHGS SCVRMPLSNS PVTNVGSRDM ICNAGTRPVS    60
GKCPVKAGGT VTVEMHQQPG DRSCNNEAIG GAHWGPVQVY LSKVEDASTA DGSTGWFKIF  120
ADTWSKKAGS SVGDDDNWGT RDLNACCGKM QVKIPADIPS GDYLLRAEAL ALHTAGQVGG  180
AQFYMSCYQI TVSGGGSASP ATVKFPGAYS ANDPGIHINI HAAVSNYVAP GPAVYSGGTT  240
KVAGSGCQGC ENTCKVGSSP TATAPSGKSG AGSDGGAGTD GGSSSSSPDT GSACSVQAYG  300
QCGGNGYSGC TQCAPGYTCK AVSPPYYSQC APSS                              334

SEQ ID NO: 41           moltype = DNA   length = 798
FEATURE                 Location/Qualifiers
source                  1..798
                        mol_type = genomic DNA
                        organism = Thielavia terrestris
SEQUENCE: 41
atgaagctga gcgttgccat cgccgtgctg gcgtcggctc ttgccgaggc tcactgtgag   60
tgcatcgtct cactccagct actgcgaagc ttgctgacga tggtcccag acaccttccc    120
cagcatcgga acaccgctg actggcagta tgtgcggatt acaacgaact accagagcaa   180
cgggccggtg acggacgtca cctcggatca aattcggtgc tacgaacgga acccaggcac   240
gggagcgcag ggcatataca acgtcaccgc cggccagacc atcaactaca acgcgaaggc  300
gtccatctcc caccggggc ccatgtcctt ctacattgct aaggttcccg ccggccaaac   360
cgctgcgacc tgggacggta aggggctgt gtggaccaag atctaccagg acatgcccaa   420
gttcggcagc agcctgacct ggcccaccat gggtaagaat tctcaccctg gaaatgaacg   480
cacatttgca cagatctaac atggcctaca ggcgccaagt ctgtcccgt caccatccct    540
cgttgcctcc agaacggcga ttaccttctg cgagccgagc acatcgctct acacagcgcg  600
agcagcgtcg gtgcgccca gttctacctc tcgtgcgccc agcttactgt cagcggcggc  660
agtggcacct ggaaccccaa gaaccgggtc tccttccccg cgcttacaa ggcaacgac     720
ccgggcatct tgatcaacat ctactacccc gtgccgacca gctactcgcc gccggcccg    780
ccggctgaga cgtgctaa                                                798

SEQ ID NO: 42           moltype = AA   length = 227
FEATURE                 Location/Qualifiers
source                  1..227
                        mol_type = protein
                        organism = Thielavia terrestris
SEQUENCE: 42
MKLSVAIAVL ASALAEAHYT FPSIGNTADW QYVRITTNYQ SNGPVTDVTS DQIRCYERNP    60
GTGAQGIYNV TAGQTINYNA KASISHPGPM SFYIAKVPAG QTAATWDGKG AVWTKIYQDM  120
PKFGSSLTWP TMGAKSVPVT IPRCLQNGDY LLRAEHIALH SASSVGGAQF YLSCAQLTVS  180
GGSGTWNPKN RVSFPGAYKA TDPGILINIY YPVPTSYSPP GPPAETC                227

SEQ ID NO: 43           moltype = DNA   length = 977
FEATURE                 Location/Qualifiers
```

```
source                  1..977
                        mol_type = genomic DNA
                        organism = Thielavia terrestris
SEQUENCE: 43
atgaagctgt catcccagct cgccgccctc acgctggccg cggcctccgt gtcaggccac     60
tacatcttcg agcagattgc ccatggcggc accaagttcc caccttacga gtacatccga    120
agaaacacga actataacag ccctgtcacc agtctctcgt cgaacgacct gcgatgcaac    180
gtaggcggcg agacggctgg caacacgacc gtcctcgacg tgaaggcggg cgactccttc    240
accttctact cggacgtggc cgtgtaccac caggggccca tctcactgtg cgtgcccggg    300
gccaactttg atcagtccca agcggactgt ccgctcgcct ggataaccac aattgactga    360
cagcccgcac agctacatgt ccaaggctcc cggctccgtc gtggactacg acggctccgg    420
cgactggttc aagatccacg actggggccc gaccttcagc aacggccagg cctcgtggcc    480
gctgcggggt gcgtcccttc cctttccctc ccccttcctc ccccttcctc ccccctttc    540
ccccctttc tgtctggtcg cacgccctgc tgacgtcccc gtagacaact accagtacaa    600
catcccgacg tgcatcccga acggcgagta cctgctgcgc atccagtcgc tggcgatcca    660
caacccgggc gccacgccgc agttctacat cagctgcgcg caggtccggg tctcgggcgg    720
cggcagcgcc tccccctccc caacggccaa gatcccggc gcgttcaagg cgaccgatcc    780
cgggtatacc gcgaatgtga gtgccctatg ttccttgccc tccttgttcc ttgctcctcc    840
ctcggcgtgc ttgaacgcta cgggctgtgg agggagggat ggatggatga ataggatgct    900
gactgatggt gggacaccag atttacaata acttccactc gtatacggtg ccgggtccgg    960
cggtctttca gtgctag                                                    977

SEQ ID NO: 44           moltype = AA  length = 223
FEATURE                 Location/Qualifiers
source                  1..223
                        mol_type = protein
                        organism = Thielavia terrestris
SEQUENCE: 44
MKLSSQLAAL TLAAASVSGH YIFEQIAHGG TKFPPYEYIR RNTNYNSPVT SLSSNDLRCN     60
VGGETAGNTT VLDVKAGDSF TFYSDVAVYH QGPISLYMSK APGSVVDYDG SGDWFKIHDW    120
GPTFSNGQAS WPLRDNYQYN IPTCIPNGEY LLRIQSLAIH NPGATPQFYI SCAQVRVSGG    180
GSASPSPTAK IPGAFKATDP GYTANIYNNF HSYTVPGPAV FQC                      223

SEQ ID NO: 45           moltype = DNA  length = 1107
FEATURE                 Location/Qualifiers
source                  1..1107
                        mol_type = genomic DNA
                        organism = Thielavia terrestris
SEQUENCE: 45
atgccttctt tcgcctccaa gactctcctt tccaccctgg cgggtgccgc atccgtggcc     60
gcccacgggc acgtgtcgaa catcgtcatc aacggggtct cgtaccaggg ttacgatccg    120
acctccttcc cttacatgca gaacccgccc atcgtggtcg gctggactgc cgccgacacg    180
gacaacggct tgttgccccc ggatgccttc gccagtgcga atatcatctg ccacaagaac    240
gccaccaacg ccaagggcca cgccgtggtc gccgcgggag acaagatctt catccagtgg    300
aacacatggc ccgagtccca ccacggcccc gtcatcgact acctcgcgag ctgcggcagc    360
gcgtcctgcg agaccgtcga caagaccaag ctcgagttct tcaagatcga cgaggtcggc    420
ctggtcgacg gcagctcggc gccgggtgtg tggggctcag accgctcat cgccaacaac    480
aactcgtggc tcgtcgagat cccgcccacc atcgcgccgg gcaactacgt cctgcgccac    540
gagatcatcg cgctgcacag cgccgaaaac gccgacggcg cccagaacta cccgcagtgc    600
ttcaacctgc agatcaccgg caccggcacc gccacccct ccggcgtccc cggcacctcg    660
ctctacaccc cgaccgaccc gggcatcctc gtcaacatct acagcgcccc gatcacctac    720
accgtcccgg ggccgccct catctccggc gccgtcagca tcgcccagtc ctcctccgcc    780
atcaccgcct ccggcaccgc cctgaccggc tctgccaccg cacccgccgc cgccgctgct    840
accacaactt ccaccaccaa cgccgcggct gctgctacct gctgctgc tgctgctggt    900
acttccacaa ccaccacag ccgccggc gtggtccaga cctcctcctc ctcctcctcc    960
gccccgtcct ctgccgccgc cgccgccacc accaccgcgg ctgccagcgc ccgcccgacc   1020
ggctgctcct ctgccgctc caggaagcag ccgcgccgcc acgcgcggga tatggtggtt   1080
gcgcgagggg ctgaggaggc aaactga                                       1107

SEQ ID NO: 46           moltype = AA  length = 368
FEATURE                 Location/Qualifiers
source                  1..368
                        mol_type = protein
                        organism = Thielavia terrestris
SEQUENCE: 46
MPSFASKTLL STLAGAASVA AHGHVSNIVI NGVSYQGYDP TSFPYMQNPP IVVGWTAADT     60
DNGFVAPDAF ASGDIICHKN ATNAKGHAVV AAGDKIFIQW NTWPESHHGP VIDYLASCGS    120
ASCETVDKTK LEFFKIDEVG LVDGSSAPGV WGSDQLIANN NSWLVEIPPT IAPGNYVLRH    180
EIIALHSAEN ADGAQNYPQC FNLQITGTGT ATPSGVPGTS LYTPTDPGIL VNIYSAPITY    240
TVPGPALISG AVSIAQSSSA ITASGTALTG SATAPAAAA TTTSTTNAAA AATSAAAAG     300
TSTTTTSAAA VVQTSSSSSS APSSAAAAAT TTAAASARPT GCSSGRSRKQ PRRHARDMVV    360
ARGAEEAN                                                              368

SEQ ID NO: 47           moltype = DNA  length = 993
FEATURE                 Location/Qualifiers
source                  1..993
                        mol_type = genomic DNA
                        organism = Thielavia terrestris
SEQUENCE: 47
```

```
atgccgcccg cactccctca actcctaacc acggtcctga ccgccctcac cctcggttcc   60
accgccctcg cccactcaca cctcgcgtac attatcgtta acggcaagct ctaccagggc  120
ttcgacccgc gcccgcacca ggccaactac ccttcccggg tcgggtggtc caccggcgcc  180
gtcgacgacg gcttcgtcac gccggccaac tactccaccc cggacatcat ttgccacatc  240
gccggcacca gcccggccgg ccacgcgccc gtgcgccggc agaccgcat ccacgtccag  300
tggaacggct ggccggtcgg ccacatcggt cccgtgctgt cgtacctcgc ccgctgcgag  360
tcggacacgg gctgcacggg ccagaacaag accgcgctgc ggtggaccaa gatcgacgac  420
tccagcccga ccatgcagaa cgtcgccggc gcgggcaccc agggcgaggg caccccccgg  480
aagcgctggg ccaccgacgt gctgatcgcc gccaacaaca gctggcaggt cgccgtgccg  540
gcggggctgc cgaccggcgc gtacgtgctg cgcaacgaga tcatcgcgct gcactacgcg  600
gcgaggaaga acggggcgca gaactatccg ctctgcatga acctgtgggt ggacgccagt  660
ggtgataata gtagtgtggc tgcaacgacg gcggcggtga cggcgggggg tctgcagatg  720
gatgcgtatg acgcgcgcgg gttctacaag gagaacgatc cgggcgtgct ggtcaatgtc  780
acggccgcgc tgtcgtcgta tgtcgtgccc gggccgacgg tggcggcgga cgccacgccg  840
gtgccgtacg cgcagcagag cccgagcgtg tcgacggcag cgggcacgcc cgtcgtcgtt  900
acaaggacta gcgagacggc gccgtacacg ggcgccatga cgccgacggt tgcggcgagg  960
atgaagggga gggggtatga tcggcggggt tag                               993

SEQ ID NO: 48         moltype = AA   length = 330
FEATURE               Location/Qualifiers
source                1..330
                      mol_type = protein
                      organism = Thielavia terrestris
SEQUENCE: 48
MPPALPQLLT TVLTALTLGS TALAHSHLAY IIVNGKLYQG FDPRPHQANY PSRVGWSTGA   60
VDDGFVTPAN YSTPDIICHI AGTSPAGHAP VRPGDRIHVQ WNGWPVGHIG PVLSYLARCE  120
SDTGCTGQNK TALRWTKIDD SSPTMQNVAG AGTQGEGTPG KRWATDVLIA ANNSWQVAVP  180
AGLPTGAYVL RNEIIALHYA ARKNGAQNYP LCMNLWVDAS GDNSSVAATT AAVTAGGLQM  240
DAYDARGFYK ENDPGVLVNV TAALSSYVVP GPTVAAGATP VPYAQQSPSV STAAGTPVVV  300
TRTSETAPYT GAMTPTVAAR MKGRGYDRRG                                   330

SEQ ID NO: 49         moltype = DNA   length = 1221
FEATURE               Location/Qualifiers
source                1..1221
                      mol_type = genomic DNA
                      organism = Thielavia terrestris
SEQUENCE: 49
atgaagacat tcaccgccct cctggccgca gccggcctcg tcgcggcca tggatatgtc    60
gacaacgcca ccattggcgg ccagttttat caggtactct accgctcac ccaaggtccg   120
ctggccacaa ctctataggt gtcataaatt aacaagccac cgtcccgcag ttctatcagg  180
tgtgctcgct accgaccatg tggtcccgtc tcagcaagcc actcacacgc ccatgatccc  240
ctagccttac gtcgacccgt atttagcaac cttggcacgt agtatttatt gtcccaaata  300
ttgagctgaa ctgcacctcc ctagaatccc gcggtgctaa cattctttca gcccgacagg  360
gtctctcgat ccatcccggg caacggcccg tcacggacg tcactctcat cgacctgcag  420
tgcaacgcca attccacccc ggccaagctc acgccactg ccgctgccgg ctcggacgtg   480
attctccgct ggacgctctg gcctgagtcg cacgttggcc ccgtcatcac ctacatggcc  540
cgctgccgcg acacgggctg ccaggactgg atgccggaca cttcgtagga gcccatcttg  600
caccatatcc atttcaaccg gccacacgca ctgacccata tgtctgtcta cccctgcagt  660
gcggtctggt tcaagatcaa ggagggcggc gcgacggca cttccaacac ctgggccgac   720
gtacgtgtac cccgtcccag agagccaaag ccccccttc aacaaagcaa acatctcaat   780
agcccgagcc tacgcactaa cccctctcct tcccccctga aaacacagac ccgctgatg   840
acggcgccca cctcgtacac gtacacgatc ccctcctgcc tgaagaaggg ctactacctg  900
gtccgccacg agatcatcgc gctgcacgcc gcctacacct acccggcgc gcagttctac   960
ccgggctgcc accagctcaa cgtcacgggc ggcgggtcca ccgtaccgtc gagcggcctg  1020
gtggccttc ccggggcgta caagggcagt gaccccggga ttacgacga tcgtataaa   1080
ggtggggttgg ctggttggcc caggtcttgg tgatggggga atgtggtgat gaggttatt  1140
atttgggatc ccgtggctaa cgtaaccctg ggtgtagcgc aaacgtacca gattcctggg  1200
ccggcggtct ttacttgctg a                                            1221

SEQ ID NO: 50         moltype = AA   length = 236
FEATURE               Location/Qualifiers
source                1..236
                      mol_type = protein
                      organism = Thielavia terrestris
SEQUENCE: 50
MKTFTALLAA AGLVAGHGYV DNATIGGQFY QNPAVLTFFQ PDRVSRSIPG NGPVTDVTLI   60
DLQCNANSTP AKLHATAAAG SDVILRWTLW PESHVGPVIT YMARCPDTGC QDWMPGTSAV  120
WFKIKEGGRD GTSNTWADTP LMTAPTSYTY TIPSCLKKGY YLVRHEIIAL HAAYTYPGAQ  180
FYPGCHQLNV TGGGSTVPSS GLVAFPGAYK GSDPGITYDA YKAQTYQIPG PAVFTC      236

SEQ ID NO: 51         moltype = DNA   length = 933
FEATURE               Location/Qualifiers
source                1..933
                      mol_type = genomic DNA
                      organism = Thielavia terrestris
SEQUENCE: 51
atggccttgc tgctcttggc aggcttggcc attctggccg gccggcctca tgcccacggc   60
ggcctcgcca actacacagt gggcaacacc tggtataggg ggtgcgtaag ggggcaccg   120
acaacgcctt cttagtaact ccaccattc gagcgggcta acaccgggcg cagctacgac  180
```

```
ccccttcacgc cggcggccga ccagatcggc cagccgtgga tgatccaacg cgcgtgggac    240
tcgatcgacc cgatcttcag cgtcaacgac aaggcgctcg cctgcaacac cccggccacg    300
gcgccgacct cttacattcc catccgcgcg ggcgagaaca tcacggccgt gtactggtac    360
tggctgcacc cggtgggccc catgacgcg tggctggcgc ggtgcgacgg cgactgccgc    420
gacgccgacg tcaacgaggc gcgctggttc aagatctgga aggccggcct gctcagcggg    480
ccgaacctgg ccgagggcat gtggtaccag aaggcgttcc agaactggga cggcagcccg    540
gacctgtggc ccgtcacgat cccggccggg ctgaagagcg gcctgtacat gatccggcac    600
gagatcttgt cgatccacgt cgaggataaa ccgcagtttt atcccgagtg tgcgcatctg    660
aatgtgaccg ggggtgggga cctgctgccg cctgatgagt ttttggtgaa gttcccgggc    720
gcttacaaag aagatagtga gtgaaacgcg aagcttcggt agccattggg ttgcgctgtt    780
ggaggttaga cccgtcgatc aagatcaata tctactcgga ccagtacgcc aatacaacgg    840
tgagtgtaac aggtcgagca aaaccaaaca gatgccgatg actgatgatc tcagaattac    900
acaattcccg gagggccgat atgggatggg tga                                 933

SEQ ID NO: 52           moltype = AA   length = 250
FEATURE                 Location/Qualifiers
source                  1..250
                        mol_type = protein
                        organism = Thielavia terrestris
SEQUENCE: 52
MALLLLAGLA ILAGPAHAHG GLANYTVGNT WYRGYDPFTP AADQIGQPWM IQRAWDSIDP    60
IFSVNDKALA CNTPATAPTS YIPIRAGENI TAVYWYWLHP VGPMTAWLAR CDGDCRDADV    120
NEARWFKIWE AGLLSGPNLA EGMWYQKAFQ NWDGSPDLWP VTIPAGLKSG LYMIRHEILS    180
IHVEDKPQFY PECAHLNVTG GGDLLPPDEF LVKFPGAYKE DNPSIKINIY SDQYANTTNY    240
TIPGGPIWDG                                                           250

SEQ ID NO: 53           moltype = DNA   length = 1584
FEATURE                 Location/Qualifiers
source                  1..1584
                        mol_type = genomic DNA
                        organism = Thielavia terrestris
SEQUENCE: 53
atgatgccgt cccttgttcg cttctcaatg ggtctggcga ccgccttcgc ctcgctgtcc    60
acagcacata ccgtcttcac cacgcttttc atcaacggcg tcgaccaagg ggacgggacc    120
tgcatccgca tggccaagaa gggcagcgtt tgcacccatc ccattgctgg tggcctcgac    180
agcccagaca tggcttgtgg tatgccctct gcgtttcccc tgcgagagct ttcctcgagc    240
taacccaatg ccgcgttgcc caggccgaga cggacaacaa gccgtggcat tcacctgccc    300
agccccggcg ggctccaagt tgagcttcga gttccgcatg tgggccgacg cctctcagcc    360
cggctctatc gacccatccc acctcggctc gacggcsatc tacctcaaac aagtctccaa    420
catcagctcc gactcggctg ccggcccctgg ctggttcaag atctacgccg agggctacga    480
cacagccgcc aagaagtggg ccacagaaa gctcatcgac aacggcggcc tgctgagcat    540
cgagcttccg cccactctgc cggcgggata ctacctcgcc cgcagcgaga tcgtcaccat    600
ccagaacgtc accaacgacc acgtcgaccc gcagttctac gttggctgcg cacagctctt    660
cgtccagggg cctccgacca cccccaccgt cccgccagac agactcgtct ccatcccggg    720
ccacgtccat ggctccgacc cggggctgac cttcaacatc tggcgcgacg acccctccaa    780
gacggcctac accgtcgtcg gcccggcccc cttctccccc accgccgccc caccccac     840
ctccaccaac accaacgggc agcaacaaca acaacgacca gataa acagacagga         900
cggcgtgatc cccgccgact gccagctcaa gaacgccaac tggtgcggcg ccgaggtgcc    960
cgcgtacgcc gacgaggccg gctgctgggc gtcgtcggcc gactgcttcg cccagctgga   1020
cgcctgctac acgtcggcgc cgcccacggg cagccgcggc tgccggctgt gggaggactg   1080
gtgcaccggc attcagcagg gctgcggcgc ggggcggtgg cgggccgc cgccctttca     1140
tgggagggg gcagcagcgg aggtgtgaac ggttcgggga cgggtggcgg tggtggtggt   1200
ggtggtggtg gcactggctc ttcttccggct tctgccccga cggagacggc ctctgctggc   1260
cgggggggcg caagaatagc tgccgtggcc ggctgcggag cgggacagg agacatggtt    1320
gaagaggttt tcctcttta ttgggagct tgcagcggct ggcggggcg ccgtggtgt        1380
ggttcgattc ttgcgaggct tatccttcat gtccttcttc cacttttgag accgaggcga   1440
gcccctcgag tccatttact tctccttcca ctgtacctca acttctgtta tccaggaacc   1500
agtggtttct ataatcgcct gagcattaaa ctaggcatat ggccaagcaa aatgtcgcct   1560
gatgtagcgc attacgtgaa ataa                                         1584

SEQ ID NO: 54           moltype = AA   length = 478
FEATURE                 Location/Qualifiers
source                  1..478
                        mol_type = protein
                        organism = Thielavia terrestris
SEQUENCE: 54
MMPSLVRFSM GLATAFASLS TAHTVFTTLF INGVDQGDGT CIRMAKKGSV CTHPIAGGLD    60
SPDMACGRDG QQAVAFTCPA PAGSKLSFEF RMWADASQPG SIDPSHLGST AIYLKQVSNI    120
SSDSAAGPGW FKIYAEGYDT AAKKWATEKL IDNGGLLSIE LPPTLPAGYY LARSEIVTIQ    180
NVTNDHVDPQ FYVGCAQLFV QGPPTTPTVP PDRLVSIPGH VHASDPGLTF NIWRDDPSKT    240
AYTVVGPAPF SPTAAPTPTS TNTNGQQQQQ QQQAIKQTDG VIPADCQLKN ANWCGAEVPA    300
YADEAGCWAS SADCFAQLDA CYTSAPPTGS RGCRLWEDWC TGIQQGCRAG RWRGPPPFHG    360
EGAAAETASA GRGGARIAAV AGCGGGTGDM VEEVFLFYWD ACSGWRRSRG GGSILARLIL    420
HVLLPLLRPR RAPRVHLLLF HLYLNFCYPG TSGFYNRLSI KLGIWPSKMS PDVAHYVK     478

SEQ ID NO: 55           moltype = DNA   length = 868
FEATURE                 Location/Qualifiers
source                  1..868
                        mol_type = genomic DNA
```

```
                        organism = Thielavia terrestris
SEQUENCE: 55
atgcagctcc tcgtgggctt gctgcttgca gccgtggctg ctcgagcaca ttgtatttct   60
acccctttcc gcgtgcctcc cagcctcaag gcaagaagac gcacgcagca gctaacggac  120
cctatcagac acatttccca gactcgtggt aaatgggcag cccgaggaca aggactggtc  180
ggttacgcgc atgaccaaga acgcgcagag caagcaggga gtccaggacc cgaccagtcc  240
cgacattcgc tgctacacgt cgcagacggc gcctaacgtg gctacggtcc ctgccggagc  300
caccgtccat tacatatcga ctcagcagat caaccacccg ggcccgacgc agtactacct  360
cgccaaggta ccggcggggt cgtcggccaa gacgtgggac gggtcagggg ccgtctggtt  420
caagatctcg accaccatgc cttacttgga caacaacaag cagcttgtct ggccgaatca  480
gagtaggaac aattcccgct ccaatcttcg atttggcctt gagctacggc cgattgcatg  540
ggagagaccg ttgactgacg gggcaaccca accttcatca gacacgtaca cgacggtcaa  600
cacgaccatc cccgccgata cgcccagtgg ggaataccte ctccgggtcg agcagatcgc  660
gctgcacctg gcctcgcagc caacggggc tcagttctac ctggcctgct cgcagatcca  720
gattacgggc ggcggcaacg gcacgcccgg cccgctagtc gcgttgccgg gggcgtacaa  780
gagcaacgac ccgggcattt tggtcaacat ctactctatg cagcccggcg attacaagcc  840
gcccgggccg ccggtgtgga gtggctga                                     868

SEQ ID NO: 56           moltype = AA  length = 230
FEATURE                 Location/Qualifiers
source                  1..230
                        mol_type = protein
                        organism = Thielavia terrestris
SEQUENCE: 56
MQLLVGLLLA AVAARAHYTF PRLVVNGQPE DKDWSVTRMT KNAQSKQGVQ DPTSPDIRCY   60
TSQTAPNVAT VPAGATVHYI STQQINHPGP TQYYLAKVPA GSSAKTWDGS GAVWFKISTT  120
MPYLDNNKQL VWPNQNTYTT VNTTIPADTP SGEYLLRVEQ IALHLASQPN GAQFYLACSQ  180
IQITGGGNGT PGPLVALPGA YKSNDPGILV NIYSMQPGDY KPPGPPVWSG            230

SEQ ID NO: 57           moltype = DNA  length = 1068
FEATURE                 Location/Qualifiers
source                  1..1068
                        mol_type = genomic DNA
                        organism = Thielavia terrestris
SEQUENCE: 57
atgaagctgt acctggcggc ctttctaggc gccgtcgcca cccgggagc gttcgctcat   60
cgtaggttcc ccgtctatct ccctaggggt agcaccacga ctaatttctc gtcgtccccc  120
tgtagaaatc cacgggattc tacttgtcaa cggcaccgaa acgccggaat ggaaatacgt  180
ccggtaatat ctaccttgct ctccttcttc cacaaccagt ctaacacatc atcagtgacg  240
tggcctggga gggcgcctac gaaccggaaa aatacccca caccgagttc tttaagacgc  300
ccccgcagac ggacataaac aacccgaaca tcacctgcgg caggaacgcg ttcgactcgg  360
ccagcaagac tgagacggcc gacatactgg ccggctcaga ggtcggcttc cgcgtctcgt  420
gggacgcgcaa cggcaagtac ggcgtgttct ggcatccggg gccgggggcag atctacctct  480
ctcgtgctcc gaacgacgac ctggaggact accgcggcga cggagactgg ttcaagatcg  540
caaccggcgc cgccgtctcc aataccgagt ggctgctgtg gaacaagcat gacgtgagcc  600
ccaacattcc tcgcccaatc gatccccaac ctggtcacca tggcggcgtc cgggatgcaa  660
agagactaac tccagaggaa cctacctagt tcaacttcac catcccaag acgacgccgc  720
cgggcaagta cctgatgcgc atcgagcagt tcatgccctc cacggtcgaa tacagccagt  780
ggtacgtcaa ctgcgcccac gtcaacatca tcggccccgg cggaggcacg ccgacgggct  840
ttgccaggtt tcccggcacc tacactgttg acgatcccgg taagccggac ctaccggaca  900
cagaggcctc gggatagctt gctaaccttg tttgctctct ctcttttctc tcccgacta   960
ggcatcaagg tgccgttgaa ccagatcgtc aacagcggag agttgccgca ggaccaactg  1020
aggctgctcg agtacaagcc cccgggccca gcgctgtgga ctggttga             1068

SEQ ID NO: 58           moltype = AA  length = 257
FEATURE                 Location/Qualifiers
source                  1..257
                        mol_type = protein
                        organism = Thielavia terrestris
SEQUENCE: 58
MKLYLAAFLG AVATPGAFAH QIHGILLVNG TETPEWKYVR DVAWEGAYEP EKYPNTEFFK   60
TPPQTDINNP NITCGRNAFD SASKTETADI LAGSEVGFRV SWDGNGKYGV FWHPGPGQIY  120
LSRAPNDDLE DYRGDGDWFK IATGAAVSNT EWLLWNKHDF NFTIPKTTPP GKYLMRIEQF  180
MPSTVEYSQW YVNCAHVNII GPGGGTPTGF ARFPGTYTVD DPGIKVPLNQ IVNSGELPQD  240
QLRLLEYKPP GPALWTG                                                 257

SEQ ID NO: 59           moltype = DNA  length = 871
FEATURE                 Location/Qualifiers
source                  1..871
                        mol_type = genomic DNA
                        organism = Thermoascus crustaceus
SEQUENCE: 59
atggcctttt cccagataat ggctattacc ggcgtttttc ttgcctctgc ttccctggtg   60
gctggccatg gctttgttca gaatatcgtg attgatgtga aaggtaccct aactacctac  120
cttactatct gatgtcattt acaagaaagg gcacagacac aagcggcaaa aaaagaaag  180
aaagaaagaa agaaagaaag ctgacaaaaa ttcaacaagt tatggcgggt acatcgtgaa  240
ccaatatcca tacatgtcag atcctccgga ggtcgtcggc tggtcctacc acgcaaccga  300
cctcggattc gtggacggta ccggatacca aggacctgat atcatctgcc acggggcgc  360
caagcctgca gccctgactg cccaagtggc cgccggagga accgtcaagc tggaatggac  420
```

```
tccatggcct gattctcacc acggcccggt gatcaactac cttgctcctt gcaacggtga    480
ctgttccacc gtggacaaga cccaattgaa attcttcaag atcgcccagg ccggtctcat    540
cgatgacaac agtcctcctg gtatctgggc ctcagacaat ctgatagcgg ccaacaacag    600
ctggactgtc accatcccaa ccacaactgc acctggaaac tatgttctaa ggcatgagat    660
cattgctctc cactcagctg ggaacaagga tggtgcgcag aactatcccc agtgcatcaa    720
cctgaaggtc actggaaatg gttctggcaa tcctcctgct ggtgctcttg gaacggcact    780
ctacaaggat acagatccgg gaattctgat caatatctac cagaaacttt ccagctatgt    840
tattcctggt cctgctttgt acactggtta g                                   871

SEQ ID NO: 60           moltype = AA  length = 251
FEATURE                 Location/Qualifiers
source                  1..251
                        mol_type = protein
                        organism = Thermoascus crustaceus
SEQUENCE: 60
MAFSQIMAIT GVFLASASLV AGHGFVQNIV IDGKSYGGYI VNQYPYMSDP PEVVGWSTTA    60
TDLGFVDGTG YQGPDIICHR GAKPAALTAQ VAAGGTVKLE WTPWPDSHHG PVINYLAPCN    120
GDCSTVDKTQ LKFFKIAQAG LIDDNSPPGI WASDNLIAAN NSWTVTIPTT TAPGNYVLRH    180
EIIALHSAGN KDGAQNYPQC INLKVTGNGS GNPPAGALGT ALYKDTDPGI LINIYQKLSS    240
YVIPGPALYT G                                                        251

SEQ ID NO: 61           moltype = DNA  length = 1102
FEATURE                 Location/Qualifiers
source                  1..1102
                        mol_type = genomic DNA
                        organism = Thermoascus crustaceus
SEQUENCE: 61
atgtcattct cgaagatact tgctatcgct ggggccatta cctacgcatc ttcagctgcc    60
gctcatggtt atgtccaggg aattgttgtc gatggcagct agtatgtcac tctgatgga    120
accttcagca cgtactgtac taacaatcag cagctacggg tggatatatgg tgacccaata    180
tccctacacc gctcaacctc cggaactcat cgcctggtcc actaaagcaa ccgatccttg    240
gtttgtggac ggcagtggct atacttctcc tgatatcatc tgccataagg gtgctgagcc    300
tggtgcccag agcgccaaag tggcagctgg agggaccgtt gagctgcagt ggacggcatg    360
gcccgagtct cacaagggcc cagttattga ctacctcgcc gcctgcgacg gggactgtag    420
atctgttgat aagactgcac taaagttctt taagattgac gagagtggtc tgattgacgg    480
caacggtgct ggaacatggg cctctgatac gttgatcaaa aataacaaca gctgactgt    540
caccatccca agcacaattg cttccggaaa ctacgtacta agcacgaaa taattgcgct    600
ccattctgcc ggaaacaaag atggtgctca gaactatccc cagtgtatca acctcgaggt    660
cactggtagt ggcaccgaaa accctgctgg cactctcgga acagcgcttt acacagacac    720
tgatcctggc cttctggtca acatctacca gggtctgtcc aactattcaa tccctggtcc    780
tgctctgtat agcggcaaca gtgataacgc tggttccctc aaccctacca ccacgccgtc    840
aattcagaat gctgctgctg ctccctccac ttccacagca tctgttgtca ctgattcttc    900
gtcagccacc cagactgcta gtgtcgccgc cacgactcca cctccacttt cggctgttac    960
agcctcacca gctcccgata ctggaagcga cgtaaccaaa tatctggatt cgatgagctc    1020
ggatgaggtc ctcaccctgg tgcgcgggac cctgtcttgg ctggtttcta acaagaaaca    1080
tgcgcgggat ctttctcact ga                                            1102

SEQ ID NO: 62           moltype = AA  length = 349
FEATURE                 Location/Qualifiers
source                  1..349
                        mol_type = protein
                        organism = Thermoascus crustaceus
SEQUENCE: 62
MSFSKILAIA GAITYASSAA AHGYVQGIVV DGSYYGGYMV TQYPYTAQPP ELIAWSTKAT    60
DLGFVDGSGY TSPDIICHKG AEPGAQSAKV AAGGTVELQW TAWPESHKGP VIDYLAACDG    120
DCSSVDKTAL KFFKIDESGL IDGNGAGTWA SDTLIKNNNS WTVTIPSTIA SGNYVLRHEI    180
IALHSAGNKD GAQNYPQCIN LEVTGSGTEN PAGTLGTALY TDTDPGLLVN IYQGLSNYSI    240
PGPALYSGNS DNAGSLNPTT TPSIQNAAAA PSTSTASVVT DSSSATQTAS VAATTPASTS    300
AVTASPAPDT GSDVTKYLDS MSSDEVLTLV RGTLSWLVSN KKHARDLSH               349

SEQ ID NO: 63           moltype = DNA  length = 1493
FEATURE                 Location/Qualifiers
source                  1..1493
                        mol_type = genomic DNA
                        organism = Thermoascus crustaceus
SEQUENCE: 63
atgttgtcat tcattcccac caagtcagct gcgctgacga ctcttctact tcttggaaca    60
gctcatggtc acactttgat gaccaccatg tttgtggacg gcgtcaacca gggagatggt    120
gtctgcattc gcatgaacaa tgacggcgga actgccaata cctatatcca gcctatccgt    180
agcaaggata tcgcctcacg gtaagtaccc gatgtcatca tactctgcca taacatccgt    240
catatctact agaatcggag caatgttaag tatttcaggg catccaaggc gaaatcggcg    300
cctcccgagt ctgcccagtc aaggcatctt ccacccctaac cttccaattc cgcgagcaac    360
ccaacaaccc aaactcctcc cctctcgatc catcgcacaa aggccccgcc gcggtgtacc    420
tgaaaaaggt cgactccgcc atcgcgagca ggagacagc tggttcaaga    480
tctgggagtc cgtctacgac gagtccacgg gcaaatgggg cacgaccaag atgatcgaga    540
acaacgggca catctccgtc aaggtgcccg atgatatcga gggtggttac tatcttgccc    600
ggacggagct gctggcgcta cattctgcgg atcaggggga tccgcagttc tatgttggct    660
gtgcgcagct gtttatcgat tcggatggga cggcgaaacc gccactgtt tctattggag    720
aggggacgta cgatctgagc atgcctgcca tgacgtataa tatctgggag acaccgttgg    780
```

```
ctctgccgta tccgatgtat gggcctcctg tctatacgcc tggctctggt tctggatcag    840
tccgtgcgac gagctcttct gctgtcccta ctgcaaccga atcctctttt gtagaggaaa    900
gagcaaaccc cgtcacggca acagtgttt attctgcaag gggcaaattc aaaacctgga    960
ttgataaact gtcatggcgc gggaaggtcc gtgagaacgt cagacaagcc gcgggaagaa   1020
gaagcactct cgtccagact gtgggtctaa agccaaaagg ctgcatcttc gtcaatggaa   1080
actggtgcgg cttcgaggtt cccgactaca acgatgcgga gagctgctgg gctgtatgtt   1140
cccctcctta gctcttaca tccctaagta ctacatttga aaacaacaaa aagaaatgta   1200
tatactaact acgtacgctc tactctaggc tccgacaac tgctgaaaac agtccgacgc   1260
ctgctggaac aagacccaac ccacgggcta caataactgc cagatctggc aggacaagaa   1320
atgcaaggtc atccaggatt cctgtagcgg acccaacccg catggaccac cgaataaggc   1380
caaggattg actccggagt ggccgccact gaagggctcg atggatacgt tctccaagcg   1440
tactatcggt taccgcgatt ggattgttag aaggagaggt gcatgagggt gta           1493

SEQ ID NO: 64          moltype = AA  length = 436
FEATURE                Location/Qualifiers
source                 1..436
                       mol_type = protein
                       organism = Thermoascus crustaceus
SEQUENCE: 64
MLSFIPTKSA ALTTLLLLGT AHAHTLMTTM FVDGVNQGDG VCIRMNNDGG TANTYIQPIT    60
SKDIACGIQG EIGASRVCPV KASSTLTFQF REQPNNPNSS PLDPSHKGPA AVYLKKVDSA   120
IASNNAAGDS WFKIWESVYD ESTGKWGTTK MIENNGHISV KVPDDIEGGY YLARTELLAL   180
HSADQGDPQF YVGCAQLFID SDGTAKPPTV SIGEGTYDLS MPAMTYNIWE TPLALPYPMY   240
GPPVYTPGSG SGSVRATSSS AVPTATESSF VEERANPVTA NSVYSARGKF KTWIDKLSWR   300
GKVRENVRQA AGRRSTLVQT VGLKPKGCIF VNGNWCGFEV PDYNDAESCW AASDNCWKQS   360
DACWNKTQPT GYNNCQIWQD KKCKVIQDSC SGPNPHGPPN KGKDLTPEWP PLKGSMDTFS   420
KRTIGYRDWI VRRRGA                                                   436

SEQ ID NO: 65          moltype = DNA  length = 1035
FEATURE                Location/Qualifiers
source                 1..1035
                       mol_type = genomic DNA
                       organism = Aspergillus aculeatus
SEQUENCE: 65
atgaagtata ttcctctcgt tattgcagtt gctgccggcc tggcacgtcc ggctactgcc    60
cactacatct tcagcaagct cgtgctgaac ggagaggcat ctgcggactg gcaatacatc   120
cgcgagacta ctcgcagcat agtctatgag ccgaccaagt acacctctac cttcgataac   180
ctaacaccca gcgatagcga cttccgctgt aatctccggtt ccttcagcaa tgctgcgaag   240
accgagtcg ctgaggttgc ggcaggcgat accatccaa tgaagctatt ctacgacacc     300
agtattgcgc atcctggccc gggacaagtt tatatgtcca aggcaccgac cggcaatgtt   360
caggaatacc aaggagacgg ggattggttc aaaatctggg aaaagaccct ttgcaacacg   420
gatggtgatc tgactacaga ggcctggtgc acctgggcca tgtcacagtt tgaatttcaa   480
atcccagctg cgaccccggc aggagactac ctagtgccga cagcatat aggcctgcat    540
ggcgctcaag cgaacgaggc cgaattcttc tacagctgtg cgcagatcaa ggttacaggc   600
tcgggaactg gatctcccag tctcacgtat caaattcctg gtctctataa cgacactatg   660
accctgttca atggcctcaa tctttggact gattcagccg agaaggtgca gctggatttc   720
ctggagacgc caattgggga cgacgtgtgg agcggagcag gctcggggag cccatctgct   780
gccacctctt cgaccagcgg tgcaactctt gcagctcagg gtacaactac ctctgccgcg   840
catgctcagg cccagaccac cattaccacc agcaccagca ccatcacgtc tctcgaatca   900
gccagctcaa ccgatctcgt tgcgcagtat ggtcagtgcg gaggccttaa ctggtccggt   960
ccaaccgagt gtgagacacc ttatacctgt gtgcagcaga acccttacta ccatcaatgc  1020
gtgaattcgt gctga                                                   1035

SEQ ID NO: 66          moltype = AA  length = 344
FEATURE                Location/Qualifiers
source                 1..344
                       mol_type = protein
                       organism = Aspergillus aculeatus
SEQUENCE: 66
MKYIPLVIAV AAGLARPATA HYIFSKLVLN GEASADWQYI RETTRSIVYE PTKYTSTFDN    60
LTPSDSDFRC NLGSFSNAAK TEVAEVAAGD TIAMKLFYDT SIAHPGPGQV YMSKAPTGNV   120
QEYQGDGDWF KIWEKTLCNT DGDLTTEAWC TWGMSQFEFQ IPAATPAGEY LVRAEHIGLH   180
GAQANEAEFF YSCAQIKVTG SGTGSPSLTY QIPGLYNDTM TLFNGLNLWT DSAEKVQLDF   240
LETPIGDDVW SGAGSGSPSA ATSSTSGATL AAQGTTTSAA HAQAQTTITT STSTITSLES   300
ASSTDLVAQY GQCGGLNWSG PTECETPYTC VQQNPYYHQC VNSC                    344

SEQ ID NO: 67          moltype = DNA  length = 1203
FEATURE                Location/Qualifiers
source                 1..1203
                       mol_type = genomic DNA
                       organism = Aspergillus aculeatus
SEQUENCE: 67
atgtctgttg ctaagtttgc tggtgttatc ctcggttcgg ccgctctcgt cgctggccac    60
ggttacgtgt cgggtcgtgt tgtcgacgga acctactgtg tgctacat tgtcacttcc    120
taccccatt ccagcgatcc cccgagacc attggatggt ctaccgaggc gaccgacttg   180
ggtttcgtcg atggtagcga gtatgctgat gccgacatca tttgccacaa gagtgccaag   240
cccggtgcca tctctgctga ggtcaaggcc ggtggtactg ttgagctcca gtggactacc   300
tggcccgaca gccaccacgg ccctgtcctg acctaccttg ccaactgcaa tggtgactgc   360
agcagcgtca ccaagaccga cctcgagttt ttcaagattg acgagagcgg tctcatcaac   420
```

```
gacgacgacg tccccggtac ctgggccagt gataacttga tcgccaacaa caacagctgg    480
actgtgacca tccctctga cattgcggct ggcaactacg tcctccgtca cgaaatcatt    540
gcccttcact ctgctggtaa caaggatggt gctcagaact accctcagtg cctcaacttg    600
aaggtcactg gcggcggtga tctcgctcct tctggcactg ctggtgagag cctgtacaag    660
gacaccgatg ctggtatcct cgtcaacatc taccagtgtc tttcctccta cgatattccc    720
ggacctgcta tgtacaacgc tacctccagc tcctccagct cctccagctc cagctccagc    780
tccagctcca gctccagctc cggctcttcc agctccgccg ccgcctccag cagctccagc    840
agctccagca ctactgccgc cgccgccgcc gctaccagcg ctgcttcttc cgtcacctct    900
gctgctggct ccgtcgttac tcagactgct accgctgttg agactgatac tgccactgtt    960
taccagacct ccactgaggt tgcgcaagtc accgtcaccg gtagcgctcc ccagcagacc    1020
taccgttgcca ctcccagcag ctccagctct gcctccagca gctccagtgc ttccgtatcc    1080
accagcacca gcctcaccag ctacttcgag tccctgagcg ctgatcagtt cctcagcgtt    1140
ctcaagcaga ctttcacctg gttggtcagc gagaagaagc acgcccgtga cctctccgcc    1200
taa                                                                  1203

SEQ ID NO: 68           moltype = AA   length = 400
FEATURE                 Location/Qualifiers
source                  1..400
                        mol_type = protein
                        organism = Aspergillus aculeatus
SEQUENCE: 68
MSVAKFAGVI LGSAALVAGH GYVSGAVVDG TYYGGYIVTS YPYSSDPPET IGWSTEATDL     60
GFVDGSEYAD ADIICHKSAK PGAISAEVKA GGTVELQWTT WPDSHHGPVL TYLANCNGDC    120
SSVTKTDLEF FKIDESGLIN DDDVPGTWAS DNLIANNNSW TVTIPSDIAA GNYVLRHEII    180
ALHSAGNKDG AQNYPQCLNL KVTGGGDLAP SGTAGESLYK DTDAGILVNI YQSLSSYDIP    240
GPAMYNATSS SSSSSSSSSS SSSSSSSGSS SSAAASSSSS SSSTTAAAAA ATSASSVTS     300
AAGSVVTQTA TAVETDTATA YQTSTEVAQV TVTGSAPQQT YVATPSSSSS ASSSSSASVS    360
TSTSLTSYFE SLSADQFLSV LKQTFTWLVS EKKHARDLSA                          400

SEQ ID NO: 69           moltype = DNA   length = 1170
FEATURE                 Location/Qualifiers
source                  1..1170
                        mol_type = genomic DNA
                        organism = Aspergillus aculeatus
SEQUENCE: 69
atgaagtcct ctactttcgg tatgctcgct ctggcagcag cagccaagat ggtcgatgcc     60
cacaccaccg tcttcgccgt ctggatcaac ggcgaggacc agggtctggg caacagtgcc    120
agtggctaca tccggtctcc ccccagcaac agccccgtca aggacgtgac ctcgaccgac    180
atcacctgca acgtcaacgg cgaccaggcc gcggctaaga ccctctccgt caagggcggt    240
gacgtcgtca ccttcgagtg gcaccacgac agccggacg cctccgacga catcatcgcc     300
tcctcccaca agggccccgt catggtctac atggccccga ccaccgccgg cagcagcggc    360
aagaactggg tcaagatcgc cgaggacgga tactccgacg gcacctgggc cgtcgacacc    420
ctgatcgcca acagcggcaa gcacaacatc accgtccccg acgtccccgc cggcgactac    480
ctcttccgcc cggagatcat cgccctccac gaggccgcaa acgagggcgg cgcccagttc    540
tacatggagt gtgtccagtt caaggtcacc tccgacggtg ccaacactct gcccgacggt    600
gtcagcctgc ccgcgcccta ctccgccact gaccccggta tcctcttcaa catgtacggc    660
tccttcgaca gctatcccat ccccgtgtcc tccgtctgga tggcactag tctggctct     720
tcctcttctt cctcttcttc ctcttccagc tcttccgccg ccgctgccgt tgttgccacc    780
tcctcttcct cttcctctgc ttccatcgag gccgtgacca ccaagggtgc cgtcgccgcc    840
gtctccaccg ccgccgccgt ggctcctacc accaccaccg ctgccccac caccttcgcc    900
acggccgtcg cctccaccaa gaaggccact gcctgccgca acaagaccaa gtcctcctcc    960
gctgccacca ccgccgccgc cgtcgccgag accaccctctt ccaccgctcg cgccaccgct    1020
gctgcttcct ctgcctcttc cgcctccggc accgccggca gtacgagcg ctgcggtggc    1080
cagggctgga ccgqtqccac cacctqcqtt qatqqctqga cctqcaaqca qtqqaacct    1140
tactactacc agtgcgttga gtctgcctag                                     1170

SEQ ID NO: 70           moltype = AA   length = 389
FEATURE                 Location/Qualifiers
source                  1..389
                        mol_type = protein
                        organism = Aspergillus aculeatus
SEQUENCE: 70
MKSSTFGMLA LAAAAKMVDA HTTVFAVWIN GEDQGLGNSA SGYIRSPPSN SPVKDVTSTD     60
ITCNVNGDQA AAKTLSVKGG DVVTFEWHHD SRDASDDIIA SSHKGPVMVY MAPTTAGSSG    120
KNWVKIAEDG YSDGTWAVDT LIANSGKHNI TVPDVPAGDY LFRPEIIALH EAENEGGAQF    180
YMECVQFKVT SDGANTLPDG VSLPGAYSAT DPGILFNMYG SFDSYPIPGP SVWDGTSSGS    240
SSSSSSSSSS SSAAAAVVAT SSSSSSASIE AVTTKGAVAA VSTAAAVAPT TTAAPTTFA     300
TAVASTKKAT ACRNKTKSSS AATTAAAVAE TTSSTAAATA AASSASSASG TAGKYERCGG    360
QGWTGATTCV DGWTCKQWNP YYYQCVESA                                      389

SEQ ID NO: 71           moltype = DNA   length = 1221
FEATURE                 Location/Qualifiers
source                  1..1221
                        mol_type = genomic DNA
                        organism = Aspergillus aculeatus
SEQUENCE: 71
atgcgtcagg ctcagtcttt gtccctcttg acagctcttc tgtctgccac gcgtgtggct     60
ggacacggtc acgtcactaa cgttgtcgtc aacggtgttt actacgaggg cttcgatatc    120
aacagcttcc cctacgagtc cgatccccct aaggtggcgg cttggaccac tcctaacact    180
```

-continued

```
ggcaacggtt tcatttcccc cagcgactac ggtaccgatg acattatttg ccaccagaat    240
gccaccaacg cccaggccca cattgttgtt gcggctggtg acaagatcaa catccagtgg    300
accgcgtggc ccgattccca ccacggtcct gtccttgact acctcgctcg ctgcgacggt    360
gagtgtgaga cggttgataa gaccactctt gagttttca agatcgacgg cgtcggtctc     420
atcagtgaca ccgaagtgcc cggtacctgg ggagatgaca gctgatcgc caacaacaac     480
agctggttgg tcgagatccc ccgaccatt gctcctggca actatgttct tcgccacgag     540
cttatcgctc tccacagcgc cggcactgaa gatggtgctc agaactaccc ccagtgtttc    600
aacctccagg tcactggctc cggtactgac gagcccgctg gtaccctcgg caccaagctc    660
tacactgagg atgaggctgg tatcgttgtg aacatctcaa cctctctgtc ttcctatgcc    720
gtccccggcc ccacccagta cagcggcgcc gtctctgtca gccaatccac ttcggccatt    780
acctccaccg gaactgctgt tgtcggtagc ggcagcgctg ttgccacctc tgccgccgcg    840
gctaccacca cgctgctgc ttcttctgcc gctgctgcta ccaccgctgc tgccgttacc     900
agcgccaatg ccaacactca gattgccag cccagcagca gctcttctta ctcccagatc     960
gccgtgcagg tgccctcctc ctggaccacc ttgtgaccg tcactcctcc cgccgccgcc    1020
gccaccaccc ctgctgccgt ccctgagcct cagacccct ctgccagctc tggagccacc    1080
actaccagca gcagcagcgg cgccgcccag tctctctacg gccagtgcgg tggtatcaac    1140
tggaccggag ctacctcttg cgttgagggc gctacttgct accagtacaa cccttactac    1200
taccagtgca tctctgccta a                                               1221

SEQ ID NO: 72            moltype = AA    length = 406
FEATURE                  Location/Qualifiers
source                   1..406
                         mol_type = protein
                         organism = Aspergillus aculeatus
SEQUENCE: 72
MRQAQSLSLL TALLSATRVA GHGHVTNVVV NGVYYEGFDI NSFPYESDPP KVAAWTTPNT     60
GNGFISPSDY GTDDIICHQN ATNAQAHIVV AAGDKINIQW TAWPDSHHGP VLDYLARCDG    120
ECETVDKTTL EFFKIDGVGL ISDTEVPGTW GDDQLIANNN SWLVEIPPTI APGNYVLRHE    180
LIALHSAGTE DGAQNYPQCF NLQVTGSGTD EPAGTLGTKL YTEDEAGIVV NIYTSLSSYA    240
VPGPTQYSGA VSVSQSTSAI TSTGTAVVGS GSAVATSAAA ATTSAAASSA AAATTAAAVT    300
SANANTQIAQ PSSSSSYSQI AVQVPSSWTT LVTVTPPAAA ATTPAAVPEP QTPSASSGAT    360
TTSSSSGAAQ SLYGQCGGIN WTGATSCVEG ATCYQYNPYY YQCISA                   406

SEQ ID NO: 73            moltype = DNA    length = 1284
FEATURE                  Location/Qualifiers
source                   1..1284
                         mol_type = genomic DNA
                         organism = Aspergillus aculeatus
SEQUENCE: 73
atgtctcttt ccaagattgc cactcttctg ctgggctcgg tctcgctggt cgctggtcat     60
gggtatgtct cgagcatcga ggtggacggt accacctatg gagggtactt ggtcgacact    120
tattactacg aatccgaccc gcccgagtta atcgcctggt ccacaaatgc cacggatgat    180
ggctatgtat cgccctccga ctacgagagc gtgaacatca tctgccacaa ggggtctgca    240
cccggcgcgt tgtcggcccc tgtcgcgccc ggaggctggg tgcagatgac ctggaacacc    300
tggcccaccg accatcacgg ccctgtcatc acgtatatgg ccaattgcca cggttcttgc    360
gcagatgtgg acaagaccac cctcgagttc ttcaagatcg atgctggcgg cttgatcgat    420
gacacggacg tgcctggaac ttgggcgacc gatgagctca ttgaagatag ctatagtcgc    480
aacatcacta tccccagcga tattgccccc gggtactatg ttttgcgaca cgagatcatt    540
gctctgcaca cgcgccgagaa cctggacgga gcccagaact accccagtg catcaatctg    600
gaagtcaccg gcagcgagac agcaaccccg agtggcacct tgggcactgc tctgtacaag    660
gagaccgacc ccggcatcta tgttgacatc tggaacacgt tgagcactac tactattccc    720
ggccccgcgc tgtacactgc tggtagcact gcgaccgcag ccgctgctgc cgataccacc    780
actacttctg ctggcaccac cgctgaggcc accaccgctg ccgccgccgt gagtaccacc    840
gcggacgctg ttccgaccga gtcttcagct ccttccgaga ccagcgcgac taccgcgaac    900
cctgctggc ccactgcgcg gcagcgacatc cgcttccagc ccggtcaggt caaggctggt    960
gcttcagtca acaactcgcg tactgagact tcctctggtg agtctgccac gacgaccaca    1020
acatcagtgg ccactgcggc ttcgagcgcg gattcgtcga cgacttctgg ggttttgagt    1080
ggcgcctgca gccaggaggg ctactggtac tgcaacgggg gcactgcgtt ccagcgctgt    1140
gtcaacgggg aatgggatgc gtcccagagt gtggctgcgg gcacggtctg caccgccggt    1200
atctcggaga ccatcaccat ttcagccgcc gccacgcgcc gggatgccat gcgtcgtcat    1260
ctggcgcgtc caagcgtca ctga                                             1284

SEQ ID NO: 74            moltype = AA    length = 427
FEATURE                  Location/Qualifiers
source                   1..427
                         mol_type = protein
                         organism = Aspergillus aculeatus
SEQUENCE: 74
MSLSKIATLL LGSVSLVAGH GYVSSIEVDG TTYGGYLVDT YYYESDPPEL IAWSTNATDD     60
GYVSPSDYES VNIICHKGSA PGALSAPVAP GGWVQMTWNT WPTDHHGPVI TYMANCHGSC    120
ADVDKTTLEF FKIDAGGLID DTDVPGTWAT DELIEDSYSR NITIPSDIAP GYYVLRHEII    180
ALHSAENLDG AQNYPQCINL EVTGSETATP SGTLGTALYK ETDPGIYVDI WNTLSTYTIP    240
GPALYTAGST ATAAAADTT TTSAGTTAEA TTAAAAVTAD ADAVPTESSA PSETSATTAN    300
PARPTAGSDI RFQPGQVKAG ASVNNSATET SSGESATTTT TSVATAASSA DSSTTSGVLS    360
GACSQEGYWY CNGGTAFQRC VNGEWDASQS VAAGTVCTAG ISETITISAA ATRRDAMRRH    420
LARPKRH                                                              427

SEQ ID NO: 75            moltype = DNA    length = 804
FEATURE                  Location/Qualifiers
```

```
source                  1..804
                        mol_type = genomic DNA
                        organism = Aspergillus aculeatus
SEQUENCE: 75
atgcttgtca aactcatctc ttttctttca gctgctacca gcgtagctgc tcatggtcat   60
gtgtcaaaca ttgtgatcaa cggggtgtcc taccgcggat gggacatcaa ttcggaccct  120
tacaattcca accctccggt ggtggttgca tggcaaacac ccaacacagc taatggcttc  180
atctccctg atgcatacga cacagatgat gttatttgcc atctgagcgc tacgaatgcc   240
agaggccacg cagtcgtcgc tgctggcgac aagatcagcc tccagtggac gacctggcct  300
gacagtcacc atgggcctgt catcagctac ctagccaact gcggctccag ctgcgagaca  360
gtcgataaga ccaccctcga gttcttcaag atcgatggtg ttggcttggt ggatgagagc  420
aatccccctg gtatctgggg agacgatgag ctcattgcca caacaactc ttggctggta   480
gagattccag ctagtatcgc gccaggatac tatgtgctgc gtcacgagtt gatcgctctg  540
catggagcag ggagtgagaa tggagcccag aattacatgc aatgtttcaa ccttcaggtt  600
actgggactg gcacggttca gccttccggg gtcctgggca cggagctgta caaacccaca  660
gacgctggaa ttcttgtcaa tatctaccag tcgctctcca cctatgttgt tcctggcccg  720
accctgatcc cccaggccgt ttccctcgtt cagtcgagct ccaccattac cgcctcgggc  780
acggcagtga caaccacggc ttga                                          804

SEQ ID NO: 76          moltype = AA  length = 267
FEATURE                Location/Qualifiers
source                 1..267
                       mol_type = protein
                       organism = Aspergillus aculeatus
SEQUENCE: 76
MLVKLISFLS AATSVAAHGH VSNIVINGVS YRGWDINSDP YNSNPPVVVA WQTPNTANGF   60
ISPDAYDTDD VICHLSATNA RGHAVVAAGD KISLQWTTWP DSHHGPVISY LANCGSSCET  120
VDKTTLEFFK IDGVGLVDES NPPGIWGDDE LIANNNSWLV EIPASIAPGY YVLRHELIAL  180
HGAGSENGAQ NYMQCFNLQV TGTGTVQPSG VLGTELYKPT DAGILVNIYQ SLSTYVVPGP  240
TLIPQAVSLV QSSSTITASG TAVTTTA                                      267

SEQ ID NO: 77          moltype = DNA  length = 822
FEATURE                Location/Qualifiers
source                 1..822
                       mol_type = genomic DNA
                       organism = Aspergillus aculeatus
SEQUENCE: 77
atgaagtatc ttgcgatctt cgcggcagca gcagctggac tggcccgccc gacagcagcg   60
cactacatct tcagcaagct gattctggac ggcgaagtct ctgaggactg gcagtatatt  120
cgtaaaacca cccgggagac atgctatttg ccgaccaagt tcaccgacac cttcgacaac  180
ttgactccga cgaccaggga tttccggtgc aatctcggct cgttcagcaa cgccgccaag  240
accgaagtgg ccgaggtgga agcgggctcc acgattggca tgcagctttt cgctggtagc  300
cacatggcgt cacccgggacc tgcgcaagtc ttcatgtcta aggccccgtc cggcaacgta  360
cagagctacg agggtgacgg ctcctggttc aagatctggg agcgtacact ctgcgacaaa  420
agtggcgatc tgactggaga tgcgtggtgt acatacggcc agaccgagat cgagtttcaa  480
atccccgagg cgaccccgac gggcgaatac ctggtccgag cggagcacat cggtcttcac  540
cgcgcacaga gtaatcaagc cgagttctac tacagctgcg ccgcaggtca aggtcacgggc  600
aatggtaccg gggtgccgag ccagacatat cagatccctg gcatgtacaa tgaccgctcg  660
gagcttttca acgggctgaa cttgtggtcc tactcggtgg agaacgtcga ggcagccatg  720
aagaattcta tcgtgggtga tgaaatttgg aatggaagtt ctgttccctc tgagtcccat  780
gtcccgaagt ataagaagag tcatgcttgt cgtgtttatt ga                      822

SEQ ID NO: 78          moltype = AA  length = 273
FEATURE                Location/Qualifiers
source                 1..273
                       mol_type = protein
                       organism = Aspergillus aculeatus
SEQUENCE: 78
MKYLAIFAAA AAGLARPTAA HYIFSKLILD GEVSEDWQYI RKTTRETCYL PTKFTDTFDN   60
LTPNDQDFRC NLGSFSNAAK TEVAEVEAGS TIGMQLFAGS HMRHPGPAQV FMSKAPSGNV  120
QSYEGDGSWF KIWERTLCDK SGDLTGDAWC TYGQTEIEFQ IPEATPTGEY LVRAEHIGLH  180
RAQSNQAEFY YSCAQVKVTG NGTGVPSQTY QIPGMYNDRS ELFNGLNLWS YSVENVEAAM  240
KNSIVGDEIW NGSSVPSESH VPKYKKSHAC RVY                                273

SEQ ID NO: 79          moltype = DNA  length = 969
FEATURE                Location/Qualifiers
source                 1..969
                       mol_type = genomic DNA
                       organism = Aurantiporus alborubescens
SEQUENCE: 79
atgcgaacca tcgccacgtt tgttacgctt gtagcctcag ttctccctgc ggtcctcgca   60
cacgaggtg tcctctccta ttcsaacggg gggaattggt actggggatg gaagcctac   120
aattcacctg acgggcagac caccatccaa cgcccgtggg caacatacaa tccgatcact  180
gatgcgacgg atcctaccat tgcttgcaac aacgacggga catctggagc tctgcagttg  240
actgcgacag tcgcggcggg atctgccatc acggcgtatt ggaaccaggt gtggccgcat  300
gataaagggc cgatgacgac atacctcgca caatgccccg gcagtacctg cacaggagtc  360
aacgcgaaga ctctgaaatg gttcaagatc gatcacgccg ggttgctttc tggtactgtc  420
tacagtggct cgtgggcatc aggcaagatg attgcacaga actcgacctg acaactacc   480
attccagcga cggtgccttc aggaactat ctgatacgtt tcgagactat tgccctgcac  540
```

```
tctttgccag cgcaattttta ccctgagtgc gcacaaattc aaatcacggg cggaggttcc    600
cgtgctccaa ccgctgcaga gcttgttagc ttccctggcg cgtacagcaa caatgatcct    660
ggtgtcaaca ttgacatcta ctccaatgcc gcgcagagtg caaccacata cgtaatacca    720
ggacctccta tgtacggcgg tgcttccgga tctggtccat cttccgcgcc tccatcaagt    780
accccaggta gttcgtccac ttcccacggt cccacgtccg tcagcagtgc cagcagtgct    840
gcaccatcga cgacaggaac cgtgacgcag tacggtcagt gcggtggcat tggttgggct    900
ggagctaccg gctgtatctc accattcaag tgcacggtca tcaacgatta ttactaccag    960
tgcctctga                                                            969

SEQ ID NO: 80            moltype = AA   length = 322
FEATURE                  Location/Qualifiers
source                   1..322
                         mol_type = protein
                         organism = Aurantiporus alborubescens
SEQUENCE: 80
MRTIATFVTL VASVLPAVLA HGGVLSYSNG GNWYWGWKPY NSPDGQTTIQ RPWATYNPIT    60
DATDPTIACN NDGTSGALQL TATVAAGSAI TAYWNQVWPH DKGPMTTYLA QCPGSTCTGV    120
NAKTLKWFKI DHAGLLSGTV YSGSWASGKM IAQNSTWTTT IPATVPSGNY LIRFETIALH    180
SLPAQFYPEC AQIQITGGGS RAPTAAELVS FPGAYSNNDP GVNIDIYSNA AQSATTYVIP    240
GPPLYGGASG SGPSSAPPSS TPGSSSTSHG PTSVSTSSSA APSTTGTVTQ YGQCGGIGWA    300
GATGCISPFK CTVINDYYYQ CL                                             322

SEQ ID NO: 81            moltype = DNA   length = 705
FEATURE                  Location/Qualifiers
source                   1..705
                         mol_type = genomic DNA
                         organism = Aurantiporus alborubescens
SEQUENCE: 81
atgaaggcta tcttggctat tttctcggcc cttgctccac ttgccgctgc gcattatacc    60
ttccctgatt ttattgtcaa cggaacaaca actgccgatt gggtctacat ccgagagcct    120
gcgaaccact actcgaatgg tcctgtaacc aacgtgaacg atccagaatt ccgatgctac    180
gagctggacc tgcaaaacac ggcagcgagt ccctcaccg ccacggtctc tgcaggctcc    240
agcgtcggct ttaaagctaa cagcgccctt taccatcctg gttatctcga tgtgtatatg    300
tccaaagcga ccccagctgc taattcaccc agtgctggaa cggacaaagc ctggttcaag    360
gtctatgaat ccgctccggt cttcgcgaat ggggccctaa gcttccctttc ggagaacatc    420
caatctttca cgttcacaat cccgaagtcc cttcccagtg gccaatatct catccgtgtg    480
gaacacatcg ctctccactc cgccagtagc tacggaggtg cacaattcta catcagctgc    540
gctcaagtca atgtcgtcaa cggcgggaac ggaaacccag accgttagt caagattccc    600
ggcgtttaca ctgggaacga gcctggcatc ctcatcaaca tctacagctt cccaccggt    660
ttcagttggc accaatcccc gggacctgct gtgtggcgtg gttga                    705

SEQ ID NO: 82            moltype = AA   length = 234
FEATURE                  Location/Qualifiers
source                   1..234
                         mol_type = protein
                         organism = Aurantiporus alborubescens
SEQUENCE: 82
MKAILAIFSA LAPLAAAHYT FPDFIVNGTT TADWVYIRET ANHYSNGPVT NVNDPEFRCY    60
ELDLQNTAAS TLTATVSAGS SVGFKANSAL YHPGYLDVYM SKATPAANSP SAGTDQSWFK    120
VYESAPVFAN GALSFPSENI QSFTFTIPKS LPSGQYLIRV EHIALHSASS YGGAQFYISC    180
AQVNVVNGGN GNPGPLVKIP GVYTGNEPGI LINIYSFPPG FSGYQSPGPA VWRG          234

SEQ ID NO: 83            moltype = DNA   length = 702
FEATURE                  Location/Qualifiers
source                   1..702
                         mol_type = genomic DNA
                         organism = Trichophaea saccata
SEQUENCE: 83
atgacgcccc tgaaactccg cccccttctc ctcctggtgc tttcacgac cctcagcctc    60
gtgcacgcgc actatcgctt ctacgaactg atcgccaacg gggccaccca cgcttccttc    120
gaatacatcc gccaatgggt gcccatctac agcaactctc ccgtaaccga cgtcaccagc    180
gtcaacctcc gctgcaacgt caacgccact cccgccgccg agtgatcac cgttgctgcc    240
ggtagcaccg tcggcttcgt agcagacaca acagtaacgc accccggtgc gttcaccgcg    300
tacatggcga aagcgcccga agacatcacg gaatgcaaga caacggggca ctggttcaag    360
atctggagaa agggtccaac gagtataacc agtagcggga taacctggga cgtcacggat    420
acccaatgga ccttcaccat ccccttccgcg cacaccaaacg gtcaataccct actccgcttc    480
gagcacatag cgctccacgc cgccagcacc gtgggggtg ctcaattcta catgtcgtgc    540
gcgcagatac aagtaacgaa cggcggcaac gggagtcccg ggccaccat caagttcccg    600
ggcggataca gcgccacaga ccccggtatc ctgatcaata tctattatcc catccccact    660
agttacacta ttcctggtcc accggtttgg accggtaagt aa                       702

SEQ ID NO: 84            moltype = AA   length = 233
FEATURE                  Location/Qualifiers
source                   1..233
                         mol_type = protein
                         organism = Trichophaea saccata
SEQUENCE: 84
MTPLKLRPLL LLVLSTTLSL VHAYRFYEL IANGATHASF EYIRQWVPIY SNSPVTDVTS     60
VNLRCNVNAT PAAEVITVAA GSTVGFVADT TVTHPGAFTA YMAKAPEDIT EWDGNGDWFK    120
```

```
IWEKGPTSIT SSGITWDVTD TQWTFTIPSA TPNGQYLLRF EHIALHAAST VGGAQFYMSC    180
AQIQVTNGGN GSPGPTIKFP GGYSATDPGI LINIYYPIPT SYTIPGPPVW TGK          233

SEQ ID NO: 85           moltype = DNA  length = 714
FEATURE                 Location/Qualifiers
source                  1..714
                        mol_type = genomic DNA
                        organism = Trichophaea saccata
SEQUENCE: 85
atgaaatgcc ttctctccct ccttctcgcc gcgacagcgg tctccgctca cacgatcttc    60
caagaaatcg gcataaacgg ggtgatgcaa gctcgctacg actacatgcg gctgccgtcc   120
tacgacggtc ccattacgga cgtaacgagc acctacatgg cgtgcaacgg tggtcccaat   180
ccattggtcc aaatctcgaa cgacgtcgct ttcgtaaaag ccggcgacag catcacgctg   240
caatgggcgc aaacgttgac gacagatttc aacacgggac tgatcatcga tccatcgcac   300
ttgggtcctg tgatggtcta catggccaaa gtaccctccg ccaccggtcc gatccccaac   360
agcggctggt tcaaaatcta cgaagacggc tacgacccga caacaaagac atgggcggta   420
accaagctca tcaacaacaa gggaaaagtg accgtcacca tcccatcgtg tctaccggca   480
ggggactact tgctgcgcgg tgaaatcatt gccttgcacg ctgctagtac ctatccgggt   540
gcacagtttt acatggagtg tgcgcagttg cggcttacca gtggcggcac taagatgcct   600
accacgtata acattccggg gatctattcg cccactgatc cgggtgttac gttcaatctt   660
tacaatggat tcacgagtta taccattcct ggcccaaggc cgtttacatg ctag         714

SEQ ID NO: 86           moltype = AA   length = 237
FEATURE                 Location/Qualifiers
source                  1..237
                        mol_type = protein
                        organism = Trichophaea saccata
SEQUENCE: 86
MKCLLSLLLA ATAVSAHTIF QEIGINGVMQ ARYDYMRLPS YDGPITDVTS TYMACNGGPN    60
PLVQISNDVA FVKAGDSITL QWAQTLTTDF NTGLIIDPSH LGPVMVYMAK VPSATGPIPN   120
SGWFKIYEDG YDPTTKTWAV TKLINNKGKV TVTIPSCLPA GDYLLRGEII ALHAASTYPG   180
AQFYMECAQL RLTSGGTKMP TTYNIPGIYS PTDPGVTFNL YNGFTSYTIP GPRPFTC      237

SEQ ID NO: 87           moltype = DNA  length = 1455
FEATURE                 Location/Qualifiers
source                  1..1455
                        mol_type = genomic DNA
                        organism = Penicillium thomii
SEQUENCE: 87
atgtctctgt ctaagatttc tggattgatc ctcggatctg ctgccttggt ggctggccac    60
ggttacgtga gcggaatcgt cgttgacgat acctactatg gtggatacct tgtcacccag   120
tacccttatg agagtgacgc cccagagctc attgcctggt cggagcaaga gaccgatctg   180
ggttacatcg atggctctga gtatgccaac tccaacatca tctgtcacaa ggaggccaaa   240
cctggtgctt tggaagcacc cgttaaggct ggtggctccg tcgagctcca gtggaccact   300
tggcctacca gccaccacgg tcctgtcatt acctacatgg ccaactgtaa cggcgactgt   360
gacgacgttg acaagactac tttgcagttc ttcaagattg accagggtgg tttgatcagc   420
gataccaccg agcccggtac ctgggcaact gacaacctca tgccaacaa caatagccgt   480
actgtcaccg tccccagcga cattgccgat ggaaactacg tcctccgtca cgagatcatt   540
gccctccact ccgccgggga gaccaacggt gcccagaact accccaatg tatcaacttg   600
aaggtcactg gcggcggtag cgctactcct tctggtaccc tgggtaccgc cctgtacaag   660
aacaccgacc ccggtatcct gatcaacatc tacttcgtc tcagcaccta cgatatcccc   720
ggcccaaccc tgtacactgc cggcgccgcc gctgctaccg ctgcctccac ggctgcctct   780
tccaccgccg ctgccgttac tactgccgac gccgtcacta ccgccgctgc cgtcaccagc   840
agctctgcat ccgtggaagt tgtgcccaca actactccca gctcatcaat cgtcagtgcc   900
ttcccaacct ggagccctc ttctacccca ccctcctcca acttccaa cggatggcgt   960
ccgtcattca gccgcggacc tggtggcccc gcttcacat ctgctcctgc tcctcagttc  1020
tccgctccta gcggcgctca gcagaagcag tctgccactg ctacccccat cgtggctacc  1080
cctgtcgtga tcaccatgac cgagaccagc acctcctggg tcaccgaaat ggttactctt  1140
actgacaagt ctgttgtgca gaccaccagc gctgtcccaa tcgtcgtcgc cgccaccact  1200
acccttaccg agggaagcga gcctgctcag acagcctccc ccagcgttgt ctccggctcc  1260
tctagctccg gctctagctc ctcatctacc accaccacct caaagacctc aactggatcc  1320
gactacgtct ccagcgactg gatgtcttac ctcagctcct tgagcgctgc tgaggtcctc  1380
cagatgctgc gccagacctt ccgttggatg gtcagcaacg acaaggtgca cgctcgtgat  1440
attaccatca actag                                                   1455

SEQ ID NO: 88           moltype = AA   length = 484
FEATURE                 Location/Qualifiers
source                  1..484
                        mol_type = protein
                        organism = Penicillium thomii
SEQUENCE: 88
MSLSKISGLI LGSAALVAGH GYVSGIVVDD TYYGGYLVTQ YPYESDAPEL IAWSEQETDL    60
GYIDGSEYAN SNIICHKEAK PGALEAPVKA GGSVELQWTT WPTSHHGPVI TYMANCNGDC   120
DDVDKTTLQF FKIDQGGLIS DTTEPGTWAT DNLIANNNSR TVTVPSDIAD GNYVLRHEII   180
ALHSAGETNG AQNYPQCINL KVTGGGSATP SGTLGTALYK NTDPGILINI YTSLSTYDIP   240
GPTLYTAGAA AATAASTAAS STAAAVTTAD AVTTAAAVTS SSASVEVVPT TTPSSSIVSA   300
FPTWSPSSTP PFSNSSNGWR PSFSRGPGGP RFTSAPAPQF SAPSGAQQKQ SATATPIVAT   360
PVVITMTETS TSWVTEMVTL TDKSVVQTTS AVPVVAATT TLTEGSEPAQ TASPSVVSGS   420
SSSGSSSSST TTSKTSTGS DYVSSDWMSY LSSLSAAEVL QMLRQTFRWM VSNDKVHARD   480
```

```
SEQ ID NO: 89            moltype = DNA   length = 1021
FEATURE                  Location/Qualifiers
source                   1..1021
                         mol_type = genomic DNA
                         organism = Talaromyces stipitatus
SEQUENCE: 89
atgccttcca ctaaagttgc tgctctatct gccgtcctgg cttttggcctc cacggttgct    60
ggccatggct ttgtgcaaaa tattgtcatt gacggtaaat cgtaagtgac ttgcttttgt   120
actatagagc tagataaata cttatactaa ataattcagc tacactggct acctcgtgaa   180
ccagtatcct taccagtcca acccaccagc tgttattggg tggtcaacca ctgcaaccga   240
cttgggatt tgtcgatggat ctggatacac caacccggat atcatctgcc acaaaaacgc   300
caaacccggt cagctttctg ctccggttgc gcaggaggc aaggttgagc tcgaatggac    360
aacatggccc gagagccatc acgggcctgt catcagctat ctcgccaatt gcaatggcga   420
ttgtactacc gtggataaga cgaagctcga atttgtcaaa atcgatcagc ggggtctgat   480
cgacgacagc aatcctcccg gtacatgggc cgccgaccag ctcatcgccg ccaacaacag   540
ctggactgta actattccgg agagcatcgc gcctggaaac tacgtccttc gccacgaaat   600
catcgctctt cactccgcca acaacgcaac cggagctcaa aactaccctc aatgcatcaa   660
cttgcaaatc actggcagcg ggacggcaaa cccatctggt accctggcg agaaactcta    720
taccccaact gacccaggta tcttggtcaa catctaccag tcattgtcgt cttatgttat   780
tcccggtccg acttgtgga gtggtgctgc agcgcacgtt gttgccactg cagccggttc    840
tgctactcgg gttgcttctg ccaccgctac tccgaccact cttgtgactg ccgtttcatc   900
gcctaccggt gctccttcag tggtgactcc tgaggctcct tcagtaacct cgttcgcccc   960
agtggtgact gttactgatg tcgttactgt gactaccgtc atcactacta ctatctctta  1020
g                                                                 1021

SEQ ID NO: 90            moltype = AA   length = 320
FEATURE                  Location/Qualifiers
source                   1..320
                         mol_type = protein
                         organism = Talaromyces stipitatus
SEQUENCE: 90
MPSTKVAALS AVLALASTVA GHGFVQNIVI DGKSYTGYLV NQYPYQSNPP AVIGWSTTAT    60
DLGFVDGSGY TNPDIICHKN AKPGQLSAPV AAGGKVELEW TTWPESHHGP VISYLANCNG   120
DCTTVDKTKL EFVKIDQRGL IDDSNPPGTW AADQLIAANN SWTVTIPESI APGNYVLRHE   180
IIALHSANNA TGAQNYPQCI NLQITGSGTA NPSGTPGEKL YTPTDPGILV NIYQSLSSYV   240
IPGPTLWSGA AAHVVATAAG SATGVASATA TPTTLVTAVS SPTGAPSVVT PEAPSVTSFA   300
PVVTVTDVVT VTTVITTTIS                                              320

SEQ ID NO: 91            moltype = DNA   length = 872
FEATURE                  Location/Qualifiers
source                   1..872
                         mol_type = genomic DNA
                         organism = Thermomyces lanuginosus
SEQUENCE: 91
atgaagggct ccagcgctgc gtcggtgctt cttaccttcc tcgcgggcat ctcccgtacc    60
tctgcgcacg gtatgtctc caacctcgtt atcaacggcg tctactatcg gggctggctc   120
cccggcgaag accccctacaa ccctgacccc cgattggcg ttggctggga gacgccaaac   180
ctgggcaacg gcttcgtgac gccgtcgaa gcgtcgaccg acgccgtcat ctgccacaag   240
gaagccacac cagcccgcgg tcatgtctcc gtgaaggccg gtgacaagat ctacatccaa   300
tggcagccga atccatggcc ggattccac cacggtgcgt caaacttctg cccgaaagct   360
gttcacactc actaacaaca ctttaggcc ccgtcctgga ctatctgcc ccttgcaacg    420
ggccctgtga gtccgtcgac aagaccagcc tgcgcttctt caagatcgac ggagtgggtc   480
ttatcgacgg ctcttctcct ccgggctact gggccgacga gaactcatt gcgaacggca    540
acgggtggct ggttcagatc cccgaggaca tcaagccggg taactacgtc ctgcgacacg   600
agatcatcgc cttgcacagc gccgggaacc cggacggcgc cagctgtac ccgcagtgct    660
tcaaccttga gattacggga tccggcaccg tcgagccgga gggcgtgcca gccaccgagt   720
tctactcgcc cgatgacccg ggcatcctgg tcaacatcta cgagccctg tccacgtatg    780
aggtgccggg tccctcgctc atcccgcagg cggttcagat cgagcagtct tcgtctgcga   840
ttacggcgac gggcacgccg acgccggcat ga                                 872

SEQ ID NO: 92            moltype = AA   length = 272
FEATURE                  Location/Qualifiers
source                   1..272
                         mol_type = protein
                         organism = Thermomyces lanuginosus
SEQUENCE: 92
MKGSSAASVL LTFLAGISRT SAHGYVSNLV INGVYYRGWL PGEDPYNPDP PIGVGWETPN    60
LGNGFVTPSE ASTDAVICHK EATPARGHVS VKAGDKIYIQ WQPNPWPDSH HGPVLDYLAP   120
CNGPCESVDK TSLRFFKIDG VGLIDGSSPP GYWADDELIA NGNGWLVQIP EDIKPGNYVL   180
RHEIIALHSA GNPDGAQLYP QCFNLEITGS GTVEPEGVPA TEFYSPDDPG ILVNIYEPLS   240
TYEVPGPSLI PQAVQIEQSS SAITATGTPT PA                                 272

SEQ ID NO: 93            moltype = DNA   length = 1039
FEATURE                  Location/Qualifiers
source                   1..1039
                         mol_type = genomic DNA
                         organism = Thermomyces lanuginosus
```

```
SEQUENCE: 93
atggcattct ctacggttac agttttttgtt acgttcctgg ccttcatctc catagcttct    60
gctcatggct tcgtgacaaa aatcaccgta ctcggagata ataataagga gtacgtctca   120
gtctcgctag gttgctaaca caggagagat cgctgaccat tgcagctacc ccggctttga   180
cccgagcact cccaaggagg ttcctccggg tctcgatgtc gcttggtcta ctagtgccag   240
tgatcaggga tacatgagca gttcaaatgc ctcgtatcac agtaaggact ttatctgcca   300
cagaaacgcc aaacctgctc cagacgcagc tcaagttcat gcgggcgaca aggtgcagct   360
tcactggact caatggcctg gacctgagga tcaccagggt cctatccttg attacctcgc   420
gagctgcaac ggaccctgct caaacgtgga gaaggcgagc cttaagtgga cgaagattga   480
cgaggcaggg cgcttttccca acggaacgtg ggcaacgaac ctgctcagga atggggaggg  540
cacgtggaat gtgacgattc catcggatct tgctcctgga gaatatgtcc tccgcaacga   600
gatcattgca cttcactcgg cgagaaatat gggtggagct cagcactaca tgcaatgtgt   660
caatctgaac gtcactggca ccggccatag agagctacag ggcgtctccg ccgcagaatt   720
ttacaatcct acggatcctg gaatttttgat taacgtctgt aaactcaaa gcctttcctc    780
ctaccatatt cccggaccta cactgttagc cgccgatacc ggcaacgacg gtggccattc   840
tgcatcatct acctttggcga ctgtgacaag cagacgtctt tccactccga gcgacgccat  900
gccccgggaat ggttcatacg gtgcaatttc gccgccctc aaacctgcta aaggattcca   960
tcctgttttgt aacgcccgat tcagacatgg cagcactttc actttgacta ccctggtcgc  1020
accaccagcc aggacctaa                                                 1039

SEQ ID NO: 94           moltype = AA  length = 327
FEATURE                 Location/Qualifiers
source                  1..327
                        mol_type = protein
                        organism = Thermomyces lanuginosus
SEQUENCE: 94
MAFSTVTVFV TFLAFISIAS AHGFVTKITV LGDNNKDYPG FDPSTPKEVP PGLDVAWSTS    60
ASDQGYMSSS NASYHSKDFI CHRNAKPAPD AAQVHAGDKV QLHWTQWPGP EDHQGPILDY   120
LASCNGPCSN VEKASLKWTK IDEAGRFPNG TWATDLLRNG GNTWNVTIPS DLAPGEYVLR   180
NEIIALHSAR NMGGAQHYMQ CVNLNVTGTG HRELQGVSAA EFYNPTDPGI LINVWQTQSL   240
SSYHIPGPTL LAADTGNDGG HSASSTLATV TSRRLSTPSD AMPGNGSYGA ISPPLKPAKG   300
FHPVCNARFR HGSTFTLTTL VAPPART                                        327

SEQ ID NO: 95           moltype = DNA  length = 881
FEATURE                 Location/Qualifiers
source                  1..881
                        mol_type = genomic DNA
                        organism = Thermomyces lanuginosus
SEQUENCE: 95
atgaaaggct ccaccactgc gtctttgctt cttccgctcc tggcgagcgt tactcgcacc    60
tctgcgcacg ggtttgtctc caacctcgtc atcaatggcg tcttctatcg gggctggctc   120
ccgaccgagg acccctacaa ggctgacccc ccgattggcg tcggctggga gacgcctaac   180
ctgggcaacg gcttcgtgct gcccgaagaa gcgtcgaccg atgccatgct ctgccacaca   240
gaggccgagc cggcccgcgg ctatgccagc gtcgctgaccg gtgacaagat ctacattcag   300
tggcagccga acccatggcc ggagtctcat acggtacgt caaactgccc attgttgcaa   360
ttcagaatca tctactaaca actcttcaag gccccgtcat tgactacctg gccccttgca   420
acggtgactg ctcgactgtc aacaagacca gtttggattc ttcaagatc acgggcgtgg   480
gcctcatcga cggctcctcc ccgcgggta agtgggctga cgacgagctc attgccaacg   540
gcaacggctg gctggtccag atccccgagg acatcaagcc gggcaactac gtcctgcgcc   600
atgagatcat cgccttgcac gaggcgttca accagaacgg cgctcagatc tacccgcagt   660
gcttcaacct ccagattacc ggctccggca ctgtcgagcc gcagggcacg ccggctaccg   720
agctgtattc gcccaccgat ccgggcattc tggttgacat ctacaacccc ttgagcacgt   780
acgtcgtgcc cggccccgacg ctcatcccgc aggcggttga gattgagcag tcttcgtcgg   840
ctgtcacggc gactggtacg ccgacgccgg cggcggcgta                          881

SEQ ID NO: 96           moltype = AA  length = 274
FEATURE                 Location/Qualifiers
source                  1..274
                        mol_type = protein
                        organism = Thermomyces lanuginosus
SEQUENCE: 96
MKGSTTASLL LPLLASVTRT SAHGFVSNLV INGVFYRGWL PTEDPYKADP PIGVGWETPN     60
LGNGFVLPEE ASTDAIVCHK EAEPARGYAS VAAGDKIYIQ WQPNPWPESH HGPVIDYLAP   120
CNGDCSTVNK TSLEFFKIDG VGLIDSSPP GKWADDELIA NGNGWLVQIP EDIKPGNYVL    180
RHEIIALHEA FNQNGAQIYP QCFNLQITGS GTVEPEGTPA TELYSPTDPG ILVDIYNPLS   240
TYVVPGPTLI PQAVEIEQSS SAVTATGTPT PAAA                                274

SEQ ID NO: 97           moltype = DNA  length = 821
FEATURE                 Location/Qualifiers
source                  1..821
                        mol_type = genomic DNA
                        organism = Humicola insolens
SEQUENCE: 97
atgaagctca gcgttgtcct cacaggcctg gcggcagccc tcgccgagcc tcattgtcag    60
tccatacgac agcgaaaccc ctggatgatc acgagactaa ccagtcctac cagacacctt   120
ccccagcgtc ggcaacaccg ccgactggca ggtcgtgcgc cagacgacca acttccagag   180
caacggcccc gtgacggacg tcaactcgga ccagatccgg tgctacgagc gcttccccgg   240
caggggggcg cccggcatct acaacgtcac cgccggccag accatctcgt acaacgccaa   300
ggcctctatc tcccacccgg gccccatggc cttctacatc gccaaggtcc ctgccggcta   360
```

```
caccgccgcc aactgggatg gcaggggcgc cgtgtggtcc aagatctacc aggacatgcc    420
gcgcattgcg gggagtctga cctggcctac caatggtacg aaatcctctt ctatccttca    480
tacttgctat tcctccaact gcctggcagc tcacactaac ttccacacac caggcgccc     540
gttccgtctc ggtaaccatc ccccgctgcc tgcaagacgg ccactacctg ttgcgcgccg    600
agcacatcgg cctgcacagc gcgagcggcg tgggcgggcg gcagttctac atctcgtgtg    660
cccagctcta cgtcagcggc ggcaccggca cttggaaccc gcgcaacaag gtcgcgttcc    720
ccggcgccta cagcccgacg cacccgggca tcatgatcaa catctactgg ccggtgccga    780
cgagctacac gccgccgggg ccgccggttg agacgtgctg a                        821

SEQ ID NO: 98         moltype = AA   length = 227
FEATURE               Location/Qualifiers
source                1..227
                      mol_type = protein
                      organism = Humicola insolens
SEQUENCE: 98
MKLSVVLTGL AAALAEAHYT FPSVGNTADW QVVRQTTNFQ SNGPVTDVNS DQIRCYERFP     60
GQGAPGIYNV TAGQTISYNA KASISHPGPM AFYIAKVPAG YTAANWDGRG AVWSKIYQDM    120
PRIAGSLTWP TNGARSVSVT IPRCLQDGHY LLRAEHIGLH SASGVGGAQF YISCAQLYVS    180
GGTGTWNPRN KVAFPGAYSP THPGIMINIY WPVPTSYTPP GPPVETC                  227

SEQ ID NO: 99         moltype = DNA   length = 1120
FEATURE               Location/Qualifiers
source                1..1120
                      mol_type = genomic DNA
                      organism = Humicola insolens
SEQUENCE: 99
atgcgcccct tcctcgccgc cctcgccgcg gccaccacgg tccacgccca cggctgggtc     60
gacaacgcca ccatcgacgg cgtcttctac cagctctacc accgtacat ggacccgtac     120
atgggcgagt tcgccccgcc tcgcatctcg cgcaagctgg tgtggaacgg ctacgtgaac    180
gacgtgacgt ccatcgacct gcaatgcggc ggacacacgg ccgaagggca aatcggcacg    240
gaacccgcgc cgctgcacgc ccccgccacg gccgggtcga cggtcaacct ccgctggacg    300
ctgtggccgg actcgcacat ggggcccatc atgacgtaca tggcgcgtg tccggacgag    360
ggttgtgata agtggttgcc gggggaggag taagtgtttc ctggcgggaa tggctgtgta    420
tttgagaagg agatattatg agtgaaactg ggagaggcga ggagaagaga tgctgcacg    480
ggttttgctc tcctcagacc agtctggttc aaaatccacg aagccggccg gtacaccacc    540
gacaagtctt accccgacga catctgggaa gttgtaagtg ccctgcctac ctatccatcc    600
ctaattccct ccctcccctc tccacctcct ccttccgcgc cccctcccc cccttattt     660
gctaaccaac ccctccctt acagaccccgc ctcatgtacc ccgccaacga aggctacaac    720
tacaccatcc ccgcctgcct cgcatccggc cactacctgg tccggcacga gatcatcgcc    780
ttacactcgg cctgggccaa aggcgaagcg cagttctatc cctcgtgcca ccagctgacc    840
gtcacctcca tcggcggtaa cgtgcgcgaa gcgccggccg agtaccgcgt cagtttcccc    900
ggcgcgtaca aggacgatga tccgggtatt ttcatcaacg tttggaaccg taagttcttt    960
ttttgttccc cttcctccca acctacctag tgtgtcgtaat gtgtccgtta aggtttgtt    1020
tgttgttgag ggatatagct gacaatggat gtgtgataac acagctggcc cctacaccat   1080
tcccggaccg ccggtctgga cgtgccccga gtctgagtaa                         1120

SEQ ID NO: 100        moltype = AA   length = 257
FEATURE               Location/Qualifiers
source                1..257
                      mol_type = protein
                      organism = Humicola insolens
SEQUENCE: 100
MRPFLAALAA ATTVHAHGWV DNATIDGVFY QLYHPYMDPY MGEFAPPRIS RKLVWNGYVN     60
DVTSIDLQCG GHTAEGQIGT EPAPLHAPAT AGSTVNLRWT LWPDSHMGPI MTYMARCPDE    120
GCDKWLPVWF KIHEAGRYTT DKSYPDDIWE VTRLMYPANE GYNYTIPACL ASGHYLVRHE    180
IIALHSAWAK GEAQFYPSCH QLTVTSIGGN VREAPAEYRV SFPGAYKDDD PGIFINVWNP    240
GPYTIPGPPV WTCPESE                                                   257

SEQ ID NO: 101        moltype = DNA   length = 878
FEATURE               Location/Qualifiers
source                1..878
                      mol_type = genomic DNA
                      organism = Humicola insolens
SEQUENCE: 101
atgagactct ccctgacaac cctcctggcc tctgccctgt ccgtccaggg tcacgccatc     60
ttccaggtgc gttcctttca ccacccacat catcatgatg aacctcaaag ttgctaaccc    120
ccgctgggca gagagttacc gtcaacggcc aggaccaagg ctcgttgact ggtctccggg    180
ccccgaataa caacaacccc gtgcagaacg tcaacagcca ggacatcatc tgtgcgctc    240
ccgggtcgcg gtcacagtcc gtcatcaacg tcaatgccgg cgaccgcatc ggtgcctggt    300
accagcatgt catcggcggc gcccagttcc ccggcgaccc ggacaacccg atcgccaggt    360
cccacaaggg ccccatctcc gtctatctgg ccaaggtgga caacgctgcc acggcgaacc    420
accagggtct gcaatggtaa acatacctcg ggtcaagtca gaacctctgt gatcgccgag    480
acgactaacc cctcttccc ataaacaggt tcaagatctg gcacgacggc ttcaacccct    540
ccaccggcaa atgggccgtc gacaccatga tcaacaacc cggctgtact tatttcaacc    600
tccccgcagtg catcgctccc ggccactatc tcatgcgcgt cgagctgctc gctctcact    660
cggccaccta ccaaggccag gcgcagttct acatctcgtg cgcccagatc aacgtccagt    720
cgggcggcaa ctttactccc tggcagacgg ttagcttccc cggcgcctac caggccaacc    780
accccggcat tcaggtcaac atttacgcgc ccatgggcca gccggataac ggcggcaggc    840
cctaccagat tccgggcccg gagccgattc agtgctga                           878
```

```
SEQ ID NO: 102          moltype = AA  length = 246
FEATURE                 Location/Qualifiers
source                  1..246
                        mol_type = protein
                        organism = Humicola insolens
SEQUENCE: 102
MRLSLTTLLA SALSVQGHAI FQRVTVNGQD QGSLTGLRAP NNNNPVQNVN SQDIICGAPG    60
SRSQSVINVN AGDRIGAWYQ HVIGGAQFPG DPDNPIARSH KGPISVYLAK VDNAATANHQ   120
GLQWFKIWHD GFNPSTRQWA VDTMINNNGW VYFNLPQCIA PGHYLMRVEL LALHSATYQG   180
QAQFYISCAQ INVQSGGNFT PWQTVSFPGA YQANHPGIQV NIYGAMGQPD NGGRPYQIPG   240
PEPIQC                                                              246

SEQ ID NO: 103          moltype = DNA  length = 1067
FEATURE                 Location/Qualifiers
source                  1..1067
                        mol_type = genomic DNA
                        organism = Humicola insolens
SEQUENCE: 103
atgggaccga cctgggcagt gattctgggg ctgattgctc cttctgtgct cagtcacagt    60
tgcgtctccc aacagacctc tcgactttta tcaagctggt actgactcat aacccaactc   120
acctagatat ccatgggatc ctcctggtca atggcacaga gacaccagag tggaaatacg   180
tcctgtatgt ttcctcatat cctagcccca ttgtacgagt tgttgacgtg atacagcgat   240
gttgcgccgg cggttccaat ttcaaaccca gactctctcc ccctggata ccaaggctat    300
aaggttgatc catcatcgg atccgggaac cccaacatca cttgtggccg gctagcattt    360
gactcggcac ccaagacgca aatgccgat gtgctagccg gtccgaggt aggattccga    420
gtctcggctg atggcttggg aaatcggat ctggagaagg gctacatccc gacgttctgg    480
cacccaggtc cggcccaggc atacttgtca cgtccccga acgacgacct gtacagctac   540
aaaggcgacg gggactggtt caagattgcc tacgctggcc cggtgacga cctgacgtgg   600
tcccttttggc cgggagtttc agatgtatgt tcatcctgtt tttgccctct                660
ccaggaccaa attattaata tcgagtcgca gttcaacttc accattccgt tgtcgacacc   720
ccctggcaag tatttgctcc gaatcgaaa cttcatgcca acggcctcga caggatatct   780
tcagttctac gtcaattgtg catttgtcaa catcattgga ccaggaggtg ggaccccgac   840
cgagttcatt cgaattcccg gggattacac gacgaggat ccaggtgagt ttgtgttatg    900
agacatgttc aactgcacc gacgaatgct tgtttcctga cagagatttg taaaaactag   960
gctttctcgt tcccccggag caaagctcct tggatggcag agtcccaagg gaccagttga  1020
aactgatgag ctacacgcca ccaggtcctg cggtgtggac ggggtga                1067

SEQ ID NO: 104          moltype = AA  length = 265
FEATURE                 Location/Qualifiers
source                  1..265
                        mol_type = protein
                        organism = Humicola insolens
SEQUENCE: 104
MGPTWAVILG LIAPSVLNIH GILLVNGTET PEWKYVLDVA PAVPISNPDS LPPGYQGYKV    60
DPIIGSGNPN ITCGRLAFDS APKTQIADVL AGSEVGFRVS ADGLGNRDLE KGYIPTFWHP  120
GPAQAYLSRA PNDDLYSYKG DGDWFKIAYA GPVDDLTWSL WPGVSDFNFT IPLSTPPGKY  180
LLRIENFMPT ASTGYLQFYV NCAFVNIIGP GGGTPTEFIR IPGDYTDEDP GFLVPPEQSS  240
LDGRVPRDQL KLMSYTPPGP AVWTG                                         265

SEQ ID NO: 105          moltype = DNA  length = 1035
FEATURE                 Location/Qualifiers
source                  1..1035
                        mol_type = genomic DNA
                        organism = Humicola insolens
SEQUENCE: 105
atgaaggccc tcaccctcct cgccgccgcg accgcggcct cggcgcacac catcttcgtg    60
cagctcgagg ccgacggcac gcgctacccc gtctcgcacg gcgtgcgcac cccgcagtac   120
gacggcccca tcaccgacgt ctcgtccaac gacctggcct gcaacggcgg gcccaacccg   180
accatgaaga cggacaagat catcaccgtg acggccgtca ggccgtcaa ggcatcttgg    240
cggcacacgc tgcagtcggg ccccaacgac gtcatggacc ccagccacaa gggcccgacg   300
ctggcgtacc tgaagaaggt ggacaacgcg ctgacggatt cgggcgtggg cggcggctgg   360
ttcaagatcc aggaggacgg gcacagcaat gggaattggg gcacgctcaa ggtaatcaac   420
aaccagggca ttcactatat cgatatcccc gactgcatcg acagcgggca gtatttgttg   480
cgggccgaga tgatcgctct gcacgctgcc gggtcgccgg gcgtgcgca gctttatgtg    540
agtttcttcc ttcttttctt ctctctcccc tttgtgataa gaataaagat ccacaccaca   600
gtcaaaccaa agcatcctaa cctcggcatc tactcacaga tggaatgcgc ccaaatcgaa   660
atcgtcggcg gcaagggcac cgtcaagccc cagacctact ccatcccggg catctacaag   720
tccaacgacc cgggcatcct catcaacatc tactccatgt cgccctcgaa ccagtacatc   780
atcccccggcc cgcccctctt cacctgcaac ggcggcggcg gcagcaacaa cggcggcggc   840
aacaacggcg gcagcaaccc cccgtccag cagcccccg ccaccaccct caccaccgcc    900
atcgcccagc ccacgcccat ctgctccgtc agcagtgggg tcagtgcgg cggccagggc   960
tatagcggct gcaccacctg cgcgtcgccg tataggtgta cgagatcaa cgcgtggtat  1020
tcgcagtgct tgtaa                                                   1035

SEQ ID NO: 106          moltype = AA  length = 310
FEATURE                 Location/Qualifiers
source                  1..310
                        mol_type = protein
```

```
                        organism = Humicola insolens
SEQUENCE: 106
MKALTLLAAA  TAASAHTIFV  QLEADGTRYP  VSHGVRTPQY  DGPITDVSSN  DLACNGGPNP   60
TMKTDKIITV  TAGSTVKAIW  RHTLQSGPND  VMDPSHKGPT  LAYLKKVDNA  LTDSGVGGGW  120
FKIQEDGHSN  GNWGTLKVIN  NQGIHYIDIP  DCIDSGQYLL  RAEMIALHAA  GSPGGAQLYM  180
ECAQIEIVGG  KGTVKPQTYS  IPGIYKSNDP  GILINIYSMS  PSSQYIIPGP  PLFTCNGGGG  240
SNNGGGNNGG  SNPPVQQPPA  TTLTTAIAQP  TPICSVQQWG  QCGGQGYSGC  TTCASPYRCN  300
EINAWYSQCL                                                              310

SEQ ID NO: 107          moltype = DNA   length = 1065
FEATURE                 Location/Qualifiers
source                  1..1065
                        mol_type = genomic DNA
                        organism = Humicola insolens
SEQUENCE: 107
atggctccca agacctcgac gttccttgcc tccctcacgg gcgccgccct cgtggctgcc   60
cacggccatg tcagccacat cattgtcaat ggcgtccagt accggaacta cgaccccacc  120
accgacttct acagcggcaa ccctccgacc gtgatcggct ggtcggccct caaccaggac  180
aacggcttca tcgagcccaa caacttcggc acccccgaca tcatctgcca taagtcggcc  240
aagcccggcg gcgccacgt cacggtgagg gccggtgaca agatcagcat cgtctggacc  300
cccgagtggc ccgagtcgca cgtcggcccc gtcatcgact accttgccgc gtgcaacggc  360
gactgcgaga cggtcgacaa gacctccctc cgcttcttca agatcgacgg cgccggctac  420
gacgccgcgg ccggccgctg gccgccgac gctctgcgcg ccaacggcaa ctcgtggctt  480
gtgcagatcc ccgccgacct caaggccgga aactacgtgc ttcggcacga gatcatcgcc  540
ctgcacggcc ccgccaaccc caacggcgcc caggcctacc cgcagtgcat caacatccgc  600
gtcaccggcg gcggcaacaa ccagccctcg ggcgtcccg cgaaccagct ctacaaggcc  660
tcggacccgg gcatcctctt caaccccctgg gtcgccaacc ctcagtaccc cgtcccgggc  720
ccggccctca tccccggcgc cgtgagctcc atccctcaga gccgctcgac cgccaccgcc  780
acgggcaccg ccaccgcgcc cggcgccgac acggacccga cggcgtcccc tcccgtcgtc  840
accaccactt ctgccccggc tcaggtgacc accaccacca ccgccgcac cacctccctg  900
cctcagatca ccaccacctt cgccaccagc accaccacgc cgcccccggc cgctaccag  960
agcaagtggg gccagtgcgg cggcaacggc tggaccggcc cgaccgtctg cgcgccgggc 1020
tcgagctgca caaagctcaa cgactggtac tcgcagtgca tctaa              1065

SEQ ID NO: 108          moltype = AA   length = 354
FEATURE                 Location/Qualifiers
source                  1..354
                        mol_type = protein
                        organism = Humicola insolens
SEQUENCE: 108
MAPKTSTFLA  SLTGAALVAA  HGHVSHIIVN  GVQYRNYDPT  TDFYSGNPPT  VIGWSALNQD   60
NGFIEPNNFG  TPDIICHKSA  KPGGGHVTVR  AGDKISIVWT  PEWPESHVGP  VIDYLAACNG  120
DCETVDKTSL  RFFKIDGAGY  DAAAGRWAAD  ALRANGNSWL  VQIPADLKAG  NYVLRHEIIA  180
LHGAANPNGA  QAYPQCINIR  VTGGGNNQPS  GVPGTQLYKA  SDPGILFNPW  VANPQYPVPG  240
PALIPGAVSS  IPQSRSTATA  TGTATRPGAD  TDPTGVPPVV  TTTSAPAQVT  TTTSSRTTSL  300
PQITTTFATS  TPPPPAATQ   SKWGQCGGNG  WTGPTVCAPG  SSCNKLNDWY  SQCI        354

SEQ ID NO: 109          moltype = DNA   length = 804
FEATURE                 Location/Qualifiers
source                  1..804
                        mol_type = genomic DNA
                        organism = Humicola insolens
SEQUENCE: 109
atgtatcttt tacctatcgc cgcggccgcc ctagcgttca ccaccaccgc atacgcccac   60
gcccaagtct acggcttgcg tgtcaacgac caacaccagg gcgatgggcg caacaaatac  120
atccgctcgc ccagcagcaa ttcccccatc cggtgggacc acgtaaccca cccattcctc  180
atctgcaaca tccgcgacga caaccaaccc ccgggtcccg cgcctgactt tgtccgcgcc  240
ttcgccggcg accgcgtggc gttccaatgg taccacgccc gccccaacga cccgacggat  300
tacgtcctcg acagctccca cctcggcgtc ctcgttacct ggatcgcgcc gtacacggac  360
gggcccggga ccggccccat ttggaccaag atccaccagg acgggtggaa cggcacgcac  420
tgggccacga gccggctcat cagcaacggc gggttcgtcg agttccggct gcccggctcg  480
ctaaagcccg ggaagtacct ggtgcggcag gagattatcg ctctgcacca ggccgacatg  540
cccggtccga accgcgggcc tgagttctac cccagctgcg cgcaattgga ggttttgggg  600
tctggtgagg cggcgccgcc gcaggggtat gatatcaaca agggatatgc ggagagcggg  660
gataagttgt ggttcaacat ttacatcaac aagaatgatg agttcaaaat gcctggaccg  720
gaggtttggg atggtgggtg tcggtttgga gagcgatggg caaccgagga accaggcaag  780
cccaaggtga accaacacgg ataa                                          804

SEQ ID NO: 110          moltype = AA   length = 267
FEATURE                 Location/Qualifiers
source                  1..267
                        mol_type = protein
                        organism = Humicola insolens
SEQUENCE: 110
MYLLPIAAAA  LAFTTTAYAH  AQVYGLRVND  QHQGDGRNKY  IRSPSSNSPI  RWDHVTHPFL   60
ICNIRDDNQP  PGPAPDFVRA  FAGDRVAFQW  YHARPNDPTD  YVLDSSHLGV  LVTWIAPYTD  120
GPGTGPIWTK  IHQDGWNGTH  WATSRLISNG  GFVEFRLPGS  LKPGKYLVRQ  EIIALHQADM  180
PGPNRGPEFY  PSCAQLEVFG  SGEAAPPQGY  DINKGYAESG  DKLWFNIYIN  KNDEFKMPGP  240
EVWDGGCRFG  ERWATEEPGK  PKVNQHG                                         267
```

```
SEQ ID NO: 111           moltype = DNA  length = 843
FEATURE                  Location/Qualifiers
source                   1..843
                         mol_type = genomic DNA
                         organism = Humicola insolens
SEQUENCE: 111
atgaagctcc tcgctcctct gatgctggct ggcgccgcca cgcccgtga gtaaccctg      60
gctggatctc atgctggtgc cagtgttcca tgactgacaa ccaccctcag acaccatctt   120
cacctccctc gaggttgatg gccgcaacta cggcacgggc aacggcgtcc gcgtcccctc   180
ctacaacggc cccgtcgagg atgtcacgtc caactcgatc gcctgcaacg gcccgccgaa   240
cccgaccagc ccgaccgaca cggtcatcac cgtccaggct ggccagaacg tgactgccat   300
ctggcggtac atgctcaaca cccagggcac ctcgcccaac gacatcatgg acagcagcca   360
caagggtcct actctcgcct acctcaagaa ggtcaacgat gcccgcactg actcgggcgt   420
cggcgatggc tggttcaaga tccagcacga cggcttcgac ggcaccacct ggggcaccga   480
gcgcgtcatc ttcggccagg gccgtcacac catcaagatc cccgagtgca tcgagcccgg   540
ccagtacctg ctgcgtgctg agatgatcgc cctccacggc gcccagaact acccgggtgc   600
tcagttctac atggagtgcg ccagctcaa cattgtcggt ggcaccggca caagaaacc   660
cagcaccgtc agcttccctg cgcttacaa ggtatgtccg agtttggtac cgagataact   720
ggagatgaga aaagtgatgc taacaaacca tgacagggca ccgaccccgg cgtcaagctc   780
agcatctggt ggccgcccgt caccaactac gtcattcccg gccccgatgt cttcaagtgc   840
taa                                                                 843

SEQ ID NO: 112           moltype = AA  length = 237
FEATURE                  Location/Qualifiers
source                   1..237
                         mol_type = protein
                         organism = Humicola insolens
SEQUENCE: 112
MKLLAPLMLA GAASAHTIFT SLEVDGRNYG TGNGVRVPSY NGPVEDVTSN SIACNGPPNP    60
TSPTDTVITV QAGQNVTAIW RYMLNTQGTS PNDIMDSSHK GPTLAYLKKV NDARTDSGVG   120
DGWFKIQHDG FDGTTWGTER VIFGQGRHTI KIPECIEPGQ YLLRAEMIAL HGAQNYPGAQ   180
FYMECAQLNI VGGTGTKKPS TVSFPGAYKG TDPGVKLSIW WPPVTNYVIP GPDVFKC     237

SEQ ID NO: 113           moltype = DNA  length = 705
FEATURE                  Location/Qualifiers
source                   1..705
                         mol_type = genomic DNA
                         organism = Humicola insolens
SEQUENCE: 113
atgaagctcc tctcaaccct cgccgccatt gcggccacct tggccacggc ggatgcgcac    60
tacatcttca acatcctgta cgtcaacggc cagcgcatgg gcggcgagta cacctacgtg   120
cggcgcaact ccaactcgta cttccccgtg ttccccgaca tcctcaactc caacgacatg   180
cgttgcaacg tgggtgccag accgggcaac acccaaaccg ccaccgtcag ggccggcgac   240
aggatcggct tcaaggtctt caacaacgag gtcatcgagc acctggtcc cggcttcatc   300
tacatgtcca agcccccggg cagcgtcaac aactatgacg gcagcgggga ctggttcaag   360
gtttacgaga ccggtctctg ccgcggtggt ggcaacgtcg acacaactg gtgctcgtac   420
tacaaggacc ggctcgagtt taccatcccg cccaagactc ctcccggcga gtatctggtg   480
cgtatcgagc atatcggtct gcacgagggc acgtcaaca gggcgcagtt ctacatcacc   540
tgcgcgcagc tcaagattga ggggcccggc ggcggcaacc cgaacccact cgtgaagatc   600
ccgggcatct acagggccaa cgaccccggc atcgcctaca caagtggac caacaacccg   660
gcgccgtaca tcatgccggg tcccaaggtg tgggatggca actaa                   705

SEQ ID NO: 114           moltype = AA  length = 234
FEATURE                  Location/Qualifiers
source                   1..234
                         mol_type = protein
                         organism = Humicola insolens
SEQUENCE: 114
MKLLSTLAAI AATLATADAH YIFNILYVNG QRMGGEYTYV RRNSNSYFPV FPDILNSNDM    60
RCNVGARPGN TQTATVRAGD RIGFKVFNNE VIEHPGPGFI YMSKAPGSVN NYDGSGDWFK   120
VYETGLCRGG GNVDTNWCSY YKDRLEFTIP PKTPPGEYLV RIEHIGLHEG HVNRAQFYIT   180
CAQLKIEGPG GGNPNPLVKI PGIYRANDPG IAYNKWTNNP APYIMPGPKV WDGN         234

SEQ ID NO: 115           moltype = DNA  length = 753
FEATURE                  Location/Qualifiers
source                   1..753
                         mol_type = genomic DNA
                         organism = Humicola insolens
SEQUENCE: 115
atgctgggaa gcgctcttct gctcctgggc actgccctgg cgccaccgc ccactacacg     60
ttccctagga tcaacagcgg cggcgactgg cagtatgtcc gccgggccga caactggcag   120
gacaacggct tcgttggcaa cgtcaactcg cctcagatcc ggtgcttcca gagcaggcac   180
caggccgcc cggccaccct caacgtcacc gccggctcca cggtgaccta ctacgccaat   240
cccaacgtct atcacccggg cccgatggcc ttctacatgg cccgcgtccc cgatgggcag   300
gatatcaact cgtggaccgg cgaggtgcc gtgtggttca agatctacca cgagcagcct   360
accgcctggg gccagcagct gaggtggtct agcgatggta cgtgaatggt gatcctgtgg   420
catctcaacc tcttccagac ttctgacccg agccccgcg ccctacagg caagaactcg   480
ttccaggttc agatcccccg ctgcatccgc tctggcact acctgctccg tgctgagcac   540
```

```
atcggcttgc acagcgccgg cagccctggt ggcgctcagt tctacatctc ttgcgcccag    600
ctcgccgtca acggcggtgg cagcaccgag cccccaaca aggtgtcctt ccctggtgcc    660
tacagcccgt ccgaccccgg cattcagatc aacatctact ggcctgttcc gacctcgtac    720
aagaaccccg gccccccggt cttccagtgc taa                                  753
```

| SEQ ID NO: 116 | moltype = AA   length = 226 |
|---|---|
| FEATURE | Location/Qualifiers |
| source | 1..226 |
| | mol_type = protein |
| | organism = Humicola insolens |

SEQUENCE: 116

```
MLGSALLLLG TALGATAHYT FPRINSGGDW QYVRRADNWQ DNGFVGNVNS PQIRCFQSRH     60
QAAPATLNVT AGSTVTYYAN PNVYHPGPMA FYMARVPDGQ DINSWTGEGA VWFKIYHEQP    120
TGLGQQLRWS SDGKNSFQVQ IPRCIRSGYY LLRAEHIGLH SAGSPGGAQF YISCAQLAVN    180
GGGSTEPPNK VSFPGAYSPS DPGIQINIYW PVPTSYKNPG PPVFQC                   226
```

| SEQ ID NO: 117 | moltype = DNA   length = 854 |
|---|---|
| FEATURE | Location/Qualifiers |
| source | 1..854 |
| | mol_type = genomic DNA |
| | organism = Humicola insolens |

SEQUENCE: 117

```
atgaagctgc ttcctgggtt gcttctggca gccacggctg cccaagccca ttgtacgttt     60
ccgatcccca agaccatctt cgagaatttt cgagccagat ctttctgaga gagttgctga    120
caattcctgc tagacacatt ccccaggctc gttgtcaacg ggcagcctga ggagagggac    180
tggtcggtca ctcggatgac aaagaaccac cagagcaggc cgggaattga aaacccaact    240
agccccgaca tccgttgcta cagctcgcag actgcccta acgtggcgat gtgccggcc     300
gggtctacca tccactacat ctcgacccaa caaatcaacc atcctggccc gactcagtac    360
tatctcgcca aggtcccagc tggtcagtca gccaagacct gggatggctc tggcaacgtg    420
tggttcaaga tcgccacgag catgccggag tacgatcaaa acaggcagct ggtttggccc    480
ggtcatagta aggactcact ctcgtccgat catctctttt gagtgagtct tgggcatacc    540
cactgactac gtctgctatg acagatacct atcagaccat caacgccacc atcccggcca    600
acacgccgag cggagagtac ctcctgcgtg tcgagcaaat tgcctccac atggccagcc    660
agccgaacaa gccccagttc tacatctcgt gctccagat tcagattacc aatggcggaa    720
acggcactcc gggccctcta gttgcattcc cgggggcata caggagccaac gaccctggca    780
tcctggtcaa tctctacagc ggcatgcagc cttcgcagta ccagccccct ggaccggccg    840
tgtggcgtgg ctga                                                       854
```

| SEQ ID NO: 118 | moltype = AA   length = 231 |
|---|---|
| FEATURE | Location/Qualifiers |
| source | 1..231 |
| | mol_type = protein |
| | organism = Humicola insolens |

SEQUENCE: 118

```
MKLLPGLLLA ATAAQAHYTF PRLVVNGQPE ERDWSVTRMT KNHQSKSGIE NPTSPDIRCY     60
SSQTAPNVAI VPAGSTIHYI STQQINHPGP TQYYLAKVPA GQSAKTWDGS GNVWFKIATS    120
MPEYDQNRQL VWPGHNTYQT INATIPANTP SGEYLLRVEQ IALHMASQPN KAQFYISCSQ    180
IQITNGGNGT PGPLVAFPGA YRSNDPGILV NLYSGMQPSQ YQPPGPAVWR G             231
```

| SEQ ID NO: 119 | moltype = DNA   length = 863 |
|---|---|
| FEATURE | Location/Qualifiers |
| source | 1..863 |
| | mol_type = genomic DNA |
| | organism = Humicola insolens |

SEQUENCE: 119

```
atgctcctga actcggtcat cggctcggcc gtcctcctgg ccaccggcgc cgccgcccac     60
ggtgccgtga ccagctacgt cattgccggg aagaactacc ctgggtaggt aacctcgtgg    120
aagcgaatgc aggcagttca ttcactaaca catacctccg ttagctacaa cggctacgcc    180
ccgtccacca ccccaacac gatccagtgg caatggtcga cctacgaccc catctactcc    240
gccaccgacc ccaagctccg ctgcaacggc ggccgctcgg ccacgcagtc cgccccggct    300
gctccgggcg acaacatcac cgccatctgg cagcagtgga cgcatagcca gggccccatc    360
ctcgtctgga tgtacaagtg tcccggcgcc ttcagctcgt gcgacggctc gggccagggc    420
tggttcaaga ttgacgaggc cggcttcaat ggcgacggca agaccgtgtt cctcgacacc    480
gagcgcccct ccggctggga gatcgccaag ctggttgcgu acaacagggu ctggaccagc    540
accatcccca agaacctggc cccgggcaac tacctggtcc gccacgagtt gattgccctt    600
caccaggcca acgcccgca gtggtaccct gagtgcgcgc aggtcgtgat caccggctcg    660
ggcactaagg agccgcctgc gtcgtacaag gctgccattc ccggctactg caaccagaac    720
gatcccaaca ttcgggtatg tgaggcctat ttggagttcg gctaaggcat gatactaact    780
ctaccccca ggttcctatc aacgaccact ccatccccca gacctacaag atccctggcc    840
ctccggtctg gcgcggcgag taa                                             863
```

| SEQ ID NO: 120 | moltype = AA   length = 248 |
|---|---|
| FEATURE | Location/Qualifiers |
| source | 1..248 |
| | mol_type = protein |
| | organism = Humicola insolens |

SEQUENCE: 120

```
MLLNSVIGSA VLLATGAAAH GAVTSYVIAG KNYPGYNGYA PSTTPNTIQW QWSTYDPIYS     60
ATDPKLRCNG GRSATQSAPA APGDNITAIW QQWTHSQGPI LVWMYKCPGA FSSCDGSGQG    120
```

```
WFKIDEAGFN GDGKTVFLDT ERPSGWEIAK LVGGNKGWTS TIPKNLAPGN YLVRHELIAL  180
HQANAPQWYP ECAQVVITGS GTKEPPASYK AAIPGYCNQN DPNIRVPIND HSIPQTYKIP  240
GPPVWRGE                                                          248

SEQ ID NO: 121          moltype = DNA   length = 883
FEATURE                 Location/Qualifiers
source                  1..883
                        mol_type = genomic DNA
                        organism = Humicola insolens
SEQUENCE: 121
atgaagctca ccacctccat cgccctgctg gctgcggccg gcgcgcaggc tcactgtacg   60
tgctccctca tctcatccat ctcctcagac catgttttac ctattggtta ctaacaagct  120
ctcacgcaga caccttcccc cgcaccaagg tcgacgcgt caccctcggggc gagtgggaga  180
cgatccgcat caccgagaac cactggtcgc acggcccccgt gacggacgtg acctcgcagg  240
ccatgacgtg ctacgagaag acgcccggcc agggcgcgcc caagacggtt aacgtgaagg  300
ccggcggcac cgtcaccttc accgtcgaca cggacgtggg ccaccgggc ccgctgcact   360
tctacttggc caaggtgccc gcgggcaaga cggccgac gtttgacggc aagggcgccg  420
tgtggttcaa gatttaccag gacggccccg gcgggttggg gaccagctcg ttgacttggc  480
ctagctttgg tgagctttct tttctttatt ttcttcaatc ctcccataat tacctcccga  540
cgaggaaata aatataccct acctgatatt aacccatccc cccccacctc ctccaggcaa  600
gaaggaagtc tctgtccaaa tccccccctg cgtgcaggac ggcgagtacc tgctgcgcgt  660
cgagcacatt gcgctgcaca gcgccgag cgtcggcggc gcgcagctct acatttcgtg  720
cgcgcaaatc aacgtcaccg gcggcaccgg cacgctcaac ccgggccagc tcgtctcgtt  780
cccgggcgcc tacaagccca ccgacccggg catcctgttc cagctctact ggccgccgcc  840
gacccagtac atcaaccccg gtccggcgcc ggtgaagtgc tga                   883

SEQ ID NO: 122          moltype = AA   length = 233
FEATURE                 Location/Qualifiers
source                  1..233
                        mol_type = protein
                        organism = Humicola insolens
SEQUENCE: 122
MKLTTSIALL AAAGAQAHYT FPRTKVDGVT SGEWETIRIT ENHWSHGPVT DVTSQAMTCY   60
EKTPGQGAPK TVNVKAGGTV TFTVDTDVGH PGPLHFYLAK VPAGKTAATF DGKGAVWFKI  120
YQDGPGGLGT SSLTWPSFGK KEVSVQIPPC VQDGEYLLRV EHIALHSAAS VGGAQLYISC  180
AQINVTGGTG TLNPGQLVSF PGAYKPTDPG ILFQLYWPPP TQYINPGPAP VKC         233

SEQ ID NO: 123          moltype = DNA   length = 928
FEATURE                 Location/Qualifiers
source                  1..928
                        mol_type = genomic DNA
                        organism = Humicola insolens
SEQUENCE: 123
atgaagactc tcgcatccgc cctcattgcc gcgggcctc tggcccagta cgccgctgcc   60
catgccattt tccagtttgc cagcagcggt ggcactgact ttgggacgtc ctgtgttagg  120
atgccggtga gtaacgggt gcccctgaac atgtgttgct cacgaaacaa ggttatgttg  180
actctataca gcccaacaac tctcccgtca cgagcgtcac cagcagtgac atggcttgca  240
atgttggcgg atctcgcggt gtatctggca tttgcgaggt gaacggtaag agttctcctc  300
agccttttct ctgtcaagca ctaaacagca ctcgctaacc atttcaatct cagccggctc  360
cgacttcacc gtcgagatgc acgcgcagcc caacgaccgg tcgtgcgcca gcgaagccat  420
tgccgcaaac cacttcgggc ccgtcatggt gtacatgcc aaggtggacg acgcacggca  480
ggcggacggt gcgtcggcgt cttggttcaa ggtggacgag ttcggctacg acgccggctc  540
caagacatgg ggaaccgaca tgctcaacaa gaactgcggc aagcggacgt tccgcatccc  600
gagcaaaatc ccgtctgggg actatctggt cgtgcggag gctattgctt tgcacaccgc  660
gggccagccg tcgggtgcgc agtttttata gagctgctat gtgagttctt ccatgcttcc  720
ccttgtggtg tcactgtata gaagatgcta atatctccca cagcaagttc gcatcaaggg  780
cagcaacaac ggtcagcttc cggctggtgt tcggattcct ggcgcctaca gcgcgacgga  840
cccgggcatc ctcgtcgata tctggggcaa tggtttcagc cagtacacta ttcctggccc  900
tcgtgtcatt gatgggagct ttttctga                                    928

SEQ ID NO: 124          moltype = AA   length = 243
FEATURE                 Location/Qualifiers
source                  1..243
                        mol_type = protein
                        organism = Humicola insolens
SEQUENCE: 124
MKTLASALIA AGLLAQYAAA HAIFQFASSG GTDFGTSCVR MPPNNSPVTS VTSSDMACNV   60
GGSRGVSGIC EVNAGSDFTV EMHAQPNDRS CASEAIGGNH FGPVMVYMAK VDDATRADGA  120
SASWFKVDEF GYDAGSKTWG TDMLNKNCGK RTFRIPSKIP SGDYLVRAEA IALHTAGQPS  180
GAQFYMSCYQ VRIKGSNNGQ LPAGVRIPGA YSATDPGILV DIWGNGFSQY TIPGPRVIDG  240
SFF                                                               243

SEQ ID NO: 125          moltype = DNA   length = 1092
FEATURE                 Location/Qualifiers
source                  1..1092
                        mol_type = genomic DNA
                        organism = Humicola insolens
SEQUENCE: 125
atgcctcgct tcaccaagtc cattgtctcg gccctggccg gcgcttccct ggtcgcagcc   60
```

```
cacggccatg tcacccacat cgtcatcaac ggcgtgctgt acccgaactt cgaccctaca    120
tcccacccett acctgcagaa cccgccgacc gttgtgggct ggaccgccgc caacaccgac   180
aacggcttcg ttgctcccga ccagttcgcc tcgggcgata tcatctgcca caaccaggcc   240
accaacgcgg gcgccacgc cgtggtcgcg gccggcgaca gatttggat ccagtgggac     300
cagtgggcc agagccacca cggccccgtc ctcgactacc tcgcctcctg cggcagctcg    360
ggctgcgagt cggtcaacaa gctcgacctc gagttcttca agatcggcga aaagggcctg   420
atcgacggct cctccgcgcc gggccggtgg cgtcggacg agctgatcgc caacaacgcc    480
ggctggctgg tccagatccc cgccgacatt gcgcccggcc actacgtcct gcgccacgaa   540
atcatcgccc tccacgccgc cggcaacca aacggcgcc agaactaccc gcagtgcttc     600
aacctcctcg tcacgggctc cggcaccgcg cggcgcagg gcgtcaaggg aacagcgctg    660
tacaccccca cgacaagggg catcttggcg ggcatctaca atgccccgt ctcgtacgag     720
attcccggcc ccgcgctcta ctccggcgcc gcaggaact tgcagcagag ctcgtcccag    780
gccacgtcga ctgccacggc tttgactggg gacgcggtgc ctgttccgac ccaagccccc   840
gtcactacca cttcctcttc ttcggccgat gccgccaccg ccacctccac caccgtccag   900
ccgccccagc aaaccaccct cacgaccgcc atcgccacgt cgaccgctgc tgctgccccg   960
acgaccaccg ccggcagcgg aaacggtggc aaccggcct tcccaacccg ctgccctggc   1020
ctggctgggc tcgggtttga caagcgccgt cgccagctcc gcgctgagga gggtgtgcag  1080
gtggttgctt ga                                                      1092

SEQ ID NO: 126          moltype = AA  length = 363
FEATURE                 Location/Qualifiers
source                  1..363
                        mol_type = protein
                        organism = Humicola insolens
SEQUENCE: 126
MPRFTKSIVS ALAGASLVAA HGHVTHIVIN GVLYPNFDPT SHPYLQNPPT VVGWTAANTD    60
NGFVAPDQFA SGDIICHNQA TNAGGHAVVA AGDKIWIQWD QWPESHHGPV LDYLASCGSS   120
GCESVNKLDL EFFKIGEKGL IDGSSAPGRW ASDELIANNA GWLVQIPADI APGHYVLRHE   180
IIALHAAGQP NGAQNYPQCF NLLVTGSGTA RPQGVKGTAL YTPNDKGILA GIYNAPVSYE   240
IPGPALYSGA ARNLQQSSSQ ATSTATALTG DAVPVPTQAP VTTTSSSSAD AATATSTTVQ   300
PPQQTTLTTA IATSTAAAAP TTTAGSGNGG NRPFPTRCPG LAGLGFDKRR RQLRAEEGVQ   360
VVA                                                                363

SEQ ID NO: 127          moltype = DNA  length = 1086
FEATURE                 Location/Qualifiers
source                  1..1086
                        mol_type = genomic DNA
                        organism = Humicola insolens
SEQUENCE: 127
atgaagggac ttctcagcat cgccgccctt tccctggcgg ttggtgaggc ttcggcccac    60
tacatcttcc agcagctctc gacgggtggc accaagcacc ccatgtggaa gtacatccgc   120
cagcacacca actacaactc tcccgtcatc gacctcgact ccaacgacct ccgctgcaat   180
gtcggtgccc ggggtgctgg aactgagacc gttacggtcg ctgccggcag cagcctgacc   240
ttccacctcg acaccccgt ctaccaccag ggcctgtgt cggtgtaagt agaagttctc     300
agacgaacca ccaatgtcgg cagataattt ctaactccga tgtccagcta tatgtccaag   360
gctcccggct ccgtgtcgga ctatgacggc agcggcggct ggttcaagat tcaagactgg   420
ggccgacct tcaccggcag cggccccacc tggaagctga atgactccta cacccttcaac   480
atcccctcgt gcattcccga cggcgagtac ctcgtccgca tccagtccct gggtatccac   540
aaccccctgg cggcgggtat tccgcagttc tatatctcgt gcgctcaggt gcgcgtcacc   600
ggcggtggca acgcgaaccc gagccgcag gtgtcgatcc caggtgcctt caaggagacc    660
gacccgggct acactgccaa cgtgagtttc catccatgct acatatccct tttacgtctt   720
cgatcccatg actaaccccc ccctgaaaag atctacaaca acttccgcag ctacaccgtc   780
cccgcccgt ccgtcttcac ctgcagcggg aacagcggcg gcggctccaa ccccagcaac    840
cctaaccccc cgaccccgac gaccttcacc acccaggtga ccaccccgac ccggcgtctc   900
ccgccctctt gcaccgtcgc gaagtggtac gtctgaaaaa aaatctcctc caggccggac   960
atgagaaaac taacatgaac gaaaaacagg ggccagtgcg gtggccaggg ctacagcggc  1020
tgcaccaact cgcgaggccgg ctcgacctgc aggcagcaga acgcttacta ttctcagtgc  1080
atctaa                                                             1086

SEQ ID NO: 128          moltype = AA  length = 296
FEATURE                 Location/Qualifiers
source                  1..296
                        mol_type = protein
                        organism = Humicola insolens
SEQUENCE: 128
MKGLLSIAAL SLAVGEASAH YIFQQLSTGG TKHPMWKYIR QHTNYNSPVI DLDSNDLRCN    60
VGARGAGTET VTVAAGSSLT FHLDTPVYHQ GPVSVYMSKA PGSVSDYDGS GGWFKIQDWG   120
PTFTGSGATW KLDDSYTFNI PSCIPDGEYL VRIQSLGIHN PWPAGIPQFY ISCAQVRVTG   180
GGNANPSPQV SIPGAFKETD PGYTANIYNN FRSYTVPGPS VFTCSGNSGG GSNPSNPNPP   240
TPTTFTTQVT TPTPASPPSC TVAKWGQCGG QGYSGCTNCE AGSTCRQQNA YYSQCI       296

SEQ ID NO: 129          moltype = DNA  length = 1032
FEATURE                 Location/Qualifiers
source                  1..1032
                        mol_type = genomic DNA
                        organism = Humicola insolens
SEQUENCE: 129
atgaggcccct tctcactcgt cgctctggcg acggccgtca gcggccacgc catcttccag    60
cgcgtgtcgt taacggcgt cgaccaaggc cagctcaagg gcgtccgcgc tcctcgagc     120
```

```
aactacccca tcgagaacgt caaccacccc gactttgcct gcaacaccaa catccagcac    180
cgcgacggca ccgtcatcaa gatccccgcc ggcgccaccg tcggcgcctg gtggcagcac    240
gagatcggcg ggccctcgtt cccgggtgac ccggataacc cgatcgctgc ttcgcacaag    300
ggtgagttcc catagataga tctcttctct cccgacccct tgtatcctct cataactaac    360
cacctcaacc ccccaggccc tatccaagtc tacctgccca aggtcgacaa cgccgcgacc    420
gcctccccca acggcctgcg gtggttcaag attgccgaga agggcctgtc gggcggcgtc    480
tgggccgtcg acgagatgat ccgcaacaac ggctggcact acttcaccat gccgcagtgc    540
atcgcgcccg gccactacct gatgcgcgtc gagctgttgg cgctgcactc ggccagcttc    600
cccgcggcg cagttcta catggagtgc gcccagatcg aggtcaccgg ctcgggcaac    660
ttctcgccct ccgagacggt cagcttcccc ggcgcctacc cggccaacca cccgggtatc    720
gtcgtcagca tctacgacgc ccagggtaac gccaacaacg gcgggcgcga gtaccagatc    780
cccgggccgc ggccgatcac ctgctccggc ggtggaagca acaatggtgg cgggaacaac    840
aatggtggtg gaaacaacaa cggcggcggc aacaacaacg gcgtgggaa caacaacggt    900
ggtggtaaca ccggtggcgg ctcggcgccg ctctggggcc agtgcggcgg caatgggtat    960
accggcccga cgacttgtgc cgagggtact tgcaagaagc agaatgactg gtactcgcag    1020
tgtacgcctt ag                                                       1032

SEQ ID NO: 130         moltype = AA   length = 318
FEATURE                Location/Qualifiers
source                 1..318
                       mol_type = protein
                       organism = Humicola insolens
SEQUENCE: 130
MRPFSLVALA TAVSGHAIFQ RVSVNGVDQG QLKGVRAPSS NYPIENVNHP DFACNTNIQH     60
RDGTVIKIPA GATVGAWWQH EIGGPSFPGD PDNPIAASHK GPIQVYLAKV DNAATASPNG    120
LRWFKIAEKG LSGGVWAVDE MIRNNGWHYF TMPQCIAPGH YLMRVELLAL HSASFPGGAQ    180
FYMECAQIEV TGSGNFSPSE TVSFPGAYPA NHPGIVVSIY DAQGNANNGG REYQIPGPRP    240
ITCSGGGSNN GGGNNNGGGN NNGGGNNNGG GNNNGGGNTG GGSAPLWGQC GGNGYTGPTT    300
CAEGTCKKQN DWYSQCTP                                                 318

SEQ ID NO: 131         moltype = DNA   length = 1113
FEATURE                Location/Qualifiers
source                 1..1113
                       mol_type = genomic DNA
                       organism = Humicola insolens
SEQUENCE: 131
atggtgttgc ggtctctctc tatcctggcc ttcgtagcca gaggcgtctt cgcccacggt     60
ggcctctcca actacacggt cggcgacacg tggtatagcg gtgcgtcca tgaacaactc    120
ctatatcttc ccccccctcca cattgcgacc gctgcacatc tcactcgtcc ataaacaaca    180
acatcaatcg gtagacactg tccaaaagct aaccaccgta cctcctgaac acagctacga    240
ccccttcacc ccgccgccg cccaactctc caaccctgg ctgatccaac gccaatggac    300
cagcatcgac ccgtcttct cccgacctc tccctacctc gctgcaact tccccggcac    360
cgcgccacca tcttacatcc tctccgcgc cggcgacact ctcaccgcg tttactggtt    420
ctggctgcac cccgtggggc cgatgagcgt ttggctggcg cggtgcgcag ggactgccg    480
cgacgaggac gtgacgcggg cgcgctggtt caagatctgg catgcggggt ttctggaggg    540
gccgaatttg gagctcggga tgtggtatca agaagttc cagcggtggg atggcgggcc    600
ggcgctctgg cgggtgagga taccgagggg gttgaagaag gggttgtaca tggtcaggca    660
tgagattttg tcgattcatg tgggtgacg gccccagttt tatcccgagt gtgcgcactt    720
gaatgtgacg gagtgtgg aggtggtagt gccgggga tggacgagaa ggttccctgg    780
ggcgtatgac gatgatggtg agtgccttgc tagacgggaa ggctctatgg atggggcgga    840
tgagacgaaa ggctggtgtg agactgtcag cactgacgc ctgcagacaa gtcagtcttc    900
atcgatatct accggccga acatgaaac aggacggta cgtgggacaag caagcctcgg    960
attttccaga ttttcgactc tgacaacgaa caggactat gatccctgg aggcccgatt    1020
tgggaaaggt acgtacaatc gcatcatctt gactctgtat tcaggggcta acataaacac    1080
agcttggggg agatggagtt atggcctgaa tga                                1113

SEQ ID NO: 132         moltype = AA   length = 259
FEATURE                Location/Qualifiers
source                 1..259
                       mol_type = protein
                       organism = Humicola insolens
SEQUENCE: 132
MVLRSLSILA FVARGVFAHG GLSNYTVGDT WYSGYDPFTP AAAQLSQPWL IQRQWTSIDP     60
LFSPTSPYLA CNFPGTAPPS YIPLRAGDIL TAVYWFWLHP VGPMSVWLAR CAGDCRDEDV    120
TRARWFKIWH AGFLEGPNLE LGMWYQKKFQ RWDGGPALWR VRIPRGLKKG LYMVRHEILS    180
IHVGGRPQFY PECAHLNVTE GGEVVVPGEW TRRFPGAYDD DDKSVFIDIY RPEHENRTDY    240
EIPGGPIWES LGEMELWPE                                                259

SEQ ID NO: 133         moltype = DNA   length = 1103
FEATURE                Location/Qualifiers
source                 1..1103
                       mol_type = genomic DNA
                       organism = Humicola insolens
SEQUENCE: 133
atgaggaccg tcttcgccgc cgcactggca gcactgctg cccggaagt cgccggccat     60
gccacgttcc agcaactctg ggttgacgga accgattata taagtgcccc cttttctcg    120
gttccatttg atatcatgat gctgacaccc ccagcacggc agcacctgcg tccgcctccc    180
cgccagcaac agcccctga ccgacgtcac cagcagcgac ttcgcctgca acatcggcgg    240
ccggcgcggt gtgggcggca aatgcccgt caaagccgg ggcgtggtca cgatcgagat    300
```

```
gcatcagcag cccaacgacc ggaactgccg cagcgaggcc atcgcggca tgcactgggg    360
tccggtgcag gtctacctca gcaaggtccc cgacgcgtcg accgccgagc cgacgcaggt    420
gggctggttc aagatcttct ccaacgcgtg ggccaagaag cccggcggca actcgggcga    480
cgacgactac tggggcacgc gcgagctcaa cggctgctgc gggcgcatgg acgtgccgat    540
ccccaccgac ctgaagacg cgcgactacct gctgcgcgcc gaggcgctgg cgctgcacgc    600
catgccgggc cagttctaca tgtcgtgcta ccagatcacc atcacgggcg gcacgggcac    660
cgcgaagccg cgcgactgtcc gcttcccgg agcgtacacc aacaacgacg ccggcatccg    720
cgccaacatc cacgccccgc tgagcaccta catcgcgccc ggcccggagg tgtactccgg    780
cggtaccacc cgggcgcccg tgagggctg cccgggatgt gctacgacct gccaggttgg    840
ctcgtcgccc agcgcgcagg ctccaggcca tggcacggcc gtgggcgggcg gagctgggca    900
cccgtctgct tgcaccgtcc aggcgtatgg ccagtcgcgt ggccaggat acacgggttg    960
caccgagtgc gcggtaagtt gggacttcct tgtcattaaa atcgcaaatg gaacggatgg    1020
gctaacattt gcgggtgcag gatggtttcg tttgccgcga cgtctcggct ccgtggtact    1080
ctcagtgcca gcctgctttc taa                                           1103

SEQ ID NO: 134         moltype = AA  length = 325
FEATURE                Location/Qualifiers
source                 1..325
                       mol_type = protein
                       organism = Humicola insolens
SEQUENCE: 134
MRTVFAAALA ALAAREVAGH ATFQQLWVDG TDYGSTCVRL PASNSPLTDV TSSDFACNIG    60
GRRGVGGKCP VKAGGVVTIE MHQQPNDRNC RSEAIGGMHW GPVQVYLSKV PDASTAEPTQ    120
VGWFKIFSNA WAKKPGGNSG DDDYWGTREL NGCCGRMDVP IPTDLEDGDY LLRAEALALH    180
AMPGQFYMSC YQITITGGTG TAKPATVRFP GAYTNNDAGI RANIHAPLST YIAPGPEVYS    240
GGTTRAPGEG CPGCATTCQV GSSPSAQAPG HGTAVGGGAG GPSACTVQAY GQCGGQGYTG    300
CTECADGFVC RDVSAPWYSQ CQPAF                                         325

SEQ ID NO: 135         moltype = DNA  length = 1039
FEATURE                Location/Qualifiers
source                 1..1039
                       mol_type = genomic DNA
                       organism = Humicola insolens
SEQUENCE: 135
atgaggctcc cccaagtggc ttccgttctg gccctcgcgg cccaggtcca cggtcacggc    60
tacatctacc gtgtcaccgc cgacaacatt gtgtaagcgc cctcagattc cggacctctt    120
cctacctggt ggctaacctt ctctcaactc ttcagctacc cgggatacga catctatgtc    180
gatcccctcc tccaaccgcc cccgtaccgc attgcctacg tggtggcca gacgggtccc    240
gtctatgata tcaacagcaa ggatatcgcc tgccagcgcg tccacagccc cgctccgggt    300
ctgattgccc aggctcgcgc gggcagcaac atcaccttct ggtggtcgcg gtggctgtac    360
agccacaagg gtcccatctc ggcatggatg gctccgtatg agggcgacat tgccaatgtg    420
gacgtcaacc agctcgagtt cttcaagatt ggcgaggagt tccacgatga accggcaag    480
tgggcggacg agaagctggt ggacgacccc gagggcaagt ggacggtcaa gatccccgcc    540
gatatcaagc ccggtctcta tgtcgtgcgc aacgaggtaa gtttcatccg tcccaaaaaa    600
ggggtcccat cccatgcatg gtgcatgccc agtctaatca tcatctcccg gatagatcat    660
cgccctccac ttcgccgtcc gcatgcctcc ctttctttgcc gccttcaccc cctcggacc    720
gcagttctac atgacctgct tcgccttcaa catcaccggc gacggcacgg ccactcccca    780
gggctacaag ttccctggcg cctacagcaa ggacgatccg gccctgtggt gggatctgga    840
ggagaacaag aacccgtacc ccggcgccgg ccccaagccc cacgtctcgg cctacgatgt    900
cgacctcgtc cccaacgagt tgtacatcgt cagcccgacg aacaacgcga cggctgatga    960
gctctactgg gaggcccaga ggcaggcgct tgctgcccag gcggcgacga cggagtactt    1020
tgactcgatt ggtggctaa                                                1039

SEQ ID NO: 136         moltype = AA  length = 298
FEATURE                Location/Qualifiers
source                 1..298
                       mol_type = protein
                       organism = Humicola insolens
SEQUENCE: 136
MRLPQVASVL ALAAQVHGHG YIYRVTADNI VYPGYDIYVD PLLQPPPYRI AYGGGQTGPV    60
YDINSKDIAC QRVHSPAPGL IAQARAGSNI TFWWSRWLYS HKGPISAWMA PYEGDIANVD    120
VNQLEFFKIG EEFHDETGKW ATEKLVDDPE GKWTVKIPAD IKPGLYVVRN EIIALHFAVR    180
MPPFFAAFTP LGPQFYMTCF AFNITGDGTA TPQGYKFPGA YSKDDPALWW DLEENKNPYP    240
GAGPKPHVSA YDVDLVPNEL YIVSPTNNAT ADELYWEAQR QALAAQAATT EYFDSIGG    298

SEQ ID NO: 137         moltype = DNA  length = 1025
FEATURE                Location/Qualifiers
source                 1..1025
                       mol_type = genomic DNA
                       organism = Humicola insolens
SEQUENCE: 137
atgcacgtcc agtctctcct tgccggagcg ctcgctctgg ctccgtcggc gtctgctcac    60
ttcctcttcc cgcacctgat gctgaacggt gtccgcacgg gagcctacga gtatgtccgg    120
gagcagact tcggcttcat gccgcacaac aacgactga tcaactccc cgatttccgt    180
tgcaacgagg ggtcctggcg tcatcgccgc gagcccaaga ccgccgtagt cactgccggc    240
gttgacgtcg tgggcttcaa cctgcacctg gactttgacc tgtaccatcc gggccccgtg    300
acggtaagca catctgagtc agaacatacc tccctgtgac gtagactaat gagtctctta    360
ccgcagatct atctctcccg cgcccccggc gacgtgcgtg actacgacgg atcggtgac    420
tggttcaagg tgtaccagct gggcacccgc caaccccttca acggcactga cgagggctgg    480
```

```
gccacttgga agatgaagaa ctggcagttc cgcctgcccg ctgagatccc ggcgggcgag    540
tacctgatgc gcatcgagca gatgagcgtg caccctcctt accgccagaa ggagtggtac    600
gtgcagtgcg cccacctaaa gatcaacagc aactacaacg ccccgcgcc cggcccgacc     660
atcaagattc ccgagggta caagatcagc gatcctgcga ttcaatatga ccagtgggcg    720
cagccgccgc cgacgtacgc gcccatgccg gaccgccgc tgtggcccaa caacaatcct     780
cagcagggca acccgaatca gggcggaaat aacggcggtg caaccaggg cggcggcaat     840
ggtggctgca ccgttccgaa gtggtatgta gagttcttca ctattatcat gagatgcagc    900
gttggacttg tgcttacacc tagaacaggg gccaatgcgg tggtcagggt tacagcgggt    960
gcaggaactg cgagtctggc tcgacatgcc gtgcccagaa cgactggtac tcgcagtgcc   1020
tgtaa                                                                1025

SEQ ID NO: 138          moltype = AA   length = 298
FEATURE                 Location/Qualifiers
source                  1..298
                        mol_type = protein
                        organism = Humicola insolens
SEQUENCE: 138
MHVQSLLAGA LALAPSASAH FLFPHLMLNG VRTGAYEYVR EHDFGFMPHN NDWINSPDFR     60
CNEGSWRHRR EPKTAVVTAG VDVVGFNLHL DFDLYHPGPV TIYLSRAPGD VRDYDGSGDW   120
FKVYQLGTRQ PFNGTDEGWA TWKMKNWQFR LPAEIPAGEY LMRIEQMSVH PPYRQKEWYV   180
QCAHLKINSN YNGPAPGPTI KIPGGYKISD PAIQYDQWAQ PPPTYAPMPG PPLWPNNNPQ   240
QGNPNQGGNN GGGNQGGGNG GCTVPKWGQC GGQGYSGCRN CESGSTCRAQ NDWYSQCL    298

SEQ ID NO: 139          moltype = DNA   length = 1035
FEATURE                 Location/Qualifiers
source                  1..1035
                        mol_type = genomic DNA
                        organism = Humicola insolens
SEQUENCE: 139
atgccaccac cactactggc caccgtcctc tccttgctag ccctcacccg cggcgccctt     60
tcccattccc acctagccca cgtcatcatc aacggccagc tctaccacgg cttcgaccca   120
cgtccaaacc aaaacaacca tccagcccgt gtcggctggt ccacgaccgc cacagatgac   180
ggcttcgtca ccccgggcaa ttactccat cccgacatca tctgccaccg cggcggcgtc    240
agcccgcgcg cccacgctcc cgtcaccgcc ggcggcaagg tccaggtcca atggaacggc   300
tggccgatcg gacacgtcgg gccgatcctg acctacgtgc ggggactgcg gggactgccg   360
ggcgccgaag aagggtgtac gggcgtggac aaaaccgacc tgcggtgac caagatcgac    420
gactcgatgc cgccgttccg gtttaccgac gccaccaagc cagtctctgg cagagcgcag   480
ttcccgatag gccaggtctg ggcgacggat gcgctggtcg aggcgaataa tagctggtcg    540
gtggtcattc ccaggaatat cccgccgggg ccgtacgttt tgaggcagga gattgtgcc    600
ctgcattacg cggcgaagtt gaacgggcg cagaactatc cgttgtgtct gaacctctgg    660
gtggaaaagg ggcagcagga tcagggagag cccttcaaat tcgatgctta cgacgcgagg   720
gagttttaca gcgaggacca tccgggtgtg ttgattgatg ttatgacgat ggttgggccg    780
agagccgtgt accggataccc tggaccgacc gtggccagga gtgccagaa aattccgcac   840
tcattgcaga cgagcgccga gacgtgggtg gaagggacgc cggtggccgt gacgagcgg    900
acggaaacgg ttcagatgga gataactacg cacctgcag gtcagggagc tggtgtgagg    960
acagctaccc ctgccatgcc aacaccaaca gtgacgaaga ggtggaaggg aagatttgag   1020
atgggtaggc catga                                                   1035

SEQ ID NO: 140          moltype = AA   length = 344
FEATURE                 Location/Qualifiers
source                  1..344
                        mol_type = protein
                        organism = Humicola insolens
SEQUENCE: 140
MPPPLLATVL SLLALTRGAL SHSHLAHVII NGQLYHGFDP RPNQNNHPAR VGWSTTATDD     60
GFVTPGNYSH PDIICHRGGV SPRAHAPVTA GGKVQVQWNG WPIGHVGPIL TYIAPCGGLP   120
GAEEGCTGVD KTDLRWTKID DSMPPFRFTD ATKPVSGRAQ FPIGQVWATD ALVEANNSWS   180
VVIPRNIPPG PYVLRQEIVA LHYAAKLNGA QNYPLCLNLW VEKGQQDQGE PFKFDAYDAR   240
EFYSEDHPGV LIDVMTMVGP RAVYRIPGPT VASGATRIPH SLQTSAETWV EGTPVAVTRA   300
TETVQMEITT TPAGQGAGVR TATPAMPTPT VTKRWKGRFE MGRP                    344

SEQ ID NO: 141          moltype = DNA   length = 1057
FEATURE                 Location/Qualifiers
source                  1..1057
                        mol_type = genomic DNA
                        organism = Humicola insolens
SEQUENCE: 141
atgaagtccc tgacctacgc cgcgctggcc gccctctggg cccagcagac cgctgctcat     60
gccaccttcc agcaactctg ggtcgacggc gtcgactacg gcagtcagtg cgccgccctg   120
ccgccgtcca actcccccat cgccagcgtc acctcgaccg ccatgcgctg caacaacggt   180
ccccgcgctg ccgccaagtg cccgtcaag gctggcggca ccgtcaccat cgagatgcac    240
caggttggtt tccttgaagt gttccctac cacatataca gaccgtagct aacacaccca    300
tccttagcaa cccggtgacc ggtcctgcaa ccaggacgcc attggcggtg cccaccacgg   360
ccccgtgatg gtgtacatgt ccaaggtctc tgatgcttc accgccgacg gctcgtcagg   420
ctggttcaag atcttccagg acggctgggc caagaacccc aacggccgcg ttggcgacga   480
cgacttctgg ggcaccaagg acctcaacac ctgctgcggc aagatgaacg tcaagatccc   540
cgccgacatc gccccggcg actacctgct ccgcgccgag gccatcgcgc tgcacgccgc   600
cggcccccagc ggtggcgccc agccctacgt cacctgctac cagctcaccg tcacgggcgg    660
cggcaacgcc aacccgccca ccgtcaactt ccccggcgcc tacagcgagc gtgacccctgg   720
```

```
catcgccgtc agcatccacg gcgctctgtc caactacgtc gtccccggtc ctccggtcta    780
ctcgggcggc agcgagaagc gcgctggcag cccctgcgag ggctgcgagg ccacctgcaa    840
ggtcggctcg agcccagcc  agactcttgc tccttccaac ccggcccga  cctctcccgc    900
caacggcggc ggcaacaacg gtggtggcaa cactggcggc ggctgcaccg tgcccaagtg    960
gcagcagtgc ggcggccagg gctactcggg ctgcaccgtc tgcgagtctg gctcgacttg   1020
ccgcgctcag aaccagtggt actctcagtg cgtgtaa                            1057

SEQ ID NO: 142          moltype = AA  length = 330
FEATURE                 Location/Qualifiers
source                  1..330
                        mol_type = protein
                        organism = Humicola insolens
SEQUENCE: 142
MKSLTYAALA ALWAQQTAAH ATFQQLWVDG VDYGSQCARL PPSNSPIASV TSTAMRCNNG     60
PRAAAKCPVK AGGTVTIEMH QQPGDRSCNQ DAIGGAHHGP VMVYMSKVSD AFTADGSSGW    120
FKIFQDGWAK NPNGRVGDDD FWGTKDLNTC CGKMNVKIPA DIAPGDYLLR AEAIALHAAG    180
PSGGAQPYVT CYQLTVTGGG NANPPTVNFP GAYSERDPGI AVSIHGALSN YVVPGPPVYS    240
GGSEKRAGSP CEGCEATCKV GSSPSQTLAP SNPAPTSPAN GGGNNGGGNT GGGCTVPKWQ    300
QCGGQGYSGC TVCESGSTCR AQNQWYSQCV                                    330

SEQ ID NO: 143          moltype = DNA  length = 772
FEATURE                 Location/Qualifiers
source                  1..772
                        mol_type = genomic DNA
                        organism = Humicola insolens
SEQUENCE: 143
atgaagctcc tcctcccgc  cctcctggct ctggccgccg agtccgtctc ggcgcactac     60
atcttccaac aactcaccgt cgccggcacc aagtacccg  tgtggaagta catccggcgc    120
aacagcaatc cggcgtggct tcaaaacggc cctgtgaccg acctcgcctc gaccgacctg    180
cgctgcaacg tgggcgggca ggtcagcaac ggcaccgaga ctctcacggt ccgcgccggc    240
gaccagttca cgttccacct cgacacggcg gtgtaccacc agggcccgac ctcgctgtac    300
atgtcgcgcg ctccgggcaa ggtggaggac tatgatggca gcgggccgtg gtttaagatt    360
tatgattggg ggccgacagg gaataattgg gtcatgaggg gtatggtttc ccctattaat    420
tattattatt gtttacttgg ggcatcatct ggtggtggtg ctggtgacga tgataagagt    480
gatggagaag gacctggctg acgacctaaa aacccgatca gattcgtaca cgtacaacat    540
cccccgctgc atccccgacg gcgagtatct cctgcgcatc cagcagctgg gtctgcacaa    600
tccgggcgcc gcgccgcagt tctacatcag ctgcgcccag atcaaggtca ccggcggcgg    660
cactaccaac ccgaccccca cggctctgat tccgggagcc ttcagggcta cggatccggg    720
atacactgtc aacgtaagtc aaactttgag caactccata tcaacctcgt ga            772

SEQ ID NO: 144          moltype = AA  length = 216
FEATURE                 Location/Qualifiers
source                  1..216
                        mol_type = protein
                        organism = Humicola insolens
SEQUENCE: 144
MKLLLPALLA LAAESVSAHY IFQQLTVAGT KYPVWKYIRR NSNPAWLQNG PVTDLASTDL     60
RCNVGGQVSN GTETLTVRAG DQFTFHLDTA VYHQGPTSLY MSRAPGKVED YDGSGPWFKI    120
YDWGPTGNNW VMRDSYTYNI PRCIPDGEYL LRIQQLGLHN PGAAPQFYIS CAQIKVTGGG    180
TTNPTPTALI PGAFRATDPG YTVNVSQTLS NSISTS                             216

SEQ ID NO: 145          moltype = DNA  length = 1536
FEATURE                 Location/Qualifiers
source                  1..1536
                        mol_type = genomic DNA
                        organism = Humicola insolens
SEQUENCE: 145
atgcgttctg tttcccttct tgcggccgct ttcgcgccgc tggctacggc acacacggtc     60
tttacagctc ttttcatcaa caatgtccac cagggcgacg gcacttgcgt ccgtatggct    120
aagcagggca acctgccac  ccatcccgtc agtctgaaca gcaatgagat ggcctggggt    180
gggtaggccc cgttcctcga gcagctgatc tcgaactaac atgttgattc ttgaactcca    240
ggtcgcgatg gccaacaacc agtggcattt acttgcccag cacctgcggg agccaagctg    300
accttattgt ttcgtatgtg ggcagatggc tctcagccag gttccatcga caagtctcac    360
gttggtccca tgtccatcta cctcaagaaa gtctcagata tgaaccacga ctcggccgca    420
gggcccgggt ggttcaagat ctggagtgag ggctacgacg ctgcgacgaa gaaatgggcc    480
acggagaaac tcatcgccaa caacggtttg ctcagcgtca acctacctcc cggcctccct    540
gcaggctact acctcgcccg ccacgaaatc gtcactctcc aaaacgtcac caacaacaag    600
gccgatccgc agttctacgt cggctgtgcg cagctgttcg tccaagggtt gggcaccgcc    660
ggctccgtgc ctgctgacaa aaccgtttcc atccccgcag atctgaaccc caacgaccgc    720
gcgctggtat tcaaccccta tcccaaaac  gctgcgacat cccaagctt  cggcccaccg    780
ctcttcttcc caaatgctgc ttcggcggga tcaacaagg  cccagtcaac actcaagcaa    840
acctccggcg tcatcccctc cgactgcctc atcaaaaacg ccaactggtg cggccgtgaa    900
gttccagact ataccaacga ggcggatgc  tggacgcgcg cggggaactg ttgggagcag    960
gctgatcaat gctacaagac agccccgcca tcgggccgca aggatgcaa  ggacctgggag   1020
gagcagaagt gcaacgtcat ccagaactcc tgtgaagcga agaggttttc ggggcccgcca   1080
aacaggggg  tcaagtttgc tgatatggat gtgaatcagc ttgttccggg ggcgatccct   1140
gaagcagtga acgccggtca gaatgggag  cggttgttg  ttgacggcac aacgagctct   1200
gcagatgaga aggcgagtgt ggatttgaca acatcgtctc taccgacgcc gacgcctgcg   1260
gctgaagaaa acgggaagga ggatgaaaga ctggctcttg atccgaccct gacggaggac   1320
```

```
gagtcgtttt tctcagttga gccaacgtct gagcccactg gtgttcaggt tgaggtgcct  1380
ttgacaactg tggtcctcct tccaacgctc acctcatctt tgaatccatt gccaaccccg  1440
acctcaattt cccagccggc tcacccggga agaccatgca caggtcgccg tcgtaggccg  1500
aggccagggt ttccgaaaca cccgcgcgat ttttaa                            1536

SEQ ID NO: 146          moltype = AA  length = 490
FEATURE                 Location/Qualifiers
source                  1..490
                        mol_type = protein
                        organism = Humicola insolens
SEQUENCE: 146
MRSVSLLAAA FAPLATAHTV FTALFINNVH QGDGTCVRMA KQGNLATHPV SLNSNEMACG   60
RDGQQPVAFT CPAPAGAKLT LLFRMWADGS QPGSIDKSHV GPMSIYLKKV SDMNTDSAAG  120
PGWFKIWSEG YDAATKKWAT EKLIANNGLL SVNLPPGLPA GYYLARHEIV TLQNVTNNKA  180
DPQFYVGCAQ LFVQGLGTAA SVPADKTVSI PGHLNPNDPA LVFNPYTQNA ATYPSFGPPL  240
FFPNAASAGS NKAQSTLKQT SGVIPSDCLI KNANWCGREV PDYTNEAGCW TAAGNCWEQA  300
DQCYKTAPPS GHKGCKTWEE QKCNVIQNSC EAKRFSGPPN RGVKFADMDV NQLVPGAIPE  360
AVNAGQNGEA VVVDGTTSSA DEKASVDLTT SSLPTPTPAA EENGKEDERL ALDPTLTEDE  420
SFFSVEPTSE PTGVQVEVPL TTVVLLPTLT SSLNPLPTPT SISQPAHPGR PCTGRRRRPR  480
PGFPKHPRDF                                                        490

SEQ ID NO: 147          moltype = DNA  length = 921
FEATURE                 Location/Qualifiers
source                  1..921
                        mol_type = genomic DNA
                        organism = Humicola insolens
SEQUENCE: 147
atgttcttcc gcaacgccgc cactcttgct ctggcctacg ccaccaccgg cgtctcggcc   60
cacgcgctca tgtacggcgt ctgggtcaac ggcgtcgacc aaggcgacgg ccgcaacgtc  120
tacatccgca cgccccccaa caacagcccg gtcaaagacc tggacatcgt ggacatcgtc  180
tgcaacgtca acggcgggcg cgccgttccg gacttcgtcc aggcctcggc ggggacacc   240
ctcaccttcg agtggctgca caacacccgc ggcgacgaca tcatcgaccg ctcccacctc  300
ggccccatca tcacctacat cgcccctttt accacgggca acccgacggg cccgtctgg   360
accaaaatcg ccgaacaggg cttcaaccct tccacccgcg gctgggccgt cgacgatctg  420
atcgacaacg gcggcaagac cgacttcgtc ctgcccgcgt ccctcgcgcc gggcaggtac  480
atcatccggc aggagatcat cgcgcaccac gagtccgaaa ccacgttcga atccaacccg  540
gcgcggggtg cccagttcta cccgtcgtgc gtgcagatcc aagtctcttc tggctcgggc  600
accgccgtgc cggatcagaa ctttgacttc aacacgggct acacgtacgc cgaccccggc  660
atccacttca acatctacac ctcgttcaac agctactcca tccccggccc gggaggttgg  720
acgggcgcta gcaccggcgg cggcaacggc aacggcaacg gcaacggcaa tgccacgcct  780
acgcagccta ctcccactcc cactgtcact cccactccca tcgagaccgc ccagccggtt  840
accacgacga ccacctcgac ccggccgttc cctacccgct gccctggccg ccgcctcaag  900
cgtgaggagc ccaaggcttg a                                            921

SEQ ID NO: 148          moltype = AA  length = 306
FEATURE                 Location/Qualifiers
source                  1..306
                        mol_type = protein
                        organism = Humicola insolens
SEQUENCE: 148
MFFRNAATLA LAYATTGVSA HALMYGVWVN GVDQGDGRNV YIRTPPNNSP VKDLASPDIV   60
CNVNGGRAVP DFVQASAGDT LTFEWLHNTR GDDIIDRSHL GPIITYIAPF TTGNPTGPVW  120
TKIAEQGFNP STRRWAVDDL IDNGGKTDFV LPASLAPGRY IIRQEIIAHH ESETTFESNP  180
ARGAQFYPSC VQIQVSSGSG TAVPDQNFDF NTGYTYADPG IHFNIYTSFN SYSIPGPEVW  240
TGASTGGGNG NGNGNGNATP TQPTPTPTVT PTPIETAQPV TTTTTSTRPF PTRCPGRRLK  300
REEPKA                                                            306

SEQ ID NO: 149          moltype = DNA  length = 1092
FEATURE                 Location/Qualifiers
source                  1..1092
                        mol_type = genomic DNA
                        organism = Humicola insolens
SEQUENCE: 149
atggctcatc catgggcacg ttgcgtctat acagccatct ggctcgctgc ctccgcttct   60
ggacgtaggt acaagactcc ggcagtgcca tttatgaacc cacaacgtgg actggtcccg  120
tgctaacaca tcacagactc gcgcgtttgg agtgtctcgg tcaatggacg ctaccaggga  180
ccgggtgttg atgactacct gcgcgcaccg ccaagtgact ctccggtggt ggacctggac  240
tcaccaaccc tcaactgcaa tgtcaatgga aacaagcctg ttccagggtt tgttgaggtg  300
tctgcgggag attctctgga atggaagtgg tactacatca acccgtacaa cccaagcgac  360
atgatcatcg cggcagaaca ccgcggaccg atcatcacct acatcacgaa ttacaccgat  420
ggccagcctc aaggagctgt ctggaccaag attgatcacg aaggctacga tcctgtgaca  480
gaccggttcg ccgtcgacaa cttgatcgcc aacaggggat ggaaagcaat caagcttccc  540
atgctcgccg acgggaagta catcctgcga caggagatca tcgcactcca cagcgcacac  600
aaccaaggcg gggcccagct gtatccgaac tgcattcaga tcaaggtcgt tggtggcaag  660
ggaagcgcgt gcccaaccag aactttgat ctcaacaagg ggtacacatc cgatcacccg  720
ggacttcggt tcaacctgtg gcaaccattc aacaattaca ccattcccgg tcctgaggtc  780
tggaaggagg ttgtggttgc gagcaatggt acaacgaaca gcaccacaaa tctcaccaac  840
aacaccggca ccggttttgc gaacagcact atggccactg tgaaacaag gaccgagagg  900
agttttatga cacttaccgc atcacattca gacactggcg tccccgccaa atctcatact  960
```

```
gtggctgtaa gctggacaac atccgccgcc gttgttgggt ctccgattag cgttaccaca   1020
actttcagtt cctttaccac aacaccggtt ccgacgaact ctaccggtgc ttatctctac   1080
cggtacaagt ga                                                       1092

SEQ ID NO: 150         moltype = AA   length = 339
FEATURE                Location/Qualifiers
source                 1..339
                       mol_type = protein
                       organism = Humicola insolens
SEQUENCE: 150
MAHPWARCVY TAIWLAASAS GHSRVWSVSV NGRYQGPGVD DYLRAPPSDS PVVDLDSPTL    60
NCNVNGNKPV PGFVEVSAGD SLEWKWYYIN PYNPSDMIIA AEHRGPIITY ITNYTDGQPQ   120
GAVWTKIDHE GYDPVTDRFA VDNLIANRGW KAIKLPMLAD GKYILRQEII ALHSAHNQGG   180
AQLYPNCIQI KVVGGKGSAV PNQNFDLNKG YTSDHPGLRF NLWQPFNNYT IPGPEVWKGV   240
VVASNGTTNS TTNLTNNTGT GFANSTMATG ETRTERSFMT LTASHSDTGV PAKSHTVAVS   300
WTTSAAVVGS PISVTTTFSS FTTTPVPTNS TGAYLYRYK                          339

SEQ ID NO: 151         moltype = DNA   length = 1005
FEATURE                Location/Qualifiers
source                 1..1005
                       mol_type = genomic DNA
                       organism = Malbranchea cinnamomea
SEQUENCE: 151
atgtcaccct ccttcaagtc cactgccatc ctcggagccg ttgctctggc cgcccgcgtg    60
cgcgcccacg gctacgtgtc tggaatcgtc gttgacggtg cttaccatgg cggttacatc   120
gtcgacaagt accccctacat gcccaaccca cccgatgtcg tcggctggtc gactacggcc   180
acggacctgg gcttcgtcgc ccctgacgcc tttggcgacc cggacatcat ctgccaccgg   240
gacggtgccc ccggtgccat ccacgccaaa gtcaacgccg gtgccaccat cgagctgcag   300
tggaacacct ggcccgaaag ccaccacggg cccgtcatcg actacctggc taactgcaac   360
ggtgactgct cgtccgtcga caagacctcg ctcaagttct tcaagatcag cgaggccgac   420
ctaaacgacg gctccaacgc ccccggccag tgggcgtccg acgatctcat tgccaacaac   480
aacagctgga ctgtgaccat ccccaagtcg atcccccgg gcaactacgt gctgcgccac    540
gagatcatcg ccctgcacag cgccggcaac cagaatggcg cgcagaacta cccccagtgc   600
ttcaacctcg agatcaccag caaacccggc gacaacccgg agggcgtgct gggaaccgag   660
ctgtacaagg ccgacgaccc gggcattctg ttcaacatct accagcccat ggactcgtac   720
ccgattcccg gccctgctct ctacaccggc ggctcttctc cctcccctaa tccgcccacc   780
tctacccagt cgcctgtgcc ccagcccacc cagtctcccc catcgggcag caaccccggc   840
aacggcaacg cgacgacga caacgacaac ggcaacgaga cccatcccc gtctctcccc    900
gtcgagatcc ctgacgacct gacctcgcgc gagctactcc ttgtggccca ggagatcatt   960
gcccgtctgc ttgagctgca gaatcagctg gtcgtctcga actaa                  1005

SEQ ID NO: 152         moltype = AA   length = 334
FEATURE                Location/Qualifiers
source                 1..334
                       mol_type = protein
                       organism = Malbranchea cinnamomea
SEQUENCE: 152
MSPSFKSTAI LGAVALAARV RAHGYVSGIV VDGAYHGGYI VDKYPYMPNP PDVVGWSTTA    60
TDLGFVAPDA FGDPDIICHR DGAPGAIHAK VNAGATIELQ WNTWPESHHG PVIDYLANCN   120
GDCSSVDKTS LKFFKISEAG LNDGSNAPGQ WASDDLIANN NSWTVTIPKS IAPGNYVLRH   180
EIIALHSAGN QNGAQNYPQC FNLEITSNGS DNPEGVLGTE LYKADDPGIL FNIYQPMDSY   240
PIPGPALYTG GSSPSPNPPT STQSPVPQPT QSPPSGSNPG NGNGDDDNDN GNETPSPSLP   300
VEIPDDLTSR ELLLVAQEII ARLLELQNQL VVSN                               334

SEQ ID NO: 153         moltype = DNA   length = 1101
FEATURE                Location/Qualifiers
source                 1..1101
                       mol_type = genomic DNA
                       organism = Talaromyces leycettanus
SEQUENCE: 153
atgcatcaac acttccgata cactgcgctc ctgacagcgt tgctgtcagc atcaacccga    60
gtcgcatccc acgccatgt cagcaacatt gtcattaatg gcgttcccta tcaaggatgg   120
gatatcgatt ccatgcccta cgagtcagac ccaccagtgg ttgtcgcctg ggagacacct   180
aacacgtcaa acgtttcat tacccccggat cagtacggca cgagtgatat tatctgccat   240
ctgaacgcaa ccaacgcaaa gggcatgcc gtcgttgctg ccggagacaa gatcagcatt    300
caatggactg cctggcccag ctccaccac ggccctgtca tcagctacct ggccaactgt    360
ggcgccagct gtgagacagt cgacaaacg acgttgcaat tctttaagat cgacaacatc   420
ggtttcatag atgactcttc ccccaggc atctggcag ccgatcaatt ggaagcaaac     480
aacaacacct ggctcgtgga tccccccg accatcgtct caggatacta cgtcctgcga    540
aacgagatca tcgccctaca cggtgcagag aatcaggatg cgcccagaa ctatccgcag    600
tgcttcaatc tgcaggtcac cggctcgggt accgataaac ccgccggcgt cttggaact   660
cagctctatt ctcccactga cccgggcatt tcgtgaaca tttacacgag ctttcgacc    720
tacatcgtcc ccggtccaac cccgtacagt ggttgggtgt ccgtcgtgca gtctagctct   780
gctatcaccg cttctggaac ccggtgacg ggcactggcg gagttagcc aaccaggct     840
gctactacga cttcttcttc tcactccacg acttctacta ctaccgggcc cactgtaacc   900
tcgactagcc acactactac cactactact cctactaccc tcagaaccac gactacaact   960
gcagctggtg gtggtgcgac acagaccgtc tacggcaat gcggcggtag tggttggact   1020
ggcgcaactg cctgcgcagc cggagctact tgcagcactc tgaatcccta ctatgccaa   1080
tgccttccta ctggtgcttg a                                            1101
```

```
SEQ ID NO: 154          moltype = AA  length = 366
FEATURE                 Location/Qualifiers
source                  1..366
                        mol_type = protein
                        organism = Talaromyces leycettanus
SEQUENCE: 154
MHQHFRYTAL LTALLSASTR VASHGHVSNI VINGVPYQGW DIDSMPYESD PPVVVAWETP    60
NTSNGFITPD QYGTSDIICH LNATNAKGHA VVAAGDKISI QWTAWPSSHH GPVISYLANC   120
GASCETVDKT TLQFFKIDNI GFIDDSSPPG IWAADQLEAN NNTWLVEIPP TIAPGYYVLR   180
NEIIALHGAE NQDGAQNYPQ CFNLQVTGSG TDKPAGVLGT QLYSPTDPGI LVNIYTSLST   240
YIVPGPTPYS GWVSVVQSSS AITASGTPVT GTGGVSPTTA ATTTSSSHST TSTTTGPTVT   300
STSHTTTTTT PTTLRTTTTT AAGGGATQTV YGQCGGSGWT GATACAAGAT CSTLNPYYAQ   360
CLPTGA                                                              366

SEQ ID NO: 155          moltype = DNA  length = 1091
FEATURE                 Location/Qualifiers
misc_feature            522..524
                        note = n is a, c, g, or t
source                  1..1091
                        mol_type = genomic DNA
                        organism = Chaetomium thermophilum
SEQUENCE: 155
atgccttcct tcgcttcgaa gactctcatt tctgccctcg ccggcgctgc cagcgtcgcc    60
gctcacggcc acgtcaagaa cttcgtcatc aacggtctgt cgtaccaggc ctacgacccg   120
accgtcttcc cgtacatgca gaaccctccc atcgtcgggc gctggacgtc ctccaacact   180
gacaacggct tcgtgggccc cgagtcctac tcgagcccg atatcatctg ccacaagtcg    240
gccacgaacg ccaagggcca tgccgtcatc aaggccggtg actctgtcta catccagtgg   300
gacacctggc ccgagtcgca ccacggcccg gtcatcgact acctgccag ctgcggcagc    360
gccggctcga agacggtcga caagacccag ctcgagttct tcaagatcgc cgaggccggt   420
ctgattgacg gctcccaggc tcccggaaag tgggctgccg atcagctcat cgcccagaac   480
aactcgtggc tggtcaccat ccccgagaat atcaagccgc tnnnggctcc tacgtcctcc   540
gccacgagat catcgccctg cacagcgctg ccagaccaa cggtgcccag aactaccccg    600
tctgcatcaa cctcgaggtc actggtgggc gcagcgacgt tccctcgggt gtcaagggta   660
ctgagctcta caagcccacc gaccccggca tcctcatcaa catctaccag tcgctctcga   720
actacaccat ccctggccct gctctgatgc ccggcgccaa gccagtcacc cagcacacct   780
cagccatcat cggcagcacc accgccatca ctggcaccgc caccgctgct ccggccgcgc   840
cgacctcgac cgccgctgcc atcaccacca gctctgctaa tgccaacccc gccccgacca   900
ccaccgcgg caaccgcaac cccgtcccga ctaccaccct ccgcacgac accatcgctc    960
ctcagcccac tgctgccccc atccagaccc cgacctccag cgtcggccgg ccccgcgcc   1020
cgacccgctg ccctggtctg gacaacttca agcgcgctcg tcgccacgct cgtgaccttg  1080
ctgccccacta a                                                      1091

SEQ ID NO: 156          moltype = AA  length = 364
FEATURE                 Location/Qualifiers
REGION                  174..176
                        note = misc_feature - Xaa can be any naturally occurring
                         amino acid
source                  1..364
                        mol_type = protein
                        organism = Chaetomium thermophilum
SEQUENCE: 156
MPSFASKTLI SALAGAASVA AHGHVKNFVI NGLSYQAYDP TVFPYMQNPP IVAGWTASNT    60
DNGFVGPESY SSPDIICHKS ATNAKGHAVI KAGDSVYIQW DTWPESHHGP VIDYLASCGS   120
AGCETVDKTQ LEFFKIAEAG LIDGSQAPGK WAADQLIAQN NSWLVTIPEN IKPXXXGSYV   180
LRHEIIALHS AGQTNGAQNY PVCINLEVTG GGSDVPSGVK GTELYKPTDP GILINIYQSL   240
SNYTIPGPAL MPGAKPVTQH TSAIIGSTTA ITGTATAAPA APTSTAAAIT TSSANANPAP   300
TTTRGNANPV PTTTLRTSTI APQPTAAPIQ TPTSSVGRPP RPTRCPGLDN FKRARRHARD   360
LAAH                                                                364

SEQ ID NO: 157          moltype = DNA  length = 1089
FEATURE                 Location/Qualifiers
source                  1..1089
                        mol_type = genomic DNA
                        organism = Trichoderma ressei
SEQUENCE: 157
atgatccaga agctttccaa cctccttgtc accgcactgg cggtggctac tggcgttgtc    60
ggacatggac atattaatga cattgtcatc aacggggtgt ggtatcaggc ctatgatcct   120
acaacgtttc catacgagtc aaacccccca atagtagtgg gctggacggc tgccgacctt   180
gacaacggta cgtgatcctc atctctatct gtacaacgct catgctaatc caactcaata   240
ggcttcgttt cacccgacgc ataccaaaac cctgacatca tctgccacaa gaatgctacg   300
aatgccaagg gcacgcgtc tgtcaaggcc ggagacacta ttctcttcca gtgggtgcca   360
gttccatggc cgcaccctgg tcccattgtc gactacctgg ccaactgcaa tggtgactgc   420
gagacgttg acaagacgac gcttgagttc ttcaagatca tggcgttgg tctcctcagc   480
ggcgggatc cggcacctg gcctcagac gtgctgatct ccaacaacaa cacctgggtc   540
gtcaagatcc ccgacaatct tgcgccaggc aattacgtgc tccgcacga gatcatcgcg   600
ttacacagcg ccgggcaggc aaacggcgct cagaactacc ccagtgcttc aacattgcc   660
gtctcaggct cgggttctct gcagcccagc ggcgttctag gaccgacct ctatcacgcg   720
acggaccctg gtgttctcat caacatctac accagcccg tcaactacat catccctgga   780
```

```
cctaccgtgg tatcaggcct gccaacgagt gttgcccagg ggagctccgc cgcgacggcc    840
accgccagcg ccactgttcc tggaggcggt agcggcccga ccagcagaac cacgacaacg    900
gcgaggacga cgcaggcctc aagcaggccc agctctacgc ctcccgcaac cacgtcggca    960
cctgctggcg gcccaaccca gactctgtac ggccagtgtg gtggcagcgg ttacagcggg   1020
cctactcgat gcgcgccgcc agccacttgc tctaccttga accctactac gcccagtgc    1080
cttaactag                                                            1089

SEQ ID NO: 158         moltype = AA  length = 344
FEATURE                Location/Qualifiers
source                 1..344
                       mol_type = protein
                       organism = Trichoderma ressei
SEQUENCE: 158
MIQKLSNLLV TALAVATGVV GHGHINDIVI NGVWYQAYDP TTFPYESNPP IVVGWTAADL     60
DNGFVSPDAY QNPDIICHKN ATNAKGHASV KAGDTILFQW VPVPWPHPGP IVDYLANCNG    120
DCETVDKTTL EFFKIDGVGL LSGGDPGTWA SDVLISNNNT WVVKIPDNLA PGNYVLRHEI    180
IALHSAGQAN GAQNYPQCFN IAVSGSGSLQ PSGVLGTDLY HATDPGVLIN IYTSPLNYII    240
PGPTVVSGLP TSVAQGSSAA TATASATVPG GGSGPTSRTT TTARTTQASS RPSSTPPATT    300
SAPAGGPTQT LYGQCGGSGY SGPTRCAPPA TCSTLNPYYA QCLN                      344

SEQ ID NO: 159         moltype = DNA  length = 759
FEATURE                Location/Qualifiers
source                 1..759
                       mol_type = genomic DNA
                       organism = Acrophialophora fusispora
SEQUENCE: 159
atgcgcatag aagctatcac aggcctcgtg ctggcctcgg ccggtgcagt gtctgcccat     60
ggctgggtcg atgtctgggc tattggcggc aagaactaca caggcttcaa ccccacggtg    120
gcgccatggg tcccggatca gggcaccatt gcgtggccgg cctggaacac cgacacagga    180
ccggtgtaca gcaaggacgt caacaccaca gacatcatct gctcaatcaa tgccaccaac    240
gccaagatct actccgaccc catcgccgct gggaacgtca tcaacctgca ctggacggtg    300
tggccagact cacaccacgg gcccatcctg tcgtacctgg ccgcgtgcaa cggcgactgc    360
gccaaggccg acaagaccaa gctcaagtgg ttcaagattg cccatgccgg tcaaatcagc    420
ctgggcaccg gcgcggggca ggttggctac tgggccagcg acaagctgca agacgacaac    480
ggcacctggc ccgtcaccat tccggcctcc atcaagcccg gcaattacgt gctgcggaac    540
gagattattg ccctccattc ggcgtacgac gtcggcgccg cccagctcta cccgcagtgc    600
gttaatatca agatcacggg caacggccgc gtcacccctg ccggcgtggt gggaaccaag    660
ctctacaagg agaccgatcc tggcctgcat ataacatct ataacgacga gtctaagcct     720
gtctatcaga tccccggccc ggccttgtgt aagtgctaa                           759

SEQ ID NO: 160         moltype = AA  length = 252
FEATURE                Location/Qualifiers
source                 1..252
                       mol_type = protein
                       organism = Acrophialophora fusispora
SEQUENCE: 160
MRIEAITGLV LASAGAVSAH GWVDVWAIGG KNYTGFNPTV APWVPDQGTI AWPAWNTDTG     60
PVYSKDVNTT DIICSINATN AKIYSDPIAA GNVINLHWTV WPDSHHGPIL SYLAACNGDC    120
AKADKTKLKW FKIAHAGQIS LGTGGGQVGY WASDKLQDDN GTWPVTIPAS IKPGNYVLRN    180
EIIALHSAYD VGAAQLYPQC VNIKITGNGR VTPAGVVGTK LYKETDPGLH YNIYNDESKP    240
VYQIPGPALC KC                                                         252

SEQ ID NO: 161         moltype = DNA  length = 1035
FEATURE                Location/Qualifiers
source                 1..1035
                       mol_type = genomic DNA
                       organism = Corynascus sepedonium
SEQUENCE: 161
atgtctaaga cttctgctct ccttgctggc ctaacgggcg cggccctcgt cgctgcccac     60
gggcacgtca gccatatcat tgtcaacggt gtctactatg agaactacga ccccacgaca    120
cactggtacc agcccaaccc accaacagtc atcggctgga cggcagccca gcaggacaac    180
ggcttcatcg agcccaacaa ctttggcacg tcggacatca tctgccacaa gagcggttct    240
ccaggcggcg gtcacgctac cgtcgctgcg ggcgacaaga tcaacatcgt ctggactccg    300
gagtggccgg actcccatat cggcccggtc attgactacc tggcgcctg caacggtgac    360
tgcgagaccg taaacaagga gtcgctgcgc ttctttaaga ttgacggggc cggctatgcc    420
aaggccgctg gccgctgggc cgccgagact ctgcgccaga acggcaacag ctggctcgtc    480
cagatcccgt ctgaccttaa ggctggcaac tacgtgctcc gccacgaaat catcgccctc    540
cacggcgcgt cggaagcgcc aacggtgctc aacgctaccg ccagtgcatc aaccttcgcg tg    600
acgggcggcg gcagcagcgt cccagcggc gtggccgcca cctcgctcta caaagcctcc    660
gacgcaggca tcctcttcaa cccctacgtc gcctctcccg attacccggt cccaggcccg    720
gcgctcattg ctggtgccgc cagctctatc gtacagagca cgtcggcagt gaccgctacc    780
gcctcggcca ccgctcccgg tggcggcggc gccaaccca accctacgcc caccaccacc    840
tcctcgagca atcccgcccc aagcaccacc ctcaggacaa ccacctcggc cgcgcaaacc    900
acgccccgc ctaccaatgg gcctcgcag acaaagtacg gtcagtgtgg tggtagggac     960
tggagcgcc caacggcgtg cgcggctggt tccagctgct cggtgctcaa cgactggtac   1020
tcccagtgcg tgtaa                                                    1035

SEQ ID NO: 162         moltype = AA  length = 344
FEATURE                Location/Qualifiers
```

```
source                    1..344
                          mol_type = protein
                          organism = Corynascus sepedonium
SEQUENCE: 162
MSKTSALLAG LTGAALVAAH GHVSHIIVNG VYYENYDPTT HWYQPNPPTV IGWTAAQQDN    60
GFIEPNNFGT SDIICHKSGS PGGGHATVAA GDKINIVWTP EWPDSHIGPV IDYLAACNGD   120
CETVNKESLR FFKIDGAGYD KAAGRWAAET LRQNGNSWLV QIPSDLKAGN YVLRHEIIAL   180
HGAGSANGAQ AYPQCINLRV TGGGSSVPSG VAGTSLYKAS DAGILFNPYV ASPDYPVPGP   240
ALIAGAASSI VQSTSAVTAT ASATAPGGGG ANPNPTPTTT SSSNPAPSTT LRTTTSAAQT   300
TPPPTNGNVQ TKYGQCGGRD WSGPTACAAG SSCSVLNDWY SQCV                    344

SEQ ID NO: 163            moltype = DNA  length = 1044
FEATURE                   Location/Qualifiers
source                    1..1044
                          mol_type = genomic DNA
                          organism = Corynascus sepedonium
SEQUENCE: 163
atgccttctt ctacctccaa gggtcttttc tccgccctca tgggcgcggc gtcggttgcc     60
gcccatggtc atgtcaccaa cattgtcatc aacggtgtgt cgtaccagaa ctacgacccg    120
accagcttcc cttacatgca gaacccgccg acggttgttg gctggacggc aagcaacact    180
gataacggct tcgtcgctcc tgatgcgttt gctagcggcg acatcatctg ccacagggac    240
gccaccaatg ctggtggtca tgccgtcgtt gctgctgcga acaaggtctt catccagtgg    300
gatacctggc ctgagtcgca ccatggcccc gtccttgatt acctcgccag ctgcggtgac    360
gccggctgcg aaacggtcga caagaacact ctcgagttct tcaagatcgg cgaggctggc    420
ctgatcgacg gcagcagtgc tcccggcaag tgggcgtcgg accagctgat tgagaacaat    480
aactcgtgga tggttcagat ccctgccaac tttgcgcccg gaaactatgt gctgcggcat    540
gagattattg ctttgcacag cgctgggcaa gctaacggtg cccaaaacta ccccagtgc    600
ttcaacctgc aagttaccgg ctccggcacg gacaagcctg ccggtgtgct cggcaccgag    660
ctctacactc ccaccgacgc cggcatcttg gccaacatct acacctcgcc tgttcagtac    720
gagattcctg gcccggctct gatctcgggc gcttcggccg ttgaacagtc ctcctcggct    780
atcaccgcct ccgccagcgc tgagaccggc tccgcacaga cacccccgc cggctctgcc    840
acggccgccc ccaccactac cactaccacg gctggctcgg atgctagcgc tacgccctcg    900
tcctcgtcca gctctggtgc gagcaccacc gccgagccca cccttcggc tactactacc    960
gccggcggca gcaccccgcg cccgaccggg tgccctggcc tgaagcgccg ccgcacgcc   1020
cgtgatgtca agctcgccct ctaa                                         1044

SEQ ID NO: 164            moltype = AA  length = 347
FEATURE                   Location/Qualifiers
source                    1..347
                          mol_type = protein
                          organism = Corynascus sepedonium
SEQUENCE: 164
MPSSTSKGLF SALMGAASVA AHGHVTNIVI NGVSYQNYDP TSFPYMQNPP TVVGWTASNT    60
DNGFVAPDAF ASGDIICHRD ATNAGGHAVV AAGDKVFIQW DTWPESHHGP VLDYLASCGD   120
AGCETVDKNT LEFFKIGEAG LIDGSSAPGK WASDQLIENN NSWMVQIPAN LAPGNYVLRH   180
EIIALHSAGQ ANGAQNYPQC FNLQVTGSGT DKPAGVLGTE LYTPTDAGIL ANIYTSPVQY   240
EIPGPALISG ASAVEQSSSA ITASASAETG SATAPPAGSA TAAPTTTTTT AGSDASATPS   300
SSSSSGASTT AEPTPSATTT AGGSTPRPTR CPGLKRRRHA RDVKLAL                 347

SEQ ID NO: 165            moltype = DNA  length = 1029
FEATURE                   Location/Qualifiers
source                    1..1029
                          mol_type = genomic DNA
                          organism = Myceliophthora thermophila
SEQUENCE: 165
atgtccaagg cctctgctct cctcgctggc ctgacgggcg cggccctcgt cgctgcacat     60
ggccacgtca gccacatcgt cgtcaacggc gtctactaca ggaactacga ccccacgaca    120
gactggtacc agcccaaccc gccaacagtc atcggctgga cggcagccga tcaggataat    180
ggcttcgttg aacccaacag ctttggcacg ccagatatca tctgccacaa gagcgccacc    240
cccggcgggc gccacgctac cgttgctgcc ggagacaaga tcaacatcgt ctggaccccc    300
gagtggcccg aatcccacat cggccccgtc attgactacc tagccgcctg caacggtgac    360
tgcgagaccg tcgacaagtc gtcgctgcgc tggttcaaga ttgacggcgc cggctacgac    420
aaggccgccg gcgctgggc cgccgacgct tgcgcgcca cggcaacag ctggctcgtc    480
cagatcccgt cggatctcaa ggccggcaac tacgtcctcc gccacgagat catcgccctc    540
cacggtgctc agagcccaa cggcgcccag gcctacccgc agtgcatcaa cctccgcgtc    600
accggcggcg gcagcaacct gccagcggc gtcgccggca cctcgctgta caaggcgacc    660
gacccgggca tcctcttcaa ccctacgtc tcctccccgg attacaccgt ccccggcccc    720
gccctcattg ccggcgccgc cagctcgatc gcccagagca cgtcggtcgc cactgccacc    780
ggcacggcca ccgttccgg cggcggcggc gccaaccta ccgccaccac caccgccgcc    840
acctccgccg cccccgagca caccctgagg acgaccacta cctcggccgc gcagactacc    900
gccccgccct ccggcgatgt gcagaccaag tacggccagt gtggtggcaa cggatggacg    960
ggcccgacgg tgtgcgcccc cggctcgagc tgctccgtcc tcaacgagtg gtactcccag   1020
tgtttgtaa                                                          1029

SEQ ID NO: 166            moltype = AA  length = 342
FEATURE                   Location/Qualifiers
source                    1..342
                          mol_type = protein
                          organism = Myceliophthora thermophila
```

```
SEQUENCE: 166
MSKASALLAG LTGAALVAAH GHVSHIVVNG VYYRNYDPTT DWYQPNPPTV IGWTAADQDN    60
GFVEPNSFGT PDIICHKSAT PGGGHATVAA GDKINIVWTP EWPESHIGPV IDYLAACNGD   120
CETVDKSSLR WFKIDGAGYD KAAGRWAADA LRANGNSWLV QIPSDLKAGN YVLRHEIIAL   180
HGAQSPNGAQ AYPQCINLRV TGGGSNLPSG VAGTSLYKAT DPGILFNPYV SSPDYTVPGP   240
ALIAGAASSI AQSTSVATAT GTATVPGGGG ANPTATTTAA TSAAPSTTLR TTTTSAAQTT   300
APPSGDVQTK YGQCGGNGWT GPTVCAPGSS CSVLNEWYSQ CL                     342

SEQ ID NO: 167             moltype = DNA   length = 765
FEATURE                    Location/Qualifiers
source                     1..765
                           mol_type = genomic DNA
                           organism = Talaromyces emersonii
SEQUENCE: 167
atgctgtctt cgaaggctcc tgtcacccct gcctttgcag gcctcgctgg ccttctgtcc    60
gccccactgg tcaaggccca tggttttgtc cagggcattg tcatcggtga ccaattctac   120
agcgggtaca tcgtcaacga gttcccctac gaatccaacc cacccccgt catcggctgg   180
gccacgacag ccaccgacct gggcttcgtc gacggcactg aataccaagg accagacatc   240
atctgccacc ggaatgcgac gcccgcgctg ctgacagccc ccgtggccgc cggcggcacc   300
gtcgagctgc agtggacgcc ctggccgtcc agccaccacg gccggtcat cacgtacctg   360
gccaactgca acggcaactg ctcgaccgtc gacaagacgc agctggagtt cttcaagatc   420
gaccagtcgg gcctgatcaa cgacactgac ccgccgggcg cctggcgtc cgacaacctc   480
atcgccaaca caacagctg gaccgtgacc atccccagca ccctcgagcc gggcaactac   540
gtgctgcgcc acgagatcat cgccctgcac tcggcgggca caaagacgg cgcccagaac   600
taccccagt gcatcaacat cgaggtcacg ggcggcggct cggtcgagcc gacgggcacg   660
ctgggcgagg atctctacca cgacacggac ccgggcattc tgatcgacat ttacgagccg   720
attgcgacgt ataccattcc aggaccgcct gagccgacgt tctag                  765

SEQ ID NO: 168             moltype = AA   length = 254
FEATURE                    Location/Qualifiers
source                     1..254
                           mol_type = protein
                           organism = Talaromyces emersonii
SEQUENCE: 168
MLSSKAPVTL AFAGLAGLLS APLVKAHGFV QGIVIGDQFY SGYIVNEFPY ESNPPPVIGW    60
ATTATDLGFV DGTEYQGPDI ICHRNATPAL LTAPVAAGGT VELQWTPWPS SHHGPVITYL   120
ANCNGNCSTV DKTQLEFFKI DQSGLINDTD PPGTWASDNL IANNNSWTVT IPSTLEPGNY   180
VLRHEIIALH SAGNKDGAQN YPQCINIEVT GGGSVEPTGT LGEDLYHDTD PGILIDIYEP   240
IATYTIPGPP EPTF                                                    254

SEQ ID NO: 169             moltype = DNA   length = 3060
FEATURE                    Location/Qualifiers
source                     1..3060
                           mol_type = genomic DNA
                           organism = Aspergillus fumigatus
SEQUENCE: 169
atgagattcg gttggctcga ggtggccgct ctgacggccg cttctgtagc caatgcccag    60
gtttgtgatg ctttcccgtc attgtttcgg atatagttga caatagtcat ggaaataatc   120
aggaattggc tttctctcca ccattctacc cttgccttg gctgatggc cagggagagt   180
gggcagatgc ccatcgacgc gccgtcgaga tcgtttctca gatgacactg gcggagaagg   240
ttaaccttac aacgggtact gggtgggttg cgactttttg gttgacagtg agctttcttc   300
actgaccatc tacacagatg ggaaatggac cgatgcgtcg gtcaaaccgg cagcgttccc   360
aggtaagctt gcaattctgc aacaacgtgc aagtgtagtt gctaaaacgc ggtggtgcag   420
acttggtatc aactggggtc tttgtggcca ggattcccct tgggtatcc gtttctgtga   480
gctatacccg cggagtcttt cagtccttgt attatgtgct gatgattgtc tctgtatagc   540
tgacctcaac tccgccttcc ctgctggtac taatgtcgcc gcgacatggg acaagacact   600
cgcctacctt cgtggcaagg ccatgggtga ggaattcaac gacaagggcg tggacatttt   660
gctggggcct gctgctggtc ctctcggcaa atacccggac ggcggcagaa tctgggaagg   720
cttctctcct gatccggttc tcactggtgt acttttcgc gaaactatca agggtatcca   780
agacgcgggt gtgattgcta ctgccaagca ttacattctg aatgaacagg agcattccg   840
acaggttggc gaggcccagg gatatgggta caacatcacg gagacgatca gctccaacgt   900
ggatgacaag accatgcacg agttgtacct tggtgagta gttgacactg caaatgagga   960
ccttgattga tttgactgac ctggaatgca ggccctttgc agatgctgtg cgcggtaaga  1020
tttttccgtag acttgaccctc gcgacgaaga aatcgctgac gaaccatcgt agctggcgtt  1080
ggcgctgtca tgtgttccta caatcaaatc aacaacagct acggttgtca aaacagtcaa  1140
actctcaaca agctcctcaa ggctgagctg gccttccaag gcttcgtcat gagtgactgg  1200
agcgctcacc acagcggtgt cggcgctgcc ctcgctgggt tggatatgtc gatgcctgga  1260
gacatttcct tcgacgacgg actctccttg tgggcacga acctaactgt cagtgttctt  1320
aacggcaccg ttccagcctg gcgtgtcgat gacatgctg ttcgtatcat gaccgcgtac  1380
tacaaggttg tcgtgaccg tcttcgtatt cccctaact tcagctcctg gacccgggat  1440
gagtacggct gggagcattc tgctgtctcc gagggagcct ggaccaaggt gaacgacttc  1500
gtcaatgtgc agcgcagtca ctctcagatc atccgtgaga ttggtgccgc tagtacagtg  1560
ctcttgaaga acacgggtgc tcttcctttg accggcaagg aggttaaagt gggtgttctc  1620
ggtgaagacc ctggttccaa cccgtggggt gctaacgact gccccgaccg cggctgtgat  1680
aacggcactc ttgctatggc ctggggtagt ggtactgcca acttccctta ccttgtcacc  1740
cccgagcagg ctaccagcg agaggtcatc agcaacggcg gcaatgtctt tgctgtgact  1800
gataacgggg ctctcagcca gatggcagat gttgcatctc aatccaggtg agtgcgggct  1860
cttagaaaaa gaacgttctc tgaatgaagt ttttaaccca ttgcgaacag cgtgtctttg  1920
gtgtttgtca acgccgactc tggagagggt ttcatcagtg tcgacggcaa cgagggtgac  1980
```

-continued

```
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc ggggagtctta cggggctccc ttgctcaccg agccaacaa tggcaatgt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaggcctg cgccaaccta tggtgagatc ggtagtgccg ccgactacct gtatcccgag    2520
ggtctcaaaa gaattaccaa gttttatttac ccttggctca actcgaccga cctcgaggat    2580
tcttctgacg acccgaacta cggctgggag gactcggagt acattcccga aggcgctagg    2640
gatgggtctc ctcaaccct cctgaaggct ggcggcgctc ctggtggtaa ccctaccctt    2700
tatcaggatc ttgttagggt gtcggccacc ataaccaaca ctggtaacgt cgccggttat    2760
gaagtccctc aattggtgag tgacccgcat gttccttgcg ttgcaatttg gctaactgac    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caagtacccc caagaaagtg    3000
cacgtcggca gctcctcgcg taagctgcct ctgagagcgc ctctgccccg tgtctactag    3060
```

SEQ ID NO: 170   moltype = AA length = 863
FEATURE      Location/Qualifiers
source       1..863
         mol_type = protein
         organism = Aspergillus fumigatus
SEQUENCE: 170

```
MRFGWLEVAA LTAASVANAQ ELAFSPPFYP SPWADGQGEW ADAHRRAVEI VSQMTLAEKV     60
NLTTGTGWEM DRCVGQTGSV PRLGINWGLC GQDSPLGIRF SDLNSAFPAG TNVAATWDKT    120
LAYLRGKAMG EEFNDKGVDI LLGPAAGPLG KYPDGGRIWE GFSPDPVLTG VLFAETIKGI    180
QDAGVIATAK HYILNEQEHF RQVGEAQGYG YNITETISSN VDDKTMHELY LWPFADAVRA    240
GVGAVMCSYN QINNSYGCQN SQTLNKLLKA ELGPQGFVMS DWSAHHSGVG AALAGLDMSM    300
PGDISFDDGL SFWGTNLTVS VLNGTVPAWR VDDMAVRIMT AYYKVGRDRL RIPPNFSSWT    360
RDEYGWEHSA VSEGAWTKVN DFVNVQRSHS QIIREIGAAS TVLLKNTGAL PLTGKEVKVG    420
VLGEDAGSNP WGANGCPDRG CDNGTLAMAW GSGTANFPYL VTPEQAIQRE VISNGGNVFA    480
VTDNGALSQM ADVASQSSVS LVFVNADSGE GFISVDGNNG DRKNLTLWKN GEAVIDTVVS    540
HCNNTIVVIH SVGPVLIDRW YDNPNVTAII WAGLPGQESG NSLVDVLYGR VNPSAKTPFT    600
WGKTRESYGA PLLTEPNNGN GAPQDDFNEG VFIDYRHFDK RNETPIYEFG HGLSYTTFGY    660
SHLRVQALNS SSSAYVPTSG ETKPAPTYGE IGSAADYLYP EGLKRITKFI YPWLNSTDLE    720
DSSDDPNYGW EDSEYIPEGA RDGSPQPLLK AGGAPGGNPT LYQDLVRVSA TITNTGNVAG    780
YEVPQLYVSL GGPNEPRVVL RKFDRIFLAP GEQKVWTTTL NRRDLANWDV EAQDWVITKY    840
PKKVHVGSSS RKLPLRAPLP RVY                                           863
```

SEQ ID NO: 171   moltype = DNA length = 40
FEATURE      Location/Qualifiers
misc_feature    1..40
         note = Artificial DNA Primer
source       1..40
         mol_type = other DNA
         organism = synthetic construct
SEQUENCE: 171

```
cacaactggg gatccatgac tttgtccaag atcacttcca                           40
```

SEQ ID NO: 172   moltype = DNA length = 40
FEATURE      Location/Qualifiers
misc_feature    1..40
         note = Artificial DNA Primer
source       1..40
         mol_type = other DNA
         organism = synthetic construct
SEQUENCE: 172

```
ggcctccgcg gccgcttaag cgttgaacag tgcaggacca                           40
```

SEQ ID NO: 173   moltype = DNA length = 40
FEATURE      Location/Qualifiers
misc_feature    1..40
         note = Artificial DNA Primer
source       1..40
         mol_type = other DNA
         organism = synthetic construct
SEQUENCE: 173

```
cacaactggg gatccatgac tttgtccaag atcacttcca                           40
```

SEQ ID NO: 174   moltype = DNA length = 40
FEATURE      Location/Qualifiers
misc_feature    1..40
         note = Artificial DNA Primer
source       1..40
         mol_type = other DNA
         organism = synthetic construct
SEQUENCE: 174

```
ggcctccgcg gccgcttaag cgttgaacag tgcaggacca                            40

SEQ ID NO: 175          moltype = DNA  length = 40
FEATURE                 Location/Qualifiers
misc_feature            1..40
                        note = Artificial DNA Primer
source                  1..40
                        mol_type = other DNA
                        organism = synthetic construct
SEQUENCE: 175
cacaactggg gatccatgct gtcttcgacg actcgcaccc                            40

SEQ ID NO: 176          moltype = DNA  length = 40
FEATURE                 Location/Qualifiers
misc_feature            1..40
                        note = Artificial DNA Primer
source                  1..40
                        mol_type = other DNA
                        organism = synthetic construct
SEQUENCE: 176
ggcctccgcg gccgcctaga acgtcggctc aggcggcccc                            40

SEQ ID NO: 177          moltype = DNA  length = 27
FEATURE                 Location/Qualifiers
misc_feature            1..27
                        note = Artificial DNA Primer
source                  1..27
                        mol_type = other DNA
                        organism = synthetic construct
SEQUENCE: 177
ctggggatcc atgtcctttt ccaagat                                          27

SEQ ID NO: 178          moltype = DNA  length = 29
FEATURE                 Location/Qualifiers
misc_feature            1..29
                        note = Artificial DNA Primer
source                  1..29
                        mol_type = other DNA
                        organism = synthetic construct
SEQUENCE: 178
ctccgcggcc gcttaaccag tatacagag                                        29

SEQ ID NO: 179          moltype = DNA  length = 25
FEATURE                 Location/Qualifiers
misc_feature            1..25
                        note = Artificial DNA Primer
source                  1..25
                        mol_type = other DNA
                        organism = synthetic construct
SEQUENCE: 179
actcaattta cctctatcca cactt                                            25

SEQ ID NO: 180          moltype = DNA  length = 25
FEATURE                 Location/Qualifiers
misc_feature            1..25
                        note = Artificial DNA Primer
source                  1..25
                        mol_type = other DNA
                        organism = synthetic construct
SEQUENCE: 180
gaattgtgag cggataacaa tttca                                            25

SEQ ID NO: 181          moltype = DNA  length = 36
FEATURE                 Location/Qualifiers
misc_feature            1..36
                        note = Artificial DNA Primer
source                  1..36
                        mol_type = other DNA
                        organism = synthetic construct
SEQUENCE: 181
cggactgcgc accatgctgt cttcgacgac tcgcac                                36

SEQ ID NO: 182          moltype = DNA  length = 35
FEATURE                 Location/Qualifiers
misc_feature            1..35
                        note = Artificial DNA Primer
source                  1..35
                        mol_type = other DNA
                        organism = synthetic construct
```

```
SEQUENCE: 182
tcgccacgga gcttatcgac ttcttctaga acgtc                          35

SEQ ID NO: 183          moltype = DNA  length = 49
FEATURE                 Location/Qualifiers
misc_feature            1..49
                        note = Artificial DNA Primer
source                  1..49
                        mol_type = other DNA
                        organism = synthetic construct
SEQUENCE: 183
acaagaatac tgatcctggc atctggtttg acatctactc ggatctgag           49

SEQ ID NO: 184          moltype = DNA  length = 49
FEATURE                 Location/Qualifiers
misc_feature            1..49
                        note = Artificial DNA Primer
source                  1..49
                        mol_type = other DNA
                        organism = synthetic construct
SEQUENCE: 184
ctcagatccg agtagatgtc aaaccagatg ccaggatcag tattcttgt           49

SEQ ID NO: 185          moltype = DNA  length = 45
FEATURE                 Location/Qualifiers
misc_feature            1..45
                        note = Artificial DNA Primer
source                  1..45
                        mol_type = other DNA
                        organism = synthetic construct
SEQUENCE: 185
atcatcgccc ttcactctgc gtttaacctg aacggcgcgc agaac               45

SEQ ID NO: 186          moltype = DNA  length = 45
FEATURE                 Location/Qualifiers
misc_feature            1..45
                        note = Artificial DNA Primer
source                  1..45
                        mol_type = other DNA
                        organism = synthetic construct
SEQUENCE: 186
gttctgcgcg ccgttcaggt taaacgcaga gtgaagggcg atgat               45

SEQ ID NO: 187          moltype = DNA  length = 46
FEATURE                 Location/Qualifiers
misc_feature            1..46
                        note = Artificial DNA Primer
source                  1..46
                        mol_type = other DNA
                        organism = synthetic construct
SEQUENCE: 187
gaagtttgtc aagatcgccg ctaagggctt gatcgacggc tccaac              46

SEQ ID NO: 188          moltype = DNA  length = 46
FEATURE                 Location/Qualifiers
misc_feature            1..46
                        note = Artificial DNA Primer
source                  1..46
                        mol_type = other DNA
                        organism = synthetic construct
SEQUENCE: 188
gttggagccg tcgatcaagc ccttagcggc gatcttgaca aacttc              46

SEQ ID NO: 189          moltype = DNA  length = 48
FEATURE                 Location/Qualifiers
misc_feature            1..48
                        note = Artificial DNA Primer
source                  1..48
                        mol_type = other DNA
                        organism = synthetic construct
SEQUENCE: 189
cttgttaacc aataccccta catggaaaac cctcccgaca ccattgcc            48

SEQ ID NO: 190          moltype = DNA  length = 48
FEATURE                 Location/Qualifiers
misc_feature            1..48
                        note = Artificial DNA Primer
source                  1..48
                        mol_type = other DNA
```

```
                              organism = synthetic construct
SEQUENCE: 190
ggcaatggtg tcgggagggt tttccatgta ggggtattgg ttaacaag                48

SEQ ID NO: 191          moltype = DNA  length = 42
FEATURE                 Location/Qualifiers
misc_feature            1..42
                        note = Artificial DNA Primer
source                  1..42
                        mol_type = other DNA
                        organism = synthetic construct
SEQUENCE: 191
ctcccgacac cattgcctgg gccaccaccg ccaccgacct cg                      42

SEQ ID NO: 192          moltype = DNA  length = 42
FEATURE                 Location/Qualifiers
misc_feature            1..42
                        note = Artificial DNA Primer
source                  1..42
                        mol_type = other DNA
                        organism = synthetic construct
SEQUENCE: 192
cgaggtcggt ggcggtggtg gcccaggcaa tggtgtcggg ag                      42

SEQ ID NO: 193          moltype = DNA  length = 46
FEATURE                 Location/Qualifiers
misc_feature            1..46
                        note = Artificial DNA Primer
source                  1..46
                        mol_type = other DNA
                        organism = synthetic construct
SEQUENCE: 193
acagatcgaa ttccagtgga cgaagtggcc agagtctcac catgga                  46

SEQ ID NO: 194          moltype = DNA  length = 46
FEATURE                 Location/Qualifiers
misc_feature            1..46
                        note = Artificial DNA Primer
source                  1..46
                        mol_type = other DNA
                        organism = synthetic construct
SEQUENCE: 194
acagatcgaa ttccagtgga cgaagtggcc agagtctcac catgga                  46

SEQ ID NO: 195          moltype = DNA  length = 37
FEATURE                 Location/Qualifiers
misc_feature            1..37
                        note = Artificial DNA Primer
source                  1..37
                        mol_type = other DNA
                        organism = synthetic construct
SEQUENCE: 195
ccagtggacg aagtggccaa agtctcacca tggaccg                            37

SEQ ID NO: 196          moltype = DNA  length = 37
FEATURE                 Location/Qualifiers
misc_feature            1..37
                        note = Artificial DNA Primer
source                  1..37
                        mol_type = other DNA
                        organism = synthetic construct
SEQUENCE: 196
cggtccatgg tgagactttg gccacttcgt ccactgg                            37

SEQ ID NO: 197          moltype = DNA  length = 47
FEATURE                 Location/Qualifiers
misc_feature            1..47
                        note = Artificial DNA Primer
source                  1..47
                        mol_type = other DNA
                        organism = synthetic construct
SEQUENCE: 197
ctggcatctg gtttgacatc tacggcgatc tgagcggtgg ataccct                 47

SEQ ID NO: 198          moltype = DNA  length = 47
FEATURE                 Location/Qualifiers
misc_feature            1..47
                        note = Artificial DNA Primer
source                  1..47
```

```
                        mol_type = other DNA
                        organism = synthetic construct
SEQUENCE: 198
agggtatcca ccgctcagat cgccgtagat gtcaaaccag atgccag              47

SEQ ID NO: 199          moltype = DNA   length = 45
FEATURE                 Location/Qualifiers
misc_feature            1..45
                        note = Artificial DNA Primer
source                  1..45
                        mol_type = other DNA
                        organism = synthetic construct
SEQUENCE: 199
atcatcgccc ttcactctgc gtttaacctg aacggcgcgc agaac                45

SEQ ID NO: 200          moltype = DNA   length = 45
FEATURE                 Location/Qualifiers
misc_feature            1..45
                        note = Artificial DNA Primer
source                  1..45
                        mol_type = other DNA
                        organism = synthetic construct
SEQUENCE: 200
gttctgcgcg ccgttcaggt taaacgcaga gtgaagggcg atgat                45

SEQ ID NO: 201          moltype = DNA   length = 44
FEATURE                 Location/Qualifiers
misc_feature            1..44
                        note = Artificial DNA Primer
source                  1..44
                        mol_type = other DNA
                        organism = synthetic construct
SEQUENCE: 201
cacgagatca tcgcccttca caccgcgggt aacctgaacg cgc                  44

SEQ ID NO: 202          moltype = DNA   length = 44
FEATURE                 Location/Qualifiers
misc_feature            1..44
                        note = Artificial DNA Primer
source                  1..44
                        mol_type = other DNA
                        organism = synthetic construct
SEQUENCE: 202
gcgccgttca ggttacccgc ggtgtgaagg gcgatgatct cgtg                 44

SEQ ID NO: 203          moltype = DNA   length = 45
FEATURE                 Location/Qualifiers
misc_feature            1..45
                        note = Artificial DNA Primer
source                  1..45
                        mol_type = other DNA
                        organism = synthetic construct
SEQUENCE: 203
atcatcgccc ttcactctgc gtttaacctg aacggcgcgc agaac                45

SEQ ID NO: 204          moltype = DNA   length = 44
FEATURE                 Location/Qualifiers
misc_feature            1..44
                        note = Artificial DNA Primer
source                  1..44
                        mol_type = other DNA
                        organism = synthetic construct
SEQUENCE: 204
cggctccaac ccacctggta tctgggcttc cgatgaactg atcg                 44

SEQ ID NO: 205          moltype = DNA   length = 45
FEATURE                 Location/Qualifiers
misc_feature            1..45
                        note = Artificial DNA Primer
source                  1..45
                        mol_type = other DNA
                        organism = synthetic construct
SEQUENCE: 205
atcatcgccc ttcactctgc gtttaacctg aacggcgcgc agaac                45

SEQ ID NO: 206          moltype = DNA   length = 44
FEATURE                 Location/Qualifiers
misc_feature            1..44
                        note = Artificial DNA Primer
```

```
source                     1..44
                           mol_type = other DNA
                           organism = synthetic construct
SEQUENCE: 206
cggctccaac ccacctggta tctgggcttc cgatgaactg atcg                    44

SEQ ID NO: 207             moltype = DNA   length = 45
FEATURE                    Location/Qualifiers
misc_feature               1..45
                           note = Artificial DNA Primer
source                     1..45
                           mol_type = other DNA
                           organism = synthetic construct
SEQUENCE: 207
cggcaccggc taccagaccc cggatattat ctgccacaga gacgc                   45

SEQ ID NO: 208             moltype = DNA   length = 45
FEATURE                    Location/Qualifiers
misc_feature               1..45
                           note = Artificial DNA Primer
source                     1..45
                           mol_type = other DNA
                           organism = synthetic construct
SEQUENCE: 208
atcatcgccc ttcactctgc gtttaacctg aacggcgcgc agaac                   45

SEQ ID NO: 209             moltype = DNA   length = 44
FEATURE                    Location/Qualifiers
misc_feature               1..44
                           note = Artificial DNA Primer
source                     1..44
                           mol_type = other DNA
                           organism = synthetic construct
SEQUENCE: 209
cggctccaac ccacctggta tctgggcttc cgatgaactg atcg                    44

SEQ ID NO: 210             moltype = DNA   length = 45
FEATURE                    Location/Qualifiers
misc_feature               1..45
                           note = Artificial DNA Primer
source                     1..45
                           mol_type = other DNA
                           organism = synthetic construct
SEQUENCE: 210
ccagtgtttc aacatccaaa tcaccggtcc tggcagtgct caggg                   45

SEQ ID NO: 211             moltype = DNA   length = 36
FEATURE                    Location/Qualifiers
misc_feature               1..36
                           note = Artificial DNA Primer
source                     1..36
                           mol_type = other DNA
                           organism = synthetic construct
SEQUENCE: 211
ccattcctgc ctgctatgcc cccggaaact acgtcc                             36

SEQ ID NO: 212             moltype = DNA   length = 33
FEATURE                    Location/Qualifiers
misc_feature               1..33
                           note = Artificial DNA Primer
source                     1..33
                           mol_type = other DNA
                           organism = synthetic construct
SEQUENCE: 212
cctggtcctg cactgttcaa ctgctaagcg gcc                                33

SEQ ID NO: 213             moltype = DNA   length = 43
FEATURE                    Location/Qualifiers
misc_feature               1..43
                           note = Artificial DNA Primer
source                     1..43
                           mol_type = other DNA
                           organism = synthetic construct
SEQUENCE: 213
tggaccgtca ccattcccaa ctgcgtcgcc cccggcaact acg                     43

SEQ ID NO: 214             moltype = DNA   length = 43
FEATURE                    Location/Qualifiers
misc_feature               1..43
```

```
                        note = Artificial DNA Primer
source                  1..43
                        mol_type = other DNA
                        organism = synthetic construct
SEQUENCE: 214
cgtagttgcc gggggcgacg cagttgggaa tggtgacggt cca            43

SEQ ID NO: 215          moltype = DNA  length = 45
FEATURE                 Location/Qualifiers
misc_feature            1..45
                        note = Artificial DNA Primer
source                  1..45
                        mol_type = other DNA
                        organism = synthetic construct
SEQUENCE: 215
ccggggccgc ctgagccgac gtgctaggcg gccgcggagg ccacc          45

SEQ ID NO: 216          moltype = DNA  length = 45
FEATURE                 Location/Qualifiers
misc_feature            1..45
                        note = Artificial DNA Primer
source                  1..45
                        mol_type = other DNA
                        organism = synthetic construct
SEQUENCE: 216
ggtggcctcc gcggccgcct agcacgtcgg ctcaggcggc cccgg          45

SEQ ID NO: 217          moltype = DNA  length = 27
FEATURE                 Location/Qualifiers
misc_feature            1..27
                        note = Artificial DNA Primer
misc_feature            10
                        note = N=DEOXYURIDINE
source                  1..27
                        mol_type = other DNA
                        organism = synthetic construct
SEQUENCE: 217
atgcagcgcn gccataacca tgagtga                              27

SEQ ID NO: 218          moltype = DNA  length = 28
FEATURE                 Location/Qualifiers
misc_feature            1..28
                        note = Artificial DNA Primer
misc_feature            10
                        note = N=DEOXYURIDINE
source                  1..28
                        mol_type = other DNA
                        organism = synthetic construct
SEQUENCE: 218
agcgctgcan aattctctta ctgtcatg                             28

SEQ ID NO: 219          moltype = DNA  length = 36
FEATURE                 Location/Qualifiers
misc_feature            1..36
                        note = Artificial DNA Primer
misc_feature            8
                        note = N=DEOXYURIDINE
source                  1..36
                        mol_type = other DNA
                        organism = synthetic construct
SEQUENCE: 219
aattaagncc tcagcgtgat ttaaaacgcc attgct                    36

SEQ ID NO: 220          moltype = DNA  length = 41
FEATURE                 Location/Qualifiers
misc_feature            1..41
                        note = Artificial DNA Primer
misc_feature            8
                        note = N=DEOXYURIDINE
source                  1..41
                        mol_type = other DNA
                        organism = synthetic construct
SEQUENCE: 220
acttaatnaa accctcagcg cagttaggtt ggtgttcttc t              41

SEQ ID NO: 221          moltype = DNA  length = 29
FEATURE                 Location/Qualifiers
misc_feature            1..29
                        note = Artificial DNA Primer
```

```
misc_feature            11
                        note = N=DEOXYURIDINE
source                  1..29
                        mol_type = other DNA
                        organism = synthetic construct
SEQUENCE: 221
agctcaagga nacctacagt tattcgaaa                                         29

SEQ ID NO: 222          moltype = DNA   length = 35
FEATURE                 Location/Qualifiers
misc_feature            1..35
                        note = Artificial DNA Primer
misc_feature            11
                        note = N=DEOXYURIDINE
source                  1..35
                        mol_type = other DNA
                        organism = synthetic construct
SEQUENCE: 222
atccttgagc ngtttcctgt gtgaaattgt tatcc                                  35

SEQ ID NO: 223          moltype = DNA   length = 37
FEATURE                 Location/Qualifiers
misc_feature            1..37
                        note = Artificial DNA Primer
misc_feature            9
                        note = N=DEOXYURIDINE
source                  1..37
                        mol_type = other DNA
                        organism = synthetic construct
SEQUENCE: 223
atctcctcng ctggtctggt taagccagcc ccgacac                                37

SEQ ID NO: 224          moltype = DNA   length = 27
FEATURE                 Location/Qualifiers
misc_feature            1..27
                        note = Artificial DNA Primer
misc_feature            9
                        note = N=DEOXYURIDINE
source                  1..27
                        mol_type = other DNA
                        organism = synthetic construct
SEQUENCE: 224
agaggagana atactctgcg ctccgcc                                           27

SEQ ID NO: 225          moltype = DNA   length = 32
FEATURE                 Location/Qualifiers
misc_feature            1..32
                        note = Artificial DNA Primer
misc_feature            9
                        note = N=DEOXYURIDINE
source                  1..32
                        mol_type = other DNA
                        organism = synthetic construct
SEQUENCE: 225
gggtttaanc ctcacacagg aaacagctat ga                                     32

SEQ ID NO: 226          moltype = DNA   length = 46
FEATURE                 Location/Qualifiers
misc_feature            1..46
                        note = Artificial DNA Primer
misc_feature            12
                        note = N=DEOXYURIDINE
source                  1..46
                        mol_type = other DNA
                        organism = synthetic construct
SEQUENCE: 226
agtgtctgcg ancgctctca ctgcccccag ttgtgtatat agagga                      46

SEQ ID NO: 227          moltype = DNA   length = 36
FEATURE                 Location/Qualifiers
misc_feature            1..36
                        note = Artificial DNA Primer
misc_feature            12
                        note = N=DEOXYURIDINE
source                  1..36
                        mol_type = other DNA
                        organism = synthetic construct
SEQUENCE: 227
atcgcagaca cngctggcgg tagacaatca atccat                                 36
```

```
SEQ ID NO: 228          moltype = DNA  length = 32
FEATURE                 Location/Qualifiers
misc_feature            1..32
                        note = Artificial DNA Primer
misc_feature            9
                        note = N=DEOXYURIDINE
source                  1..32
                        mol_type = other DNA
                        organism = synthetic construct
SEQUENCE: 228
ggacttaang gatctaagat gagctcatgg ct                                    32

SEQ ID NO: 229          moltype = DNA  length = 24
FEATURE                 Location/Qualifiers
misc_feature            1..24
                        note = Artificial DNA Primer
source                  1..24
                        mol_type = other DNA
                        organism = synthetic construct
SEQUENCE: 229
acgccattgc tatgatgctt gaag                                             24

SEQ ID NO: 230          moltype = DNA  length = 21
FEATURE                 Location/Qualifiers
misc_feature            1..21
                        note = Artificial DNA Primer
source                  1..21
                        mol_type = other DNA
                        organism = synthetic construct
SEQUENCE: 230
tggtgaggtg ctatcgtcct t                                                21

SEQ ID NO: 231          moltype = DNA  length = 21
FEATURE                 Location/Qualifiers
misc_feature            1..21
                        note = Artificial DNA Primer
source                  1..21
                        mol_type = other DNA
                        organism = synthetic construct
SEQUENCE: 231
cttcctgtag gtgcaccgaa g                                                21

SEQ ID NO: 232          moltype = DNA  length = 21
FEATURE                 Location/Qualifiers
misc_feature            1..21
                        note = Artificial DNA Primer
source                  1..21
                        mol_type = other DNA
                        organism = synthetic construct
SEQUENCE: 232
acagaacgat atcggacctc g                                                21

SEQ ID NO: 233          moltype = DNA  length = 23
FEATURE                 Location/Qualifiers
misc_feature            1..23
                        note = Artificial DNA Primer
source                  1..23
                        mol_type = other DNA
                        organism = synthetic construct
SEQUENCE: 233
tcgttatgtt aagtcttcta tca                                              23

SEQ ID NO: 234          moltype = DNA  length = 21
FEATURE                 Location/Qualifiers
misc_feature            1..21
                        note = Artificial DNA Primer
source                  1..21
                        mol_type = other DNA
                        organism = synthetic construct
SEQUENCE: 234
agagctcgaa gttcctccga g                                                21

SEQ ID NO: 235          moltype = DNA  length = 22
FEATURE                 Location/Qualifiers
misc_feature            1..22
                        note = Artificial DNA Primer
source                  1..22
                        mol_type = other DNA
```

```
                             organism = synthetic construct
SEQUENCE: 235
tatcacgagg ccctttcgtc tc                                              22

SEQ ID NO: 236           moltype = DNA  length = 22
FEATURE                  Location/Qualifiers
misc_feature             1..22
                         note = Artificial DNA Primer
source                   1..22
                         mol_type = other DNA
                         organism = synthetic construct
SEQUENCE: 236
tccgtcggct cctctccttc gt                                              22

SEQ ID NO: 237           moltype = DNA  length = 24
FEATURE                  Location/Qualifiers
misc_feature             1..24
                         note = Artificial DNA Primer
source                   1..24
                         mol_type = other DNA
                         organism = synthetic construct
SEQUENCE: 237
tgcatatcct ctgacagtat atga                                            24

SEQ ID NO: 238           moltype = DNA  length = 23
FEATURE                  Location/Qualifiers
misc_feature             1..23
                         note = Artificial DNA Primer
source                   1..23
                         mol_type = other DNA
                         organism = synthetic construct
SEQUENCE: 238
cagtgaagag ggcagtcgat agt                                             23

SEQ ID NO: 239           moltype = DNA  length = 22
FEATURE                  Location/Qualifiers
misc_feature             1..22
                         note = Artificial DNA Primer
source                   1..22
                         mol_type = other DNA
                         organism = synthetic construct
SEQUENCE: 239
acgaggaaca tggctatctg ga                                              22

SEQ ID NO: 240           moltype = DNA  length = 23
FEATURE                  Location/Qualifiers
misc_feature             1..23
                         note = Artificial DNA Primer
source                   1..23
                         mol_type = other DNA
                         organism = synthetic construct
SEQUENCE: 240
tcagctcatt ctgggaggtg gga                                             23

SEQ ID NO: 241           moltype = DNA  length = 22
FEATURE                  Location/Qualifiers
misc_feature             1..22
                         note = Artificial DNA Primer
source                   1..22
                         mol_type = other DNA
                         organism = synthetic construct
SEQUENCE: 241
actccaggat cctttaaatc ca                                              22

SEQ ID NO: 242           moltype = DNA  length = 21
FEATURE                  Location/Qualifiers
misc_feature             1..21
                         note = Artificial DNA Primer
source                   1..21
                         mol_type = other DNA
                         organism = synthetic construct
SEQUENCE: 242
actggcaagg gatgccatgc t                                               21

SEQ ID NO: 243           moltype = DNA  length = 22
FEATURE                  Location/Qualifiers
misc_feature             1..22
                         note = Artificial DNA Primer
source                   1..22
```

```
                              mol_type = other DNA
                              organism = synthetic construct
SEQUENCE: 243
tgatcatata accaattgcc ct                                              22

SEQ ID NO: 244        moltype = DNA   length = 22
FEATURE               Location/Qualifiers
misc_feature          1..22
                      note = Artificial DNA Primer
source                1..22
                      mol_type = other DNA
                      organism = synthetic construct
SEQUENCE: 244
agttgtgtat atagaggatt ga                                              22

SEQ ID NO: 245        moltype = DNA   length = 23
FEATURE               Location/Qualifiers
misc_feature          1..23
                      note = Artificial DNA Primer
source                1..23
                      mol_type = other DNA
                      organism = synthetic construct
SEQUENCE: 245
tggtccttcg ctcgtgatgt gga                                             23

SEQ ID NO: 246        moltype = DNA   length = 20
FEATURE               Location/Qualifiers
misc_feature          1..20
                      note = Artificial DNA Primer
source                1..20
                      mol_type = other DNA
                      organism = synthetic construct
SEQUENCE: 246
agtcctcagc gttaccggca                                                 20

SEQ ID NO: 247        moltype = DNA   length = 20
FEATURE               Location/Qualifiers
misc_feature          1..20
                      note = Artificial DNA Primer
source                1..20
                      mol_type = other DNA
                      organism = synthetic construct
SEQUENCE: 247
accctcagct gtgtccggga                                                 20

SEQ ID NO: 248        moltype = DNA   length = 21
FEATURE               Location/Qualifiers
misc_feature          1..21
                      note = Artificial DNA Primer
source                1..21
                      mol_type = other DNA
                      organism = synthetic construct
SEQUENCE: 248
tggtatgtga acgccagtct g                                               21

SEQ ID NO: 249        moltype = DNA   length = 28
FEATURE               Location/Qualifiers
misc_feature          1..28
                      note = Artificial DNA Primer
misc_feature          8
                      note = N=DEOXYURIDINE
source                1..28
                      mol_type = other DNA
                      organism = synthetic construct
SEQUENCE: 249
agagcganat gtcctttcc aagataat                                         28

SEQ ID NO: 250        moltype = DNA   length = 49
FEATURE               Location/Qualifiers
misc_feature          1..49
                      note = Artificial DNA Primer
misc_feature          8
                      note = N=DEOXYURIDINE
source                1..49
                      mol_type = other DNA
                      organism = synthetic construct
SEQUENCE: 250
tctgcganTT agtgatggtg gtgatgatga ccagtataca gaggaggac                 49
```

| | | |
|---|---|---|
| SEQ ID NO: 251 | moltype = DNA   length = 28 | |
| FEATURE | Location/Qualifiers | |
| misc_feature | 1..28 | |
| | note = Artificial DNA Primer | |
| misc_feature | 8 | |
| | note = N=DEOXYURIDINE | |
| source | 1..28 | |
| | mol_type = other DNA | |
| | organism = synthetic construct | |
| SEQUENCE: 251 | | |
| agagcganat gctgtcttcg acgactcg | | 28 |
| | | |
| SEQ ID NO: 252 | moltype = DNA   length = 49 | |
| FEATURE | Location/Qualifiers | |
| misc_feature | 1..49 | |
| | note = Artificial DNA Primer | |
| misc_feature | 8 | |
| | note = N=DEOXYURIDINE | |
| source | 1..49 | |
| | mol_type = other DNA | |
| | organism = synthetic construct | |
| SEQUENCE: 252 | | |
| tctgcganct agtgatggtg gtgatgatgg aacgtcggct caggcggcc | | 49 |
| | | |
| SEQ ID NO: 253 | moltype = DNA   length = 33 | |
| FEATURE | Location/Qualifiers | |
| misc_feature | 1..33 | |
| | note = Artificial DNA Primer | |
| misc_feature | 8 | |
| | note = N=DEOXYURIDINE | |
| source | 1..33 | |
| | mol_type = other DNA | |
| | organism = synthetic construct | |
| SEQUENCE: 253 | | |
| agagcganat gtctgttgct aagtttgctg gtg | | 33 |
| | | |
| SEQ ID NO: 254 | moltype = DNA   length = 49 | |
| FEATURE | Location/Qualifiers | |
| misc_feature | 1..49 | |
| | note = Artificial DNA Primer | |
| misc_feature | 8 | |
| | note = N=DEOXYURIDINE | |
| source | 1..49 | |
| | mol_type = other DNA | |
| | organism = synthetic construct | |
| SEQUENCE: 254 | | |
| tctgcgantt agtgatggtg gtgatgatgg gcggagaggt cacgggcgt | | 49 |
| | | |
| SEQ ID NO: 255 | moltype = DNA   length = 32 | |
| FEATURE | Location/Qualifiers | |
| misc_feature | 1..32 | |
| | note = Artificial DNA Primer | |
| misc_feature | 8 | |
| | note = N=DEOXYURIDINE | |
| source | 1..32 | |
| | mol_type = other DNA | |
| | organism = synthetic construct | |
| SEQUENCE: 255 | | |
| agagcganat gccttctact aaagtcgctg cc | | 32 |
| | | |
| SEQ ID NO: 256 | moltype = DNA   length = 49 | |
| FEATURE | Location/Qualifiers | |
| misc_feature | 1..49 | |
| | note = Artificial DNA Primer | |
| misc_feature | 8 | |
| | note = N=DEOXYURIDINE | |
| source | 1..49 | |
| | mol_type = other DNA | |
| | organism = synthetic construct | |
| SEQUENCE: 256 | | |
| tctgcgantc agtgatggtg gtgatgatga aggacagtag tggtgatga | | 49 |
| | | |
| SEQ ID NO: 257 | moltype = DNA   length = 40 | |
| FEATURE | Location/Qualifiers | |
| misc_feature | 1..40 | |
| | note = Artificial DNA Primer | |
| misc_feature | 8 | |
| | note = N=DEOXYURIDINE | |
| source | 1..40 | |

```
                    mol_type = other DNA
                    organism = synthetic construct
SEQUENCE: 257
agagcganat gccttctttc gcctccaaga ctctcctttc                              40

SEQ ID NO: 258      moltype = DNA  length = 49
FEATURE             Location/Qualifiers
misc_feature        1..49
                    note = Artificial DNA Primer
misc_feature        8
                    note = N=DEOXYURIDINE
source              1..49
                    mol_type = other DNA
                    organism = synthetic construct
SEQUENCE: 258
tctgcgantc agtgatggtg gtgatgatgg tttgcctcct cagccccctc                   49

SEQ ID NO: 259      moltype = DNA  length = 20
FEATURE             Location/Qualifiers
misc_feature        1..20
                    note = Artificial DNA Primer
source              1..20
                    mol_type = other DNA
                    organism = synthetic construct
SEQUENCE: 259
cccagttatc aactaccttg                                                    20

SEQ ID NO: 260      moltype = DNA  length = 20
FEATURE             Location/Qualifiers
misc_feature        1..20
                    note = Artificial DNA Primer
source              1..20
                    mol_type = other DNA
                    organism = synthetic construct
SEQUENCE: 260
ctcaatttac ctctatccac                                                    20

SEQ ID NO: 261      moltype = DNA  length = 20
FEATURE             Location/Qualifiers
misc_feature        1..20
                    note = Artificial DNA Primer
source              1..20
                    mol_type = other DNA
                    organism = synthetic construct
SEQUENCE: 261
tataaccaat tgccctcatc                                                    20

SEQ ID NO: 262      moltype = DNA  length = 20
FEATURE             Location/Qualifiers
misc_feature        1..20
                    note = Artificial DNA Primer
source              1..20
                    mol_type = other DNA
                    organism = synthetic construct
SEQUENCE: 262
gcaccgtcga gctgcagtgg                                                    20

SEQ ID NO: 263      moltype = DNA  length = 20
FEATURE             Location/Qualifiers
misc_feature        1..20
                    note = Artificial DNA Primer
source              1..20
                    mol_type = other DNA
                    organism = synthetic construct
SEQUENCE: 263
ccttgccaac tgcaatggtg                                                    20

SEQ ID NO: 264      moltype = DNA  length = 28
FEATURE             Location/Qualifiers
misc_feature        1..28
                    note = Artificial DNA Primer
source              1..28
                    mol_type = other DNA
                    organism = synthetic construct
SEQUENCE: 264
ggactgcgca ccatgccttc tactaaag                                           28

SEQ ID NO: 265      moltype = DNA  length = 34
FEATURE             Location/Qualifiers
```

```
misc_feature            1..34
                        note = Artificial DNA Primer
source                  1..34
                        mol_type = other DNA
                        organism = synthetic construct
SEQUENCE: 265
gccacggagc ttaattaatc aaaggacagt agtg                                34

SEQ ID NO: 266          moltype = DNA  length = 20
FEATURE                 Location/Qualifiers
misc_feature            1..20
                        note = Artificial DNA Primer
source                  1..20
                        mol_type = other DNA
                        organism = synthetic construct
SEQUENCE: 266
caatggcaat tgttctaccg                                                20

SEQ ID NO: 267          moltype = DNA  length = 20
FEATURE                 Location/Qualifiers
misc_feature            1..20
                        note = Artificial DNA Primer
source                  1..20
                        mol_type = other DNA
                        organism = synthetic construct
SEQUENCE: 267
cgacggcagc tcggcgcccg                                                20

SEQ ID NO: 268          moltype = DNA  length = 31
FEATURE                 Location/Qualifiers
misc_feature            1..31
                        note = Artificial DNA Primer
source                  1..31
                        mol_type = other DNA
                        organism = synthetic construct
SEQUENCE: 268
gcatttatca gggttattgt ctcatgagcg g                                   31

SEQ ID NO: 269          moltype = DNA  length = 26
FEATURE                 Location/Qualifiers
misc_feature            1..26
                        note = Artificial DNA Primer
source                  1..26
                        mol_type = other DNA
                        organism = synthetic construct
SEQUENCE: 269
gctgataaat ctggagccgg tgagcg                                         26

SEQ ID NO: 270          moltype = DNA  length = 30
FEATURE                 Location/Qualifiers
misc_feature            1..30
                        note = Artificial DNA Primer
source                  1..30
                        mol_type = other DNA
                        organism = synthetic construct
SEQUENCE: 270
ccagaccagc agaggagata atactctgcg                                     30

SEQ ID NO: 271          moltype = DNA  length = 32
FEATURE                 Location/Qualifiers
misc_feature            1..32
                        note = Artificial DNA Primer
source                  1..32
                        mol_type = other DNA
                        organism = synthetic construct
SEQUENCE: 271
caaggatacc tacagttatt cgaaacctcc tg                                  32

SEQ ID NO: 272          moltype = DNA  length = 49
FEATURE                 Location/Qualifiers
misc_feature            1..49
                        note = Artificial DNA Primer
source                  1..49
                        mol_type = other DNA
                        organism = synthetic construct
SEQUENCE: 272
gtggctggcc atggcttcgt tatcaacatc gtgattgatg gtaaaaagt                49

SEQ ID NO: 273          moltype = DNA  length = 33
```

```
FEATURE                 Location/Qualifiers
misc_feature            1..33
                        note = Artificial DNA Primer
source                  1..33
                        mol_type = other DNA
                        organism = synthetic construct
SEQUENCE: 273
aacgaagcca tggccagcca ctagagaagc aga                              33

SEQ ID NO: 274          moltype = DNA  length = 49
FEATURE                 Location/Qualifiers
misc_feature            1..49
                        note = Artificial DNA Primer
source                  1..49
                        mol_type = other DNA
                        organism = synthetic construct
SEQUENCE: 274
gttatggcgg gtatctagtg aacatctatc catacatgtc caatcctcc             49

SEQ ID NO: 275          moltype = DNA  length = 35
FEATURE                 Location/Qualifiers
misc_feature            1..35
                        note = Artificial DNA Primer
source                  1..35
                        mol_type = other DNA
                        organism = synthetic construct
SEQUENCE: 275
gttcactaga tacccgccat aactgtcgat tgtca                            35

SEQ ID NO: 276          moltype = DNA  length = 49
FEATURE                 Location/Qualifiers
misc_feature            1..49
                        note = Artificial DNA Primer
source                  1..49
                        mol_type = other DNA
                        organism = synthetic construct
SEQUENCE: 276
gttatggcgg gtatctagtg aacgtctatc catacatgtc caatcctcc             49

SEQ ID NO: 277          moltype = DNA  length = 35
FEATURE                 Location/Qualifiers
misc_feature            1..35
                        note = Artificial DNA Primer
source                  1..35
                        mol_type = other DNA
                        organism = synthetic construct
SEQUENCE: 277
gttcactaga tacccgccat aactgtcgat tgtca                            35

SEQ ID NO: 278          moltype = DNA  length = 49
FEATURE                 Location/Qualifiers
misc_feature            1..49
                        note = Artificial DNA Primer
source                  1..49
                        mol_type = other DNA
                        organism = synthetic construct
SEQUENCE: 278
tgctccgtgc aatggtgatt gtaggactgt ggataagacc caattagaa             49

SEQ ID NO: 279          moltype = DNA  length = 35
FEATURE                 Location/Qualifiers
misc_feature            1..35
                        note = Artificial DNA Primer
source                  1..35
                        mol_type = other DNA
                        organism = synthetic construct
SEQUENCE: 279
acaatcacca ttgcacggag caaggtagtt gataa                            35

SEQ ID NO: 280          moltype = DNA  length = 51
FEATURE                 Location/Qualifiers
misc_feature            1..51
                        note = Artificial DNA Primer
source                  1..51
                        mol_type = other DNA
                        organism = synthetic construct
SEQUENCE: 280
attagaattc ttcaaaattg ccgaggaggg tctcatcaat gatgacaatc c          51
```

```
SEQ ID NO: 281         moltype = DNA   length = 37
FEATURE                Location/Qualifiers
misc_feature           1..37
                       note = Artificial DNA Primer
source                 1..37
                       mol_type = other DNA
                       organism = synthetic construct
SEQUENCE: 281
ctcggcaatt ttgaagaatt ctaattgggt cttatcc                              37

SEQ ID NO: 282         moltype = DNA   length = 51
FEATURE                Location/Qualifiers
misc_feature           1..51
                       note = Artificial DNA Primer
source                 1..51
                       mol_type = other DNA
                       organism = synthetic construct
SEQUENCE: 282
attagaattc ttcaaaattg ccgagaaagg tctcatcaat gatgacaatc c              51

SEQ ID NO: 283         moltype = DNA   length = 37
FEATURE                Location/Qualifiers
misc_feature           1..37
                       note = Artificial DNA Primer
source                 1..37
                       mol_type = other DNA
                       organism = synthetic construct
SEQUENCE: 283
ctcggcaatt ttgaagaatt ctaattgggt cttatcc                              37

SEQ ID NO: 284         moltype = DNA   length = 51
FEATURE                Location/Qualifiers
misc_feature           1..51
                       note = Artificial DNA Primer
source                 1..51
                       mol_type = other DNA
                       organism = synthetic construct
SEQUENCE: 284
attagaattc ttcaaaattg ccgagctggg tctcatcaat gatgacaatc c              51

SEQ ID NO: 285         moltype = DNA   length = 37
FEATURE                Location/Qualifiers
misc_feature           1..37
                       note = Artificial DNA Primer
source                 1..37
                       mol_type = other DNA
                       organism = synthetic construct
SEQUENCE: 285
ctcggcaatt ttgaagaatt ctaattgggt cttatcc                              37

SEQ ID NO: 286         moltype = DNA   length = 48
FEATURE                Location/Qualifiers
misc_feature           1..48
                       note = Artificial DNA Primer
source                 1..48
                       mol_type = other DNA
                       organism = synthetic construct
SEQUENCE: 286
gatagcagcc aacaacagct gggtcgtcac cattccaacc acaattgc                  48

SEQ ID NO: 287         moltype = DNA   length = 35
FEATURE                Location/Qualifiers
misc_feature           1..35
                       note = Artificial DNA Primer
source                 1..35
                       mol_type = other DNA
                       organism = synthetic construct
SEQUENCE: 287
ccagctgttg ttggctgcta tcagattgtc tgaag                                35

SEQ ID NO: 288         moltype = DNA   length = 48
FEATURE                Location/Qualifiers
misc_feature           1..48
                       note = Artificial DNA Primer
source                 1..48
                       mol_type = other DNA
                       organism = synthetic construct
SEQUENCE: 288
gatagcagcc aacaacagct gggaggtcac cattccaacc acaattgc                  48
```

| | | |
|---|---|---|
| SEQ ID NO: 289 | moltype = DNA length = 35 | |
| FEATURE | Location/Qualifiers | |
| misc_feature | 1..35 | |
| | note = Artificial DNA Primer | |
| source | 1..35 | |
| | mol_type = other DNA | |
| | organism = synthetic construct | |
| SEQUENCE: 289 | | |
| ccagctgttg ttggctgcta tcagattgtc tgaag | | 35 |
| | | |
| SEQ ID NO: 290 | moltype = DNA length = 47 | |
| FEATURE | Location/Qualifiers | |
| misc_feature | 1..47 | |
| | note = Artificial DNA Primer | |
| source | 1..47 | |
| | mol_type = other DNA | |
| | organism = synthetic construct | |
| SEQUENCE: 290 | | |
| ggcatgagat tattgctctt cacaaagctc agaaccagga tggtgcc | | 47 |
| | | |
| SEQ ID NO: 291 | moltype = DNA length = 36 | |
| FEATURE | Location/Qualifiers | |
| misc_feature | 1..36 | |
| | note = Artificial DNA Primer | |
| source | 1..36 | |
| | mol_type = other DNA | |
| | organism = synthetic construct | |
| SEQUENCE: 291 | | |
| gtgaagagca ataatctcat gcctcagaac atagtt | | 36 |
| | | |
| SEQ ID NO: 292 | moltype = DNA length = 47 | |
| FEATURE | Location/Qualifiers | |
| misc_feature | 1..47 | |
| | note = Artificial DNA Primer | |
| source | 1..47 | |
| | mol_type = other DNA | |
| | organism = synthetic construct | |
| SEQUENCE: 292 | | |
| ggcatgagat tattgctctt cacttcgctc agaaccagga tggtgcc | | 47 |
| | | |
| SEQ ID NO: 293 | moltype = DNA length = 36 | |
| FEATURE | Location/Qualifiers | |
| misc_feature | 1..36 | |
| | note = Artificial DNA Primer | |
| source | 1..36 | |
| | mol_type = other DNA | |
| | organism = synthetic construct | |
| SEQUENCE: 293 | | |
| gtgaagagca ataatctcat gcctcagaac atagtt | | 36 |
| | | |
| SEQ ID NO: 294 | moltype = DNA length = 47 | |
| FEATURE | Location/Qualifiers | |
| misc_feature | 1..47 | |
| | note = Artificial DNA Primer | |
| source | 1..47 | |
| | mol_type = other DNA | |
| | organism = synthetic construct | |
| SEQUENCE: 294 | | |
| ggcatgagat tattgctctt cacactgctc agaaccagga tggtgcc | | 47 |
| | | |
| SEQ ID NO: 295 | moltype = DNA length = 36 | |
| FEATURE | Location/Qualifiers | |
| misc_feature | 1..36 | |
| | note = Artificial DNA Primer | |
| source | 1..36 | |
| | mol_type = other DNA | |
| | organism = synthetic construct | |
| SEQUENCE: 295 | | |
| gtgaagagca ataatctcat gcctcagaac atagtt | | 36 |
| | | |
| SEQ ID NO: 296 | moltype = DNA length = 47 | |
| FEATURE | Location/Qualifiers | |
| misc_feature | 1..47 | |
| | note = Artificial DNA Primer | |
| source | 1..47 | |
| | mol_type = other DNA | |
| | organism = synthetic construct | |
| SEQUENCE: 296 | | |

```
ggcatgagat tattgctctt cactatgctc agaaccagga tggtgcc                    47

SEQ ID NO: 297          moltype = DNA   length = 36
FEATURE                 Location/Qualifiers
misc_feature            1..36
                        note = Artificial DNA Primer
source                  1..36
                        mol_type = other DNA
                        organism = synthetic construct
SEQUENCE: 297
gtgaagagca ataatctcat gcctcagaac atagtt                                36

SEQ ID NO: 298          moltype = DNA   length = 46
FEATURE                 Location/Qualifiers
misc_feature            1..46
                        note = Artificial DNA Primer
source                  1..46
                        mol_type = other DNA
                        organism = synthetic construct
SEQUENCE: 298
gcccagaact atccccagtg cgtcaatctg caggtcactg gaggtg                     46

SEQ ID NO: 299          moltype = DNA   length = 32
FEATURE                 Location/Qualifiers
misc_feature            1..32
                        note = Artificial DNA Primer
source                  1..32
                        mol_type = other DNA
                        organism = synthetic construct
SEQUENCE: 299
gcactgggga tagttctggg caccatcctg gt                                    32

SEQ ID NO: 300          moltype = DNA   length = 46
FEATURE                 Location/Qualifiers
misc_feature            1..46
                        note = Artificial DNA Primer
source                  1..46
                        mol_type = other DNA
                        organism = synthetic construct
SEQUENCE: 300
tggaggtggt tctgataacc ctgagggaac tcttggaacg gcactc                     46

SEQ ID NO: 301          moltype = DNA   length = 33
FEATURE                 Location/Qualifiers
misc_feature            1..33
                        note = Artificial DNA Primer
source                  1..33
                        mol_type = other DNA
                        organism = synthetic construct
SEQUENCE: 301
agggttatca gaaccacctc cagtgacctg cag                                   33

SEQ ID NO: 302          moltype = DNA   length = 46
FEATURE                 Location/Qualifiers
misc_feature            1..46
                        note = Artificial DNA Primer
source                  1..46
                        mol_type = other DNA
                        organism = synthetic construct
SEQUENCE: 302
cctgctggaa ctcttggaac gtgcctctac cacgataccg atcctg                     46

SEQ ID NO: 303          moltype = DNA   length = 33
FEATURE                 Location/Qualifiers
misc_feature            1..33
                        note = Artificial DNA Primer
source                  1..33
                        mol_type = other DNA
                        organism = synthetic construct
SEQUENCE: 303
cgttccaaga gttccagcag ggttatcaga acc                                   33

SEQ ID NO: 304          moltype = DNA   length = 46
FEATURE                 Location/Qualifiers
misc_feature            1..46
                        note = Artificial DNA Primer
source                  1..46
                        mol_type = other DNA
                        organism = synthetic construct
```

```
SEQUENCE: 304
cctgctggaa ctcttggaac ggagctctac cacgataccg atcctg            46

SEQ ID NO: 305          moltype = DNA   length = 33
FEATURE                 Location/Qualifiers
misc_feature            1..33
                        note = Artificial DNA Primer
source                  1..33
                        mol_type = other DNA
                        organism = synthetic construct
SEQUENCE: 305
cgttccaaga gttccagcag ggttatcaga acc                          33

SEQ ID NO: 306          moltype = DNA   length = 46
FEATURE                 Location/Qualifiers
misc_feature            1..46
                        note = Artificial DNA Primer
source                  1..46
                        mol_type = other DNA
                        organism = synthetic construct
SEQUENCE: 306
cctgctggaa ctcttggaac gcagctctac cacgataccg atcctg            46

SEQ ID NO: 307          moltype = DNA   length = 33
FEATURE                 Location/Qualifiers
misc_feature            1..33
                        note = Artificial DNA Primer
source                  1..33
                        mol_type = other DNA
                        organism = synthetic construct
SEQUENCE: 307
cgttccaaga gttccagcag ggttatcaga acc                          33

SEQ ID NO: 308          moltype = DNA   length = 47
FEATURE                 Location/Qualifiers
misc_feature            1..47
                        note = Artificial DNA Primer
source                  1..47
                        mol_type = other DNA
                        organism = synthetic construct
SEQUENCE: 308
catccctggt cctcctctgt atagggtca tcatcaccac catcact             47

SEQ ID NO: 309          moltype = DNA   length = 35
FEATURE                 Location/Qualifiers
misc_feature            1..35
                        note = Artificial DNA Primer
source                  1..35
                        mol_type = other DNA
                        organism = synthetic construct
SEQUENCE: 309
atacagagga ggaccaggga tgatatagct ggaaa                        35

SEQ ID NO: 310          moltype = DNA   length = 47
FEATURE                 Location/Qualifiers
misc_feature            1..47
                        note = Artificial DNA Primer
source                  1..47
                        mol_type = other DNA
                        organism = synthetic construct
SEQUENCE: 310
ctacagcggg tacatcgtca acgtcttccc ctacgaatcc aacccac            47

SEQ ID NO: 311          moltype = DNA   length = 33
FEATURE                 Location/Qualifiers
misc_feature            1..33
                        note = Artificial DNA Primer
source                  1..33
                        mol_type = other DNA
                        organism = synthetic construct
SEQUENCE: 311
gttgacgatg tacccgctgt agctgttggg agt                          33

SEQ ID NO: 312          moltype = DNA   length = 44
FEATURE                 Location/Qualifiers
misc_feature            1..44
                        note = Artificial DNA Primer
source                  1..44
                        mol_type = other DNA
```

-continued

```
                        organism = synthetic construct
SEQUENCE: 312
gtcgacggca caggatacca acagccggac atcatctgcc accg                  44

SEQ ID NO: 313          moltype = DNA   length = 31
FEATURE                 Location/Qualifiers
misc_feature            1..31
                        note = Artificial DNA Primer
source                  1..31
                        mol_type = other DNA
                        organism = synthetic construct
SEQUENCE: 313
ttggtatcct gtgccgtcga cgaagcccag g                                31

SEQ ID NO: 314          moltype = DNA   length = 44
FEATURE                 Location/Qualifiers
misc_feature            1..44
                        note = Artificial DNA Primer
source                  1..44
                        mol_type = other DNA
                        organism = synthetic construct
SEQUENCE: 314
cgccgtgcaa cggcaactgc cgcaccgtcg acaagacgac gctg                  44

SEQ ID NO: 315          moltype = DNA   length = 31
FEATURE                 Location/Qualifiers
misc_feature            1..31
                        note = Artificial DNA Primer
source                  1..31
                        mol_type = other DNA
                        organism = synthetic construct
SEQUENCE: 315
gcagttgccg ttgcacggcg ccaggtaggt g                                31

SEQ ID NO: 316          moltype = DNA   length = 47
FEATURE                 Location/Qualifiers
misc_feature            1..47
                        note = Artificial DNA Primer
source                  1..47
                        mol_type = other DNA
                        organism = synthetic construct
SEQUENCE: 316
cgtcgatggt agcgagtatg ctcaggccga catcatttgc cacaaga               47

SEQ ID NO: 317          moltype = DNA   length = 34
FEATURE                 Location/Qualifiers
misc_feature            1..34
                        note = Artificial DNA Primer
source                  1..34
                        mol_type = other DNA
                        organism = synthetic construct
SEQUENCE: 317
agcatactcg ctaccatcga cgaaacccaa gtcg                             34

SEQ ID NO: 318          moltype = DNA   length = 47
FEATURE                 Location/Qualifiers
misc_feature            1..47
                        note = Artificial DNA Primer
source                  1..47
                        mol_type = other DNA
                        organism = synthetic construct
SEQUENCE: 318
cgtcgatggt agcgagtatg ctaccgccga catcatttgc cacaaga               47

SEQ ID NO: 319          moltype = DNA   length = 34
FEATURE                 Location/Qualifiers
misc_feature            1..34
                        note = Artificial DNA Primer
source                  1..34
                        mol_type = other DNA
                        organism = synthetic construct
SEQUENCE: 319
agcatactcg ctaccatcga cgaaacccaa gtcg                             34

SEQ ID NO: 320          moltype = DNA   length = 48
FEATURE                 Location/Qualifiers
misc_feature            1..48
                        note = Artificial DNA Primer
source                  1..48
```

```
                            mol_type = other DNA
                            organism = synthetic construct
SEQUENCE: 320
ctcgagtttt tcaagattga cgagtgcggt ctcatcaacg acgacgac              48

SEQ ID NO: 321          moltype = DNA  length = 35
FEATURE                 Location/Qualifiers
misc_feature            1..35
                        note = Artificial DNA Primer
source                  1..35
                        mol_type = other DNA
                        organism = synthetic construct
SEQUENCE: 321
ctcgtcaatc ttgaaaaact cgaggtcggt cttgg                            35

SEQ ID NO: 322          moltype = DNA  length = 48
FEATURE                 Location/Qualifiers
misc_feature            1..48
                        note = Artificial DNA Primer
source                  1..48
                        mol_type = other DNA
                        organism = synthetic construct
SEQUENCE: 322
ctcgagtttt tcaagattga cgagggtggt ctcatcaacg acgacgac              48

SEQ ID NO: 323          moltype = DNA  length = 35
FEATURE                 Location/Qualifiers
misc_feature            1..35
                        note = Artificial DNA Primer
source                  1..35
                        mol_type = other DNA
                        organism = synthetic construct
SEQUENCE: 323
ctcgtcaatc ttgaaaaact cgaggtcggt cttgg                            35

SEQ ID NO: 324          moltype = DNA  length = 45
FEATURE                 Location/Qualifiers
misc_feature            1..45
                        note = Artificial DNA Primer
source                  1..45
                        mol_type = other DNA
                        organism = synthetic construct
SEQUENCE: 324
acgacgacga cgtccccggt atctgggcca gtgataactt gatcg                 45

SEQ ID NO: 325          moltype = DNA  length = 31
FEATURE                 Location/Qualifiers
misc_feature            1..31
                        note = Artificial DNA Primer
source                  1..31
                        mol_type = other DNA
                        organism = synthetic construct
SEQUENCE: 325
accggggacg tcgtcgtcgt tgatgagacc g                                31

SEQ ID NO: 326          moltype = DNA  length = 47
FEATURE                 Location/Qualifiers
misc_feature            1..47
                        note = Artificial DNA Primer
source                  1..47
                        mol_type = other DNA
                        organism = synthetic construct
SEQUENCE: 326
gatcgccaac aacaacagct gggtcgtgac catcccctct gacattg               47

SEQ ID NO: 327          moltype = DNA  length = 35
FEATURE                 Location/Qualifiers
misc_feature            1..35
                        note = Artificial DNA Primer
source                  1..35
                        mol_type = other DNA
                        organism = synthetic construct
SEQUENCE: 327
ccagctgttg ttgttggcga tcaagttatc actgg                            35

SEQ ID NO: 328          moltype = DNA  length = 47
FEATURE                 Location/Qualifiers
misc_feature            1..47
                        note = Artificial DNA Primer
```

```
source                          1..47
                                mol_type = other DNA
                                organism = synthetic construct
SEQUENCE: 328
gatcgccaac aacaacagct ggttcgtgac catcccctct gacattg         47

SEQ ID NO: 329          moltype = DNA   length = 35
FEATURE                 Location/Qualifiers
misc_feature            1..35
                        note = Artificial DNA Primer
source                  1..35
                        mol_type = other DNA
                        organism = synthetic construct
SEQUENCE: 329
ccagctgttg ttgttggcga tcaagttatc actgg                      35

SEQ ID NO: 330          moltype = DNA   length = 45
FEATURE                 Location/Qualifiers
misc_feature            1..45
                        note = Artificial DNA Primer
source                  1..45
                        mol_type = other DNA
                        organism = synthetic construct
SEQUENCE: 330
tggactgtga ccatccctc tcgtattgcg gctggcaact acgtc             45

SEQ ID NO: 331          moltype = DNA   length = 33
FEATURE                 Location/Qualifiers
misc_feature            1..33
                        note = Artificial DNA Primer
source                  1..33
                        mol_type = other DNA
                        organism = synthetic construct
SEQUENCE: 331
agagggatg gtcacagtcc agctgttgtt gtt                         33

SEQ ID NO: 332          moltype = DNA   length = 48
FEATURE                 Location/Qualifiers
misc_feature            1..48
                        note = Artificial DNA Primer
source                  1..48
                        mol_type = other DNA
                        organism = synthetic construct
SEQUENCE: 332
gtcacgaaat cattgccctt cacaaggctg gtaacaagga tggtgctc        48

SEQ ID NO: 333          moltype = DNA   length = 34
FEATURE                 Location/Qualifiers
misc_feature            1..34
                        note = Artificial DNA Primer
source                  1..34
                        mol_type = other DNA
                        organism = synthetic construct
SEQUENCE: 333
gtgaagggca atgatttcgt gacggaggac gtag                       34

SEQ ID NO: 334          moltype = DNA   length = 48
FEATURE                 Location/Qualifiers
misc_feature            1..48
                        note = Artificial DNA Primer
source                  1..48
                        mol_type = other DNA
                        organism = synthetic construct
SEQUENCE: 334
gtcacgaaat cattgccctt cacaccgctg gtaacaagga tggtgctc        48

SEQ ID NO: 335          moltype = DNA   length = 34
FEATURE                 Location/Qualifiers
misc_feature            1..34
                        note = Artificial DNA Primer
source                  1..34
                        mol_type = other DNA
                        organism = synthetic construct
SEQUENCE: 335
gtgaagggca atgatttcgt gacggaggac gtag                       34

SEQ ID NO: 336          moltype = DNA   length = 48
FEATURE                 Location/Qualifiers
misc_feature            1..48
```

```
                         note = Artificial DNA Primer
source                   1..48
                         mol_type = other DNA
                         organism = synthetic construct
SEQUENCE: 336
gtcacgaaat cattgccctt cactacgctg gtaacaagga tggtgctc                48

SEQ ID NO: 337           moltype = DNA  length = 34
FEATURE                  Location/Qualifiers
misc_feature             1..34
                         note = Artificial DNA Primer
source                   1..34
                         mol_type = other DNA
                         organism = synthetic construct
SEQUENCE: 337
gtgaagggca atgatttcgt gacggaggac gtag                                34

SEQ ID NO: 338           moltype = DNA  length = 45
FEATURE                  Location/Qualifiers
misc_feature             1..45
                         note = Artificial DNA Primer
source                   1..45
                         mol_type = other DNA
                         organism = synthetic construct
SEQUENCE: 338
gctcagaact accctcagtg catcaacttg aaggtcactg gcggc                    45

SEQ ID NO: 339           moltype = DNA  length = 33
FEATURE                  Location/Qualifiers
misc_feature             1..33
                         note = Artificial DNA Primer
source                   1..33
                         mol_type = other DNA
                         organism = synthetic construct
SEQUENCE: 339
gcactgaggg tagttctgag caccatcctt gtt                                 33

SEQ ID NO: 340           moltype = DNA  length = 45
FEATURE                  Location/Qualifiers
misc_feature             1..45
                         note = Artificial DNA Primer
source                   1..45
                         mol_type = other DNA
                         organism = synthetic construct
SEQUENCE: 340
gctcagaact accctcagtg cgtcaacttg aaggtcactg gcggc                    45

SEQ ID NO: 341           moltype = DNA  length = 33
FEATURE                  Location/Qualifiers
misc_feature             1..33
                         note = Artificial DNA Primer
source                   1..33
                         mol_type = other DNA
                         organism = synthetic construct
SEQUENCE: 341
gcactgaggg tagttctgag caccatcctt gtt                                 33

SEQ ID NO: 342           moltype = DNA  length = 46
FEATURE                  Location/Qualifiers
misc_feature             1..46
                         note = Artificial DNA Primer
source                   1..46
                         mol_type = other DNA
                         organism = synthetic construct
SEQUENCE: 342
ccttctggca ctgctggtga gatgctgtac aaggacaccg atgctg                   46

SEQ ID NO: 343           moltype = DNA  length = 32
FEATURE                  Location/Qualifiers
misc_feature             1..32
                         note = Artificial DNA Primer
source                   1..32
                         mol_type = other DNA
                         organism = synthetic construct
SEQUENCE: 343
ctcaccagca gtgccagaag gagcgagatc ac                                  32

SEQ ID NO: 344           moltype = DNA  length = 46
FEATURE                  Location/Qualifiers
```

```
misc_feature              1..46
                          note = Artificial DNA Primer
source                    1..46
                          mol_type = other DNA
                          organism = synthetic construct
SEQUENCE: 344
ccttctggca ctgctggtga gcagctgtac aaggacaccg atgctg           46

SEQ ID NO: 345            moltype = DNA  length = 32
FEATURE                   Location/Qualifiers
misc_feature              1..32
                          note = Artificial DNA Primer
source                    1..32
                          mol_type = other DNA
                          organism = synthetic construct
SEQUENCE: 345
ctcaccagca gtgccagaag gagcgagatc ac                          32

SEQ ID NO: 346            moltype = DNA  length = 45
FEATURE                   Location/Qualifiers
misc_feature              1..45
                          note = Artificial DNA Primer
source                    1..45
                          mol_type = other DNA
                          organism = synthetic construct
SEQUENCE: 346
actgctggtg agagcctgta ccgtgacacc gatgctggta tcctc             45

SEQ ID NO: 347            moltype = DNA  length = 32
FEATURE                   Location/Qualifiers
misc_feature              1..32
                          note = Artificial DNA Primer
source                    1..32
                          mol_type = other DNA
                          organism = synthetic construct
SEQUENCE: 347
gtacaggctc tcaccagcag tgccagaagg ag                          32

SEQ ID NO: 348            moltype = DNA  length = 47
FEATURE                   Location/Qualifiers
misc_feature              1..47
                          note = Artificial DNA Primer
source                    1..47
                          mol_type = other DNA
                          organism = synthetic construct
SEQUENCE: 348
ctcctacgat attcccggac ctcccatgta caacgctacc tccagct          47

SEQ ID NO: 349            moltype = DNA  length = 34
FEATURE                   Location/Qualifiers
misc_feature              1..34
                          note = Artificial DNA Primer
source                    1..34
                          mol_type = other DNA
                          organism = synthetic construct
SEQUENCE: 349
aggtccggga atatcgtagg aggaaagaga ctgg                        34

SEQ ID NO: 350            moltype = DNA  length = 52
FEATURE                   Location/Qualifiers
misc_feature              1..52
                          note = Artificial DNA Primer
source                    1..52
                          mol_type = other DNA
                          organism = synthetic construct
SEQUENCE: 350
caaaacatcg ttatcgacgg taaattttaa gcagtgatgc atccattatt aa    52

SEQ ID NO: 351            moltype = DNA  length = 36
FEATURE                   Location/Qualifiers
misc_feature              1..36
                          note = Artificial DNA Primer
source                    1..36
                          mol_type = other DNA
                          organism = synthetic construct
SEQUENCE: 351
tttaccgtcg ataacgatgt tttgcacaaa accatg                      36

SEQ ID NO: 352            moltype = DNA  length = 48
```

```
FEATURE            Location/Qualifiers
misc_feature       1..48
                   note = Artificial DNA Primer
source             1..48
                   mol_type = other DNA
                   organism = synthetic construct
SEQUENCE: 352
agttactctg gataccttgt gaatatcttc ccctacgagt ccaaccca            48

SEQ ID NO: 353     moltype = DNA  length = 38
FEATURE            Location/Qualifiers
misc_feature       1..38
                   note = Artificial DNA Primer
source             1..38
                   mol_type = other DNA
                   organism = synthetic construct
SEQUENCE: 353
attcacaagg tatccagagt aactgatttt tttgtaag                       38

SEQ ID NO: 354     moltype = DNA  length = 48
FEATURE            Location/Qualifiers
misc_feature       1..48
                   note = Artificial DNA Primer
source             1..48
                   mol_type = other DNA
                   organism = synthetic construct
SEQUENCE: 354
agttactctg gataccttgt gaatgtcttc ccctacgagt ccaaccca            48

SEQ ID NO: 355     moltype = DNA  length = 38
FEATURE            Location/Qualifiers
misc_feature       1..38
                   note = Artificial DNA Primer
source             1..38
                   mol_type = other DNA
                   organism = synthetic construct
SEQUENCE: 355
attcacaagg tatccagagt aactgatttt tttgtaag                       38

SEQ ID NO: 356     moltype = DNA  length = 47
FEATURE            Location/Qualifiers
misc_feature       1..47
                   note = Artificial DNA Primer
source             1..47
                   mol_type = other DNA
                   organism = synthetic construct
SEQUENCE: 356
tgtgaatcag ttcccctacg agcttaaccc accagctgtt attgggt             47

SEQ ID NO: 357     moltype = DNA  length = 34
FEATURE            Location/Qualifiers
misc_feature       1..34
                   note = Artificial DNA Primer
source             1..34
                   mol_type = other DNA
                   organism = synthetic construct
SEQUENCE: 357
ctcgtagggg aactgattca caaggtatcc agag                           34

SEQ ID NO: 358     moltype = DNA  length = 45
FEATURE            Location/Qualifiers
misc_feature       1..45
                   note = Artificial DNA Primer
source             1..45
                   mol_type = other DNA
                   organism = synthetic construct
SEQUENCE: 358
ccaccagctg ttattgggtg gtgcacaact gcaaccgacc tggga               45

SEQ ID NO: 359     moltype = DNA  length = 32
FEATURE            Location/Qualifiers
misc_feature       1..32
                   note = Artificial DNA Primer
source             1..32
                   mol_type = other DNA
                   organism = synthetic construct
SEQUENCE: 359
ccacccaata acagctggtg ggttggactc gt                             32
```

| | | |
|---|---|---|
| SEQ ID NO: 360 | moltype = DNA   length = 45 | |
| FEATURE | Location/Qualifiers | |
| misc_feature | 1..45 | |
| | note = Artificial DNA Primer | |
| source | 1..45 | |
| | mol_type = other DNA | |
| | organism = synthetic construct | |
| SEQUENCE: 360 | | |
| ccaccagctg ttattgggtg ggagacaact gcaaccgacc tggga | | 45 |
| | | |
| SEQ ID NO: 361 | moltype = DNA   length = 32 | |
| FEATURE | Location/Qualifiers | |
| misc_feature | 1..32 | |
| | note = Artificial DNA Primer | |
| source | 1..32 | |
| | mol_type = other DNA | |
| | organism = synthetic construct | |
| SEQUENCE: 361 | | |
| ccacccaata acagctggtg ggttggactc gt | | 32 |
| | | |
| SEQ ID NO: 362 | moltype = DNA   length = 49 | |
| FEATURE | Location/Qualifiers | |
| misc_feature | 1..49 | |
| | note = Artificial DNA Primer | |
| source | 1..49 | |
| | mol_type = other DNA | |
| | organism = synthetic construct | |
| SEQUENCE: 362 | | |
| ctagactttg tcaagattga ccaatgcggt ttgatcgacg atactaccc | | 49 |
| | | |
| SEQ ID NO: 363 | moltype = DNA   length = 37 | |
| FEATURE | Location/Qualifiers | |
| misc_feature | 1..37 | |
| | note = Artificial DNA Primer | |
| source | 1..37 | |
| | mol_type = other DNA | |
| | organism = synthetic construct | |
| SEQUENCE: 363 | | |
| ttggtcaatc ttgacaaagt ctagcttagt cttatcc | | 37 |
| | | |
| SEQ ID NO: 364 | moltype = DNA   length = 45 | |
| FEATURE | Location/Qualifiers | |
| misc_feature | 1..45 | |
| | note = Artificial DNA Primer | |
| source | 1..45 | |
| | mol_type = other DNA | |
| | organism = synthetic construct | |
| SEQUENCE: 364 | | |
| acgatactac cccccgggt atctgggctt ccgacaaact tatcg | | 45 |
| | | |
| SEQ ID NO: 365 | moltype = DNA   length = 32 | |
| FEATURE | Location/Qualifiers | |
| misc_feature | 1..32 | |
| | note = Artificial DNA Primer | |
| source | 1..32 | |
| | mol_type = other DNA | |
| | organism = synthetic construct | |
| SEQUENCE: 365 | | |
| acccgggggg gtagtatcgt cgatcaaacc ac | | 32 |
| | | |
| SEQ ID NO: 366 | moltype = DNA   length = 45 | |
| FEATURE | Location/Qualifiers | |
| misc_feature | 1..45 | |
| | note = Artificial DNA Primer | |
| source | 1..45 | |
| | mol_type = other DNA | |
| | organism = synthetic construct | |
| SEQUENCE: 366 | | |
| gctgccaaca acagctggac ttgcactatc ccctccacca tcgcg | | 45 |
| | | |
| SEQ ID NO: 367 | moltype = DNA   length = 34 | |
| FEATURE | Location/Qualifiers | |
| misc_feature | 1..34 | |
| | note = Artificial DNA Primer | |
| source | 1..34 | |
| | mol_type = other DNA | |
| | organism = synthetic construct | |
| SEQUENCE: 367 | | |
| agtccagctg ttgttggcag cgataagttt gtcg | | 34 |

```
SEQ ID NO: 368          moltype = DNA  length = 45
FEATURE                 Location/Qualifiers
misc_feature            1..45
                        note = Artificial DNA Primer
source                  1..45
                        mol_type = other DNA
                        organism = synthetic construct
SEQUENCE: 368
gctgccaaca acagctggac tcttactatc ccctccacca tcgcg              45

SEQ ID NO: 369          moltype = DNA  length = 34
FEATURE                 Location/Qualifiers
misc_feature            1..34
                        note = Artificial DNA Primer
source                  1..34
                        mol_type = other DNA
                        organism = synthetic construct
SEQUENCE: 369
agtccagctg ttgttggcag cgataagttt gtcg                          34

SEQ ID NO: 370          moltype = DNA  length = 46
FEATURE                 Location/Qualifiers
misc_feature            1..46
                        note = Artificial DNA Primer
source                  1..46
                        mol_type = other DNA
                        organism = synthetic construct
SEQUENCE: 370
ccaacaacag ctggactgta actcttccct ccaccatcgc gcctgg             46

SEQ ID NO: 371          moltype = DNA  length = 35
FEATURE                 Location/Qualifiers
misc_feature            1..35
                        note = Artificial DNA Primer
source                  1..35
                        mol_type = other DNA
                        organism = synthetic construct
SEQUENCE: 371
agttacagtc cagctgttgt tggcagcgat aagtt                         35

SEQ ID NO: 372          moltype = DNA  length = 47
FEATURE                 Location/Qualifiers
misc_feature            1..47
                        note = Artificial DNA Primer
source                  1..47
                        mol_type = other DNA
                        organism = synthetic construct
SEQUENCE: 372
ctggactgta actatcccct cccgcatcgc gcctggaaac tacgttt            47

SEQ ID NO: 373          moltype = DNA  length = 33
FEATURE                 Location/Qualifiers
misc_feature            1..33
                        note = Artificial DNA Primer
source                  1..33
                        mol_type = other DNA
                        organism = synthetic construct
SEQUENCE: 373
ggagggata gttacagtcc agctgttgtt ggc                            33

SEQ ID NO: 374          moltype = DNA  length = 46
FEATURE                 Location/Qualifiers
misc_feature            1..46
                        note = Artificial DNA Primer
source                  1..46
                        mol_type = other DNA
                        organism = synthetic construct
SEQUENCE: 374
gccacgaaat cattgctctt cacaaggctg gaaacgcaga cggtgc             46

SEQ ID NO: 375          moltype = DNA  length = 35
FEATURE                 Location/Qualifiers
misc_feature            1..35
                        note = Artificial DNA Primer
source                  1..35
                        mol_type = other DNA
                        organism = synthetic construct
SEQUENCE: 375
```

```
gtgaagagca atgatttcgt ggcgcaaaac gtagt                                    35

SEQ ID NO: 376          moltype = DNA   length = 46
FEATURE                 Location/Qualifiers
misc_feature            1..46
                        note = Artificial DNA Primer
source                  1..46
                        mol_type = other DNA
                        organism = synthetic construct
SEQUENCE: 376
gccacgaaat cattgctctt cactttgctg gaaacgcaga cggtgc                        46

SEQ ID NO: 377          moltype = DNA   length = 35
FEATURE                 Location/Qualifiers
misc_feature            1..35
                        note = Artificial DNA Primer
source                  1..35
                        mol_type = other DNA
                        organism = synthetic construct
SEQUENCE: 377
gtgaagagca atgatttcgt ggcgcaaaac gtagt                                    35

SEQ ID NO: 378          moltype = DNA   length = 46
FEATURE                 Location/Qualifiers
misc_feature            1..46
                        note = Artificial DNA Primer
source                  1..46
                        mol_type = other DNA
                        organism = synthetic construct
SEQUENCE: 378
gccacgaaat cattgctctt cacaccgctg gaaacgcaga cggtgc                        46

SEQ ID NO: 379          moltype = DNA   length = 35
FEATURE                 Location/Qualifiers
misc_feature            1..35
                        note = Artificial DNA Primer
source                  1..35
                        mol_type = other DNA
                        organism = synthetic construct
SEQUENCE: 379
gtgaagagca atgatttcgt ggcgcaaaac gtagt                                    35

SEQ ID NO: 380          moltype = DNA   length = 46
FEATURE                 Location/Qualifiers
misc_feature            1..46
                        note = Artificial DNA Primer
source                  1..46
                        mol_type = other DNA
                        organism = synthetic construct
SEQUENCE: 380
gccacgaaat cattgctctt cactacgctg gaaacgcaga cggtgc                        46

SEQ ID NO: 381          moltype = DNA   length = 35
FEATURE                 Location/Qualifiers
misc_feature            1..35
                        note = Artificial DNA Primer
source                  1..35
                        mol_type = other DNA
                        organism = synthetic construct
SEQUENCE: 381
gtgaagagca atgatttcgt ggcgcaaaac gtagt                                    35

SEQ ID NO: 382          moltype = DNA   length = 46
FEATURE                 Location/Qualifiers
misc_feature            1..46
                        note = Artificial DNA Primer
source                  1..46
                        mol_type = other DNA
                        organism = synthetic construct
SEQUENCE: 382
tgcccaaaac taccctcaat gcgtcaactt ggagatcacc ggcagc                        46

SEQ ID NO: 383          moltype = DNA   length = 32
FEATURE                 Location/Qualifiers
misc_feature            1..32
                        note = Artificial DNA Primer
source                  1..32
                        mol_type = other DNA
                        organism = synthetic construct
```

```
SEQUENCE: 383
gcattgaggg tagttttggg caccgtctgc gt                                       32

SEQ ID NO: 384          moltype = DNA  length = 44
FEATURE                 Location/Qualifiers
misc_feature            1..44
                        note = Artificial DNA Primer
source                  1..44
                        mol_type = other DNA
                        organism = synthetic construct
SEQUENCE: 384
gcagcggaac cgccgctccc gagggtaccg ctggcgaaaa gctc                          44

SEQ ID NO: 385          moltype = DNA  length = 30
FEATURE                 Location/Qualifiers
misc_feature            1..30
                        note = Artificial DNA Primer
source                  1..30
                        mol_type = other DNA
                        organism = synthetic construct
SEQUENCE: 385
gggagcggcg gttccgctgc cggtgatctc                                          30

SEQ ID NO: 386          moltype = DNA  length = 46
FEATURE                 Location/Qualifiers
misc_feature            1..46
                        note = Artificial DNA Primer
source                  1..46
                        mol_type = other DNA
                        organism = synthetic construct
SEQUENCE: 386
accgctggcg aaaagctcta ccgctctact gaccccggta tcttgg                        46

SEQ ID NO: 387          moltype = DNA  length = 32
FEATURE                 Location/Qualifiers
misc_feature            1..32
                        note = Artificial DNA Primer
source                  1..32
                        mol_type = other DNA
                        organism = synthetic construct
SEQUENCE: 387
gtagagcttt tcgccagcgg taccagaggg ag                                       32

SEQ ID NO: 388          moltype = DNA  length = 45
FEATURE                 Location/Qualifiers
misc_feature            1..45
                        note = Artificial DNA Primer
source                  1..45
                        mol_type = other DNA
                        organism = synthetic construct
SEQUENCE: 388
gacctacgtt attcccggac cacccctgtg gagcggtgct gccaa                         45

SEQ ID NO: 389          moltype = DNA  length = 34
FEATURE                 Location/Qualifiers
misc_feature            1..34
                        note = Artificial DNA Primer
source                  1..34
                        mol_type = other DNA
                        organism = synthetic construct
SEQUENCE: 389
tggtccggga ataacgtagg tcgacaagga ttgg                                     34

SEQ ID NO: 390          moltype = DNA  length = 46
FEATURE                 Location/Qualifiers
misc_feature            1..46
                        note = Artificial DNA Primer
source                  1..46
                        mol_type = other DNA
                        organism = synthetic construct
SEQUENCE: 390
taccagggtt acgatccgac catcttccct tacatgcaga acccgc                        46

SEQ ID NO: 391          moltype = DNA  length = 31
FEATURE                 Location/Qualifiers
misc_feature            1..31
                        note = Artificial DNA Primer
source                  1..31
                        mol_type = other DNA
```

```
                        organism = synthetic construct
SEQUENCE: 391
ggtcggatcg taaccctggt acgagacccc g                                          31

SEQ ID NO: 392          moltype = DNA  length = 46
FEATURE                 Location/Qualifiers
misc_feature            1..46
                        note = Artificial DNA Primer
source                  1..46
                        mol_type = other DNA
                        organism = synthetic construct
SEQUENCE: 392
taccagggtt acgatccgac cgtcttccct tacatgcaga acccgc                          46

SEQ ID NO: 393          moltype = DNA  length = 31
FEATURE                 Location/Qualifiers
misc_feature            1..31
                        note = Artificial DNA Primer
source                  1..31
                        mol_type = other DNA
                        organism = synthetic construct
SEQUENCE: 393
ggtcggatcg taaccctggt acgagacccc g                                          31

SEQ ID NO: 394          moltype = DNA  length = 44
FEATURE                 Location/Qualifiers
misc_feature            1..44
                        note = Artificial DNA Primer
source                  1..44
                        mol_type = other DNA
                        organism = synthetic construct
SEQUENCE: 394
ccgacctcct tcccttacat gctcaacccg cccatcgtgg tcgg                            44

SEQ ID NO: 395          moltype = DNA  length = 33
FEATURE                 Location/Qualifiers
misc_feature            1..33
                        note = Artificial DNA Primer
source                  1..33
                        mol_type = other DNA
                        organism = synthetic construct
SEQUENCE: 395
catgtaaggg aaggaggtcg gatcgtaacc ctg                                        33

SEQ ID NO: 396          moltype = DNA  length = 45
FEATURE                 Location/Qualifiers
misc_feature            1..45
                        note = Artificial DNA Primer
source                  1..45
                        mol_type = other DNA
                        organism = synthetic construct
SEQUENCE: 396
ttgccccgga tgccttcgcc accggcgata tcatctgcca caaga                           45

SEQ ID NO: 397          moltype = DNA  length = 31
FEATURE                 Location/Qualifiers
misc_feature            1..31
                        note = Artificial DNA Primer
source                  1..31
                        mol_type = other DNA
                        organism = synthetic construct
SEQUENCE: 397
ggcgaaggca tccggggcaa caaagccgtt g                                          31

SEQ ID NO: 398          moltype = DNA  length = 45
FEATURE                 Location/Qualifiers
misc_feature            1..45
                        note = Artificial DNA Primer
source                  1..45
                        mol_type = other DNA
                        organism = synthetic construct
SEQUENCE: 398
cgagttcttc aagatcgacg agtgcggcct ggtcgacggc agctc                           45

SEQ ID NO: 399          moltype = DNA  length = 34
FEATURE                 Location/Qualifiers
misc_feature            1..34
                        note = Artificial DNA Primer
source                  1..34
```

```
                          mol_type = other DNA
                          organism = synthetic construct
SEQUENCE: 399
ctcgtcgatc ttgaagaact cgagcttggt cttg                                     34

SEQ ID NO: 401            moltype = DNA   length = 34
FEATURE                   Location/Qualifiers
misc_feature              1..34
                          note = Artificial DNA Primer
source                    1..34
                          mol_type = other DNA
                          organism = synthetic construct
SEQUENCE: 400
cgagttcttc aagatcgacg agggcggcct ggtcgacggc agctc                         45

SEQ ID NO: 401            moltype = DNA   length = 34
FEATURE                   Location/Qualifiers
misc_feature              1..34
                          note = Artificial DNA Primer
source                    1..34
                          mol_type = other DNA
                          organism = synthetic construct
SEQUENCE: 401
ctcgtcgatc ttgaagaact cgagcttggt cttg                                     34

SEQ ID NO: 402            moltype = DNA   length = 43
FEATURE                   Location/Qualifiers
misc_feature              1..43
                          note = Artificial DNA Primer
source                    1..43
                          mol_type = other DNA
                          organism = synthetic construct
SEQUENCE: 402
acggcagctc ggcgcccggt atctggggct ccgaccagct cat                           43

SEQ ID NO: 403            moltype = DNA   length = 28
FEATURE                   Location/Qualifiers
misc_feature              1..28
                          note = Artificial DNA Primer
source                    1..28
                          mol_type = other DNA
                          organism = synthetic construct
SEQUENCE: 403
accgggcgcc gagctgccgt cgaccagg                                            28

SEQ ID NO: 404            moltype = DNA   length = 44
FEATURE                   Location/Qualifiers
misc_feature              1..44
                          note = Artificial DNA Primer
source                    1..44
                          mol_type = other DNA
                          organism = synthetic construct
SEQUENCE: 404
gccaacaaca actcgtggct cctcgagatc ccgcccacca tcgc                          44

SEQ ID NO: 405            moltype = DNA   length = 32
FEATURE                   Location/Qualifiers
misc_feature              1..32
                          note = Artificial DNA Primer
source                    1..32
                          mol_type = other DNA
                          organism = synthetic construct
SEQUENCE: 405
gagccacgag ttgttgttgg cgatgagctg gt                                       32

SEQ ID NO: 406            moltype = DNA   length = 43
FEATURE                   Location/Qualifiers
misc_feature              1..43
                          note = Artificial DNA Primer
source                    1..43
                          mol_type = other DNA
                          organism = synthetic construct
SEQUENCE: 406
cctacaccgt cccggggccg ccgctcatct ccggcgccgt cag                           43

SEQ ID NO: 407            moltype = DNA   length = 29
FEATURE                   Location/Qualifiers
misc_feature              1..29
                          note = Artificial DNA Primer
```

```
source                  1..29
                        mol_type = other DNA
                        organism = synthetic construct
SEQUENCE: 407
cggccccggg acggtgtagg tgatcgggg                                         29

SEQ ID NO: 408          moltype = DNA  length = 884
FEATURE                 Location/Qualifiers
source                  1..884
                        mol_type = genomic DNA
                        organism = Talaromyces thermophilus
SEQUENCE: 408
atgaaagccc ccagcgctgc gtcgatcctc cttcctttcc ttgcgagcat cacccgtacc        60
tctgcccacg ggttcgtctc caatatcgtc attaatggtg tctcgtatcg gggctggctc       120
cccaatgaag accccataaa acctgagccc ccgattggcg tgggttggga gacgcccaac       180
ctgagcaacg gcttcgtgac gcccgaagaa gcgttgaccg atgcgatcgt ctgccacaag       240
gaggccaagc cggcccgcgg ctatgccagc gtcgcagccg gcgacaagat ctatatccaa       300
tggcagccga ttccatggcc ggagtctcac catggtgcgt tagactctct cattgttttg       360
cagtcaagcc tcgcccaact gacaacattc tcttccaagg accgtcctg gactatctgg        420
ccccttgcaa cggcgactgc cagaacgtca acaagtccag cctggagttt ttcaagatcg       480
acggcaaagg actcatcgac ggctcctccc cgccgggctt ctgggccgac gacgaactta       540
tcgccaacgg caacggctgg ctggtccaga tccccgagga catcaagccg ggcaactacg       600
tgctgcgaca tgagatcatc gccttgcatg agggattcaa ccagaacggc gcccagctgt       660
atccccagtg cttcaacctg cagattacgg atctggcac cgttgagccg agggaacgc         720
ccgccacgga gctgtattcg ccaccgaccc cgggcattct ggtcgacatc tacaaccct        780
tgagcacgta tgtggtgccg ggccccacgc tcatcccaca ggcggttgag atcgaacagt       840
cttcgtcggc ggttacggcg acagggacgc caacgccggc ttaa                        884

SEQ ID NO: 409          moltype = AA  length = 272
FEATURE                 Location/Qualifiers
source                  1..272
                        mol_type = protein
                        organism = Talaromyces thermophilus
SEQUENCE: 409
MKAPSAASIL LPFLASITRT SAHGFVSNIV INGVSYRGWL PNEDPYKPEP PIGVGWETPN        60
LSNGFVTPEE ALTDAIVCHK EAKPARGYAS VAAGDKIYIQ WQPIPWPESH HGPVLDYLAP       120
CNGDCQNVNK SSLEFFKIDG KGLIDGSSPP GFWADDELIA NGNGWLVQIP EDIKPGNYVL       180
RHEIIALHEG FNQNGAQLYP QCFNLQITGS GTVEPEGTPA TELYSPTDPG ILVDIYNPLS       240
TYVVPGPTLI PQAVEIEQSS SAVTATGTPT PA                                    272

SEQ ID NO: 410          moltype = DNA  length = 885
FEATURE                 Location/Qualifiers
source                  1..885
                        mol_type = genomic DNA
                        organism = Talaromyces thermophilus
SEQUENCE: 410
atgaagggct ccagcgctgc gtcggtgctt cttgctctcc tcgcgggcat tacccgtacc        60
tctgcccacg ggtatgtctc caacattgtt gtcaacggtg tctactatcg aggctggctg       120
cccggcgaag accccataaa ccctgacccc ccgatcggcg tgggctggga gacgcccaac       180
ctgggcaacg gcttcgtgac gcctgaagaa gcgtcgaccg atgccatcat ctgccacaag       240
gaggccaagc cggcccgcgg ccatgccacc gtgaaagccg gcgacaagat ctacatccaa       300
tggcagccga tccctggcc ggagtccac acggtgcgt agcatttcct tgagactctg         360
attgtgcat tccagtctca cccactaaca atacttctag gccccgtcct cgactatctg        420
gccgcttgca acggcgactg cgagaccgtc gacaagacca gcctgcggtt cttcaagatc       480
tccaacaagg gtctcatcga cggctcttcc ccgccgggct actgggctga cgatcagctc       540
atcgagaacg gtaacggatg gctggttcag attcccgagg acatcaagcc gggcaactac       600
gtgctgcgac acgagatcat cgcttttgcac gcagcgggca acccgaacgg cgcccagctg      660
tatccgcagt gcttcaacct gcatattacg ggttccggca ccgtcgagcc gcagggaata      720
ccagccaccg agctgtactc gcccgatgac ccgggcattc tgatcaacat ctaccagccc      780
ttgaccacgt atgaggtgcc gggccccacg cccatcccac aggcggttga gattgagcag      840
tcttcgtccg cgattaccgc gactggaacg ccaacgccgg catga                       885

SEQ ID NO: 411          moltype = AA  length = 272
FEATURE                 Location/Qualifiers
source                  1..272
                        mol_type = protein
                        organism = Talaromyces thermophilus
SEQUENCE: 411
MKGSSAASVL LALLAGITRT SAHGYVSNIV VNGVYYRGWL PGEDPYNPDP PIGVGWETPN        60
LGNGFVTPEE ASTDAIICHK EAKPARGHAT VKAGDKIYIQ WQPIPWPESH HGPVLDYLAA       120
CNGDCETVDK TSLRFFKISN KGLIDGSSPP GYWADDQLIE NGNGWLVQIP EDIKPGNYVL       180
RHEIIALHAA GNPNGAQLYP QCFNLHITGS GTVEPQGIPA TELYSPDDPG ILINIYQPLT       240
TYEVPGPTPI PQAVEIEQSS SAITATGTPT PA                                    272
```